US012624052B2

(12) United States Patent
Lin et al.

(10) Patent No.: US 12,624,052 B2
(45) Date of Patent: *May 12, 2026

(54) KRAS MODULATORS AND USES THEREOF

(71) Applicant: Quanta Therapeutics, Inc., South San Francisco, CA (US)

(72) Inventors: Hong Lin, Exton, PA (US); Juan Luengo, Phoenixville, PA (US); Neil Johnson, Downingtown, PA (US); Audrey Hospital, Robbinsville, NJ (US)

(73) Assignee: QUANTA THERAPEUTICS, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/413,444

(22) Filed: Jan. 16, 2024

(65) Prior Publication Data

US 2025/0042921 A1 Feb. 6, 2025

Related U.S. Application Data

(63) Continuation of application No. 18/362,576, filed on Jul. 31, 2023, now Pat. No. 11,912,723, which is a continuation of application No. PCT/US2023/062235, filed on Feb. 8, 2023.

(60) Provisional application No. 63/384,374, filed on Nov. 18, 2022, provisional application No. 63/378,843, filed on Oct. 7, 2022, provisional application No. 63/373,302, filed on Aug. 23, 2022, provisional application No. 63/368,584, filed on Jul. 15, 2022, provisional application No. 63/308,424, filed on Feb. 9, 2022.

(51) Int. Cl.
*C07D 519/00* (2006.01)

(52) U.S. Cl.
CPC ................................. *C07D 519/00* (2013.01)

(58) Field of Classification Search
CPC .................................................... C07D 519/00
USPC ......................................................... 514/300
See application file for complete search history.

(56) References Cited

U.S. PATENT DOCUMENTS

| | | | |
|---|---|---|---|
| 10,647,715 B2 | 5/2020 | Marx et al. | |
| 10,689,377 B2 | 6/2020 | Blake et al. | |
| 10,822,312 B2 | 11/2020 | Li et al. | |
| 11,267,812 B2 | 3/2022 | Fischer et al. | |
| 11,312,724 B2 | 4/2022 | Li et al. | |
| 11,912,723 B2 | 2/2024 | Lin et al. | |
| 2005/0234108 A1 | 10/2005 | Himmelsbach et al. | |
| 2011/0166135 A1 | 7/2011 | Morimoto et al. | |
| 2013/0012485 A1 | 1/2013 | Bäschlin et al. | |
| 2016/0136180 A1 | 5/2016 | Himmelsbach et al. | |
| 2020/0331911 A1 | 10/2020 | Marx et al. | |

| | | | |
|---|---|---|---|
| 2021/0380574 A1 | 12/2021 | Abbott et al. | |
| 2022/0402916 A1 | 12/2022 | Hoover et al. | |
| 2023/0135152 A1 | 5/2023 | Smrcina et al. | |
| 2024/0199650 A1 | 6/2024 | Lin et al. | |

FOREIGN PATENT DOCUMENTS

| | | |
|---|---|---|
| CN | 112409331 A | 2/2021 |
| CN | 113396147 A | 9/2021 |
| CN | 114685460 A | 7/2022 |
| JP | 2020111571 A | 7/2020 |
| JP | 2021532157 A | 11/2021 |
| WO | WO-2005003099 A2 | 1/2005 |
| WO | WO-2010064705 A1 | 6/2010 |
| WO | WO-2010120996 A1 | 10/2010 |
| WO | WO-2014172639 A1 | 10/2014 |
| WO | WO-2016081679 A1 | 5/2016 |
| WO | WO-2017087528 A1 | 5/2017 |
| WO | WO-2017201161 A1 | 11/2017 |
| WO | WO-2018212774 A1 | 11/2018 |
| WO | WO-2019013311 A1 | 1/2019 |
| WO | WO-2020028706 A1 | 2/2020 |
| WO | WO-2020146613 A1 | 7/2020 |
| WO | WO-2020236940 A1 | 11/2020 |
| WO | WO-2020239123 A1 | 12/2020 |
| WO | WO-2021041671 A1 | 3/2021 |
| WO | WO-2021093758 A1 | 5/2021 |
| WO | WO-2021106231 A1 | 6/2021 |
| WO | WO-2021129820 A1 | 7/2021 |
| WO | WO-2021139748 A1 | 7/2021 |
| WO | WO-2021245055 A1 | 12/2021 |
| WO | WO-2022002102 A1 | 1/2022 |
| WO | WO-2022031678 A1 | 2/2022 |
| WO | WO-2022040469 A1 | 2/2022 |
| WO | WO-2022042630 A1 | 3/2022 |
| WO | WO-2022047260 A1 | 3/2022 |
| WO | WO-2022061251 A1 | 3/2022 |
| WO | WO-2022105857 A1 | 5/2022 |
| WO | WO-2022105859 A1 | 5/2022 |

(Continued)

OTHER PUBLICATIONS

PCT/US2022/024111 International Search Report and Written Opinion dated Aug. 1, 2022.
PCT/US2022/031846 International Search Report and Written Opinion dated Oct. 5, 2022.
PCT/US2022/032680 International Search Report and Written Opinion dated Oct. 26, 2022.
PCT/US2022/081393 International Search Report and Written Opinion dated May 9, 2023.
PCT/US2023/062235 International Search Report and Written Opinion dated Aug. 17, 2023.
PUBCHEM-SID:325121534 Deposit Date: Jan. 25, 2017 (Jan. 25, 2017) pp. 1-7; p. 2.

(Continued)

*Primary Examiner* — Kahsay Habte
(74) *Attorney, Agent, or Firm* — WILSON SONSINI GOODRICH & ROSATI

(57) ABSTRACT

Provided herein are KRAS modulating compounds, such as compounds of Formula (I), (II) (II*) (III) or pharmaceutically acceptable salts, solvates, stereoisomers, atom labelled, or tautomers of any of the foregoing, useful for modulating KRAS GD12 and/or other G12 mutants.

28 Claims, No Drawings

(56) References Cited

FOREIGN PATENT DOCUMENTS

| | | | |
|---|---|---|---|
| WO | WO-2022109487 A1 | 5/2022 | |
| WO | WO-2022115439 A1 | 6/2022 | |
| WO | WO-2022127827 A1 | 6/2022 | |
| WO | WO-2022132200 A1 | 6/2022 | |
| WO | WO-2022133038 A1 | 6/2022 | |
| WO | WO-2022135470 A1 | 6/2022 | |
| WO | WO-2022135546 A1 * | 6/2022 | .............. A61P 35/00 |
| WO | WO-2022148422 A1 | 7/2022 | |
| WO | WO-2022156761 A1 | 7/2022 | |
| WO | WO-2022170999 A1 | 8/2022 | |
| WO | WO-2022173870 A1 | 8/2022 | |
| WO | WO-2022177917 A2 | 8/2022 | |
| WO | WO-2022184178 A1 | 9/2022 | |
| WO | WO-2022187527 A1 | 9/2022 | |
| WO | WO-2022187528 A1 | 9/2022 | |
| WO | WO-2022188729 A1 | 9/2022 | |
| WO | WO-2022192790 A1 | 9/2022 | |
| WO | WO-2022192794 A1 | 9/2022 | |
| WO | WO-2022193982 A1 | 9/2022 | |
| WO | WO-2022194066 A1 | 9/2022 | |
| WO | WO-2022194191 A1 | 9/2022 | |
| WO | WO-2022194192 A1 | 9/2022 | |
| WO | WO-2022194245 A1 | 9/2022 | |
| WO | WO-2022214102 A1 | 10/2022 | |
| WO | WO-2022217118 A1 | 10/2022 | |
| WO | WO-2022221386 A1 | 10/2022 | |
| WO | WO-2022221739 A1 | 10/2022 | |
| WO | WO-2022228543 A1 | 11/2022 | |
| WO | WO-2022232331 A1 | 11/2022 | |
| WO | WO-2022232332 A1 | 11/2022 | |
| WO | WO-2022247760 A1 | 12/2022 | |
| WO | WO-2022251576 A1 | 12/2022 | |
| WO | WO-2022256459 A1 | 12/2022 | |
| WO | WO-2022261210 A1 | 12/2022 | |
| WO | WO-2022266069 A1 | 12/2022 | |
| WO | WO-2022266249 A1 | 12/2022 | |
| WO | WO-2022268051 A1 | 12/2022 | |
| WO | WO-2022269508 A1 | 12/2022 | |
| WO | WO-2022269525 A1 | 12/2022 | |
| WO | WO-2022271658 A1 | 12/2022 | |
| WO | WO-2022271823 A1 | 12/2022 | |
| WO | WO-2022271923 A1 | 12/2022 | |
| WO | WO-2023001123 A1 | 1/2023 | |
| WO | WO-2023001141 A1 | 1/2023 | |
| WO | WO-2023274324 A1 | 1/2023 | |
| WO | WO-2023274383 A1 | 1/2023 | |
| WO | WO-2023278600 A1 | 1/2023 | |
| WO | WO-2023280026 A1 | 1/2023 | |
| WO | WO-2023280136 A1 | 1/2023 | |
| WO | WO-2023280280 A1 | 1/2023 | |
| WO | WO-2023283213 A1 | 1/2023 | |
| WO | WO-2023060362 A1 | 4/2023 | |
| WO | WO-2023061294 A1 | 4/2023 | |
| WO | WO-2023061463 A1 | 4/2023 | |
| WO | WO-2023064857 A1 | 4/2023 | |
| WO | WO-2023066371 A1 | 4/2023 | |
| WO | WO-2023067546 A1 | 4/2023 | |
| WO | WO-2023072188 A1 | 5/2023 | |
| WO | WO-2023072297 A1 | 5/2023 | |
| WO | WO-2023077441 A1 | 5/2023 | |
| WO | WO-2023081476 A1 | 5/2023 | |
| WO | WO-2023081840 A1 | 5/2023 | |
| WO | WO-2023086383 A1 | 5/2023 | |
| WO | WO-2023097227 A1 | 6/2023 | |
| WO | WO-2023098425 A1 | 6/2023 | |
| WO | WO-2023098426 A1 | 6/2023 | |
| WO | WO-2023098832 A1 | 6/2023 | |
| WO | WO-2023099592 A1 | 6/2023 | |
| WO | WO-2023099608 A1 | 6/2023 | |
| WO | WO-2023099612 A1 | 6/2023 | |
| WO | WO-2023099620 A1 | 6/2023 | |
| WO | WO-2023099623 A1 | 6/2023 | |
| WO | WO-2023099624 A1 | 6/2023 | |
| WO | WO-2023101928 A1 | 6/2023 | |
| WO | WO-2023103523 A1 | 6/2023 | |
| WO | WO-2023103906 A1 | 6/2023 | |
| WO | WO-2023104018 A1 | 6/2023 | |
| WO | WO-2023105491 A1 | 6/2023 | |
| WO | WO-2023114733 A1 | 6/2023 | |
| WO | WO-2023116934 A1 | 6/2023 | |
| WO | WO-2023117681 A1 | 6/2023 | |
| WO | WO-2023119677 A1 | 6/2023 | |
| WO | WO-2023120742 A1 | 6/2023 | |
| WO | WO-2023125627 A1 | 7/2023 | |
| WO | WO-2023125989 A1 | 7/2023 | |
| WO | WO-2023130012 A1 | 7/2023 | |
| WO | WO-2023133181 A1 | 7/2023 | |
| WO | WO-2023133183 A1 | 7/2023 | |
| WO | WO-2023134465 A1 | 7/2023 | |
| WO | WO-2023137223 A1 | 7/2023 | |
| WO | WO-2023138524 A1 | 7/2023 | |
| WO | WO-2023138589 A1 | 7/2023 | |
| WO | WO-2023141570 A2 | 7/2023 | |
| WO | WO-2023143312 A1 | 8/2023 | |
| WO | WO-2023143623 A1 | 8/2023 | |
| WO | WO-2023150284 A2 | 8/2023 | |
| WO | WO-2023151621 A1 | 8/2023 | |
| WO | WO-2023152255 A1 | 8/2023 | |
| WO | WO-2023154766 | 8/2023 | |
| WO | WO-2023230190 A1 | 11/2023 | |
| WO | WO-2024192424 A1 | 9/2024 | |
| WO | WO-2025016899 A1 | 1/2025 | |

OTHER PUBLICATIONS

U.S. Appl. No. 18/362,576 Notice of Allowance dated Dec. 6, 2023.

U.S. Appl. No. 18/362,576 Office Action dated Nov. 8, 2023.

CAS Number Citation: Chemical Abstracts Service. CAS Registry: RN3056973-98-6. Spiro[azetidine-3,4'(6'H)-thieno[3, 4-b]thiophene]-3'-carbonitril 2'-amino-1-[4-[[1-(3-amino-2-pyrazinyl)ethyl]methylamino]-6-[[(2R,7aS)-2-fluorotetrahydro-1H-pyrrolizi n-7a(5H)-yl]methoxy]-1,3,5-tri azin-2-yl]—p. 1. STN Entry Date Oct. 8, 2024.

Lashford, L. et al. Phase I Study of Temozolomide in Paediatric Patients With Advanced Cancer. British Journal of Cancer 78(5):652-661 (1998).

PCT/US2023/023445 International Search Report and Written Opinion dated Sep. 6, 2023.

PCT/US2024/020319 International Search Report and Written Opinion dated Jul. 8, 2024.

U.S. Appl. No. 18/503,626 Corrected Notice of Allowability dated Oct. 3, 2024.

U.S. Appl. No. 18/503,626 Notice of Allowance dated Jun. 17, 2024.

Hallin et al. The KRASG12C Inhibitor, MRTX849, Provides Insight Toward Therapeutic Susceptibility of KRAS Mutant Cancers in Mouse Models and Patients. Cancer Discov. 10(1):54-71 (2019).

* cited by examiner

KRAS MODULATORS AND USES THEREOF

CROSS-REFERENCE

This application is a continuation of U.S. application Ser. No. 18/362,576, filed on Jul. 31, 2023, which is a continuation of International Patent Application PCT/US23/62235, filed on Feb. 8, 2023, which claims the benefit of U.S. Provisional Patent Applications Nos. 63/308,424 filed on Feb. 9, 2022; 63/368,584 filed on Jul. 15, 2022; 63/373,302 filed on Aug. 23, 2022; 63/378,843 filed on Oct. 7, 2022; and 63/384,374 filed on Nov. 18, 2022; each of which is incorporated herein by reference in its entirety.

BACKGROUND OF THE INVENTION

The small GTPase protein Kirsten Rat Sarcoma 2 Viral Oncogene Homolog (KRAS) is a member of the Ras family of cell signaling switches, regulating growth and survival of normal and cancerous cells (e.g., see Cully, M. and J. Downward, SnapShot: Ras Signaling. Cell, 2008. 133(7): p. 1292-1292 e1). KRAS mutations drive approximately 25% of human cancers by aberrant regulation of the mitogen-activated protein kinase (MAPK) signaling cascade and other effector pathways (e.g., see Stephen, A. G., et al., Dragging ras back in the ring. Cancer Cell, 2014. 25(3): p. 272-81). Though Ras has been recognized as a target in cancer for about 40 years, Ras-driven cancers remain among the most difficult to treat due to insensitivity to available targeted therapies. Ras, encoded by the three major genes KRAS, NRAS and HRAS, has the highest frequency of mutation of any oncogene. All oncogenic Ras mutations drive the switch to accumulate in the active GTP-bound state. The most common Ras mutation found across human tumor types is KRAS G12D (e.g., see The AACR Project GENIE Consortium. Cancer Discovery, 2017. 7(8): p. 818-831. Dataset Version 4). Activating mutations in codon 12 impair the small GTPases' ability to perform their role in hydrolyzing GTP. This regulatory impairment is fundamental for initiating and maintaining tumor progression.

Despite extensive efforts, small molecules have not been identified which block effector binding or restore GTPase activating protein (GAP) sensitivity, though some have been found which block interaction of Ras with the guanine nucleotide exchange factor (GEF), SOS, which activates Ras at the plasma membrane. KRAS G12C mutations, most common in lung adenocarcinoma, have been clinically shown to be susceptible to direct inhibition by covalent modification with small molecule inhibitors trapping the protein in the inactive GDP-bound state. KRAS G12D mutation confers a significantly slower intrinsic rate of GTP hydrolysis than G12C, resulting in more constitutive activation. Thus, pharmacological targeting the of inactive state is unlikely to achieve similar results against G12D, despite the existence of a similar binding pocket in the GDP-state. Additionally, a cysteine present at the site of the activating mutation yields itself to covalent chemistry, while aspartic acid does not provide typical medicinal chemistry approaches for selective covalent modification.

In order to potentially exploit the accumulation of KRAS G12D and other mutant variants in the GTP-bound state as a vulnerability to achieve selective inhibition of cancer cells while sparing normal Ras function, it is attractive for small molecule inhibitors to bind selectively to the GTP-state and stabilize a conformation that is incompetent for oncogenic signaling interactions with effector proteins. Furthermore, it has been shown that only constitutive activation of Raf, MEK and ERK kinases in the MAPK cascade downstream of Ras can bypass the requirement for Ras proteins in proliferative signaling (e.g., see Drosten, M., et al., Genetic analysis of Ras signalling pathways in cell proliferation, migration and survival. EMBO J, 2010. 29(6): p. 1091-104). As all evidence has indicated that MAPK signaling is essential for the growth effects of Ras in cancer, KRAS-mutant-selective inhibition in this pathway is considered the critical functional readout for potential clinical benefit of novel therapeutic approaches.

SUMMARY OF THE INVENTION

There is a need to develop new inhibitors for KRAS-driven cancers that demonstrate inhibition of MAPK signals via a mechanism of action that is selective for binding to the active GTP-bound state over the inactive GDP-bound state.

The present disclosure relates to Formula (I) or Formula (II) or Formula (III), including stereoisomers, tautomers, solvates, and pharmaceutically acceptable salts thereof, and to uses thereof in, for example, inhibiting KRas G12D and/or other G12 mutants.

In an aspect, the present disclosure provides a compound represented by the structure of Formula (I):

Formula (I)

or a pharmaceutically acceptable salt thereof wherein:

$R^1$ is selected from $C_3$-$C_{12}$ carbocycle and 5- to 15-membered heterocycle, each of which are optionally substituted with one or more substituents independently selected from halogen, $-B(OR^{20})_2$, $-OR^{20}$, $-SR^{20}$, $-S(O)_2(R^{20})$, $-S(O)_2N(R^{20})_2$, $-S(O)N(R^{20})_2$, $-S(O)R^{20}(=NR^{20})$, $-NR^{20}S(O)_2R^{20}c$, $-C(O)N(R^{20})_2$, $-C(=NR^{20})N(R^{20})_2$, $-C(O)NR^{20}OR^{20}$, $-N(R^{20})C(O)R^{20}$, $-N(R^{20})C(O)N(R^{20})_2$, $-N(R^{20})C(O)OR^{20}$, $-N(R^{20})_2$, $-C(O)R^{20}$, $-C(O)OR^{20}$, $-OC(O)R^{20}$, $-OC(O)N(R^{20})_2$, $-NO_2$, $=O$, $=N(R^{20})$, $=NO(R^{20})$, $-CN$, $-NHCN$, $C_{1-6}$ alkyl-$N(R^{20})_2$, $C_{1-6}$ aminoalkyl, $C_{1-6}$ alkoxy, $C_{1-6}$ hydroxyalkyl, $C_{1-6}$ cyanoalkyl, $C_{1-6}$haloalkyl, $C_{1-6}$ alkyl, $C_{2-6}$ alkenyl, $C_{2-6}$ alkynyl, $C_3$-$C_{12}$ carbocycle and 5- to 12-membered heterocycle, wherein the $C_3$-$C_{12}$ carbocycle and 5- to 12-membered heterocycle are each optionally substituted independently with one or more $R^{1*}$;

each $R^{1*}$ is independently selected from halogen, $-B(OR^{20})_2$, $-OR^{20}$, $-SR^{20}$, $-S(O)_2(R^{20})$, $-S(O)_2N(R^{20})_2$, $-S(O)N(R^{20})_2$, $-S(O)R^{20}(=NR^{20})$, $-NR^{20}S(O)_2R^{20}$, $-C(O)N(R^{20})_2$, $-C(O)NR^{20}OR^{20}$, $-N(R^{20})C(O)R^{20}$, $-N(R^{20})C(O)N(R^{20})_2$, $-N(R^{20})C(O)OR^{20}$, $-N(R^{20})_2$, $-C(O)R^{20}$, $-C(O)OR^{20}$, $-OC(O)R^{20}$, $-OC(O)N(R^{20})_2$, $-NO_2$, $=O$, $=N(R^{20})$, $=NO(R^{20})$, $-CN$, $-NHCN$, $C_{1-6}$ alkyl-$N(R^{20})_2$, $C_{1-6}$ aminoalkyl, $C_{1-6}$alkoxy, $C_{1-6}$ hydroxyalkyl, $C_{1-6}$ cyanoalkyl, $C_{1-6}$haloalkyl, $C_{1-6}$alkyl, $C_{2-6}$alkenyl, $C_{2-6}$ alkynyl, and $C_3$-$C_{12}$ carbocycle;

Y is selected from a bond, O, S and $NR^5$;

$R^2$ is selected from hydrogen, $-N(R^{21})_2$, $-L-N(R^{21})_2$, $-L-OR^{21}$, heterocycle, $C_1$-$C_6$ alkyl, $-L$-heterocycle, $-L$-aryl, $-L$-heteroaryl, $-L$-cycloalkyl, $-L$-NHC(=NH)

$NH_2$, -L-C(O)N$(R^{21})_2$, -L-$C_1$-$C_6$ haloalkyl, -L-OR$^{21}$, -L-NR$^{21}$C(O)-aryl, -L-COOH, -L-NR$^2$'S(O)$_2$(R$^{21}$), -L-S(O)$_2$N$(R^{21})_2$, -L-N$(R^{21})$C(O)(OR$^{21}$), -L-OC(O)N $(R^{21})_2$, and -LC(=O)OC$_1$-$C_6$ alkyl, wherein the heterocycle and the aryl portion of -L-NR$^5$C(O)-aryl and the heterocycle portion of -L-heterocycle and the cycloalkyl portion of the -L-cycloalkyl are optionally substituted with one or more R$^6$, and wherein the aryl or heteroaryl of the -L-aryl and the -L-heteroaryl are optionally substituted with one or more R$^7$;

each L is independently selected from a $C_1$-$C_4$ alkylene optionally substituted with one or more substituents selected from hydroxy, $C_1$-$C_4$ hydroxyalkyl, $C_1$-$C_4$ alkyl, $C_3$-$C_6$ carbocycle, or 3- to 8-membered heterocycle, wherein the $C_3$-$C_6$ carbocycle and 3- to 8-membered heterocycle are optionally substituted with one or more substituents selected from halogen, —OH, —NO$_2$, =O, =S, —CN, $C_{1-6}$ aminoalkyl, $C_{1-6}$ alkoxy, $C_{1-6}$ hydroxyalkyl, $C_{1-6}$ haloalkyl; and wherein optionally two substituents on the same carbon atom of L come together to form a $C_3$-$C_6$ carbocycle or 3- to 8-membered heterocycle wherein the $C_3$-$C_6$ carbocycle and 3- to 8-membered heterocycle are optionally substituted with one or more substituents selected from halogen, —OH, —NO$_2$, =O, =S, —CN, $C_{1-6}$ aminoalkyl, $C_{1-6}$ alkoxy, $C_{1-6}$ hydroxyalkyl, $C_{1-6}$ haloalkyl;

each R$^4$ is independently selected from $C_{1-6}$ alkyl, $C_{2-6}$ alkenyl, $C_{2-6}$ alkynyl, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{3-12}$ carbocycle, and 3- to 12-membered heterocycle, wherein $C_{3-12}$ carbocycle and 3- to 12-membered heterocycle are each optionally substituted with one or more substituents independently selected from halogen, —OH, —CN, —NO$_2$, —NH$_2$, —NH(C$_{1-6}$ alkyl), —N(C$_{1-6}$ alkyl)$_2$, $C_{1-10}$ alkyl, —C$_{1-10}$ haloalkyl, —O—C$_{1-10}$ alkyl, oxo, $C_{3-12}$ carbocycle, and 3- to 12-membered heterocycle;

each R$^5$ is independently selected from hydrogen or $C_1$-$C_6$ alkyl;

each R$^6$ is independently selected from halogen, hydroxy, $C_1$-$C_3$ hydroxyalkyl, $C_1$-$C_3$ alkyl, oxo, $C_1$-$C_3$ haloalkyl, $C_1$-$C_3$ alkoxy, cyano, =CH$_2$, =NO—C$_1$-$C_3$ alkyl, $C_1$-$C_3$ aminoalkyl, —N(R$^5$)S(O)$_2$(R$^5$), -Q-phenyl, -Q-phenylSO$_2$F, —NHC(O)phenyl, —NHC(O) phenylSO$_2$F, $C_1$-$C_3$ alkyl substituted pyrazolyl, tert-butyldimethylsilyloxyCH$_2$—, —N(R$^5$)$_2$, (C$_1$-$C_3$ alkoxy)C$_1$-$C_3$ alkyl-, (C$_1$-$C_3$ alkyl)C(=O), oxo, (C$_1$-$C_3$ haloalkyl)C(=O)—, —SO$_2$F, (C$_1$-$C_3$ alkoxy)C$_1$-$C_3$ alkoxy, —CH$_2$OC(O)N(R$^5$)$_2$, —CH$_2$NHC(O)OC$_1$-$C_6$ alkyl, —CH$_2$NHC(O)N(R$^5$)$_2$, —CH$_2$NHC(O)C$_1$-$C_6$ alkyl, —CH$_2$(pyrazolyl), —CH$_2$NHSO$_2$C$_1$-$C_6$ alkyl, —CH$_2$OC(O)heterocycle, —OC(O)N(R$^5$)$_2$, —OC(O) NH(C$_1$-$C_3$ alkyl)O(C$_1$-$C_3$ alkyl), —OC(O)NH(C$_1$-$C_3$ alkyl)O(C$_1$-$C_3$ alkyl)phenyl(C$_1$-$C_3$ alkyl)N(CH$_3$)$_2$, —OC(O)NH(C$_1$-$C_3$ alkyl)O(C$_1$-$C_3$ alkyl)phenyl, —OC(O)heterocycle, —O—C$_1$-$C_3$ alkyl, and —CH$_2$heterocycle, wherein the phenyl of —NHC(O) phenyl and —OC(O)NH(C$_1$-$C_3$ alkyl)(C$_1$-$C_3$ alkyl) phenyl are optionally substituted with one or more substituents selected from —C(O)H and OH, and wherein the alkyl of —O—C$_1$-$C_3$ alkyl is optionally substituted with substituents selected from heterocycle, oxo and hydroxy; and wherein the heterocycle of —CH$_2$heterocyclyl is optionally substituted with oxo;

each R$^7$ is independently selected from halogen, hydroxy, HC(=O)—, $C_1$-$C_4$ alkyl, $C_1$-$C_4$ alkoxy, $C_1$-$C_4$ haloalkyl, $C_1$-$C_4$ hydroxyalkyl, or —N(R$^5$)$_2$;

each R$^{20}$ is independently selected from hydrogen; and $C_{1-6}$ alkyl, $C_{3-12}$ carbocycle, and 3- to 12-membered heterocycle, each of which is optionally substituted with one or more substituents independently selected from halogen, —OH, —CN, —NO$_2$, —NH$_2$, —N(C$_{1-6}$ alkyl)$_2$, $C_{1-10}$ alkyl, —C$_{1-10}$ haloalkyl, —O—C$_{1-10}$ alkyl, oxo, =NH, $C_{3-12}$ carbocycle, and 3- to 12-membered heterocycle;

each R$^{21}$ is independently selected from hydrogen; and $C_{1-6}$ alkyl, $C_{3-12}$ carbocycle, and 3- to 12-membered heterocycle, each of which is optionally substituted with one or more substituents independently selected from halogen, —OH, —CN, —NO$_2$, —NH$_2$, —N(C$_{1-6}$ alkyl)$_2$, $C_{1-10}$ alkyl, —C$_{1-10}$ haloalkyl, —O—C$_{1-10}$ alkyl, oxo, $C_{3-12}$ carbocycle, and 3- to 12-membered heterocycle;

each Q is independently selected from a bond, S, and O;

B is selected from a heterocycle and carbocycle, wherein the heterocycle and carbocycle are optionally substituted with one or more substituents independently selected from halogen, cyano, hydroxy, =O, —NO$_2$, $C_1$-$C_4$ alkyl, $C_{1-6}$ aminoalkyl, —S—C$_1$-$C_3$ alkyl, $C_2$-$C_4$ alkenyl, $C_2$-$C_4$ alkynyl, $C_2$-$C_4$ hydroxyalkynyl, $C_1$-$C_3$ cyanoalkyl, triazolyl, $C_1$-$C_3$ haloalkyl, —O—C$_1$-$C_3$ haloalkyl, —S—C$_1$-$C_3$ haloalkyl, $C_1$-$C_3$ alkoxy, $C_1$-$C_3$ hydroxyalkyl, —CH$_2$C(=O)N(R$^5$)$_2$, —C$_3$-$C_4$ alkynyl (NR$^5$)$_2$, —N(R$^5$)$_2$, (C$_1$-$C_3$ alkoxy)haloC$_1$-$C_3$ alkyl-, $C_{1-6}$ alkyl-N(R$^{20}$)$_2$, $C_3$-$C_{12}$ carbocycle and 5- to 12-membered heterocycle, wherein $C_3$-$C_{12}$ carbocycle and 5- to 12-membered heterocycle are each optionally substituted with one or more substituents selected from halogen, —OH, —NO$_2$, —NH$_2$, =O, =S, —CN, $C_{1-6}$ aminoalkyl, $C_{1-6}$ alkoxy, $C_{1-6}$ hydroxyalkyl, $C_{1-6}$ haloalkyl, and wherein B forms a spirocycle with Ring A; and Ring A is selected from a heterocycle and carbocycle, wherein the heterocycle or carbocycle is optionally substituted with one or more substituents selected from R$^4$.

In certain embodiments, the disclosure provides a pharmaceutical composition comprising a compound or salt of Formula (I) and a pharmaceutically acceptable excipient.

In certain embodiments, the disclosure provides a method of treating a disease or disorder, using a compound or salt of Formula (I). In certain embodiments, the disclosure provides a method of treating a disease or disorder, using a compound or salt of Formula (I) and a pharmaceutically acceptable excipient.

In certain embodiments, the disclosure provides a method of inhibiting KRas G12D and/or other G12 mutants, using a compound or salt of Formula (I). In certain embodiments, the disclosure provides a method of inhibiting KRas G12D and/or other G12 mutants, using a compound or salt of Formula (I) and a pharmaceutically acceptable excipient.

In an aspect, the present disclosure provides a compound represented by the structure of Formula (II):

Formula (II)

or a pharmaceutically acceptable salt thereof wherein:

M is selected from O, S, SO, $SO_2$, and $NR^3$;

$R^1$ is selected from $C_3$-$C_{12}$ carbocycle and 5- to 15-membered heterocycle, each of which are optionally substituted with one or more substituents independently selected from halogen, $-B(OR^{20})_2$, $-OR^{20}$, $-SR^{20}$, $-S(O)_2(R^{20})$, $-S(O)_2N(R^{20})_2$, $-S(O)N(R^{20})_2$, $-S(O)R^{20}(=NR^{20})$, $-NR^{20}S(O)_2R^{20}$, $-C(O)N(R^{20})_2$, $-C(=NR^{20})N(R^{20})_2$, $-C(O)NR^{20}OR^{20}$, $-N(R^{20})C(O)R^{20}$, $-N(R^{20})C(O)N(R^{20})_2$, $-N(R^{20})C(O)OR^{20}$, $-N(R^{20})_2$, $-C(O)R^{20}$, $-C(O)OR^{20}$, $-OC(O)R^{20}$, $-OC(O)N(R^{20})_2$, $-NO_2$, $=O$, $=N(R^{20})$, $=NO(R^{20})$, $-CN$, $-NHCN$, $C_{1-6}$ alkyl-$N(R^{20})_2$, $C_{1-6}$ aminoalkyl, $C_{1-6}$ alkoxy, $C_{1-6}$ hydroxyalkyl, $C_{1-6}$ cyanoalkyl, $C_{1-6}$haloalkyl, $C_{1-6}$ alkyl-$SO_2R^{20}$, $C_{1-6}$ alkyl, $C_{2-6}$ alkenyl, $C_{2-6}$ alkynyl, $C_3$-$C_{12}$ carbocycle and 5- to 12-membered heterocycle, wherein the $C_3$-$C_{12}$ carbocycle and 5- to 12-membered heterocycle are each optionally substituted independently with one or more $R^{1*}$; and wherein when M is $NR^3$, Y is O, and $R^1$ is piperazine, the piperazine is substituted with one or more $R^9$;

each $R^{1*}$ is independently selected from halogen, $-B(OR^{20})_2$, $-OR^{20}$, $-SR^{20}$, $-S(O)_2(R^{20})$, $-S(O)_2N(R^{20})_2$, $-S(O)N(R^{20})_2$, $-S(O)R^{20}(=NR^{20})$, $-NR^{20}S(O)_2R^{20}$, $-C(O)N(R^{20})_2$, $-C(O)NR^{20}OR^{20}$, $-N(R^{20})C(O)R^{20}$, $-N(R^{20})C(O)N(R^{20})_2$, $-N(R^{20})C(O)OR^{20}$, $-N(R^{20})_2$, $-C(O)R^{20}$, $-C(O)OR^{20}$, $-OC(O)R^{20}$, $-OC(O)N(R^{20})_2$, $-NO_2$, $=O$, $=N(R^{20})$, $=NO(R^{20})$, $-CN$, $-NHCN$, $C_{1-6}$ alkyl-$N(R^{20})_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, and $C_3$-$C_{12}$ carbocycle;

Y is selected from a bond, O, S and $NR^5$;

$R^2$ is selected from -L-$N(R^{21})_2$, -L-$OR^{21}$, heterocycle, $C_1$-$C_6$ alkyl, -L-heterocycle, -L-aryl, -L-heteroaryl, -L-cycloalkyl, -L-$N(R^{21})_2$, -L-$NHC(=NH)NH_2$, -L-$C(O)N(R^{21})_2$, -L-$C_1$-$C_6$ haloalkyl, -L-$OR^{21}$, -L-$NR^{21}C(O)$-aryl, -L-COOH, -L-$NR^{21}S(O)_2(R^{21})$, -L-$S(O)_2N(R^{21})_2$, -L-$N(R^{21})C(O)(OR^{21})$, -L-$OC(O)N(R^{21})_2$, or -LC$(=O)OC_1$-$C_6$ alkyl, wherein the heterocycle, the aryl portion of -L-$NR^{21}C(O)$-aryl, the heterocycle portion of -L-heterocycle, the cycloalkyl portion of the -L-cycloalkyl are each optionally substituted with one or more $R^6$, and wherein the aryl portion of the -L- aryl and the heteroaryl portion of the -L-heteroaryl are each optionally substituted with one or more $R^7$, and wherein when Y is a bond, O, or S, $R^2$ is further selected from hydrogen;

each L is independently selected from a $C_1$-$C_4$ alkylene optionally substituted with one or more substituents selected from hydroxy, $C_1$-$C_4$ hydroxyalkyl, $C_1$-$C_4$ alkyl, $C_3$-$C_6$ carbocycle, or 3- to 8-membered heterocycle, wherein the $C_3$-$C_6$ carbocycle and 3- to 8-membered heterocycle are optionally substituted with one or more substituents selected from halogen, $-OH$, $-NO_2$, $=O$, $=S$, $-CN$, $C_{1-6}$ aminoalkyl, $C_{1-6}$ alkoxy, $C_{1-6}$ hydroxyalkyl, $C_{1-6}$ haloalkyl; and wherein optionally two substituents on the same carbon atom of L come together to form a $C_3$-$C_6$ carbocycle or 3- to 8-membered heterocycle, wherein the $C_3$-$C_6$ carbocycle and 3- to 8-membered heterocycle are each optionally substituted with one or more substituents selected from halogen, $-OH$, $-NO_2$, $=O$, $=S$, $-CN$, $C_{1-6}$ aminoalkyl, $C_{1-6}$ alkoxy, $C_{1-6}$ hydroxyalkyl, $C_{1-6}$ haloalkyl;

$R^3$ is selected from hydrogen, $C_{1-6}$ alkyl, $C_{2-6}$ alkenyl, $C_{2-6}$ alkynyl, $C_{1-6}$ alkyl-$N(R^{20})_2$, $C_{1-6}$ aminoalkyl, $C_{1-6}$ alkoxy, $C_{1-6}$ hydroxyalkyl, $C_{1-6}$ cyanoalkyl, $C_{1-6}$haloalkyl, $C_{1-6}$ alkoxyalkyl, $C_{3-12}$ carbocycle, and 3- to 12-membered heterocycle, wherein $C_{3-12}$ carbocycle and 3- to 12-membered heterocycle are each optionally substituted with one or more substituents independently selected from halogen, $-OH$, $-CN$, $-NO_2$, $-NH_2$, $-N(C_{1-6}$ alkyl$)_2$, $C_{1-10}$ alkyl, $-C_{1-10}$ haloalkyl, $-O-C_{1-10}$ alkyl, oxo, $C_{3-12}$ carbocycle, and 3- to 12-membered heterocycle;

n is selected from 0 to 2;

each $R^4$ is independently selected from $C_{1-6}$ alkyl, $C_{2-6}$ alkenyl, $C_{2-6}$ alkynyl, oxo, hydroxyl, halogen, $C_{3-12}$ carbocycle, and 3- to 12-membered heterocycle, wherein the $C_1$-$C_6$ alkyl, $C_{3-12}$ carbocycle, and 3- to 12-membered heterocycle are each optionally substituted with one or more substituents independently selected from cyano, halogen, $-OR^5$, and $-N(R^5)_2$;

each $R^5$ is independently selected from hydrogen or $C_1$-$C_6$ alkyl;

each $R^6$ is independently selected from halogen, hydroxy, $C_1$-$C_3$ hydroxyalkyl, $C_1$-$C_3$ alkyl, oxo, $C_1$-$C_3$ haloalkyl, $C_1$-$C_3$ alkoxy, cyano, $=CH_2$, $=NO-C_1$-$C_3$ alkyl, $C_1$-$C_3$ aminoalkyl, $-N(R^5)S(O)_2(R^5)$, -Q-phenyl, -Q-phenyl$SO_2F$, $-NHC(O)phenyl$, $-NHC(O)phenylSO_2F$, $C_1$-$C_3$ alkyl substituted pyrazolyl, tert-butyldimethylsilyloxy$CH_2$—, $-N(R^5)_2$, $(C_1$-$C_3$ alkoxy$)C_1$-$C_3$ alkyl-, $(C_1$-$C_3$ alkyl$)C(=O)$, oxo, $(C_1$-$C_3$ haloalkyl$)C(=O)$—, $-SO_2F$, $(C_1$-$C_3$ alkoxy$)C_1$-$C_3$ alkoxy, $-CH_2OC(O)N(R^5)_2$, $-CH_2NHC(O)OC_1$-$C_6$ alkyl, $-CH_2NHC(O)N(R^5)_2$, $-CH_2NHC(O)C_1$-$C_6$ alkyl, $-CH_2(pyrazolyl)$, $-CH_2NHSO_2C_1$-$C_6$ alkyl, $-CH_2OC(O)heterocycle$, $-OC(O)N(R^5)_2$, $-OC(O)NH(C_1$-$C_3$ alkyl$)O(C_1$-$C_3$ alkyl), $-OC(O)NH(C_1$-$C_3$ alkyl$)O(C_1$-$C_3$ alkyl)phenyl$(C_1$-$C_3$ alkyl$)N(CH_3)_2$, $-OC(O)NH(C_1$-$C_3$ alkyl$)O(C_1$-$C_3$ alkyl)phenyl, $-OC(O)heterocycle$, $-O-C_1$-$C_3$ alkyl, and $-CH_2heterocycle$, wherein the phenyl of $-NHC(O)$ phenyl and $-OC(O)NH(C_1$-$C_3$ alkyl$)(C_1$-$C_3$ alkyl) phenyl are each optionally substituted with one or more substituents selected from $-C(O)H$ and OH, and wherein the alkyl of $-O-C_1$-$C_3$ alkyl is optionally substituted with substituents selected from heterocycle, oxo and hydroxy; and wherein the heterocycle of $-CH_2$heterocyclyl is optionally substituted with oxo;

each Q is independently selected from a bond, S, and 0;

each $R^7$ is independently selected from halogen, hydroxy, $HC(=O)$—, $C_1$-$C_4$ alkyl, $C_1$-$C_4$ alkoxy, $C_1$-$C_4$ haloalkyl, $C_1$-$C_4$ hydroxyalkyl, or $-N(R^5)_2$;

each $R^9$ is independently selected from halogen, $-B(OR^{20})_2$, $-OR^{20}$, $-SR^{20}$, $-S(O)_2(R^{20})$, $-S(O)_2N(R^{20})_2$, $-NR^{20}S(O)_2R^{20}$, $-N(R^{20})C(O)R^{20}$, $-N(R^{20})C(O)N(R^{20})_2$, $-N(R^{20})C(O)OR^{20}$, $-N(R^{20})_2$, $-NO_2$, $=O$, $=NO(R^{20})$, $-CN$, $-NHCN$, $C_{1-6}$ aminoalkyl, $C_{1-6}$ alkoxy, $C_{1-6}$ hydroxyalkyl, and $C_{1-6}$ haloalkyl;

each $R^{20}$ is independently selected from hydrogen; and $C_{1-6}$ alkyl, $C_{3-12}$ carbocycle, and 3- to 12-membered heterocycle, each of which is optionally substituted with one or more substituents independently selected from halogen, $-OH$, $-CN$, $-NO_2$, $-NH_2$, $-N(C_{1-6}$ alkyl$)_2$, $C_{1-10}$ alkyl, $-C_{1-10}$ haloalkyl, $-O-C_{1-10}$ alkyl, oxo, $=NH$, $C_{3-12}$ carbocycle, and 3- to 12-membered heterocycle;

each $R^{21}$ is independently selected from hydrogen; and $C_{1-6}$ alkyl, $C_{3-12}$ carbocycle, and 3- to 12-membered heterocycle, each of which is optionally substituted with one or more substituents independently selected from halogen, —OH, —CN, —NO$_2$, —NH$_2$, —N(C$_{1-6}$ alkyl)$_2$, C$_{1-10}$ alkyl, —C$_{1-10}$ haloalkyl, —O—C$_{1-10}$ alkyl, oxo, C$_{3-12}$ carbocycle, and 3- to 12-membered heterocycle; and B is selected from a heterocycle and carbocycle, wherein the heterocycle and carbocycle are each optionally substituted with one or more substituents independently selected from halogen, cyano, hydroxy, =O, —NO$_2$, C$_1$-C$_4$ alkyl, C$_{1-6}$ aminoalkyl, —S—C$_1$-C$_3$ alkyl, C$_2$-C$_4$ alkenyl, C$_2$-C$_4$ alkynyl, C$_2$-C$_4$ hydroxy-alkynyl, C$_1$-C$_3$ cyanoalkyl, triazolyl, C$_1$-C$_3$ haloalkyl, —O—C$_1$-C$_3$ haloalkyl, —S—C$_1$-C$_3$ haloalkyl, C$_1$-C$_3$ alkoxy, C$_1$-C$_3$ hydroxyalkyl, —CH$_2$C(=O)N(R$^5$)$_2$, —C$_3$-C$_4$ alkynyl(NR$^5$)$_2$, —N(R$^5$)$_2$, (C$_1$-C$_3$ alkoxy)ha-loC$_1$-C$_3$ alkyl-, C$_{1-6}$ alkyl-N(R$^{20}$)$_2$, C$_3$-C$_{12}$ carbocycle and 5- to 12-membered heterocycle, wherein C$_3$-C$_{12}$ carbocycle and 5- to 12-membered heterocycle are each optionally substituted with one or more substituents selected from halogen, —OH, —NO$_2$, —NH$_2$, =O, =S, —CN, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$ haloalkyl.

In certain embodiments, the disclosure provides a pharmaceutical composition comprising a compound or salt of Formula (II) and a pharmaceutically acceptable excipient.

In certain embodiments, the disclosure provides a method of treating a disease or disorder, using a compound or salt of Formula (II). In certain embodiments, the disclosure provides a method of treating a disease or disorder, using a compound or salt of Formula (II) and a pharmaceutically acceptable excipient.

In certain embodiments, the disclosure provides a method of inhibiting KRas G12D and/or other G12 mutants, using a compound or salt of Formula (II). In certain embodiments, the disclosure provides a method of inhibiting KRas G12D and/or other G12 mutants, using a compound or salt of Formula (II) and a pharmaceutically acceptable excipient.

In an aspect, the present disclosure provides a compound represented by the structure of Formula (III):

Formula (III)

or a pharmaceutically acceptable salt thereof wherein:

R$^1$ is selected from C$_3$-C$_{12}$ carbocycle and 5- to 15-membered heterocycle, each of which are optionally substituted with one or more substituents independently selected from halogen, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, —C(O)N(R$^{20}$)$_2$, —C(=NR$^{20}$)N(R$^{20}$)$_2$, —C(O)NR$^{20}$OR$^{20}$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =N(R$^{20}$), =NO(R$^{20}$), —CN, —NHCN, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{1-6}$ alkyl, C$_{2-6}$ alkenyl, C$_{2-6}$ alkynyl, C$_3$-C$_{12}$ carbocycle and 5- to 12-membered heterocycle, wherein the C$_3$-C$_{12}$ carbocycle and 5- to 12-membered heterocycle are each optionally substituted independently with one or more R$^{1*}$;

each R$^{1*}$ is independently selected from halogen, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, —C(O)N(R$^{20}$)$_2$, —C(O)NR$^{20}$OR$^{20}$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =N(R$^{20}$), =NO(R$^{20}$), —CN, —NHCN, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{1-6}$ alkyl, C$_{2-6}$ alkenyl, C$_{2-6}$ alkynyl, and C$_3$-C$_{12}$ carbocycle;

R$^2$ is selected from -L-NR$^2$'S(O)$_2$(R$^{21}$), -L-S(O)$_2$N(R$^{21}$)$_2$, -L-N(R$^{21}$)C(O)(OR$^{21}$), -L-OC(O)N(R$^{21}$)$_2$, and L-bicyclic heterocycle, wherein the bicyclic heterocycle is optionally substituted with one or more R$^6$;

each L is independently selected from a C$_1$-C$_4$ alkylene optionally substituted with one or more substituents selected from hydroxy, C$_1$-C$_4$ hydroxyalkyl, C$_1$-C$_4$ alkyl, C$_3$-C$_6$ carbocycle, or 3- to 8-membered heterocycle, wherein the C$_3$-C$_6$ carbocycle and 3- to 8-membered heterocycle are optionally substituted with one or more substituents selected from halogen, —OH, —NO$_2$, =O, =S, —CN, C$_{1-6}$ aminoalkyl, C$_{1-6}$ alkoxy, C$_{1-6}$ hydroxyalkyl, C$_{1-6}$ haloalkyl; and wherein optionally two substituents on the same carbon atom of L come together to form a C$_3$-C$_6$ carbocycle or 3- to 8-membered heterocycle, wherein the C$_3$-C$_6$ carbocycle and 3- to 8-membered heterocycle are each optionally substituted with one or more substituents selected from halogen, —OH, —NO$_2$, =O, =S, —CN, C$_{1-6}$ aminoalkyl, C$_{1-6}$ alkoxy, C$_{1-6}$ hydroxyalkyl, C$_{1-6}$ haloalkyl;

n is selected from 0 to 3;

each R$^4$ is independently selected from C$_{1-6}$ alkyl, C$_{2-6}$ alkenyl, C$_{2-6}$ alkynyl, oxo, hydroxyl, halogen, C$_{3-12}$ carbocycle, and 3- to 12-membered heterocycle, wherein the C$_1$-C$_6$ alkyl, C$_{3-12}$ carbocycle, and 3- to 12-membered heterocycle are each optionally substituted with one or more substituents independently selected from cyano, halogen, —OR$^5$, and —N(R$^5$)$_2$;

B is selected from a heterocycle and carbocycle, wherein the heterocycle or carbocycle is optionally substituted with one or more substituents independently selected from halogen, cyano, hydroxy, =O, —NO$_2$, C$_1$-C$_4$ alkyl, C$_{1-6}$ aminoalkyl, —S—C$_1$-C$_3$ alkyl, C$_2$-C$_4$ alkenyl, C$_2$-C$_4$ alkynyl, C$_2$-C$_4$ hydroxyalkynyl, C$_1$-C$_3$ cyanoalkyl, triazolyl, C$_1$-C$_3$ haloalkyl, —O—C$_1$-C$_3$ haloalkyl, —S—C$_1$-C$_3$ haloalkyl, C$_1$-C$_3$ alkoxy, C$_1$-C$_3$ hydroxyalkyl, —CH$_2$C(=O)N(R$^5$)$_2$, —C$_3$-C$_4$ alkynyl(NR$^5$)$_2$, —N(R$^5$)$_2$, (C$_1$-C$_3$ alkoxy)haloC$_1$-C$_3$ alkyl-, C$_{1-6}$ alkyl-N(R$^{20}$)$_2$, C$_3$-C$_{12}$ carbocycle and 5- to 12-membered heterocycle, wherein C$_3$-C$_{12}$ carbocycle and 5- to 12-membered heterocycle are each optionally substituted with one or more substituents selected from halogen, —OH, —NO$_2$, —NH$_2$, =O, =S, —CN, C$_{1-6}$ aminoalkyl, C$_{1-6}$ alkoxy, C$_{1-6}$ hydroxyalkyl, C$_{1-6}$ haloalkyl;

Y is selected from a bond, O, S and NR$^5$;

each R$^6$ is independently selected from halogen, hydroxy, C$_1$-C$_3$ hydroxyalkyl, C$_1$-C$_3$ alkyl, oxo, C$_1$-C$_3$ haloalkyl, C$_1$-C$_3$ alkoxy, cyano, =CH$_2$, =NO—C$_1$-C$_3$ alkyl, C$_1$-C$_3$ aminoalkyl, —N(R$^5$)S(O)$_2$(R$^5$), -Q-phenyl, -Q-phenylSO$_2$F, —NHC(O)phenyl, —NHC(O)phenylSO$_2$F, C$_1$-C$_3$ alkyl substituted pyrazolyl, tertbutyldimethylsilyloxyCH$_2$—, —N(R$^5$)$_2$, (C$_1$-C$_3$ alkoxy)C$_1$-C$_3$ alkyl-, (C$_1$-C$_3$ alkyl)C(=O), oxo, (C$_1$-C$_3$ haloalkyl)C(=O)—, —SO$_2$F, (C$_1$-C$_3$ alkoxy)C$_1$-C$_3$ alkoxy, —CH$_2$OC(O)N(R$^5$)$_2$, —CH$_2$NHC(O)OC$_1$-C$_6$ alkyl, —CH$_2$NHC(O)N(R$^5$)$_2$, —CH$_2$NHC(O)C$_1$-C$_6$ alkyl, —CH$_2$(pyrazolyl), —CH$_2$NHSO$_2$C$_1$-C$_6$ alkyl, —CH$_2$OC(O)heterocycle, —OC(O)N(R$^5$)$_2$, —OC(O) NH(C$_1$-C$_3$ alkyl)O(C$_1$-C$_3$ alkyl), —OC(O)NH(C$_1$-C$_3$ alkyl)O(C$_1$-C$_3$ alkyl)phenyl(C$_1$-C$_3$ alkyl)N(CH$_3$)$_2$, —OC(O)NH(C$_1$-C$_3$ alkyl)O(C$_1$-C$_3$ alkyl)phenyl, —OC(O)heterocycle, —O—C$_1$-C$_3$ alkyl, and —CH$_2$heterocycle, wherein the phenyl of —NHC(O) phenyl and —OC(O)NH(C$_1$-C$_3$ alkyl)(C$_1$-C$_3$ alkyl) phenyl are optionally substituted with one or more substituents selected from —C(O)H and OH, and wherein the alkyl of —O—C$_1$-C$_3$ alkyl is optionally substituted with substituents selected from heterocycle, oxo and hydroxy; and wherein the heterocycle of —CH$_2$heterocyclyl is optionally substituted with oxo; each Q is independently selected from a bond, S. and 0; each R$^{20}$ is independently selected from hydrogen; and C$_{1-6}$ alkyl, C$_{3-12}$ carbocycle, and 3- to 12-membered heterocycle, each of which is optionally substituted with one or more substituents independently selected from halogen, —OH, —CN, —NO$_2$, —NH$_2$, —N(C$_{1-6}$ alkyl)$_2$, C$_{1-10}$ alkyl, —C$_{1-10}$ haloalkyl, —O—C$_{1-10}$ alkyl, oxo, C$_{3-12}$ carbocycle, and 3- to 12-membered heterocycle;
each R$^{21}$ is independently selected from hydrogen; and C$_{1-6}$ alkyl, C$_{3-12}$ carbocycle, and 3- to 12-membered heterocycle, each of which is optionally substituted with one or more substituents independently selected from halogen, —OH, —CN, —NO$_2$, —NH$_2$, —N(C$_{1-6}$ alkyl)$_2$, C$_{1-10}$ alkyl, —C$_{1-10}$ haloalkyl, —O—C$_{1-10}$ alkyl, oxo, C$_{3-12}$ carbocycle, and 3- to 12-membered heterocycle; and
each R$^5$ is independently selected from hydrogen or C$_1$-C$_6$ alkyl.

In certain embodiments, the disclosure provides a pharmaceutical composition comprising a compound or salt of Formula (III) and a pharmaceutically acceptable excipient.

In certain embodiments, the disclosure provides a method of treating a disease or disorder, using a compound or salt of Formula (III). In certain embodiments, the disclosure provides a method of treating a disease or disorder, using a compound or salt of Formula (III) and a pharmaceutically acceptable excipient.

In certain embodiments, the disclosure provides a method of inhibiting KRas G12D and/or other G12 mutants, using a compound or salt of Formula (III). In certain embodiments, the disclosure provides a method of inhibiting KRas G12D and/or other G12 mutants, using a compound or salt of Formula (III) and a pharmaceutically acceptable excipient.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

The following description sets forth numerous exemplary configurations, methods, parameters, and the like. It should be recognized, however, that such description is not intended as a limitation on the scope of the present disclosure, but is instead provided as a description of exemplary embodiments.

In the following description, certain specific details are set forth in order to provide a thorough understanding of various embodiments of the disclosure. However, one skilled in the art will understand that the disclosure may be practiced without these details.

Definitions

Unless defined otherwise, all technical and scientific terms used herein have the same meaning as is commonly understood by one of skill in the art to which this invention belongs. All patents and publications referred to herein are incorporated by reference.

"Alkyl" refers to a straight or branched hydrocarbon chain radical consisting solely of carbon and hydrogen atoms, containing no unsaturation, and preferably having from one to fifteen carbon atoms (i.e., C$_1$-C$_{15}$ alkyl). In certain embodiments, an alkyl comprises one to thirteen carbon atoms (i.e., C$_1$-C$_{13}$ alkyl). In certain embodiments, an alkyl comprises one to eight carbon atoms (i.e., C$_1$-C$_8$ alkyl). In other embodiments, an alkyl comprises one to five carbon atoms (i.e., C$_1$-C$_5$ alkyl). In other embodiments, an alkyl comprises one to four carbon atoms (i.e., C$_1$-C$_4$ alkyl). In other embodiments, an alkyl comprises one to three carbon atoms (i.e., C$_1$-C$_3$ alkyl). In other embodiments, an alkyl comprises one to two carbon atoms (i.e., C$_1$-C$_2$ alkyl). In other embodiments, an alkyl comprises one carbon atom (i.e., C$_1$ alkyl). In other embodiments, an alkyl comprises five to fifteen carbon atoms (i.e., C$_5$-C$_{15}$ alkyl). In other embodiments, an alkyl comprises five to eight carbon atoms (i.e., C$_5$-C$_8$ alkyl). In other embodiments, an alkyl comprises two to five carbon atoms (i.e., C$_2$-C$_5$ alkyl). In other embodiments, an alkyl comprises three to five carbon atoms (i.e., C$_3$-C$_5$ alkyl). In certain embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond.

The term "C$_{x-y}$," when used in conjunction with a chemical moiety, such as alkyl, alkenyl, or alkynyl is meant to include groups that contain from x to y carbons in the chain. For example, the term "C$_{1-6}$alkyl" refers to substituted or unsubstituted saturated hydrocarbon groups, including straight-chain alkyl and branched-chain alkyl groups that contain from 1 to 6 carbons. The term —C$_{x-y}$alkylene- refers to a substituted or unsubstituted alkylene chain with from x to y carbons in the alkylene chain. For example —C$_{1-6}$ alkylene- may be selected from methylene, ethylene, propylene, butylene, pentylene, and hexylene, any one of which is optionally substituted.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and preferably having from two to twelve carbon atoms (i.e., C$_2$-C$_{12}$ alkenyl). In certain embodiments, an alkenyl comprises two to eight carbon atoms (i.e., C$_2$-C$_8$ alkenyl). In certain embodiments, an alkenyl comprises two to six carbon atoms (i.e., C$_2$-C$_6$ alkenyl). In other embodiments, an alkenyl comprises two to four carbon atoms (i.e., $C_2$-$C_4$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like.

"Alkynyl" refers to a straight or branched hydrocarbon chain radical group consisting solely of carbon and hydrogen atoms, containing at least one carbon-carbon triple bond, and preferably having from two to twelve carbon atoms (i.e., $C_2$-$C_{12}$ alkynyl). In certain embodiments, an alkynyl comprises two to eight carbon atoms (i.e., $C_2$-$C_8$ alkynyl). In other embodiments, an alkynyl comprises two to six carbon atoms (i.e., $C_2$-$C_6$ alkynyl). In other embodiments, an alkynyl comprises two to four carbon atoms (i.e., $C_2$-$C_4$ alkynyl). The alkynyl is attached to the rest of the molecule by a single bond, for example, ethynyl, propynyl, butynyl, pentynyl, hexynyl, and the like.

The terms "$C_{x-y}$alkenyl" and "$C_{x-y}$alkynyl" refer to substituted or unsubstituted unsaturated aliphatic groups analogous in length and possible substitution to the alkyls described above, but that contain at least one double or triple bond, respectively. The term —C-alkenylene-refers to a substituted or unsubstituted alkenylene chain with from x to y carbons in the alkenylene chain. For example, —$C_{2-6}$ alkenylene- may be selected from ethenylene, propenylene, butenylene, pentenylene, and hexenylene, any one of which is optionally substituted. An alkenylene chain may have one double bond or more than one double bond in the alkenylene chain. The term —C-alkynylene- refers to a substituted or unsubstituted alkynylene chain with from x to y carbons in the alkenylene chain. For example, —$C_{2-6}$alkenylene- may be selected from ethynylene, propynylene, butynylene, pentynylene, and hexynylene, any one of which is optionally substituted. An alkynylene chain may have one triple bond or more than one triple bond in the alkynylene chain.

"Alkylene" or "alkylene chain" refers to a straight or branched divalent hydrocarbon chain linking the rest of the molecule to a radical group, consisting solely of carbon and hydrogen, containing no unsaturation, and preferably having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group may be through any two carbons within the chain. In certain embodiments, an alkylene comprises one to ten carbon atoms (i.e., $C_1$-$C_8$ alkylene). In certain embodiments, an alkylene comprises one to eight carbon atoms (i.e., $C_1$-$C_8$ alkylene). In other embodiments, an alkylene comprises one to five carbon atoms (i.e., $C_1$-$C_5$ alkylene). In other embodiments, an alkylene comprises one to four carbon atoms (i.e., $C_1$-$C_4$ alkylene). In other embodiments, an alkylene comprises one to three carbon atoms (i.e., $C_1$-$C_3$ alkylene). In other embodiments, an alkylene comprises one to two carbon atoms (i.e., $C_1$-$C_2$ alkylene). In other embodiments, an alkylene comprises one carbon atom (i.e., $C_1$ alkylene). In other embodiments, an alkylene comprises five to eight carbon atoms (i.e., $C_5$-$C_8$ alkylene). In other embodiments, an alkylene comprises two to five carbon atoms (i.e., $C_2$-$C_5$ alkylene). In other embodiments, an alkylene comprises three to five carbon atoms (i.e., $C_3$-$C_5$ alkylene).

"Alkenylene" or "alkenylene chain" refers to a straight or branched divalent hydrocarbon chain linking the rest of the molecule to a radical group, consisting solely of carbon and hydrogen, containing at least one carbon-carbon double bond, and preferably having from two to twelve carbon atoms. The alkenylene chain is attached to the rest of the molecule through a single bond and to the radical group through a single bond. The points of attachment of the alkenylene chain to the rest of the molecule and to the radical group may be through any two carbons within the chain. In certain embodiments, an alkenylene comprises two to ten carbon atoms (i.e., $C_2$-$C_{10}$ alkenylene). In certain embodiments, an alkenylene comprises two to eight carbon atoms (i.e., $C_2$-$C_8$ alkenylene). In other embodiments, an alkenylene comprises two to five carbon atoms (i.e., $C_2$-$C_5$ alkenylene). In other embodiments, an alkenylene comprises two to four carbon atoms (i.e., $C_2$-$C_4$ alkenylene). In other embodiments, an alkenylene comprises two to three carbon atoms (i.e., $C_2$-$C_3$ alkenylene). In other embodiments, an alkenylene comprises two carbon atom (i.e., $C_2$ alkenylene). In other embodiments, an alkenylene comprises five to eight carbon atoms (i.e., $C_5$-$C_8$ alkenylene). In other embodiments, an alkenylene comprises three to five carbon atoms (i.e., $C_3$-$C_5$ alkenylene).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and preferably having from two to twelve carbon atoms. The alkynylene chain is attached to the rest of the molecule through a single bond and to the radical group through a single bond. The points of attachment of the alkynylene chain to the rest of the molecule and to the radical group may be through any two carbons within the chain. In certain embodiments, an alkynylene comprises two to ten carbon atoms (i.e., $C_2$-$C_{10}$ alkynylene). In certain embodiments, an alkynylene comprises two to eight carbon atoms (i.e., $C_2$-$C_8$ alkynylene). In other embodiments, an alkynylene comprises two to five carbon atoms (i.e., $C_2$-$C_5$ alkynylene). In other embodiments, an alkynylene comprises two to four carbon atoms (i.e., $C_2$-$C_4$ alkynylene). In other embodiments, an alkynylene comprises two to three carbon atoms (i.e., $C_2$-$C_3$ alkynylene). In other embodiments, an alkynylene comprises two carbon atom (i.e., $C_2$ alkynylene). In other embodiments, an alkynylene comprises five to eight carbon atoms (i.e., $C_5$-$C_8$ alkynylene). In other embodiments, an alkynylene comprises three to five carbon atoms (i.e., $C_3$-$C_5$ alkynylene).

"Aryl" refers to a radical derived from an aromatic monocyclic or aromatic multicyclic hydrocarbon ring system by removing a hydrogen atom from a ring carbon atom. The aromatic monocyclic or aromatic multicyclic hydrocarbon ring system contains only hydrogen and carbon and from five to eighteen carbon atoms, where at least one of the rings in the ring system is aromatic, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene.

"Aralkyl" refers to a radical of the formula —$R^c$-aryl where $R^c$ is an alkylene chain as defined above, for example, methylene, ethylene, and the like.

"Aralkenyl" refers to a radical of the formula —$R^d$-aryl where $R^d$ is an alkenylene chain as defined above. "Aralkynyl" refers to a radical of the formula —$R^e$-aryl, where $R^e$ is an alkynylene chain as defined above.

"Carbocycle" refers to a saturated, unsaturated or aromatic rings in which each atom of the ring is carbon. Carbocycle may include 3- to 10-membered monocyclic rings, 6- to 12-membered bicyclic rings, and 6- to 12-membered bridged rings. Each ring of a bicyclic carbocycle may be selected from saturated, unsaturated, and aromatic rings. An aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, are included in the definition of carbocyclic. Exemplary carbocycles include cyclopentyl, cyclohexyl, cyclohexenyl, adamantyl, phenyl, indanyl, and naphthyl. Bicyclic carbocycles may be fused, bridged or spiro-ring systems. In some cases, spiro-ring carbocycles have at least two molecular rings with only one common atom.

The term "unsaturated carbocycle" refers to carbocycles with at least one degree of unsaturation and excluding aromatic carbocycles. Examples of unsaturated carbocycles include cyclohexadiene, cyclohexene, and cyclopentene.

"Cycloalkyl" refers to a fully saturated monocyclic or polycyclic hydrocarbon radical consisting solely of carbon and hydrogen atoms, which includes fused or bridged ring systems, and preferably having from three to twelve carbon atoms. In certain embodiments, a cycloalkyl comprises three to ten carbon atoms. In other embodiments, a cycloalkyl comprises five to seven carbon atoms. The cycloalkyl may be attached to the rest of the molecule by a single bond. Examples of monocyclic cycloalkyls include, e.g., cyclopropyl, cyclobutyl, cyclopentyl, cyclohexyl, cycloheptyl, and cyclooctyl. Polycyclic cycloalkyl radicals include, for example, adamantyl, norbomyl (i.e., bicyclo[2.2.1]heptanyl), norbornenyl, decalinyl, 7,7-dimethyl-bicyclo[2.2.1] heptanyl, and the like.

"Cycloalkenyl" refers to an unsaturated non-aromatic monocyclic or polycyclic hydrocarbon radical consisting solely of carbon and hydrogen atoms, which includes fused or bridged ring systems, preferably having from three to twelve carbon atoms and comprising at least one double bond. In certain embodiments, a cycloalkenyl comprises three to ten carbon atoms. In other embodiments, a cycloalkenyl comprises five to seven carbon atoms. The cycloalkenyl may be attached to the rest of the molecule by a single bond. Examples of monocyclic cycloalkenyls includes, e.g., cyclopentenyl, cyclohexenyl, cycloheptenyl, and cyclooctenyl.

"Cycloalkylalkyl" refers to a radical of the formula —$R^c$-cycloalkyl where $R^c$ is an alkylene chain as described above.

"Cycloalkylalkoxy" refers to a radical bonded through an oxygen atom of the formula —O—$R^c$-cycloalkyl where $R^c$ is an alkylene chain as described above.

"Halo" or "halogen" refers to halogen substituents such as bromo, chloro, fluoro and iodo substituents.

As used herein, the term "haloalkyl" or "haloalkane" refers to an alkyl radical, as defined above, that is substituted by one or more halogen radicals, for example, trifluoromethyl, dichloromethyl, bromomethyl, 2,2,2-trifluoroethyl, 1-fluoromethyl-2-fluoroethyl, and the like. In some embodiments, the alkyl part of the fluoroalkyl radical is optionally further substituted. Examples of halogen substituted alkanes ("haloalkanes") include halomethane (e.g., chloromethane, bromomethane, fluoromethane, iodomethane), di- and trihalomethane (e.g., trichloromethane, tribromomethane, trifluoromethane, triiodomethane), 1-haloethane, 2-haloethane, 1,2-dihaloethane, 1-halopropane, 2-halopropane, 3-halopropane, 1,2-dihalopropane, 1,3-dihalopropane, 2,3-dihalopropane, 1,2,3-trihalopropane, and any other suitable combinations of alkanes (or substituted alkanes) and halogens (e.g., Cl, Br, F, I, etc.). When an alkyl group is substituted with more than one halogen radicals, each halogen may be independently selected e.g., 1-chloro,2-fluoroethane.

"Fluoroalkyl" refers to an alkyl radical, as defined above, that is substituted by one or more fluoro radicals, for example, trifluoromethyl, difluoromethyl, fluoromethyl, 2,2, 2-trifluoroethyl, 1-fluoromethyl-2-fluoroethyl, and the like.

"Aminoalkyl" refers to an alkyl radical, as defined above, that is substituted by one or more amine radicals, for example, propan-2-amine, butane-1,2-diamine, pentane-1,2, 4-triamine and the like.

"Hydroxyalkyl" refers to an alkyl radical, as defined above, that is substituted by one or more hydroxy radicals, for example, propan-1-ol, butane-1,4-diol, pentane-1,2,4-triol, and the like.

"Alkoxyalkyl" refers to an alkyl radical, as defined above, that is substituted by one or more alkoxy radicals, for example, methoxymethane, 1,3-dimethoxybutane, 1-methoxypropane, 2-ethoxypentane, and the like.

"Cyanoalkyl" as used herein refers to an alkyl radical, as defined above, that is substituted by one or more cyano radicals, for example, acetonitrile, 2-ethyl-3-methylsuccinonitrile, butyronitrile, and the like.

"Heterocycle" as used herein refers to a saturated, unsaturated or aromatic ring comprising one or more heteroatoms. Exemplary heteroatoms include N, O, Si, P, B, and S atoms. The heterocycle may be attached to the rest of the molecule through any atom of the heterocycle, valence permitting, such as a carbon or nitrogen atom of the heterocycle. Heterocycles include 3- to 10-membered monocyclic rings, 6- to 12-membered bicyclic rings, and 6- to 12-membered bridged rings. A bicyclic heterocycle includes any combination of saturated, unsaturated and aromatic bicyclic rings, as valence permits. In an exemplary embodiment, an aromatic ring, e.g., pyridyl, may be fused to a saturated or unsaturated ring, e.g., cyclohexane, cyclopentane, morpholine, piperidine or cyclohexene. A bicyclic heterocycle includes any combination of ring sizes such as 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems. Bicyclic heterocycles may be fused, bridged, or spiro-ring systems. A spiro-ring system may be referred as a "spiroheterocycle", "spiro heterocycle", or "spiro-heterocycle". In some cases, spiro-heterocycles, Spiro heterocycles, or spirolheterocycles have at least two molecular rings with only one common atom. The spiro-heterocycle, spiro heterocycle, or spiroheterocycle comprises one or more heteroatoms.

"Heterocyclene" refers to a divalent heterocycle linking the rest of the molecule to a radical group.

"Heteroaryl" or "aromatic heterocycle" refers to a radical derived from a heteroaromatic ring radical that comprises one to eleven carbon atoms and at least one heteroatom wherein each heteroatom may be selected from N, O, and S. As used herein, the heteroaryl ring may be selected from monocyclic or bicyclic and fused or bridged ring systems rings wherein at least one of the rings in the ring system is aromatic, i.e., it contains a cyclic, delocalized (4n+2) π-electron system in accordance with the Hückel theory. The heteroatom(s) in the heteroaryl radical may be optionally oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl. Examples of heteroaryls include, but are not limited to, pyridine, pyrimidine, oxazole, furan, pyran, thiophene, isoxazole, benzimidazole, benzthiazole, and imidazopyridine.

An "X-membered heteroaryl" refers to the number of endocylic atoms, i.e., X, in the ring. For example, a 5-membered heteroaryl ring or 5-membered aromatic heterocycle has 5 endocyclic atoms, e.g., triazole, oxazole, thiophene, etc.

The term "unsaturated heterocycle" refers to heterocycles with at least one degree of unsaturation and excluding aromatic heterocycles. Examples of unsaturated heterocycles include dihydropyrrole, dihydrofuran, oxazoline, pyrazoline, and dihydropyridine. Heterocycles may be optionally substituted by one or more substituents such as those substituents described herein.

The term "substituted" refers to moieties having substituents replacing a hydrogen on one or more carbons or substitutable heteroatoms, e.g., NH, of the structure. It will be understood that "substitution" or "substituted with" includes the implicit proviso that such substitution is in accordance with permitted valence of the substituted atom and the substituent, and that the substitution results in a stable compound, i.e., a compound which does not spontaneously undergo transformation such as by rearrangement, cyclization, elimination, etc. In certain embodiments, substituted refers to moieties having substituents replacing two hydrogen atoms on the same carbon atom, such as substituting the two hydrogen atoms on a single carbon with an oxo, imino or thioxo group. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms.

In some embodiments, substituents may include any substituents described herein, for example: halogen, hydroxy, oxo ($=O$), thioxo ($=S$), cyano ($—CN$), nitro ($—NO_2$), imino ($=N—H$), oximo ($=N—OH$), hydrazino ($=N—NH_2$), $—R^b—OR^a$, $—R^b—OC(O)—R^a$, $—R^b—OC(O)—OR^a$, $—R^b—OC(O)—N(R^a)_2$, $—R^b—N(R^a)_2$, $—R^b—C(O)R^a$, $—R^b—C(O)OR^a$, $—R^b—C(O)N(R^a)_2$, $—R^b—O—R^c—C(O)N(R^a)_2$, $—R^b—N(R^a)C(O)OR^a$, $—R^b—N(R^1)C(O)R^a$, $—R^b—N(R^a)S(O)_tR^a$ (where t is 1 or 2), $—R^b—S(O)_tR^a$ (where t is 1 or 2), $—R^b—S(O)_tOR^a$ (where t is 1 or 2), and $—R^b—S(O)_tN(R^1)_2$ (where t is 1 or 2); and alkyl, alkenyl, alkynyl, aryl, aralkyl, aralkenyl, aralkynyl, cycloalkyl, cycloalkylalkyl, and heterocycle, any of which may be optionally substituted by alkyl, alkenyl, alkynyl, halogen, haloalkyl, haloalkenyl, haloalkynyl, oxo ($=O$), thioxo ($=S$), cyano ($—CN$), nitro ($—NO_2$), imino ($=N—H$), oximo ($=N—OH$), hydrazine ($=N—NH_2$), $—R^b—OR^a$, $—R^b—OC(O)—R^a$, $—R^b—OC(O)—OR^a$, $—R^b—OC(O)—N(R^a)_2$, $—R^b—N(R^a)_2$, $—R^b—C(O)R^1$, $—R^b—C(O)OR^a$, $—R^b—C(O)N(R^1)_2$, $—R^b—O—R^c—C(O)N(R^a)_2$, $—R^b—N(R^1)C(O)OR^1$, $—R^b—N(R^1)C(O)R^1$, $—R^b—N(R^a)S(O)_tR^a$ (where t is 1 or 2), $—R^b—S(O)_tR^a$ (where t is 1 or 2), $—R^b—S(O)_tOR^1$ (where t is 1 or 2) and $—R^b—S(O)_tN(R^a)_2$ (where t is 1 or 2); wherein each $R^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each $R^a$, valence permitting, may be optionally substituted with alkyl, alkenyl, alkynyl, halogen, haloalkyl, haloalkenyl, haloalkynyl, oxo ($=O$), thioxo ($=S$), cyano ($—CN$), nitro ($—NO_2$), imino ($=N—H$), oximo ($=N—OH$), hydrazine ($=N—NH_2$), $—R^b—OR^a$, $—R^b—OC(O)—R^a$, $—R^b—OC(O)—OR^a$, $—R^b—OC(O)—N(R^a)_2$, $—R^b—N(R^a)_2$, $—R^b—C(O)R^a$, $—R^b—C(O)OR^a$, $—R^b—C(O)N(R^a)_2$, $—R^b—O—R^c—C(O)N(R^a)_2$, $—R^b—N(R^a)C(O)OR^a$, $—R^b—N(R^a)C(O)R^a$, $—R^b—N(R^a)S(O)_tR^a$ (where t is 1 or 2), $—R^b—S(O)_tR^a$ (where t is 1 or 2), $—R^b—S(O)_tOR^1$ (where t is 1 or 2) and $—R^b—S(O)_tN(R^a)_2$ (where t is 1 or 2); and wherein each $R^b$ is independently selected from a direct bond or a straight or branched alkylene, alkenylene, or alkynylene chain, and each $R^c$ is a straight or branched alkylene, alkenylene or alkynylene chain.

As used herein, the term "electrophile" or "electrophilic moiety" is any moiety capable of reacting with a nucleophile (e.g., a moiety having a lone pair of electrons, a negative charge, a partial negative charge and/or an excess of electrons, for example an $—SH$ group). Electrophiles typically are electron poor or comprise atoms which are electron poor. In certain embodiments, an electrophile contains a positive charge or partial positive charge, has a resonance structure which contains a positive charge or partial positive charge, or is a moiety in which delocalization or polarization of electrons results in one or more atoms which contains a positive charge or partial positive charge. In some embodiments, an electrophile comprises a conjugated double bond, for example an α,β-unsaturated carbonyl or α,β-unsaturated thiocarbonyl compound.

As used herein, the term "optional" or "optionally" means that the subsequently described event of circumstances may or may not occur, and that the description includes instances where the event or circumstance occurs and instances in which it does not. For example, "optionally substituted aryl" means that the aryl group may or may not be substituted and that the description includes both substituted aryl groups and aryl groups having no substitution.

As used in the specification and claims, the singular form "a", "an" and "the" includes plural references unless the context clearly dictates otherwise.

The term "salt" or "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In certain embodiments, the term "prevent" or "preventing" as related to a disease or disorder may refer to a compound that, in a statistical sample, reduces the occurrence of the disorder or condition in the treated sample relative to an untreated control sample, or delays the onset or reduces the severity of one or more symptoms of the disorder or condition relative to the untreated control sample.

The terms "treat," "treating" or "treatment," as used herein, may include alleviating, abating or ameliorating a disease or condition symptoms, preventing additional symptoms, ameliorating or preventing the underlying causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The term "G12 mutants", as used herein, refers to other oncogenic alleles of KRAS at amino acid position 12 (ie. G12X).

Compounds of the Disclosure

The following is a discussion of compounds and salts thereof that may be used in the methods of the disclosure.

In some aspects, the present disclosure provides a compound represented by the structure of Formula (I):

Formula (I)

or a pharmaceutically acceptable salt thereof wherein:

$R^1$ is selected from $C_3$-$C_{12}$ carbocycle and 5- to 15-membered heterocycle, each of which are optionally substituted with one or more substituents independently selected from halogen, $-B(OR^{20})_2$, $-OR^{20}$, $-SR^{20}$, $-S(O)_2(R^{20})$, $-S(O)_2N(R^{20})_2$, $-S(O)N(R^{20})_2$, $-S(O)R^{20}(=NR^{20})$, $-NR^{20}S(O)_2R^{20}$, $-C(O)N(R^{20})_2$, $-C(=NR^{20})N(R^{20})_2$, $-C(O)NR^{20}OR^{20}$, $-N(R^{20})C(O)R^{20}$, $-N(R^{20})C(O)N(R^{20})_2$, $-N(R^{20})C(O)OR^{20}$, $-N(R^{20})_2$, $-C(O)R^{20}$, $-C(O)OR^{20}$, $-OC(O)R^{20}$, $-OC(O)N(R^{20})_2$, $-NO_2$, $=O$, $=N(R^{20})$, $=NO(R^{20})$, $-CN$, $-NHCN$, $C_{1-6}$ alkyl-$N(R^{20})_2$, $C_{1-6}$ aminoalkyl, $C_{1-6}$ alkoxy, $C_{1-6}$ hydroxyalkyl, $C_{1-6}$ cyanoalkyl, $C_{1-6}$haloalkyl, $C_{1-6}$ alkyl, $C_{2-6}$ alkenyl, $C_{2-6}$ alkynyl, $C_3$-$C_{12}$ carbocycle and 5- to 12-membered heterocycle, wherein the $C_3$-$C_{12}$ carbocycle and 5- to 12-membered heterocycle are each optionally substituted independently with one or more $R^{1*}$;

$R^{1*}$ is independently selected from halogen, $-B(OR^{20})_2$, $-OR^{20}$, $-SR^{20}$, $-S(O)_2(R^{20}$ each R), $-S(O)_2N(R^{20})_2$, $-S(O)N(R^{20})_2$, $-S(O)R^{20}(=NR^{20})$, $-NR^{20}S(O)_2R^{20}$, $-C(O)N(R^{20})_2$, $-C(O)NR^{20}OR^{20}$, $-N(R^{20})C(O)R^{20}$, $-N(R^{20})C(O)N(R^{20})_2$, $-N(R^{20})C(O)OR^{20}$, $-N(R^{20})_2$, $-C(O)R^{20}$, $-C(O)OR^{20}$, $-OC(O)R^{20}$, $-OC(O)N(R^{20})_2$, $-NO_2$, $=O$, $=N(R^{20})$, $=NO(R^{20})$, $-CN$, $-NHCN$, $C_{1-6}$ alkyl-$N(R^{20})_2$, $C_{1-6}$ aminoalkyl, $C_{1-6}$alkoxy, $C_{1-6}$ hydroxyalkyl, $C_{1-6}$ cyanoalkyl, $C_{1-6}$haloalkyl, $C_{1-6}$alkyl, $C_{2-6}$alkenyl, $C_{2-6}$ alkynyl, and $C_3$-$C_{12}$ carbocycle;

Y is selected from a bond, O, S and $NR^5$;

$R^2$ is selected from hydrogen, $-N(R^{21})_2$, -L-$N(R^{21})_2$, -L-$OR^{21}$, heterocycle, $C_1$-$C_6$ alkyl, -L-heterocycle, -L-aryl, -L-heteroaryl, -L-cycloalkyl, -L-$N(R^{21})_2$, -L-NHC(=NH)$NH_2$, -L-C(O)N$(R^{21})_2$, -L-$C_1$-$C_6$ haloalkyl, -L-$OR^{21}$, -L-$NR^{21}C(O)$-aryl, -L-COOH, -L-$NR^{21}S(O)_2(R^{21})$, -L-$S(O)_2N(R^{21})_2$, -L-$N(R^{21})C(O)(OR^{21})$, -L-$OC(O)N(R^{21})_2$, or -L$C(=O)OC_1$-$C_6$ alkyl, wherein the heterocycle and the aryl portion of -L-$NR^5C(O)$-aryl and the heterocycle portion of -L-heterocycle and the cycloalkyl portion of the -L-cycloalkyl are optionally substituted with one or more $R^6$, and wherein the aryl or heteroaryl of the -L-aryl and the -L-heteroaryl are optionally substituted with one or more $R^7$;

each L is independently selected from a $C_1$-$C_4$ alkylene optionally substituted with one or more substituents selected from hydroxy, $C_1$-$C_4$ hydroxyalkyl, $C_1$-$C_4$ alkyl, $C_3$-$C_6$ carbocycle, or 3- to 8-membered heterocycle, wherein the $C_3$-$C_6$ carbocycle and 3- to 8-membered heterocycle are optionally substituted with one or more substituents selected from halogen, $-OH$, $-NO_2$, $=O$, $=S$, $-CN$, $C_{1-6}$ aminoalkyl, $C_{1-6}$ alkoxy, $C_{1-6}$ hydroxyalkyl, $C_{1-6}$ haloalkyl; and wherein optionally two substituents on the same carbon atom of L come together to form a $C_3$-$C_6$ carbocycle or 3- to 8-membered heterocycle wherein the $C_3$-$C_6$ carbocycle and 3- to 8-membered heterocycle are optionally substituted with one or more substituents selected from halogen, —OH, —NO$_2$, =O, =S, —CN, C$_{1-6}$ aminoalkyl, C$_{1-6}$ alkoxy, C$_{1-6}$ hydroxyalkyl, C$_{1-6}$ haloalkyl;

each R$^4$ is independently selected from C$_{1-6}$ alkyl, C$_{2-6}$ alkenyl, C$_{2-6}$ alkynyl, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{3-12}$ carbocycle, and 3- to 12-membered heterocycle, wherein C$_{3-12}$ carbocycle and 3- to 12-membered heterocycle are each optionally substituted with one or more substituents independently selected from halogen, —OH, —CN, —NO$_2$, —NH$_2$, —NH(C$_{1-6}$ alkyl), —N(C$_{1-6}$ alkyl)$_2$, C$_{1-10}$ alkyl, —C$_{1-10}$ haloalkyl, —O—C$_{1-10}$ alkyl, oxo, C$_{3-12}$ carbocycle, and 3- to 12-membered heterocycle;

each R$^5$ is independently selected from hydrogen and C$_1$-C$_6$ alkyl;

each R$^6$ is independently selected from halogen, hydroxy, C$_1$-C$_3$ hydroxyalkyl, C$_1$-C$_3$ alkyl, oxo, C$_1$-C$_3$ haloalkyl, C$_1$-C$_3$ alkoxy, cyano, =CH$_2$, =NO—C$_1$-C$_3$ alkyl, C$_1$-C$_3$ aminoalkyl, —N(R$^5$)S(O)$_2$(R$^5$), -Q-phenyl, -Q-phenylSO$_2$F, —NHC(O)phenyl, —NHC(O) phenylSO$_2$F, C$_1$-C$_3$ alkyl substituted pyrazolyl, tert-butyldimethylsilyloxyCH$_2$—, —N(R$^5$)$_2$, (C$_1$-C$_3$ alkoxy)C$_1$-C$_3$ alkyl-, (C$_1$-C$_3$ alkyl)C(=O), oxo, (C$_1$-C$_3$ haloalkyl)C(=O)—, —SO$_2$F, (C$_1$-C$_3$ alkoxy)C$_1$-C$_3$ alkoxy, —CH$_2$OC(O)N(R$^5$)$_2$, —CH$_2$NHC(O)OC$_1$-C$_6$ alkyl, —CH$_2$NHC(O)N(R$^5$)$_2$, —CH$_2$NHC(O)C$_1$-C$_6$ alkyl, —CH$_2$(pyrazolyl), —CH$_2$NHSO$_2$C$_1$-C$_6$ alkyl, —CH$_2$OC(O)heterocycle, —OC(O)N(R$^5$)$_2$, —OC(O) NH(C$_1$-C$_3$ alkyl)O(C$_1$-C$_3$ alkyl), —OC(O)NH(C$_1$-C$_3$ alkyl)O(C$_1$-C$_3$ alkyl)phenyl(C$_1$-C$_3$ alkyl)N(CH$_3$)$_2$, —OC(O)NH(C$_1$-C$_3$ alkyl)O(C$_1$-C$_3$ alkyl)phenyl, —OC(O)heterocycle, —O—C$_1$-C$_3$ alkyl, and —CH$_2$heterocycle, wherein the phenyl of —NHC(O) phenyl and —OC(O)NH(C$_1$-C$_3$ alkyl)(C$_1$-C$_3$ alkyl) phenyl are optionally substituted with one or more substituents selected from —C(O)H and OH, and wherein the alkyl of —O—C$_1$-C$_3$ alkyl is optionally substituted with substituents selected from heterocycle, oxo and hydroxy; and wherein the heterocycle of —CH$_2$heterocyclyl is optionally substituted with oxo;

each R$^7$ is independently selected from halogen, hydroxy, HC(=O)—, C$_1$-C$_4$ alkyl, C$_1$-C$_4$ alkoxy, C$_1$-C$_4$ haloalkyl, C$_1$-C$_4$ hydroxyalkyl, or —N(R$^5$)$_2$;

each R$^{20}$ is independently selected from hydrogen; and C$_{1-6}$ alkyl, C$_{3-12}$ carbocycle, and 3- to 12-membered heterocycle, each of which is optionally substituted with one or more substituents independently selected from halogen, —OH, —CN, —NO$_2$, —NH$_2$, —N(C$_{1-6}$ alkyl)$_2$, C$_{1-10}$ alkyl, —C$_{1-10}$ haloalkyl, —O—C$_{1-10}$ alkyl, oxo, =NH, C$_{3-12}$ carbocycle, and 3- to 12-membered heterocycle;

each R$^{21}$ is independently selected from hydrogen; and C$_{1-6}$ alkyl, C$_{3-12}$ carbocycle, and 3- to 12-membered heterocycle, each of which is optionally substituted with one or more substituents independently selected from halogen, —OH, —CN, —NO$_2$, —NH$_2$, —N(C$_{1-6}$ alkyl)$_2$, C$_{1-10}$ alkyl, —C$_{1-10}$ haloalkyl, —O—C$_{1-10}$ alkyl, oxo, C$_{3-12}$ carbocycle, and 3- to 12-membered heterocycle;

each Q is independently selected from a bond, S, and O;

B is selected from a heterocycle and carbocycle, wherein the heterocycle and carbocycle are optionally substituted with one or more substituents independently selected from halogen, cyano, hydroxy, =O, —NO$_2$, C$_1$-C$_4$ alkyl, C$_{1-6}$ aminoalkyl, —S—C$_1$-C$_3$ alkyl, C$_2$-C$_4$ alkenyl, C$_2$-C$_4$ alkynyl, C$_2$-C$_4$ hydroxyalkynyl, C$_1$-C$_3$ cyanoalkyl, triazolyl, C$_1$-C$_3$ haloalkyl, —O—C$_1$-C$_3$ haloalkyl, —S—C$_1$-C$_3$ haloalkyl, C$_1$-C$_3$ alkoxy, C$_1$-C$_3$ hydroxyalkyl, —CH$_2$C(=O)N(R$^5$)$_2$, —C$_3$-C$_4$ alkynyl (NR$^5$)$_2$, —N(R$^5$)$_2$, (C$_1$-C$_3$ alkoxy)haloC$_1$-C$_3$ alkyl-, C$_{1-6}$ alkyl-N(R$^{20}$)$_2$, C$_3$-C$_{12}$ carbocycle and 5- to 12-membered heterocycle, wherein C$_3$-C$_{12}$ carbocycle and 5- to 12-membered heterocycle are each optionally substituted with one or more substituents selected from halogen, —OH, —NO$_2$, —NH$_2$, =O, =S, —CN, C$_{1-6}$ aminoalkyl, C$_{1-6}$ alkoxy, C$_{1-6}$ hydroxyalkyl, C$_{1-6}$ haloalkyl, and wherein B forms a spirocycle with Ring A; and Ring A is selected from a heterocycle and carbocycle, wherein the heterocycle or carbocycle is optionally substituted with one or more substituents selected from R$^4$.

In some embodiments, Formula (I) is represented by Formula (II), Formula (II*), or Formula (III).

In some embodiments, for a compound or salt of Formula (I), Ring A is selected from a heterocycle wherein the heterocycle is optionally substituted with one or more substituents selected from R$^4$. In some cases, Ring A includes at least one heteroatom selected from nitrogen, sulfur, and oxygen. In some cases, the heteroatom of Ring A is nitrogen, wherein the nitrogen is optionally substituted with R$^3$, wherein R$^3$ is selected from hydrogen, C$_{1-6}$ alkyl, C$_{2-6}$ alkenyl, C$_{2-6}$ alkynyl, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{3-12}$ carbocycle, and 3- to 12-membered heterocycle, wherein C$_{3-12}$ carbocycle and 3- to 12-membered heterocycle are each optionally substituted with one or more substituents independently selected from halogen, —OH, —CN, —NO$_2$, —NH$_2$, —N(C$_{1-6}$ alkyl)$_2$, C$_{1-10}$ alkyl, —C$_{1-10}$ haloalkyl, —O—C$_{1-10}$ alkyl, oxo, C$_{3-12}$ carbocycle, and 3- to 12-membered heterocycle. In some cases, the heteroatom of Ring A is sulfur, wherein the sulfur is optionally substituted with 1 or 2 oxygen atoms. In some cases, the heteroatom of Ring A is oxygen.

In some embodiments, for a compound or salt of Formula (I), Ring A is selected from a carbocycle, wherein the carbocycle is optionally substituted with one or more substituents selected from R$^4$.

In some embodiments, for a compound or salt of Formula (I), R$^2$ is selected from -L-NR$^{21}$S(O)$_2$(R$^{21}$) and -L-S(O)$_2$N (R$^{21}$)$_2$.

In some embodiments, for a compound or salt of Formula (I), R$^2$ is selected from -L-N(R$^{21}$)C(O)(OR$^{21}$), and -L-OC (O)N(R$^{21}$)$_2$.

In some embodiments, for a compound or salt of Formula (I), each R$^{21}$ is independently selected from hydrogen; C$_{1-6}$ alkyl, C$_{3-12}$ carbocycle, and 3- to 12-membered heterocycle, each of which is optionally substituted with one or more substituents independently selected from halogen, —OH, —CN, —NO$_2$, —NH$_2$, —N(C$_{1-6}$ alkyl)$_2$, C$_{1-10}$ alkyl, —C$_{1-10}$ haloalkyl, —O—C$_{1-10}$ alkyl, and oxo. In some cases, each R$^{21}$ is independently selected from hydrogen; C$_{1-6}$ alkyl, C$_{3-12}$ carbocycle, and 3- to 12-membered heterocycle. In some cases, each R$^{21}$ is independently selected from hydrogen and C$_{1-6}$ alkyl.

In some embodiments, for a compound or salt of Formula (I), R$^2$ is selected from L-bicyclic heterocycle, wherein the bicyclic heterocycle is optionally substituted with one or more R$^6$.

In some embodiments, for a compound or salt of Formula (I), R$^2$ is selected from L-pyrrolizine, wherein the pyrrolizine is optionally substituted with one or more R$^6$.

In some embodiments, for a compound or salt of Formula (I), each L is independently selected from an optionally substituted $C_1$-$C_4$ alkylene; and wherein optionally two substituents on the same carbon atom of L come together to form a $C_3$-$C_6$ carbocycle, wherein the $C_3$-$C_6$ carbocycle is optionally substituted with one or more substituents selected from halogen, —OH, —$NO_2$, =O, =S, —CN, $C_{1-6}$ aminoalkyl, $C_{1-6}$ alkoxy, $C_{1-6}$ hydroxyalkyl, $C_{1-6}$ haloalkyl. In some cases, the optional substituents of L are selected from $C_1$-$C_4$ hydroxyalkyl, $C_1$-$C_4$ alkyl, $C_3$-$C_6$ carbocycle; and wherein optionally two substituents on the same carbon atom of L come together to form a $C_3$-$C_6$ carbocycle or 3- to 8-membered heterocycle wherein the $C_3$-$C_6$ carbocycle and 3- to 8-membered heterocycle are optionally substituted with one or more substituents selected from halogen and $C_{1-6}$ haloalkyl.

In some embodiments, for a compound or salt of Formula (I), each L is independently selected from a substituted $C_1$-$C_4$ alkylene, wherein two substituents on the same carbon atom of L come together to form a $C_3$-$C_6$ carbocycle. In some cases, the $C_3$-$C_6$ carbocycle is optionally substituted with one or more substituents selected from halogen, —OH, —$NO_2$, =O, =S, —CN, $C_{1-6}$ aminoalkyl, $C_{1-6}$ alkoxy, $C_{1-6}$ hydroxyalkyl, $C_{1-6}$ haloalkyl.

In some embodiments, for a compound or salt of Formula (I), wherein each L is independently selected from a substituted $C_1$-$C_4$ alkylene, and wherein two substituents on the same carbon atom of L come together to form a $C_3$-$C_6$ carbocycle. In some cases, each L is independently selected from a substituted $C_3$ alkylene, and wherein two substituents on the same carbon atom of L come together to form a $C_3$ carbocycle. In some cases, each L is independently selected from In some embodiments, for a compound or salt of Formula (I), $R^2$ is selected from -L-heterocycle, wherein the heterocycle portion of -L-heterocycle is optionally substituted with one or more $R^6$. In some cases, the heterocycle is a saturated heterocycle. In some cases, the heterocycle has at least one nitrogen atom and at least one sulfur atom. In some cases, the heterocycle has at least one nitrogen atom. In some cases, the heterocycle has at least one sulfur atom.

In some embodiments, for a compound or salt of Formula (I), $R^2$ is selected from wherein the heterocycle portion is optionally substituted with one or more $R^6$.

In some embodiments, for a compound or salt of Formula (I), Y—$R^2$ is selected from wherein the heterocycle portion is optionally substituted with one or more $R^6$.

In some embodiments, for a compound or salt of Formula (I), Y—$R^2$ is selected from wherein the heterocycle portion is optionally substituted with one or more $R^6$.

In some embodiments, for a compound or salt of Formula Y—$R^2$ is selected from wherein the heterocycle portion is optionally substituted with one or more $R^6$.

In some embodiments, for a compound or salt of Formula (I), $R^2$ is selected from -L-saturated heterocycle, wherein the saturated heterocycle portion of the -L-saturated heterocycle is optionally substituted with one or more $R^6$, and contains one nitrogen atom and one sulfur atom. In some cases, Y—$R^2$ selected from

23

-continued wherein the heterocycle portion is optionally substituted with one or more $R^6$. In some cases, $Y$—$R^2$ is selected from wherein the heterocycle portion is optionally substituted with one or more substituents selected from $C_1$-$C_3$ alkyl and oxo. In some cases, $Y$—$R^2$ is selected from In some cases, $Y$—$R^2$ is selected from In some embodiments, for a compound or salt of Formula (I), each $R^6$ is independently selected from halogen, —OH, $C_1$-$C_3$ hydroxyalkyl, $C_1$-$C_3$ alkyl, $C_1$-$C_3$ haloalkyl, $C_1$-$C_3$ alkoxy, —CN, $C_1$-$C_3$ aminoalkyl, -Q-phenyl, -Q-phenylSO$_2$F, —NHC(O)phenyl, —NHC(O)phenylSO$_2$F, $C_1$-$C_3$ alkyl substituted pyrazolyl, —N($R^5$)$_2$, ($C_1$-$C_3$ alkoxy)

24

$C_1$-$C_3$ alkyl-, ($C_1$-$C_3$ alkyl)C(=O), oxo, ($C_1$-$C_3$ haloalkyl) C(=O)—, —SO$_2$F, ($C_1$-$C_3$ alkoxy)$C_1$-$C_3$ alkoxy, —CH$_2$OC (O)N($R^5$)$_2$, —CH$_2$NHC(O)OC$_1$-$C_6$ alkyl, —CH$_2$NHC(O)N ($R^5$)$_2$, —CH$_2$NHC(O)C$_1$-$C_6$ alkyl, —CH$_2$(pyrazolyl), —CH$_2$NHSO$_2$C$_1$-$C_6$ alkyl, —CH$_2$OC(O)heterocycle, —OC (O)N($R^5$)$_2$, —OC(O)NH(C$_1$-$C_3$ alkyl)O(C$_1$-$C_3$ alkyl), —OC (O)NH(C$_1$-$C_3$ alkyl)O(C$_1$-$C_3$ alkyl)phenyl(C$_1$-$C_3$ alkyl)N (CH$_3$)$_2$, —OC(O)NH(C$_1$-$C_3$ alkyl)O(C$_1$-$C_3$ alkyl)phenyl, —OC(O)heterocycle, and —CH$_2$heterocycle, wherein the phenyl of —NHC(O)phenyl and —OC(O)NH(C$_1$-$C_3$ alkyl) (C$_1$-$C_3$ alkyl)phenyl are each optionally substituted with —C(O)H and OH, and wherein the heterocycle of —CH$_2$heterocyclyl is optionally substituted with oxo.

In some embodiments, for a compound or salt of Formula (I), each $R^6$ is independently selected from halogen, —OH, $C_1$-$C_3$ hydroxyalkyl, $C_1$-$C_3$ alkyl, $C_1$-$C_3$ haloalkyl, $C_1$-$C_3$ alkoxy, —CN, and $C_1$-$C_3$ aminoalkyl.

In some embodiments, for a compound or salt of Formula (I), each $R^6$ is independently selected from halogen, —OH, $C_1$-$C_3$ hydroxyalkyl, $C_1$-$C_3$ alkyl, $C_1$-$C_3$ aminoalkyl, $C_1$-$C_3$ haloalkyl, $C_1$-$C_3$ alkoxy, —N($R^5$)$_2$, and oxo. In some cases, each $R^6$ is independently selected from —OH, $C_1$-$C_3$ hydroxyalkyl, $C_1$-$C_3$ alkyl, $C_1$-$C_3$ aminoalkyl, $C_1$-$C_3$ alkoxy, and —N($R^5$)$_2$. In some cases, each $R^6$ is independently selected from $C_1$-$C_3$ alkyl, $C_1$-$C_3$ alkoxy, and —N($R^5$)$_2$.

In some embodiments, for a compound or salt of Formula (I), $R^6$ is selected from halogen, —OH, $C_1$-$C_3$ hydroxyalkyl, $C_1$-$C_3$ alkyl, $C_1$-$C_3$ haloalkyl, $C_1$-$C_3$ alkoxy, —CN, and $C_1$-$C_3$ aminoalkyl. In some cases, $R^6$ is selected from halogen and $C_1$-$C_3$ alkyl. In some cases, $R^6$ is halogen. In some cases, $R^6$ is $C_1$-$C_3$ alkyl. In some cases, $R^6$ is selected from halogen and $C_1$-$C_3$ alkyl. In some cases, $R^6$ is selected from methyl and fluorine.

In some embodiments, for a compound or salt of Formula (I), $R^2$ is selected from In some embodiments, for a compound or salt of Formula (I), $Y$—$R^2$ is selected from In some embodiments, for a compound or salt of Formula (I), Y—$R^2$ is selected from In some embodiments, for a compound or salt of Formula (I), Y—$R^2$ is In some embodiments, for a compound or salt of Formula (I), Y—$R^2$ is selected from -continued , and In some embodiments, for a compound or salt of Formula (I), B is an optionally substituted 5- to 15-membered heterocycle or optionally substituted $C_3$-$C_{15}$ carbocycle. In some cases, B is an optionally substituted 5- to 15-membered heterocycle. In some cases, B is an optionally substituted $C_3$-$C_{15}$ carbocycle.

In some embodiments, for a compound or salt of Formula (I), B is an optionally substituted 8- to 15-membered fused heterocycle or optionally substituted $C_8$-$C_{15}$ fused carbocycle. In some cases, B is an optionally substituted 8- to 15-membered fused heterocycle. In some cases, B is an optionally substituted $C_8$-$C_{15}$ fused carbocycle.

In some embodiments, for a compound or salt of Formula (I), for B, the optionally substituted 8- to 15-membered fused heterocycle or optionally substituted $C_8$-$C_{15}$ fused carbocycle are each bicyclic or tricyclic. In some cases, for B, the optionally substituted 8- to 15-membered fused heterocycle are each bicyclic or tricyclic. In some cases, for B, the optionally substituted 8- to 15-membered fused heterocycle or optionally substituted $C_8$-$C_{15}$ fused carbocycle are each bicyclic or tricyclic.

In some embodiments, for a compound or salt of Formula (I), B the heterocycle or carbocycle are each independently bicyclic. In some cases, the heterocycle is bicyclic. In some cases, the carbocycle is bicyclic.

In some embodiments, for a compound or salt of Formula (I), B the heterocycle or carbocycle are each independently tricyclic. In some cases, the heterocycle is tricyclic. In some cases, the carbocycle is tricyclic.

In some embodiments, for a compound or salt of Formula (I), B, the optionally substituted 8- to 15-membered fused heterocycle or optionally substituted $C_8$-$C_{15}$ fused carbocycle is selected from each of which is optionally substituted with one or more substituents.

In some embodiments, for a compound or salt of Formula (I), for B, the optionally substituted 8- to 15-membered fused heterocycle or optionally substituted $C_8$-$C_{15}$ fused carbocycle is selected from each of which is optionally substituted with one or more substituents.

In some embodiments, for a compound or salt of Formula (I), for B, the optionally substituted 8- to 15-membered fused heterocycle or optionally substituted $C_8$-$C_{15}$ fused carbocycle is selected from, each of which is optionally substituted with one or more substituents.

In some embodiments, for a compound or salt of Formula (I), for B, the one or more optional substituents of the heterocycle and carbocycle are independently selected at each occurrence from halogen, $C_1$-$C_3$ alkyl, —B(OR$^{20}$)$_2$, —OR$^{20}$, —C(O)N(R$^{20}$)$_2$, —N(R$^{20}$)$_2$, =O, —CN, —NHCN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{2-6}$ alkenyl, and $C_{2-6}$ alkynyl. In some cases, the one or more optional substituents of the heterocycle and carbocycle are independently selected at each occurrence from halogen, oxo, —NH$_2$, $C_1$-$C_3$ alkyl, —B(OR$^{20}$)$_2$, —OH, —C(O)N(R$^{20}$)$_2$, =O, —CN, $C_{1-6}$ alkoxy, and $C_{2-6}$ alkynyl. In some cases, the one or more optional substituents of the heterocycle and carbocycle are independently selected at each occurrence from halogen, oxo, —NH$_2$, $C_1$-$C_3$ alkyl, —B(OH)$_2$, —OH, —C(O)NH$_2$, —NH$_2$, =O, —CN, $C_{1-6}$ alkoxy, and $C_{2-6}$ alkynyl. In some cases, the one or more optional substituents of the heterocycle and carbocycle are independently selected at each occurrence from oxo, —NH$_2$, —CN, halogen, $C_1$-$C_3$ alkyl. In some cases, the one or more optional substituents of the heterocycle or carbocycle are independently selected from oxo, —NH$_2$, halogen, $C_1$-$C_3$ alkyl.

In some embodiments, for a compound or salt of Formula (I), B is selected from

-continued

In some embodiments, for a compound or salt of Formula (I), each $R^4$ is independently selected from $C_{1-6}$ alkyl, $C_{2-6}$ alkenyl, $C_{2-6}$ alkynyl, oxo, hydroxyl, halogen. Ins some cases, each $R^4$ is independently selected from $C_{1-6}$ alkyl, oxo, and halogen.

In some embodiments, for a compound or salt of Formula (I), n is selected from 1 and 2. In some cases, n is 0.

In some embodiments, for a compound or salt of Formula (I), Y is O.

In some embodiments, for a compound or salt of Formula (I), $R^1$ is selected from optionally substituted 5- to 12-membered heterocycle.

In some embodiments, for a compound or salt of Formula (I), $R^1$ is selected from $C_3$-$C_{12}$ carbocycle and 5- to 12-membered heterocycle, each of which are optionally substituted with one or more substituents independently selected from halogen, $-B(OR^{20})_2$, $-OR^{20}$, $SR^{20}$, $-S(O)_2(R^{20})$, $-S(O)_2N(R^{20})_2$, $-NR^{20}S(O)_2R^{20}$, $C(O)N(R^{20})_2$, $-N(R^{20})C(O)R^{20}$, $-N(R^{20})C(O)N(R^{20})_2$, $-N(R^{20})C(O)OR^{20}$, $-N(R^{20})_2$, $-C(O)R^{20}$, $C(O)OR^{20}$, $-OC(O)R^{20}$, $-OC(O)N(R^{20})_2$, $-NO_2$, $=O$, $=NO(R^{20})$, CN, $C_{1-6}$ aminoalkyl, $C_{1-6}$alkoxy, $C_{1-6}$ hydroxyalkyl, $C_{1-6}$ cyanoalkyl, $C_{1-6}$haloalkyl, $C_{1-6}$ alkyl, $C_{2-6}$ alkenyl, and $C_{2-6}$ alkynyl.

In some embodiments, for a compound or salt of Formula (I), $R^1$ is selected from $C_3$-$C_{12}$ carbocycle and 5- to 12-membered heterocycle, each of which are optionally substituted with one or more substituents independently selected from halogen, $-B(OR^{20})_2$, $-OR^{20}$, $-SR^{20}$, $-S(O)_2(R^{20})$, $-C(O)N(R^{20})_2$, $-C(O)NR^{20}-OR^{20}$, $-S(O)_2N(R^{20})_2$, $-NR^{20}S(O)_2R^{20}$, $-N(R^{20})C(O)R^{20}$, $-N(R^{20})C(O)$ $N(R^{20})_2$, $N(R^{20})C(O)OR^{20}$, $-N(R^{20})_2$, $-C(O)R^{20}$, $-C(O)$ $OR^{20}$, $-OC(O)R^{20}$, $OC(O)N(R^{20})_2$, $-NO_2$, $=O$, $=NO$ $(R^{20})$, $-CN$, $-NHCN$, $C_{1-6}$ aminoalkyl, $C_{1-6}$ alkoxy, $C_{1-6}$ hydroxyalkyl, $C_{1-6}$ haloalkyl, $C_{1-6}$ alkyl, $C_{2-6}$ alkenyl, and $C_{2-6}$ alkynyl.

In some embodiments, for a compound or salt of Formula (I), for B, the one or more optional substituents of the heterocycle or carbocycle are independently selected from oxo, $-NH_2$, CN, halogen, $C_1$-$C_3$ alkyl.

In some embodiments, for a compound or salt of Formula (I), B is selected from

31

In some embodiments, for a compound or salt of Formula (I), $R^1$ is selected from $C_3$-$C_{12}$ carbocycle and 5- to 12-membered heterocycle, each of which are optionally substituted with one or more substituents independently selected from —S(O)$_2$(R$^{20}$), —S(O)$_2$N(R$^{20}$)$_2$, —NR$^{20}$S(O)$_2$R$^{20}$, —N(R$^{20}$)C(O)OR$^{20}$, and —OC(O)N(R$^{20}$)$_2$.

In some embodiments, for a compound or salt of Formula (I), $R^1$ is selected from 5- to 12-membered heterocycle, wherein the 5- to 12-membered heterocycle is optionally substituted with one or more substituents independently selected from halogen, —OH, —N(R$^{20}$)$_2$, —NO$_2$, =O, —CN, $C_{1-6}$ aminoalkyl, $C_{1-6}$alkoxy, $C_{1-6}$ hydroxyalkyl, and $C_{1-6}$haloalkyl.

In some embodiments, for a compound or salt of Formula (I), $R^1$ is selected from 5- to 12-membered heterocycle, wherein the 5- to 12-membered heterocycle is optionally substituted with one or more substituents independently selected from halogen, —OH, —N(R$^{20}$)$_2$, —NO$_2$, $C_{1-6}$ aminoalkyl, $C_{1-6}$alkoxy, $C_{1-6}$ hydroxyalkyl, and $C_{1-6}$ haloalkyl.

In some embodiments, for a compound or salt of Formula (I), $R^{20}$ of $R^1$ is selected from hydrogen and $C_{1-3}$ alkyl.

In some embodiments, for a compound or salt of Formula (I), the 5- to 12-membered heterocycle of $R^1$ is an unsaturated heterocycle.

In some embodiments, for a compound or salt of Formula (I), the 5- to 12-membered heterocycle of $R^1$ is a saturated heterocycle.

In some embodiments, for a compound or salt of Formula (I), 5- to 12-membered heterocycle of $R^1$ is a bridged heterocycle.

In some embodiments, for a compound or salt of Formula (I), $R^1$ is selected from

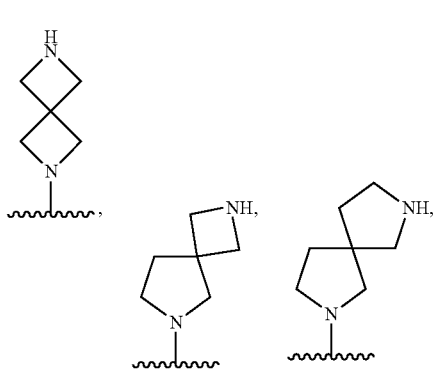

32

-continued

33

-continued

34 each of which is optionally substituted with one or more substituents independently selected from halogen, —OH, —N(R$^{20}$)$_2$, —NO$_2$, C$_{1-6}$ aminoalkyl, C$_{1-6}$ alkoxy, =O, —CN, C$_{1-6}$ hydroxyalkyl, and C$_{1-6}$ haloalkyl.

In some embodiments, for a compound or salt of Formula (I), R$^1$ is selected from In some embodiments, for a compound or salt of Formula (I), L is selected from C$_1$-C$_4$ alkylene.

In some embodiments, for a compound or salt of Formula (I), L is selected from unsubstituted C$_1$-C$_4$ alkylene.

In some embodiments, for a compound or salt of Formula (I), R$^2$ is -L-heterocycle, optionally substituted with one or more R$^6$, wherein the heterocycle portion is a bicyclic heterocycle. In some cases, the bicyclic heterocycle contains at least 1 nitrogen atom. In some cases, the bicyclic heterocycle contains at most 1 nitrogen atom.

In some embodiments, for a compound or salt of Formula (I), Y—R$^2$ is selected from wherein the heterocycle portion is optionally substituted with one or more R$^6$.

In some embodiments, for a compound or salt of Formula (I), R$^6$ of R$^2$ is independently selected at each occurrence from halogen, hydroxy, C$_1$-C$_3$ hydroxyalkyl, C$_1$-C$_3$ alkyl, C$_1$-C$_3$ haloalkyl, C$_1$-C$_3$ alkoxy, cyano, and C$_1$-C$_3$ aminoalkyl.

In some embodiments, for a compound or salt of Formula (I), R$^6$ of R$^2$ is independently selected at each occurrence from C$_1$-C$_3$ alkyl and halogen.

In some embodiments, for a compound or salt of Formula (I), Y—R$^2$ is selected from and each of which is optionally substituted with one or more substituents independently selected from halogen, —OH, —N(R$^{20}$)$_2$, —NO$_2$, C$_{1-6}$ aminoalkyl, C$_{1-6}$ alkoxy, =O, —CN, C$_{1-6}$ hydroxyalkyl, and C$_{1-6}$ haloalkyl.

In some embodiments, for a compound or salt of Formula (I), R$^1$ is selected from In some aspects, the present disclosure provides a compound represented by the structure of Formula (II):

A compound of Formula (II)

Formula (II)

or a pharmaceutically acceptable salt thereof wherein:

M is selected from O, S, SO, $SO_2$, and $NR^3$;

$R^1$ is selected from $C_3$-$C_{12}$ carbocycle and 5- to 15-membered heterocycle, each of which are optionally substituted with one or more substituents independently selected from halogen, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, —C(O)N(R$^{20}$)$_2$, —C(=NR$^{20}$)N(R$^{20}$)$_2$, —C(O)NR$^{20}$OR$^{20}$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =N(R$^{20}$), =NO(R$^{20}$), —CN, —NHCN, $C_{1-6}$ alkyl-N(R$^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$haloalkyl, $C_{1-6}$ alkyl-SO$_2$R$^{20}$, $C_{1-6}$ alkyl, $C_{2-6}$ alkenyl, $C_{2-6}$ alkynyl, $C_3$-$C_{12}$ carbocycle and 5- to 12-membered heterocycle, wherein the $C_3$-$C_{12}$ carbocycle and 5- to 12-membered heterocycle are each optionally substituted independently with one or more $R^{1*}$; and wherein when M is $NR^3$, Y is O, and $R^1$ is piperazine, the piperazine is substituted with one or more $R^9$;

each $R^{1*}$ is independently selected from halogen, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, —C(O)N(R$^{20}$)$_2$, —C(O)NR$^{20}$OR$^{20}$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =N(R$^{20}$), =NO(R$^{20}$), —CN, —NHCN, $C_{1-6}$ alkyl-N(R$^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, and $C_3$-$C_{12}$ carbocycle;

Y is selected from a bond, O, S and $NR^5$;

$R^2$ is selected from -L-N(R$^{21}$)$_2$, -L-OR$^{21}$, heterocycle, $C_1$-$C_6$ alkyl, -L-heterocycle, -L-aryl, -L-heteroaryl, -L-cycloalkyl, -L-NHC(=NH)NH$_2$, -L-C(O)N(R$^{21}$)$_2$, -L-$C_1$-$C_6$ haloalkyl, -L-OR$^{21}$, -L-NR$^{21}$C(O)-aryl, -L-COOH, -L-NR$^{21}$S(O)$_2$(R$^{21}$), -L-S(O)$_2$N(R$^{21}$)$_2$, -L-N(R$^{21}$)C(O)(OR$^{21}$), -L-OC(O)N(R$^{21}$)$_2$, and -LC(=O)OC$_1$-$C_6$ alkyl, wherein the heterocycle, the aryl portion of -L-NR$^{21}$C(O)-aryl, the heterocycle portion of -L-heterocycle, the cycloalkyl portion of the -L-cycloalkyl are each optionally substituted with one or more $R^6$, and wherein the aryl portion of the -L- aryl and the heteroaryl portion of the -L-heteroaryl are each optionally substituted with one or more $R^7$, and wherein when Y is a bond, O, or S. $R^2$ is further selected from hydrogen;

each L is independently selected from a $C_1$-$C_4$ alkylene optionally substituted with one or more substituents selected from hydroxy, $C_1$-$C_4$ hydroxyalkyl, $C_1$-$C_4$ alkyl, $C_3$-$C_6$ carbocycle, or 3- to 8-membered heterocycle, wherein the $C_3$-$C_6$ carbocycle and 3- to 8-membered heterocycle are optionally substituted with one or more substituents selected from halogen, —OH, —NO$_2$, =O, =S, —CN, $C_{1-6}$ aminoalkyl, $C_{1-6}$ alkoxy, $C_{1-6}$ hydroxyalkyl, $C_{1-6}$ haloalkyl; and wherein optionally two substituents on the same carbon atom of L come together to form a $C_3$-$C_6$ carbocycle or 3- to 8-membered heterocycle, wherein the $C_3$-$C_6$ carbocycle and 3- to 8-membered heterocycle are each optionally substituted with one or more substituents selected from halogen, —OH, —NO$_2$, =O, =S, —CN, $C_{1-6}$ aminoalkyl, $C_{1-6}$ alkoxy, $C_{1-6}$ hydroxyalkyl, $C_{1-6}$ haloalkyl;

$R^3$ is selected from hydrogen, $C_{1-6}$ alkyl, $C_{2-6}$ alkenyl, $C_{2-6}$ alkynyl, $C_{1-6}$ alkyl-N(R$^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$haloalkyl, $C_{1-6}$ alkoxyalkyl, $C_{3-12}$ carbocycle, and 3- to 12-membered heterocycle, wherein $C_{3-12}$ carbocycle and 3- to 12-membered heterocycle are each optionally substituted with one or more substituents independently selected from halogen, —OH, —CN, —NO$_2$, —NH$_2$, —N(C$_{1-6}$ alkyl)$_2$, $C_{1-10}$ alkyl, —C$_{1-10}$ haloalkyl, —O—C$_{1-10}$ alkyl, oxo, $C_{3-12}$ carbocycle, and 3- to 12-membered heterocycle;

n is selected from 0 to 2;

each $R^4$ is independently selected from $C_{1-6}$ alkyl, $C_{2-6}$ alkenyl, $C_{2-6}$ alkynyl, oxo, hydroxyl, halogen, $C_{3-12}$ carbocycle, and 3- to 12-membered heterocycle, wherein the $C_1$-$C_6$ alkyl, $C_{3-12}$ carbocycle, and 3- to 12-membered heterocycle are each optionally substituted with one or more substituents independently selected from cyano, halogen, —OR$^5$, and —N(R$^5$)$_2$;

each $R^5$ is independently selected from hydrogen or $C_1$-$C_6$ alkyl;

each $R^6$ is independently selected from halogen, hydroxy, $C_1$-$C_3$ hydroxyalkyl, $C_1$-$C_3$ alkyl, oxo, $C_1$-$C_3$ haloalkyl, $C_1$-$C_3$ alkoxy, cyano, =CH$_2$, =NO—C$_1$-$C_3$ alkyl, $C_1$-$C_3$ aminoalkyl, —N(R$^5$)S(O)$_2$(R$^5$), -Q-phenyl, -Q-phenylSO$_2$F, —NHC(O)phenyl, —NHC(O)phenylSO$_2$F, $C_1$-$C_3$ alkyl substituted pyrazolyl, tert-butyldimethylsilyloxyCH$_2$—, —N(R$^5$)$_2$, (C$_1$-$C_3$ alkoxy)C$_1$-$C_3$ alkyl-, (C$_1$-$C_3$ alkyl)C(=O), oxo, (C$_1$-$C_3$ haloalkyl)C(=O)—, —SO$_2$F, (C$_1$-$C_3$ alkoxy)C$_1$-$C_3$ alkoxy, —CH$_2$OC(O)N(R$^5$)$_2$, —CH$_2$NHC(O)OC$_1$-$C_6$ alkyl, —CH$_2$NHC(O)N(R$^5$)$_2$, —CH$_2$NHC(O)C$_1$-$C_6$ alkyl, —CH$_2$(pyrazolyl), —CH$_2$NHSO$_2$C$_1$-$C_6$ alkyl, —CH$_2$OC(O)heterocycle, —OC(O)N(R$^5$)$_2$, —OC(O)NH(C$_1$-$C_3$ alkyl)O(C$_1$-$C_3$ alkyl), —OC(O)NH(C$_1$-$C_3$ alkyl)O(C$_1$-$C_3$ alkyl)phenyl(C$_1$-$C_3$ alkyl)N(CH$_3$)$_2$, —OC(O)NH(C$_1$-$C_3$ alkyl)O(C$_1$-$C_3$ alkyl)phenyl, —OC(O)heterocycle, —O—C$_1$-$C_3$ alkyl, and —CH$_2$heterocycle, wherein the phenyl of —NHC(O) phenyl and —OC(O)NH(C$_1$-$C_3$ alkyl)(C$_1$-$C_3$ alkyl) phenyl are each optionally substituted with one or more substituents selected from —C(O)H and OH, and wherein the alkyl of —O—C$_1$-$C_3$ alkyl is optionally substituted with substituents selected from heterocycle, oxo and hydroxy; and wherein the heterocycle of —CH$_2$heterocyclyl is optionally substituted with oxo;

each Q is independently selected from a bond, S, and 0;

each $R^7$ is independently selected from halogen, hydroxy, HC(=O)—, $C_1$-$C_4$ alkyl, $C_1$-$C_4$ alkoxy, $C_1$-$C_4$ haloalkyl, $C_1$-$C_4$ hydroxyalkyl, or —N(R$^5$)$_2$;

each $R^9$ is independently selected from halogen, —B(OR$^{20}$)$_2$, —OR$^{20}$, —SR$^{20}$, —S(O)$_2$(R$^{20}$), —S(O)$_2$N(R$^{20}$)$_2$, —NR$^{20}$S(O)$_2$R$^{20}$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —NO$_2$, =O, =NO(R$^{20}$), —CN, —NHCN, C$_{1-6}$ aminoalkyl, C$_{1-6}$ alkoxy, C$_{1-6}$ hydroxyalkyl, and C$_{1-6}$ haloalkyl;

each R$^{20}$ is independently selected from hydrogen; and C$_{1-6}$ alkyl, C$_{3-12}$ carbocycle, and 3- to 12-membered heterocycle, each of which is optionally substituted with one or more substituents independently selected from halogen, —OH, —CN, —NO$_2$, —NH$_2$, —N(C$_{1-6}$ alkyl)$_2$, C$_{1-10}$ alkyl, —C$_{1-10}$ haloalkyl, —O—C$_{1-10}$ alkyl, oxo, =NH, C$_{3-12}$ carbocycle, and 3- to 12-membered heterocycle;

each R$^{21}$ is independently selected from hydrogen; and C$_{1-6}$ alkyl, C$_{3-12}$ carbocycle, and 3- to 12-membered heterocycle, each of which is optionally substituted with one or more substituents independently selected from halogen, —OH, —CN, —NO$_2$, —NH$_2$, —N(C$_{1-6}$ alkyl)$_2$, C$_{1-10}$ alkyl, —C$_{1-10}$ haloalkyl, —O—C$_{1-10}$ alkyl, oxo, C$_{3-12}$ carbocycle, and 3- to 12-membered heterocycle; and B is selected from a heterocycle and carbocycle, wherein the heterocycle and carbocycle are each optionally substituted with one or more substituents independently selected from halogen, cyano, hydroxy, =O, —NO$_2$, C$_1$-C$_4$ alkyl, C$_{1-6}$ aminoalkyl, —S—C$_1$-C$_3$ alkyl, C$_2$-C$_4$ alkenyl, C$_2$-C$_4$ alkynyl, C$_2$-C$_4$ hydroxyalkynyl, C$_1$-C$_3$ cyanoalkyl, triazolyl, C$_1$-C$_3$ haloalkyl, —O—C$_1$-C$_3$ haloalkyl, —S—C$_1$-C$_3$ haloalkyl, C$_1$-C$_3$ alkoxy, C$_1$-C$_3$ hydroxyalkyl, —CH$_2$C(=O)N(R$^5$)$_2$, —C$_3$-C$_4$ alkynyl(NR$^5$)$_2$, —N(R$^5$)$_2$, (C$_1$-C$_3$ alkoxy)halo C$_1$-C$_3$ alkyl-, C$_{1-6}$ alkyl-N(R$^{20}$)$_2$, C$_3$-C$_{12}$ carbocycle and 5- to 12-membered heterocycle, wherein C$_3$-C$_{12}$ carbocycle and 5- to 12-membered heterocycle are each optionally substituted with one or more substituents selected from halogen, —OH, —NO$_2$, —NH$_2$, =O, =S, —CN, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$ haloalkyl.

In some embodiments, for a compound or salt of Formula (II), R$^2$ is selected from -L-NR$^{21}$S(O)$_2$(R$^{21}$) and -L-S(O)$_2$N(R$^{21}$)$_2$.

In some embodiments, for a compound or salt of Formula (II), R$^2$ is selected from -L-N(R$^{21}$)C(O)(OR$^{21}$), and -L-OC(O)N(R$^{21}$)$_2$.

In some embodiments, for a compound or salt of Formula (II), each R$^{2'}$ is independently selected from hydrogen; C$_{1-6}$ alkyl, C$_{3-12}$ carbocycle, and 3- to 12-membered heterocycle, each of which is optionally substituted with one or more substituents independently selected from halogen, —OH, —CN, —NO$_2$, —NH$_2$, —N(C$_{1-6}$ alkyl)$_2$, C$_{1-10}$ alkyl, —C$_{1-10}$ haloalkyl, —O—C$_{1-10}$ alkyl, and oxo. In some cases, each R$^{21}$ is independently selected from hydrogen; C$_{1-6}$ alkyl, C$_{3-12}$ carbocycle, and 3- to 12-membered heterocycle. In some cases, each R$^{21}$ is independently selected from hydrogen and C$_{1-6}$ alkyl.

In some embodiments, for a compound or salt of Formula (II), R$^3$ is selected from hydrogen and C$_{1-6}$ alkyl.

In some embodiments, for a compound or salt of Formula (II), M is selected from 0, NH, and NMe. In some cases, M is O. In some cases, M is selected from NH and NMe.

In some embodiments, for a compound or salt of Formula (II), B is an optionally substituted 5- to 15-membered heterocycle or optionally substituted C$_3$-C$_{15}$ carbocycle. In some cases, B is an optionally substituted 5- to 15-membered heterocycle. In some cases, B is an optionally substituted C$_3$-C$_{15}$ carbocycle. In some cases, B is an optionally substituted 8- to 15-membered heterocycle. In some cases, B is an optionally substituted C$_8$-C$_{15}$ carbocycle.

In some embodiments, for a compound or salt of Formula (II), B is an optionally substituted 8- to 15-membered fused heterocycle or optionally substituted C$_8$-C$_{15}$ fused carbocycle. In some cases, B is an optionally substituted 8- to 15-membered fused heterocycle. In some cases, B is an optionally substituted C$_8$-C$_{15}$ fused carbocycle.

In some embodiments, for a compound or salt of Formula (II), for B, the optionally substituted 8- to 15-membered fused heterocycle or optionally substituted C$_8$-C$_{15}$ fused carbocycle are each bicyclic or tricyclic. In some cases, for B, the optionally substituted 8- to 15-membered fused heterocycle are each bicyclic or tricyclic. In some cases, for B, the optionally substituted 8- to 15-membered fused heterocycle or optionally substituted C$_8$-C$_{15}$ fused carbocycle are each bicyclic or tricyclic.

In some embodiments, for a compound or salt of Formula (II), for B, the optionally substituted 8- to 15-membered heterocycle contains at least one nitrogen atom. In some cases, the optionally substituted 8- to 15-membered heterocycle contains at least one sulfur atom. In some cases, the optionally substituted 8- to 15-membered heterocycle contains at most one nitrogen atom. In some cases, the optionally substituted 8- to 15-membered heterocycle contains at most one sulfur atom. In some cases, the optionally substituted 8- to 15-membered heterocycle contains at least two heteroatoms.

In some embodiments, for a compound or salt of Formula (II), B the heterocycle or carbocycle are each independently bicyclic. In some cases, the heterocycle is bicyclic. In some cases, the carbocycle is bicyclic.

In some embodiments, for a compound or salt of Formula (II), B the heterocycle or carbocycle are each independently tricyclic. In some cases, the heterocycle is tricyclic. In some cases, the carbocycle is tricyclic.

In some embodiments, for a compound or salt of Formula (II), B, the optionally substituted 8- to 15-membered fused heterocycle or optionally substituted C$_8$-C$_{15}$ fused carbocycle is selected from each of which is optionally substituted with one or more substituents.

In some embodiments, for a compound or salt of Formula (II), for B, the optionally substituted 8- to 15-membered fused heterocycle or optionally substituted C$_8$-C$_{15}$ fused carbocycle is selected from each of which is optionally substituted with one or more substituents.

In some embodiments, for a compound or salt of Formula (II), for B, the optionally substituted 8- to 15-membered fused heterocycle or optionally substituted $C_8$-$C_{15}$ fused carbocycle is selected from, and each of which is optionally substituted with one or more substituents.

In some embodiments, for a compound or salt of Formula (II), for B, the one or more optional substituents of the heterocycle and carbocycle are independently selected at each occurrence from halogen, $C_1$-$C_3$ alkyl, —B(OR$^{20}$)$_2$, —OR$^{20}$, —C(O)N(R$^{20}$)$_2$, —N(R$^{20}$)$_2$, =O, —CN, —NHCN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{2-6}$ alkenyl, and $C_{2-6}$ alkynyl. In some cases, the one or more optional substituents of the heterocycle and carbocycle are independently selected at each occurrence from halogen, oxo, —NH$_2$, $C_1$-$C_3$ alkyl, —B(OR$^{20}$)$_2$, —OH, —C(O)N(R$^{20}$)$_2$, =O, —CN, $C_{1-6}$ alkoxy, and $C_{2-6}$ alkynyl. In some cases, the one or more optional substituents of the heterocycle and carbocycle are independently selected at each occurrence from halogen, oxo, —NH$_2$, $C_1$-$C_3$ alkyl, —B(OH)$_2$, —OH, —C(O)NH$_2$, —NH$_2$, =O, —CN, $C_{1-6}$ alkoxy, and $C_{2-6}$ alkynyl. In some cases, the one or more optional substituents of the heterocycle and carbocycle are independently selected at each occurrence from oxo, —NH$_2$, —CN, halogen, $C_1$-$C_3$ alkyl. In some cases, the one or more optional substituents of the heterocycle or carbocycle are independently selected from oxo, —NH$_2$, halogen, $C_1$-$C_3$ alkyl.

In some embodiments, for a compound or salt of Formula (II), B is selected from

41

42

In some embodiments, for a compound or salt of Formula (II), B is selected from

In some embodiments, for a compound or salt of Formula (II), each R$^4$ is independently selected from C$_{1-6}$ alkyl, C$_{2-6}$ alkenyl, C$_{2-6}$ alkynyl, oxo, hydroxyl, halogen. Ins some cases, each R$^4$ is independently selected from C$_{1-6}$ alkyl, oxo, and halogen.

In some embodiments, for a compound or salt of Formula (II), n is selected from 1 and 2. In some cases, n is 0.

In some embodiments, for a compound or salt of Formula (II), Y is O.

In some embodiments, for a compound or salt of Formula (II), R$^1$ is selected from optionally substituted 5- to 12-membered heterocycle.

In some embodiments, for a compound or salt of Formula (II), R$^1$ is selected from 5- to 12-membered heterocycle, wherein the 5- to 12-membered heterocycle is optionally substituted with one or more substituents independently selected from halogen, —OH, —N(R$^{20}$)$_2$, —NO$_2$, =O, —CN, C$_{1-6}$ aminoalkyl, C$_{1-6}$ alkoxy, C$_{1-6}$ hydroxyalkyl, and C$_{1-6}$ haloalkyl.

In some embodiments, for a compound or salt of Formula (II), R$^1$ is selected from C$_3$-C$_{12}$ carbocycle and 5- to 12-membered heterocycle, each of which are optionally substituted with one or more substituents independently selected from halogen, —B(OR$^{20}$)$_2$, —OR$^{20}$, SR$^{20}$, —S(O)$_2$ (R$^{20}$), —S(O)$_2$N(R$^{20}$)$_2$, —NR$^{20}$S(O)$_2$R$^{20}$, —C(O)N(R$^{20}$)$_2$, —N(R$^{20}$)C(O)R$^{20}$, —N(R$^{20}$)C(O)N(R$^{20}$)$_2$, —N(R$^{20}$)C(O) OR$^{20}$, —N(R$^{20}$)$_2$, —C(O)R$^{20}$, C(O)OR$^{20}$, —OC(O)R$^{20}$, —OC(O)N(R$^{20}$)$_2$, —NO$_2$, =O, =NO(R$^{20}$), CN, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{1-6}$ alkyl, C$_{2-6}$ alkenyl, and C$_{2-6}$ alkynyl.

In some embodiments, for a compound or salt of Formula (II), R$^1$ is selected from C$_3$-C$_{12}$ carbocycle and 5- to 12-membered heterocycle, each of which are optionally substituted with one or more substituents independently selected from —S(O)$_2$(R$^{20}$), —S(O)$_2$N(R$^{20}$)$_2$, —NR$^{20}$ S(O)$_2$R$^{20}$, —N(R$^{20}$)C(O)OR$^{20}$, and —OC(O)N(R$^{20}$)$_2$.

In some embodiments, for a compound or salt of Formula (II), R$^1$ is selected from 5- to 12-membered heterocycle, wherein the 5- to 12-membered heterocycle is optionally substituted with one or more substituents independently selected from halogen, —OH, —N(R$^{20}$)$_2$, —NO$_2$, C$_{1-6}$ aminoalkyl, C$_{1-6}$ alkoxy, C$_{1-6}$ hydroxyalkyl, and C$_{1-6}$ haloalkyl.

In some embodiments, for a compound or salt of Formula (II), R$^{20}$ of R$^1$ is selected from hydrogen and C$_{1-3}$ alkyl.

In some embodiments, for a compound or salt of Formula (II), the 5- to 12-membered heterocycle of R$^1$ is an unsaturated heterocycle.

In some embodiments, for a compound or salt of Formula (II), the 5- to 12-membered heterocycle of R$^1$ is a saturated heterocycle.

In some embodiments, for a compound or salt of Formula (II), 5- to 12-membered heterocycle of R$^1$ is a bridged heterocycle.

In some embodiments, for a compound or salt of Formula (II), R$^1$ is selected from

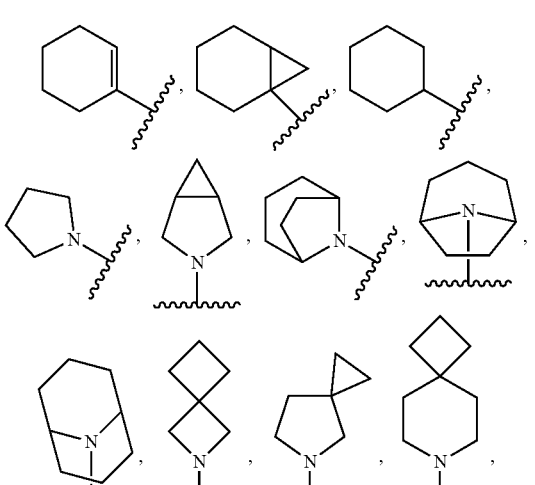

44

-continued

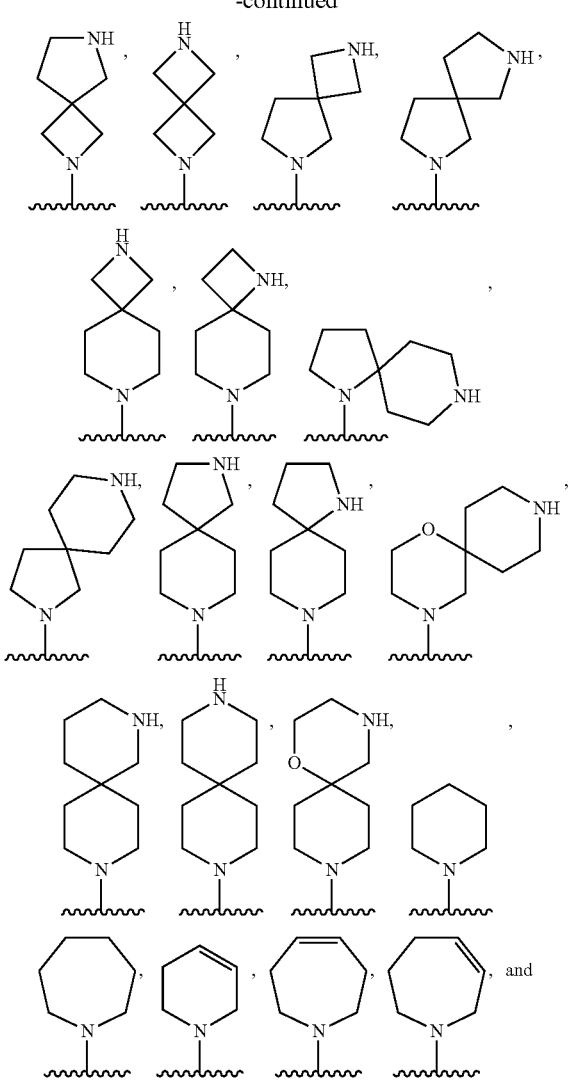

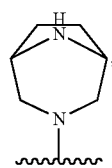

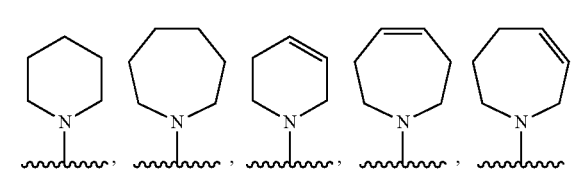

each of which is optionally substituted with one or more substituents independently selected from halogen, —OH, —N(R$^{20}$)$_2$, —NO$_2$, C$_{1-6}$ aminoalkyl, C$_{1-6}$ alkoxy, =O, —CN, C$_{1-6}$ hydroxyalkyl, and C$_{1-6}$ haloalkyl.

In some embodiments, for a compound or salt of Formula (II), R$^1$ is selected from -continued and each of which is optionally substituted with one or more substituents independently selected from halogen, —OH, —N(R$^{20}$)$_2$, —NO$_2$, C$_{1-6}$ aminoalkyl, C$_{1-6}$alkoxy, =O, —CN, C$_{1-6}$ hydroxyalkyl, and C$_{1-6}$haloalkyl.

In some embodiments, for a compound or salt of Formula (II), R$^1$ is selected from and In some embodiments, for a compound or salt of Formula (II), R$^1$ is selected from an optionally substituted saturated 6- to 7-membered heterocycle. In some cases, R$^1$ is selected from an optionally substituted saturated 6-membered heterocycle. In some cases, R$^1$ is selected from which is optionally substituted. In some cases, the optional one or more substituents are independently selected from halogen, —CN, —NHCN, C$_{1-6}$ cyanoalkyl, and C$_{1-6}$ alkyl. In some cases, the optional one or more substituents are independently selected from —CN, —NHCN, C$_{1-6}$ cyanoalkyl, and C$_{1-6}$ alkyl. In some cases, the optional one or more substituents are independently selected from —CN, —NHCN, C$_{1-6}$ cyanoalkyl, and C$_{1-6}$ alkyl. In some cases, the optional one or more substituents are independently selected from —NHCN, and C$_{1-6}$ alkyl. In some cases, R$^1$ is selected from which is substituted with one or more substituents selected from —NHCN, and C$_{1-6}$ alkyl. In some cases, R$^1$ is selected

46 and

In some embodiments, for a compound or salt of Formula (II), R$^1$ is selected from a substituted saturated 6-membered heterocycle, wherein the saturated 6-membered heterocycle is substituted with at least one —NHCN, and optionally one or more C$_{1-6}$ alkyl; M is O; n is 0; B is selected from an optionally substituted 8- to 15-membered fused heterocycle and optionally substituted C$_8$-C$_{15}$ fused carbocycle, each of which is optionally substituted with one or more substituents independently selected from halogen, oxo, —NH$_2$, C$_1$-C$_3$ alkyl, —OH, —C(O)NH$_2$, —NH$_2$, =O, —CN, C$_{1-6}$ alkoxy, C$_{1-6}$ hydroxyalkyl, and C$_{2-6}$ alkynyl; Y is O; R$^2$ is selected from -L-heterocycle, wherein the heterocycle portion is optionally substituted with one or more substituents independently selected from halogen, hydroxy, C$_1$-C$_4$ alkyl, C$_1$-C$_4$ alkoxy, C$_1$-C$_4$ haloalkyl, C$_1$-C$_4$ hydroxyalkyl, or —N(R$^5$)$_2$; and L is selected from C$_1$-C$_4$ alkylene. In some cases, R$^1$ is selected from and In some cases, B is selected from OH, Br, N, OH, , Cl , and

NH$_2$.

In some cases, B is selected from

In some cases, B is

In some embodiments, for a compound or salt of Formula (II), each $R^9$ is independently selected from halogen, —B(OR$^{20}$)$_2$, —OR$^{20}$, —SR$^{20}$, —S(O)$_2$(R$^{20}$), —S(O)$_2$N (R$^{20}$)$_2$, —NR$^{20}$S(O)$_2$R$^{20}$, —N(R$^{20}$)C(O)R$^{20}$, —N(R$^{20}$)C (O)N(R$^{20}$)$_2$, —N(R$^{20}$)C(O)OR$^{20}$, —N(R$^{20}$)$_2$, —NO$_2$, =O, =NO(R$^{20}$), —CN, —NHCN, C$_{1-6}$ aminoalkyl, C$_{1-6}$ alkoxy, C$_{1-6}$ hydroxyalkyl, and C$_{1-6}$haloalkyl. In some cases, each $R^9$ is independently selected from halogen, —B(OR$^{20}$)$_2$, —OR$^{20}$, —SR$^{20}$, —S(O)$_2$(R$^{20}$), —S(O)$_2$N(R$^{20}$)$_2$, —NR$^{20}$S (O)$_2$R$^{20}$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —NO$_2$, =O, =NO(R$^{20}$), —CN, —NHCN. In some cases, each $R^9$ is independently selected from halogen, —SR$^{20}$, —S(O)$_2$(R$^{20}$), —S(O)$_2$N (R$^{20}$)$_2$, —N(R$^{20}$)$_2$, —NO$_2$, =O, and =NO(R$^{20}$). In some cases, each $R^9$ is independently selected from halogen, and —N(R$^{20}$)$_2$.

In some embodiments, for a compound or salt of Formula (II), each L is independently selected from an optionally substituted C$_1$-C$_4$ alkylene; and wherein optionally two substituents on the same carbon atom of L come together to form a C$_3$-C$_6$ carbocycle, wherein the C$_3$-C$_6$ carbocycle is optionally substituted with one or more substituents selected from halogen, —OH, —NO$_2$, =O, =S, —CN, C$_{1-6}$ aminoalkyl, C$_{1-6}$ alkoxy, C$_{1-6}$ hydroxyalkyl, C$_{1-6}$ haloalkyl. In some cases, the optional substituents of L are selected from C$_1$-C$_4$ hydroxyalkyl, C$_1$-C$_4$ alkyl, C$_3$-C$_6$ carbocycle; and wherein optionally two substituents on the same carbon atom of L come together to form a C$_3$-C$_6$ carbocycle or 3- to 8-membered heterocycle wherein the C$_3$-C$_6$ carbocycle and 3- to 8-membered heterocycle are optionally substituted with one or more substituents selected from halogen and C$_{1-6}$ haloalkyl.

In some embodiments, for a compound or salt of Formula (II), each L is independently selected from a substituted C$_1$-C$_4$ alkylene, wherein two substituents on the same carbon atom of L come together to form a C$_3$-C$_6$ carbocycle. In some cases, the C$_3$-C$_6$ carbocycle is optionally substituted with one or more substituents selected from halogen, —OH, —NO$_2$, =O, =S, —CN, C$_{1-6}$ aminoalkyl, C$_{1-6}$ alkoxy, C$_{1-6}$ hydroxyalkyl, C$_{1-6}$ haloalkyl.

In some embodiments, for a compound or salt of Formula (II), wherein each L is independently selected from a substituted C$_1$-C$_4$ alkylene, and wherein two substituents on the same carbon atom of L come together to form a C$_3$-C$_6$ carbocycle. In some cases, each L is independently selected from a substituted C$_3$ alkylene, and wherein two substituents on the same carbon atom of L come together to form a C$_3$ carbocycle. In some cases, each L is independently selected from In some embodiments, for a compound or salt of Formula (II), $R^2$ is selected from -L-heterocycle, wherein the heterocycle portion of -L-heterocycle is optionally substituted with one or more $R^6$. In some cases, the heterocycle is a saturated heterocycle. In some cases, the heterocycle has at least one nitrogen atom and at least one sulfur atom. In some cases, the heterocycle has at least one nitrogen atom. In some cases, the heterocycle has at least one sulfur atom.

In some embodiments, for a compound or salt of Formula (II), $R^2$ is selected from wherein the heterocycle portion is optionally substituted with one or more $R^6$.

In some embodiments, for a compound or salt of Formula (II), Y—R$^2$ is selected from wherein the heterocycle portion is optionally substituted with one or more $R^6$.

In some embodiments, for a compound or salt of Formula (II), Y—R$^2$ is selected from wherein the heterocycle portion is optionally substituted with one or more $R^6$.

In some embodiments, for a compound or salt of Formula (II), Y—R$^2$ is selected from wherein the heterocycle portion is optionally substituted with one or more R$^6$.

In some embodiments, for a compound or salt of Formula (II), R$^2$ is selected from -L-saturated heterocycle, wherein the saturated heterocycle portion of the -L-saturated heterocycle is optionally substituted with one or more R$^6$, and contains one nitrogen atom and one sulfur atom. In some cases, Y—R$^2$ is selected from wherein the heterocycle portion is optionally substituted with one or more R$^6$. In some cases, Y—R$^2$ is selected from wherein the heterocycle portion is optionally substituted with one or more substituents selected from C$_1$-C$_3$ alkyl and oxo. In some cases, Y—R$^2$ is selected from In some cases, Y—R$^2$ is selected from In some embodiments, for a compound or salt of Formula (II), each R$^6$ is independently selected from halogen, —OH, C$_1$-C$_3$ hydroxyalkyl, C$_1$-C$_3$ alkyl, C$_1$-C$_3$ haloalkyl, C$_1$-C$_3$ alkoxy, —CN, C$_1$-C$_3$ aminoalkyl, -Q-phenyl, -Q-phenylSO$_2$F, —NHC(O)phenyl, —NHC(O)phenylSO$_2$F, C$_1$-C$_3$ alkyl substituted pyrazolyl, —N(R$^5$)$_2$, (C$_1$-C$_3$ alkoxy) C$_1$-C$_3$ alkyl-, (C$_1$-C$_3$ alkyl)C(═O), oxo, (C$_1$-C$_3$ haloalkyl) C(═O)—, —SO$_2$F, (C$_1$-C$_3$ alkoxy)C$_1$-C$_3$ alkoxy, —CH$_2$OC (O)N(R$^5$)$_2$, —CH$_2$NHC(O)OC$_1$-C$_6$ alkyl, —CH$_2$NHC(O)N (R$^5$)$_2$, —CH$_2$NHC(O)C$_1$-C$_6$ alkyl, —CH$_2$(pyrazolyl), —CH$_2$NHSO$_2$C$_1$-C$_6$ alkyl, —CH$_2$OC(O)heterocycle, —OC (O)N(R$^5$)$_2$, —OC(O)NH(C$_1$-C$_3$ alkyl)O(C$_1$-C$_3$ alkyl), —OC (O)NH(C$_1$-C$_3$ alkyl)O(C$_1$-C$_3$ alkyl)phenyl(C$_1$-C$_3$ alkyl)N (CH$_3$)$_2$, —OC(O)NH(C$_1$-C$_3$ alkyl)O(C$_1$-C$_3$ alkyl)phenyl, —OC(O)heterocycle, and —CH$_2$heterocycle, wherein the phenyl of —NHC(O)phenyl and —OC(O)NH(C$_1$-C$_3$ alkyl) (C$_1$-C$_3$ alkyl)phenyl are each optionally substituted with —C(O)H and OH, and wherein the heterocycle of —CH$_2$heterocyclyl is optionally substituted with oxo.

In some embodiments, for a compound or salt of Formula (II), each R$^6$ is independently selected from halogen, —OH, C$_1$-C$_3$ hydroxyalkyl, C$_1$-C$_3$ alkyl, C$_1$-C$_3$ haloalkyl, C$_1$-C$_3$ alkoxy, —CN, and C$_1$-C$_3$ aminoalkyl.

In some embodiments, for a compound or salt of Formula (II), each R$^6$ is independently selected from halogen, —OH, C$_1$-C$_3$ hydroxyalkyl, C$_1$-C$_3$ alkyl, C$_1$-C$_3$ aminoalkyl, C$_1$-C$_3$ haloalkyl, C$_1$-C$_3$ alkoxy, —N(R$^5$)$_2$, and oxo. In some cases, each R$^6$ is independently selected from —OH, C$_1$-C$_3$ hydroxyalkyl, C$_1$-C$_3$ alkyl, C$_1$-C$_3$ aminoalkyl, C$_1$-C$_3$ alkoxy, and —N(R$^5$)$_2$. In some cases, each R$^6$ is independently selected from C$_1$-C$_3$ alkyl, C$_1$-C$_3$ alkoxy, and —N(R$^5$)$_2$.

In some embodiments, for a compound or salt of Formula (II), $R^6$ is selected from halogen, —OH, $C_1$-$C_3$ hydroxyalkyl, $C_1$-$C_3$ alkyl, $C_1$-$C_3$ haloalkyl, $C_1$-$C_3$ alkoxy, —CN, and $C_1$-$C_3$ aminoalkyl. In some cases, $R^6$ is selected from halogen and $C_1$-$C_3$ alkyl. In some cases, $R^6$ is halogen. In some cases, $R^6$ is $C_1$-$C_3$ alkyl. In some cases, $R^6$ is selected from halogen and $C_1$-$C_3$ alkyl. In some cases, $R^6$ is selected from methyl and fluorine.

In some embodiments, for a compound or salt of Formula (II), $R^2$ is selected from , and In some embodiments, for a compound or salt of Formula (II), Y—$R^2$ is selected from , and In some embodiments, for a compound or salt of Formula (II), Y—$R^2$ is selected from , and -continued In some embodiments, for a compound or salt of Formula (II), Y—$R^2$ is In some embodiments, for a compound or salt of Formula (II), Y—$R^2$ is selected from

, ,

,

, ,

, and

In some embodiments, for a compound or salt of Formula (II), L is selected from $C_1$-$C_4$ alkylene.

In some embodiments, for a compound or salt of Formula (II), L is selected from unsubstituted $C_1$-$C_4$ alkylene.

In some embodiments, for a compound or salt of Formula (II), $R^2$ is -L-heterocycle, optionally substituted with one or more $R^6$, wherein the heterocycle portion is a bicyclic heterocycle. In some cases, the bicyclic heterocycle contains at least 1 nitrogen atom. In some cases, the bicyclic heterocycle contains at most 1 nitrogen atom.

In some embodiments, for a compound or salt of Formula (II), $R^2$ is selected from L-bicyclic heterocycle, wherein the bicyclic heterocycle is optionally substituted with one or more $R^6$.

In some embodiments, for a compound or salt of Formula (II), $R^2$ is selected from L-pyrrolizine, wherein the pyrrolizine is optionally substituted with one or more $R^6$.

In some embodiments, for a compound or salt of Formula (II), Y—$R^2$ is selected from wherein the heterocycle portion is optionally substituted with one or more $R^6$.

In some embodiments, for a compound or salt of Formula (II), $R^6$ of $R^2$ is independently selected at each occurrence from halogen, hydroxy, $C_1$-$C_3$ hydroxyalkyl, $C_1$-$C_3$ alkyl, $C_1$-$C_3$ haloalkyl, $C_1$-$C_3$ alkoxy, cyano, and $C_1$-$C_3$ aminoalkyl. In some cases, $R^6$ of $R^2$ is independently selected at each occurrence from $C_1$-$C_3$ alkyl and halogen. In some cases, Y—$R^2$ is selected from In some embodiments, for a compound or salt of Formula (II), M is selected from $NR^3$.

In some cases, M is selected from NH and NMe. In some cases, M is selected from NMe and $NCH_2CH_3$. In some cases, M is NMe. In some cases, M is selected from $C_{1-6}$ cyanoalkyl. In some cases, M is selected from $C_2$ cyanoalkyl. In some cases, M is selected from NH. In some cases, $R^3$ is selected from hydrogen, $C_{1-6}$ alkyl, $C_{2-6}$ alkenyl, $C_{2-6}$ alkynyl, $C_{1-6}$ alkyl-$N(R^{20})_2$, $C_{1-6}$ aminoalkyl, $C_{1-6}$alkoxy, $C_{1-6}$ hydroxyalkyl, $C_{1-6}$ cyanoalkyl, $C_{1-6}$alkoxyalkyl, and $C_{1-6}$haloalkyl. In some cases, $R^3$ is selected from hydrogen, $C_{1-6}$ alkyl, $C_{1-6}$ alkyl-$N(R^{20})_2$, $C_{1-6}$ aminoalkyl, $C_{1-6}$ alkoxy, $C_{1-6}$ hydroxyalkyl, $C_{1-6}$ cyanoalkyl, $C_{1-6}$ alkoxyalkyl, and $C_{1-6}$ haloalkyl. In some cases, $R^3$ is selected from $C_{1-6}$ alkyl, $C_{1-6}$ alkyl-$N(R^{20})_2$, $C_{1-6}$ aminoalkyl, $C_{1-6}$ alkoxy, $C_{1-6}$ hydroxyalkyl, $C_{1-6}$ cyanoalkyl, $C_{1-6}$ alkoxyalkyl, and $C_{1-6}$ haloalkyl. In some cases, $R^3$ is selected from $C_{2-6}$ alkyl, $C_{1-6}$ alkyl-$N(R^{20})_2$, $C_{1-6}$ aminoalkyl, $C_{1-6}$ alkoxy, $C_{1-6}$ hydroxyalkyl, $C_{1-6}$ cyanoalkyl, $C_{1-6}$ alkoxyalkyl, and $C_{1-6}$ haloalkyl. In some cases, $R^3$ is selected from $C_{1-6}$ alkyl-$N(R^{20})_2$, $C_{1-6}$ aminoalkyl, $C_{1-6}$ alkoxy, $C_{1-6}$ hydroxyalkyl, $C_{1-6}$ cyanoalkyl, $C_{1-6}$ alkoxyalkyl, and $C_{1-6}$ haloalkyl. In some cases, $R^3$ is selected from $C_{1-6}$ cyanoalkyl, $C_{1-6}$ alkoxyalkyl, and $C_{1-6}$haloalkyl. In some cases, $R^3$ is selected from hydrogen, $C_{1-6}$ alkyl, $C_{1-6}$ alkyl-$N(R^{20})_2$, $C_{1-6}$ aminoalkyl, $C_{1-6}$ alkoxy, $C_{1-6}$ hydroxyalkyl, $C_{1-6}$ cyanoalkyl, and $C_{1-6}$haloalkyl. In some cases, $R^3$ is selected from $C_{1-6}$ alkoxyalkyl, $C_{1-6}$ cyanoalkyl, and $C_{1-6}$ alkyl. In some cases, $R^3$ is In some cases, is selected from $C_{2-6}$ alkyl.

In some embodiments, for a compound or salt of Formula (II), M is $NR^3$, B is selected from each of which is optionally substituted; n is 0; Y is O; $R^2$ is selected from L-heterocycle, wherein the heterocycle is optionally substituted with one or more $R^6$; $R^1$ is selected from which is optionally substituted. In some cases, $R^1$ is which is optionally substituted with one or more substituents independently selected from halogen, —OH, —$S(O)_2(R^{20})$, —$S(O)_2N(R^{20})_2$, —$S(O)N(R^{20})_2$, —$S(O)R^{20}$(=$NR^{20}$), —$C(O)N(R^{20})_2$, —$C(O)NR^{20}OR^{20}$, —$N(R^{20})_2$, —$C(O)R^{20}$, —$NO_2$, =O, —CN, $C_{1-6}$ alkyl-$N(R^{20})_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, and $C_{2-6}$ alkynyl. In some cases, $R^1$ is In some cases, $R^1$ is In some cases, $R^1$ is In some cases, $R^1$ is In some cases, the heterocycle of L-heterocycle is bicyclic. In some cases, the heterocycle of L-heterocycle is monocyclic. In some cases, L is selected from an $C_1$-$C_4$ alkylene. In some cases, L is selected from an unsubstituted $C_1$-$C_4$ alkylene. In some cases, L is independently selected from a substituted $C_1$-$C_4$ alkylene, wherein two substituents on the same carbon atom of L come together to form a $C_3$-$C_6$ carbocycle. In some cases, Y—$R^2$ is selected from In some cases, Y—$R^2$ is selected from In some cases, B is selected from is substituted with one or more substituents. In some cases, B is which is substituted with one or more substituents. In some cases, B is selected from which is substituted with one or more substituents. In some cases, for B, the one or more substituents are independently selected from halogen, oxo, —NH₂, C₁-C₃ alkyl, —B(OH)₂, —OH, —C(O)NH₂, —NH₂, =O, —CN, —O—C₁-C₃ haloalkyl, C₁₋₆ alkoxy, C₁₋₆ hydroxyalkyl, and C₂₋₆ alkynyl. In some cases, B is substituted with at least one halogen. In some cases, B is substituted with at least one chlorine. In some cases, B is substituted with at least one fluorine. In some cases, B is selected from -continued In some cases, B is selected from which is substituted with one or more substituents selected from halogen, —O—C₁-C₃ haloalkyl, and C₁₋₆ haloalkyl. In some cases, B is which is substituted with one or more substituents selected from halogen. In some cases, B is selected from In some cases, B is which is substituted with one or more substituents selected from fluorine. In some cases, B is selected from In some cases, B is which is substituted with one or more substituents selected from chlorine. In some cases, B is selected from In some cases, $R^3$ is selected from hydrogen and $C_{1-6}$ alkyl. In some cases, $R^3$ is selected from $C_{1-6}$ alkyl. In some cases, $R^3$ is methyl. In some cases, each $R^6$ is selected from halogen, oxo, and $C_{1-6}$ alkyl. In some cases, each $R^6$ is selected from halogen, and $C_{1-6}$ alkyl. In some cases, each $R^6$ is selected from halogen. In some cases, $R^1$ is selected from In some cases, $R^1$ is In some cases, B is In some aspects, the present disclosure provides a compound represented by the structure of Formula (III):

Formula (III)

or a pharmaceutically acceptable salt thereof wherein:

$R^1$ is selected from $C_3$-$C_{12}$ carbocycle and 5- to 15-membered heterocycle, each of which are optionally substituted with one or more substituents independently selected from halogen, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, —C(O)N(R$^{20}$)$_2$, —C(=NR$^{20}$)N(R$^{20}$)$_2$, —C(O)NR$^{20}$OR$^{20}$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =N(R$^{20}$), =NO(R$^{20}$), —CN, —NHCN, $C_{1-6}$ alkyl-N(R$^{20}$)$_2$, $C_{1-6}$ aminoalkyl, $C_{1-6}$ alkoxy, $C_{1-6}$ hydroxyalkyl. $C_{1-6}$ cyanoalkyl, $C_{1-6}$haloalkyl. $C_{1-6}$ alkyl, $C_{2-6}$ alkenyl, $C_{2-6}$ alkynyl, $C_3$-$C_{12}$ carbocycle and 5- to 12-membered heterocycle, wherein the $C_3$-$C_{12}$ carbocycle and 5- to 12-membered heterocycle are each optionally substituted independently with one or more $R^{1*}$;

each $R^{1*}$ is independently selected from halogen, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, —C(O)N(R$^{20}$)$_2$, —C(O)NR$^{20}$OR$^{20}$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =N(R$^{20}$), =NO(R$^{20}$), —CN, —NHCN, $C_{1-6}$ alkyl-N(R$^{20}$)$_2$, $C_{1-6}$ aminoalkyl, $C_{1-6}$alkoxy, $C_{1-6}$ hydroxyalkyl, $C_{1-6}$ cyanoalkyl, $C_{1-6}$haloalkyl, $C_{1-6}$alkyl, $C_{2-6}$alkenyl, $C_{2-6}$ alkynyl, and $C_3$-$C_{12}$ carbocycle;

$R^2$ is selected from -L-NR$^{2'}$S(O)$_2$(R$^{21}$), -L-S(O)$_2$N(R$^{21}$)$_2$, -L-N(R$^{21}$)C(O)(OR$^{21}$), -L-OC(O)N(R$^{21}$)$_2$, and L-bicyclic heterocycle, wherein the bicyclic heterocycle is optionally substituted with one or more R$^6$;

each L is independently selected from a $C_1$-$C_4$ alkylene optionally substituted with one or more substituents selected from hydroxy, $C_1$-$C_4$ hydroxyalkyl, $C_1$-$C_4$ alkyl, $C_3$-$C_6$ carbocycle, or 3- to 8-membered heterocycle, wherein the $C_3$-$C_6$ carbocycle and 3- to 8-membered heterocycle are optionally substituted with one or more substituents selected from halogen, —OH, —NO$_2$, =O, =S, —CN, $C_{1-6}$ aminoalkyl, $C_{1-6}$ alkoxy, $C_{1-6}$ hydroxyalkyl, $C_{1-6}$ haloalkyl; and wherein optionally two substituents on the same carbon atom of L come together to form a $C_3$-$C_6$ carbocycle or 3- to 8-membered heterocycle, wherein the $C_3$-$C_6$ carbocycle and 3- to 8-membered heterocycle are each optionally substituted with one or more substituents selected from halogen, —OH, —NO$_2$, =O, =S, —CN, $C_{1-6}$ aminoalkyl, $C_{1-6}$ alkoxy, $C_{1-6}$ hydroxyalkyl, $C_{1-6}$ haloalkyl;

n is selected from 0 to 3;

each $R^4$ is independently selected from $C_{1-6}$ alkyl, $C_{2-6}$ alkenyl, $C_{2-6}$ alkynyl, oxo, hydroxyl, halogen, $C_{3-12}$ carbocycle, and 3- to 12-membered heterocycle, wherein the $C_1$-$C_6$ alkyl, $C_{3-12}$ carbocycle, and 3- to 12-membered heterocycle are each optionally substituted with one or more substituents independently selected from cyano, halogen, —OR$^5$, and —N(R$^5$)$_2$;

B is selected from a heterocycle and carbocycle, wherein the heterocycle or carbocycle is optionally substituted with one or more substituents independently selected from halogen, cyano, hydroxy, =O, —NO$_2$, $C_1$-$C_4$ alkyl, $C_{1-6}$ aminoalkyl, —S—$C_1$-$C_3$ alkyl, $C_2$-$C_4$ alkenyl, $C_2$-$C_4$ alkynyl, $C_2$-$C_4$ hydroxyalkynyl, $C_1$-$C_3$ cyanoalkyl, triazolyl, $C_1$-$C_3$ haloalkyl, —O—$C_1$-$C_3$ haloalkyl, —S—$C_1$-$C_3$ haloalkyl, $C_1$-$C_3$ alkoxy, $C_1$-$C_3$ hydroxyalkyl, —CH$_2$C(=O)N(R$^5$)$_2$, —$C_3$-$C_4$ alkynyl (NR$^5$)$_2$, —N(R$^5$)$_2$, (C$_1$-$C_3$ alkoxy)haloC$_1$-$C_3$ alkyl-, $C_{1-6}$ alkyl-N(R$^{20}$)$_2$, $C_3$-$C_{12}$ carbocycle and 5- to 12-membered heterocycle, wherein $C_3$-$C_{12}$ carbocycle and 5- to 12-membered heterocycle are each optionally substituted with one or more substituents selected from halogen, —OH, —NO$_2$, —NH$_2$, =O, =S, —CN, $C_{1-6}$ aminoalkyl, $C_{1-6}$ alkoxy, $C_{1-6}$ hydroxyalkyl, $C_{1-6}$ haloalkyl;

Y is selected from a bond, O, S and NR$^5$;

each $R^6$ is independently selected from halogen, hydroxy, $C_1$-$C_3$ hydroxyalkyl, $C_1$-$C_3$ alkyl, oxo, $C_1$-$C_3$ haloalkyl, $C_1$-$C_3$ alkoxy, cyano, =CH$_2$, =NO—$C_1$-$C_3$ alkyl, $C_1$-$C_3$ aminoalkyl, —N(R$^5$)S(O)$_2$(R$^5$), -Q-phenyl, -Q-phenylSO$_2$F, —NHC(O)phenyl, —NHC(O) phenylSO$_2$F, $C_1$-$C_3$ alkyl substituted pyrazolyl, tert-butyldimethylsilyloxyCH$_2$—, —N(R$^5$)$_2$, (C$_1$-$C_3$ alkoxy)C$_1$-$C_3$ alkyl-, (C$_1$-$C_3$ alkyl)C(=O), oxo, (C$_1$-$C_3$ haloalkyl)C(=O)—, —SO$_2$F, (C$_1$-$C_3$ alkoxy)C$_1$-$C_3$ alkoxy, —CH$_2$OC(O)N(R$^5$)$_2$, —CH$_2$NHC(O)OC$_1$-$C_6$ alkyl, —CH$_2$NHC(O)N(R$^5$)$_2$, —CH$_2$NHC(O)C$_1$-$C_6$ alkyl, —CH$_2$(pyrazolyl), —CH$_2$NHSO$_2$C$_1$-$C_6$ alkyl, —CH$_2$OC(O)heterocycle, —OC(O)N(R$^5$)$_2$, —OC(O) NH(C$_1$-$C_3$ alkyl)O(C$_1$-$C_3$ alkyl), —OC(O)NH(C$_1$-$C_3$ alkyl)O(C$_1$-$C_3$ alkyl)phenyl(C$_1$-$C_3$ alkyl)N(CH$_3$)$_2$, —OC(O)NH(C$_1$-$C_3$ alkyl)O(C$_1$-$C_3$ alkyl)phenyl, —OC(O)heterocycle, —O—$C_1$-$C_3$ alkyl, and —CH$_2$heterocycle, wherein the phenyl of —NHC(O) phenyl and —OC(O)NH(C$_1$-$C_3$ alkyl)(C$_1$-$C_3$ alkyl) phenyl are optionally substituted with one or more substituents selected from —C(O)H and OH, and wherein the alkyl of —O—$C_1$-$C_3$ alkyl is optionally substituted with substituents selected from heterocycle, oxo and hydroxy; and wherein the heterocycle of —CH$_2$heterocyclyl is optionally substituted with oxo;

each Q is independently selected from a bond, S, and O;

each $R^{20}$ is independently selected from hydrogen; and $C_{1-6}$ alkyl, $C_{3-12}$ carbocycle, and 3- to 12-membered heterocycle, each of which is optionally substituted with one or more substituents independently selected from halogen, —OH, —CN, —NO$_2$, —NH$_2$, —N(C$_{1-6}$ alkyl)$_2$, $C_{1-10}$ alkyl, —$C_{1-10}$ haloalkyl, —O—$C_{1-10}$ alkyl, oxo, $C_{3-12}$ carbocycle, and 3- to 12-membered heterocycle;

each $R^{21}$ is independently selected from hydrogen; and $C_{1-6}$ alkyl, $C_{3-12}$ carbocycle, and 3- to 12-membered heterocycle, each of which is optionally substituted with one or more substituents independently selected from halogen, —OH, —CN, —NO$_2$, —NH$_2$, —N(C$_{1-6}$ alkyl)$_2$, $C_{1-10}$ alkyl, —$C_{1-10}$ haloalkyl, —O—$C_{1-10}$ alkyl, oxo, $C_{3-12}$ carbocycle, and 3- to 12-membered heterocycle; and each $R^5$ is independently selected from hydrogen or $C_1$-$C_6$ alkyl.

In some embodiments, for a compound or salt of Formula (III), $R^1$ is selected from $C_3$-$C_{12}$ carbocycle and 5- to 12-membered heterocycle, each of which are optionally substituted with one or more substituents independently selected from halogen, —B(OR$^{20}$)$_2$, —OR$^{20}$, —SR$^{20}$, —S(O)$_2$(R$^{20}$), —C(O)N(R$^{20}$)$_2$, —C(O)NR$^{20}$—OR$^{20}$, —S(O)$_2$N(R$^{20}$)$_2$, —NR$^{20}$S(O)$_2$R$^{20}$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =NO(R$^{20}$), —CN, —NHCN, $C_{1-6}$ aminoalkyl, $C_{1-6}$ alkoxy, $C_{1-6}$ hydroxyalkyl, $C_{1-6}$ haloalkyl, $C_{1-6}$ alkyl, $C_{2-6}$ alkenyl, and $C_{2-6}$ alkynyl.

In some embodiments, for a compound or salt of Formula (III), $R^2$ is selected from -L-NR$^{21}$S(O)$_2$(R$^{21}$) and -L-S(O)$_2$ N(R$^{21}$)$_2$.

In some embodiments, for a compound or salt of Formula (III), $R^2$ is selected from -L-N(R$^{21}$)C(O)(OR$^{21}$), and -L-OC (O)N(R$^{21}$)$_2$.

In some embodiments, for a compound or salt of Formula (III), each R$^{2'}$ is independently selected from hydrogen; $C_{1-6}$ alkyl, $C_{3-12}$ carbocycle, and 3- to 12-membered heterocycle, each of which is optionally substituted with one or more substituents independently selected from halogen, —OH, —CN, —NO$_2$, —NH$_2$, —N(C$_{1-6}$ alkyl)$_2$, $C_{1-10}$ alkyl, —$C_{1-10}$ haloalkyl, —O—$C_{1-10}$ alkyl, and oxo. In some cases, each R$^{21}$ is independently selected from hydrogen; $C_{1-6}$ alkyl, $C_{3-12}$ carbocycle, and 3- to 12-membered heterocycle. In some cases, each R$^{21}$ is independently selected from hydrogen and $C_{1-6}$ alkyl.

In some embodiments, for a compound or salt of Formula (III), $R^2$ is selected from L-bicyclic heterocycle, wherein the bicyclic heterocycle is optionally substituted with one or more R$^6$.

In some embodiments, for a compound or salt of Formula (III), $R^2$ is selected from L-pyrrolizine, wherein the pyrrolizine is optionally substituted with one or more R$^6$.

In some embodiments, for a compound or salt of Formula (III), B is an optionally substituted 5- to 15-membered heterocycle or optionally substituted $C_3$-$C_{15}$ carbocycle. In some cases, B is an optionally substituted 5- to 15-membered heterocycle. In some cases, B is an optionally substituted 8- to 15-membered heterocycle. In some cases, B is an optionally substituted $C_3$-$C_{15}$ carbocycle. In some cases, B is an optionally substituted $C_8$-$C_{15}$ carbocycle.

In some embodiments, for a compound or salt of Formula (III), B is an optionally substituted 8- to 15-membered fused heterocycle or optionally substituted $C_8$-$C_{15}$ fused carbocycle. In some cases, B is an optionally substituted 8- to 15-membered fused heterocycle. In some cases, B is an optionally substituted $C_8$-$C_{15}$ fused carbocycle.

In some embodiments, for a compound or salt of Formula (III), for B, the optionally substituted 8- to 15-membered heterocycle contains at least one nitrogen atom. In some cases, the optionally substituted 8- to 15-membered heterocycle contains at least one sulfur atom. In some cases, the optionally substituted 8- to 15-membered heterocycle contains at most one nitrogen atom. In some cases, the optionally substituted 8- to 15-membered heterocycle contains at most one sulfur atom. In some cases, the optionally substituted 8- to 15-membered heterocycle contains at least two heteroatoms.

In some embodiments, for a compound or salt of Formula (III), for B, the optionally substituted 8- to 15-membered fused heterocycle or optionally substituted $C_8$-$C_{15}$ fused carbocycle are each bicyclic or tricyclic. In some cases, for B, the optionally substituted 8- to 15-membered fused heterocycle are each bicyclic or tricyclic. In some cases, for B, the optionally substituted 8- to 15-membered fused heterocycle or optionally substituted $C_8$-$C_{15}$ fused carbocycle are each bicyclic or tricyclic.

In some embodiments, for a compound or salt of Formula (III), B the heterocycle or carbocycle are each independently bicyclic. In some cases, the heterocycle is bicyclic. In some cases, the carbocycle is bicyclic.

In some embodiments, for a compound or salt of Formula (III), B the heterocycle or carbocycle are each independently tricyclic. In some cases, the heterocycle is tricyclic. In some cases, the carbocycle is tricyclic.

In some embodiments, for a compound or salt of Formula (III), B, the optionally substituted 8- to 15-membered fused heterocycle or optionally substituted $C_8$-$C_{15}$ fused carbocycle is selected from each of which is optionally substituted with one or more substituents.

In some embodiments, for a compound or salt of Formula (III), for B, the optionally substituted 8- to 15-membered fused heterocycle or optionally substituted $C_8$-$C_{15}$ fused carbocycle is selected from each of which is optionally substituted with one or more substituents.

In some embodiments, for a compound or salt of Formula (III), for B, the optionally substituted 8- to 15-membered fused heterocycle or optionally substituted $C_8$-$C_{15}$ fused carbocycle is selected from, and of which is optionally substituted with one or more substituents.

In some embodiments, for a compound or salt of Formula (III), for B, the one or more optional substituents of the heterocycle and carbocycle are independently selected at each occurrence from halogen, $C_1$-$C_3$ alkyl, —B(OR$^{20}$)$_2$, —OR$^{20}$, —C(O)N(R$^{20}$)$_2$, —N(R$^{20}$)$_2$, =O, —CN, —NHCN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{2-6}$ alkenyl, and $C_{2-6}$ alkynyl. In some cases, the one or more optional substituents of the heterocycle and carbocycle are independently selected at each occurrence from halogen, oxo, —NH$_2$, $C_1$-$C_3$ alkyl, —B(OR$^{20}$)$_2$, —OH, —C(O)N(R$^{20}$)$_2$, =O, —CN, $C_{1-6}$ alkoxy, $C_{1-6}$ hydroxyalkyl, and $C_{2-6}$ alkynyl. In some cases, the one or more optional substituents of the heterocycle and carbocycle are independently selected at each occurrence from halogen, oxo, —NH$_2$, $C_1$-$C_3$ alkyl, —B(OH)$_2$, —OH, —C(O)NH$_2$, —NH$_2$, =O, —CN, $C_{1-6}$ alkoxy, $C_{1-6}$ hydroxyalkyl, and $C_{2-6}$ alkynyl. In some cases, the one or more optional substituents of the heterocycle and carbocycle are independently selected at each occurrence from oxo, —NH$_2$, —CN, halogen, $C_1$-$C_3$ alkyl. In some cases, the one or more optional substituents of the heterocycle or carbocycle are independently selected from oxo, —NH$_2$, halogen, $C_1$-$C_3$ alkyl.

In some embodiments, for a compound or salt of Formula (III), B is selected from

66

-continued

In some embodiments, for a compound or salt of Formula (III), for B, the one or more optional substituents of the heterocycle or carbocycle are independently selected from oxo, —NH₂, halogen, C₁-C₃ alkyl.

In some embodiments, for a compound or salt of Formula (III), B is selected from In some embodiments, for a compound or salt of Formula (III), each $R^4$ is independently selected from $C_{1-6}$ alkyl, $C_{2-6}$ alkenyl, $C_{2-6}$ alkynyl, oxo, hydroxyl, halogen. Ins some cases, each $R^4$ is independently selected from $C_{1-6}$ alkyl, oxo, and halogen.

In some embodiments, for a compound or salt of Formula (III), n is selected from 1 and 2. In some cases, n is 0.

In some embodiments, for a compound or salt of Formula (III), Y is O.

In some embodiments, for a compound or salt of Formula (III), $R^1$ is selected from optionally substituted 5- to 12-membered heterocycle.

In some embodiments, for a compound or salt of Formula (III), $R^1$ is selected from $C_3$-$C_{12}$ carbocycle and 5- to 12-membered heterocycle, each of which are optionally substituted with one or more substituents independently selected from halogen, —B(OR$^{20}$)$_2$, —OR$^{20}$, SR$^{20}$, —S(O)$_2$ (R$^{20}$), —S(O)$_2$N(R$^{20}$)$_2$, —NR$^{20}$S(O)$_2$R$^{20}$, C(O)N(R$^{20}$)$_2$, —N(R$^{20}$)C(O)R$^{20}$, —N(R$^{20}$)C(O)N(R$^{20}$)$_2$, —N(R$^{20}$)C(O) OR$^{20}$, —N(R$^{20}$)$_2$, —C(O)R$^{20}$, C(O)OR$^{20}$, —OC(O)R$^{20}$, —OC(O)N(R$^{20}$)$_2$, —NO$_2$, =O, =NO(R$^{20}$), CN, $C_{1-6}$ aminoalkyl, $C_{1-6}$alkoxy, $C_{1-6}$ hydroxyalkyl, $C_{1-6}$ cyanoalkyl, $C_{1-6}$haloalkyl, $C_{1-6}$ alkyl, $C_{2-6}$ alkenyl, and $C_{2-6}$ alkynyl.

In some embodiments, for a compound or salt of Formula (III), $R^1$ is selected from $C_3$-$C_{12}$ carbocycle and 5- to 12-membered heterocycle, each of which are optionally substituted with one or more substituents independently selected from halogen, —B(OR$^{20}$)$_2$, —OR$^{20}$, SR$^{20}$, —S(O)$_2$ (R$^{20}$), —S(O)$_2$N(R$^{20}$)$_2$, —NR$^{20}$S(O)$_2$R$^{20}$, C(O)N(R$^{20}$)$_2$, —N(R$^{20}$)C(O)R$^{20}$, —N(R$^{20}$)C(O)N(R$^{20}$)$_2$, —N(R$^{20}$)C(O) OR$^{20}$, —N(R$^{20}$)$_2$, —C(O)R$^{20}$, C(O)OR$^{20}$, —OC(O)R$^{20}$, —OC(O)N(R$^{20}$)$_2$, —NO$_2$, =O, =NO(R$^{20}$), CN, $C_{1-6}$ aminoalkyl, $C_{1-6}$ alkoxy, $C_{1-6}$ hydroxyalkyl, $C_{1-6}$ haloalkyl, $C_{1-6}$ alkyl, $C_{2-6}$ alkenyl, and $C_{2-6}$ alkynyl.

In some embodiments, for a compound or salt of Formula (III), $R^1$ is selected from $C_3$-$C_{12}$ carbocycle and 5- to 12-membered heterocycle, each of which are optionally substituted with one or more substituents independently selected from —S(O)$_2$(R$^{20}$), —S(O)$_2$N(R$^{20}$)$_2$, —NR$^{20}$S(O)$_2$ R$^{20}$, —N(R$^{20}$)C(O)OR$^{20}$, and —OC(O)N(R$^{20}$)$_2$.

In some embodiments, for a compound or salt of Formula (III), $R^1$ is selected from 5- to 12-membered heterocycle, wherein the 5- to 12-membered heterocycle is optionally substituted with one or more substituents independently selected from halogen, —OH, —N(R$^{20}$)$_2$, —NO$_2$, =O, —CN, $C_{1-6}$ aminoalkyl, $C_{1-6}$ alkoxy, $C_{1-6}$ hydroxyalkyl, and $C_{1-6}$ haloalkyl.

In some embodiments, for a compound or salt of Formula (III), $R^1$ is selected from 5- to 12-membered heterocycle, wherein the 5- to 12-membered heterocycle is optionally substituted with one or more substituents independently selected from halogen, —OH, —N(R$^{20}$)$_2$, —NO$_2$, $C_{1-6}$ aminoalkyl, $C_{1-6}$ alkoxy, $C_{1-6}$ hydroxyalkyl, and $C_{1-6}$ haloalkyl.

In some embodiments, for a compound or salt of Formula (III), $R^{20}$ of $R^1$ is selected from hydrogen and $C_{1-3}$ alkyl.

In some embodiments, for a compound or salt of Formula (III), the 5- to 12-membered heterocycle of $R^1$ is an unsaturated heterocycle.

In some embodiments, for a compound or salt of Formula (III), the 5- to 12-membered heterocycle of $R^1$ is a saturated heterocycle.

In some embodiments, for a compound or salt of Formula (III), 5- to 12-membered heterocycle of $R^1$ is a bridged heterocycle.

In some embodiments, for a compound or salt of Formula (III), $R^1$ is selected from

69

-continued

70

In some embodiments, for a compound or salt of Formula (III), $R^1$ is selected from an optionally substituted saturated 6- to 7-membered heterocycle. In some cases, $R^1$ is selected from an optionally substituted saturated 6-membered heterocycle. In some cases, $R^1$ is selected from which is optionally substituted. In some cases, the optional one or more substituents are independently selected from halogen, —CN, —NHCN, $C_{1-6}$ cyanoalkyl, and $C_{1-6}$ alkyl. In some cases, the optional one or more substituents are independently selected from —CN, —NHCN, $C_{1-6}$ cyanoalkyl, and $C_{1-6}$ alkyl. In some cases, the optional one or more substituents are independently selected from —CN, —NHCN, $C_{1-6}$ cyanoalkyl, and $C_{1-6}$ alkyl. In some cases, the optional one or more substituents are independently selected from —NHCN, and $C_{1-6}$ alkyl. In some cases, $R^1$ is selected from which is substituted with one or more substituents selected from —NHCN, and $C_{1-6}$ alkyl. In some cases, $R^1$ is selected from

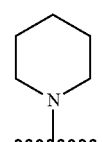

each of which is optionally substituted with one or more substituents independently selected from halogen, —OH, —N(R$^{20}$)$_2$, —NO$_2$, $C_{1-6}$ aminoalkyl, $C_{1-6}$ alkoxy, =O, —CN, $C_{1-6}$ hydroxyalkyl, and $C_{1-6}$ haloalkyl.

In some embodiments, for a compound or salt of Formula (III), $R^1$ is selected from each of which is optionally substituted with one or more substituents independently selected from halogen, —OH, —N(R$^{20}$)$_2$, —NO$_2$, $C_{1-6}$ aminoalkyl, $C_{1-6}$ alkoxy, =O, —CN, $C_{1-6}$ hydroxyalkyl, and $C_{1-6}$ haloalkyl.

In some embodiments, for a compound or salt of Formula (III), $R^1$ is selected from In some embodiments, for a compound or salt of Formula (III), $R^1$ is selected from a substituted saturated 6-membered heterocycle, wherein the saturated 6-membered heterocycle is substituted with at least one —NHCN, and optionally one or more $C_{1-6}$ alkyl; M is O; n is 0; B is selected from an optionally substituted 8- to 15-membered fused heterocycle and optionally substituted $C_8$-$C_{15}$ fused carbocycle, each of which is optionally substituted with one or more substituents independently selected from halogen, oxo, —NH$_2$, $C_1$-$C_3$ alkyl, —OH, —C(O)NH$_2$, —NH$_2$, =O, —CN, $C_{1-6}$ alkoxy, $C_{1-6}$ hydroxyalkyl, and $C_{2-6}$ alkynyl; Y is O; $R^2$ is selected from -L-bicyclic heterocycle, wherein the bicyclic hetero-cycle portion is optionally substituted with one or more substituents independently selected from halogen, hydroxy, $C_1$-$C_4$ alkyl, $C_1$-$C_4$ alkoxy, $C_1$-$C_4$ haloalkyl, $C_1$-$C_4$ hydroxy-alkyl, or —N($R^5$)$_2$; and L is selected from $C_1$-$C_4$ alkylene. In some cases, $R^1$ is selected from In some cases, B is selected from In some cases, B is selected from In some cases, B is In some embodiments, for a compound or salt of Formula (III), L is selected from $C_1$-$C_4$ alkylene.

In some embodiments, for a compound or salt of Formula (III), each L is independently selected from an optionally substituted $C_1$-$C_4$ alkylene; and wherein optionally two substituents on the same carbon atom of L come together to form a $C_3$-$C_6$ carbocycle, wherein the $C_3$-$C_6$ carbocycle is optionally substituted with one or more substituents selected from halogen, —OH, —NO$_2$, =O, =S, —CN, $C_{1-6}$ ami-noalkyl, $C_{1-6}$ alkoxy, $C_{1-6}$ hydroxyalkyl, $C_{1-6}$ haloalkyl. In some cases, the optional substituents of L are selected from $C_1$-$C_4$ hydroxyalkyl, $C_1$-$C_4$ alkyl, $C_3$-$C_6$ carbocycle; and wherein optionally two substituents on the same carbon atom of L come together to form a $C_3$-$C_6$ carbocycle or 3- to 8-membered heterocycle wherein the $C_3$-$C_6$ carbocycle and 3- to 8-membered heterocycle are optionally substituted with one or more substituents selected from halogen and $C_{1-6}$ haloalkyl.

In some embodiments, for a compound or salt of Formula (III), each L is independently selected from a substituted $C_1$-$C_4$ alkylene, wherein two substituents on the same car-bon atom of L come together to form a $C_3$-$C_6$ carbocycle. In some cases, the $C_3$-$C_6$ carbocycle is optionally substituted with one or more substituents selected from halogen, —OH, —NO$_2$, =O, =S, —CN, $C_{1-6}$ aminoalkyl, $C_{1-6}$ alkoxy, $C_{1-6}$ hydroxyalkyl, $C_{1-6}$ haloalkyl.

In some embodiments, for a compound or salt of Formula (III), wherein each L is independently selected from a substituted $C_1$-$C_4$ alkylene, and wherein two substituents on the same carbon atom of L come together to form a $C_3$-$C_6$ carbocycle. In some cases, each L is independently selected from a substituted $C_3$ alkylene, and wherein two substituents on the same carbon atom of L come together to form a $C_3$ carbocycle. In some cases, each L is independently selected from In some embodiments, for a compound or salt of Formula (III), $R^2$ is selected from -L-heterocycle, wherein the heterocycle portion of -L-heterocycle is optionally substituted with one or more $R^6$. In some cases, the heterocycle is a saturated heterocycle. In some cases, the heterocycle has at least one nitrogen atom and at least one sulfur atom. In some cases, the heterocycle has at least one nitrogen atom. In some cases, the heterocycle has at least one sulfur atom.

In some embodiments, for a compound or salt of Formula (III) $R^2$ is selected from and , wherein the heterocycle portion is optionally substituted with one or more $R^6$.

In some embodiments, for a compound or salt of Formula (III), Y—$R^2$ is selected from and , wherein the heterocycle portion is optionally substituted with one or more $R^6$.

In some embodiments, for a compound or salt of Formula (III), Y—$R^2$ is selected from , and

, wherein the heterocycle portion is optionally substituted with one or more $R^6$.

In some embodiments, for a compound or salt of Formula (III), Y—$R^2$ is selected from

74

, ,

, , and

, wherein the heterocycle portion is optionally substituted with one or more $R^6$.

In some embodiments, for a compound or salt of Formula (III), $R^2$ is selected from -L-saturated heterocycle, wherein the saturated heterocycle portion of the -L-saturated heterocycle is optionally substituted with one or more $R^6$, and contains one nitrogen atom and one sulfur atom. In some cases, Y—$R^2$ is selected from , , and

, wherein the heterocycle portion is optionally substituted with one or more $R^6$. In some cases, Y—$R^2$ is selected from , , and

, wherein the heterocycle portion is optionally substituted with one or more substituents selected from $C_1$-$C_3$ alkyl and oxo. In some cases, Y—$R^2$ is selected from In some cases, Y—$R^2$ is selected from In some embodiments, for a compound or salt of Formula (III), each $R^6$ is independently selected from halogen, —OH, $C_1$-$C_3$ hydroxyalkyl, $C_1$-$C_3$ alkyl, $C_1$-$C_3$ haloalkyl, $C_1$-$C_3$ alkoxy, —CN, $C_1$-$C_3$ aminoalkyl, -Q-phenyl, -Q-phenylSO$_2$F, —NHC(O)phenyl, —NHC(O)phenylSO$_2$F, $C_1$-$C_3$ alkyl substituted pyrazolyl, —N($R^5$)$_2$, ($C_1$-$C_3$ alkoxy) $C_1$-$C_3$ alkyl-, ($C_1$-$C_3$ alkyl)C(=O), oxo, ($C_1$-$C_3$ haloalkyl) C(=O)—, —SO$_2$F, ($C_1$-$C_3$ alkoxy)$C_1$-$C_3$ alkoxy, —CH$_2$OC (O)N($R^5$)$_2$, —CH$_2$NHC(O)OC$_1$-$C_6$ alkyl, —CH$_2$NHC(O)N ($R^5$)$_2$, —CH$_2$NHC(O)C$_1$-$C_6$ alkyl, —CH$_2$(pyrazolyl), —CH$_2$NHSO$_2$C$_1$-$C_6$ alkyl, —CH$_2$OC(O)heterocycle, —OC (O)N($R^5$)$_2$, —OC(O)NH($C_1$-$C_3$ alkyl)O($C_1$-$C_3$ alkyl), —OC (O)NH($C_1$-$C_3$ alkyl)O($C_1$-$C_3$ alkyl)phenyl($C_1$-$C_3$ alkyl)N (CH$_3$)$_2$, —OC(O)NH($C_1$-$C_3$ alkyl)O($C_1$-$C_3$ alkyl)phenyl, —OC(O)heterocycle, and —CH$_2$heterocycle, wherein the phenyl of —NHC(O)phenyl and —OC(O)NH($C_1$-$C_3$ alkyl) ($C_1$-$C_3$ alkyl)phenyl are each optionally substituted with —C(O)H and OH, and wherein the heterocycle of —CH$_2$heterocyclyl is optionally substituted with oxo.

In some embodiments, for a compound or salt of Formula (III), each $R^6$ is independently selected from halogen, —OH, $C_1$-$C_3$ hydroxyalkyl, $C_1$-$C_3$ alkyl, $C_1$-$C_3$ haloalkyl, $C_1$-$C_3$ alkoxy, —CN, and $C_1$-$C_3$ aminoalkyl.

In some embodiments, for a compound or salt of Formula (III), each $R^6$ is independently selected from halogen, —OH, $C_1$-$C_3$ hydroxyalkyl, $C_1$-$C_3$ alkyl, $C_1$-$C_3$ aminoalkyl, $C_1$-$C_3$ haloalkyl, $C_1$-$C_3$ alkoxy, —N($R^5$)$_2$, and oxo. In some cases, each $R^6$ is independently selected from —OH, $C_1$-$C_3$ hydroxyalkyl, $C_1$-$C_3$ alkyl, $C_1$-$C_3$ aminoalkyl, $C_1$-$C_3$ alkoxy, and —N($R^5$)$_2$. In some cases, each $R^6$ is independently selected from $C_1$-$C_3$ alkyl, $C_1$-$C_3$ alkoxy, and —N($R^5$)$_2$.

In some embodiments, for a compound or salt of Formula (III), $R^6$ is selected from halogen, —OH, $C_1$-$C_3$ hydroxyalkyl, $C_1$-$C_3$ alkyl, $C_1$-$C_3$ haloalkyl, $C_1$-$C_3$ alkoxy, —CN, and $C_1$-$C_3$ aminoalkyl. In some cases, $R^6$ is selected from halogen and $C_1$-$C_3$ alkyl. In some cases, $R^6$ is halogen. In some cases, $R^6$ is $C_1$-$C_3$ alkyl. In some cases, $R^6$ is selected from halogen and $C_1$-$C_3$ alkyl. In some cases, $R^6$ is selected from methyl and fluorine.

In some embodiments, for a compound or salt of Formula (III), $R^2$ is selected from In some embodiments, for a compound or salt of Formula (III), Y—$R^2$ is selected from In some embodiments, for a compound or salt of Formula (III), Y—$R^2$ is selected from In some embodiments, for a compound or salt of Formula (III), Y—R$^2$ is In some embodiments, for a compound or salt of Formula (III), L is selected from unsubstituted C$_1$-C$_4$ alkylene.

In some embodiments, for a compound or salt of Formula (III), Y—R$^2$ is selected from wherein the heterocycle portion is optionally substituted with one or more R$^6$.

In some embodiments, for a compound or salt of Formula (III), R$^6$ of R$^2$ is independently selected at each occurrence from halogen, hydroxy, C$_1$-C$_3$ hydroxyalkyl, C$_1$-C$_3$ alkyl, C$_1$-C$_3$ haloalkyl, C$_1$-C$_3$ alkoxy, cyano, and C$_1$-C$_3$ aminoalkyl.

In some embodiments, for a compound or salt of Formula (III), R$^6$ of R$^2$ is independently selected at each occurrence from C$_1$-C$_3$ alkyl and halogen.

In some embodiments, for a compound or salt of Formula (III), Y—R$^2$ is selected from In some embodiments, for a compound or salt of Formula (I), Formula (II), or Formula (III), the carbocycle of R$^1$ is selected from C$_3$-C$_{12}$ carbocycle, C$_3$-C$_{10}$ carbocycle, C$_3$-C$_9$ carbocycle, C$_3$-C$_8$ carbocycle, or C$_3$-C$_6$ carbocycle. In some cases, the carbocycle of R$^1$ is selected from C$_3$-C$_{12}$ carbocycle, C$_4$-C$_{12}$ carbocycle, C$_5$-C$_{12}$ carbocycle, C$_6$-C$_{12}$ carbocycle, C$_7$-C$_{12}$ carbocycle, C$_8$-C$_{12}$ carbocycle, or C$_9$-C$_{12}$ carbocycle.

In some embodiments, for a compound of Formula (I), the heterocycle of R$^1$ is a 5- to 12-membered heterocycle, 6- to 12-membered heterocycle, 7- to 12-membered heterocycle, or 8- to 12-membered heterocycle. In some cases, the heterocycle of R$^1$ is a 5- to 11-membered heterocycle, 5- to 10-membered heterocycle, 5- to 9-membered heterocycle, or 5- to 8-membered heterocycle. In some cases, the hetero-cycle of R$^1$ is a 6- to 11-membered heterocycle, 6- to 10-membered heterocycle, 6- to 9-membered heterocycle, or 6- to 8-membered heterocycle. In some cases, the hetero-cycle of R$^1$ is a 7- to 11-membered heterocycle, 7- to 10-membered heterocycle, 7- to 9-membered heterocycle, or 7- to 8-membered heterocycle. In some cases, the hetero-cycle of R$^1$ is a 5- to 6-membered heterocycle or 5- to 9-membered heterocycle. In some cases, the heterocycle of R$^1$ is an 8- to 9-membered heterocycle. In some cases, the heterocycle of R$^1$ is saturated. The heterocycle may be optionally substituted as described elsewhere herein.

In some embodiments, for a compound or salt of Formula (I), Formula (II), or Formula (III), the heterocycle of R$^1$ is a 5- to 12-membered monocyclic heterocycle, 6- to 12-membered monocyclic heterocycle, 7- to 12-membered monocyclic heterocycle, or 8- to 12-membered monocyclic heterocycle. In some cases, the heterocycle of R$^1$ is a 5- to 11-membered monocyclic heterocycle, 5- to 10-membered monocyclic heterocycle, 5- to 9-membered monocyclic heterocycle, or 5- to 8-membered monocyclic heterocycle. In some cases, the heterocycle of R$^1$ is a 6- to 11-membered monocyclic heterocycle, 6- to 10-membered monocyclic heterocycle, 6- to 9-membered monocyclic heterocycle, or 6- to 8-membered monocyclic heterocycle. In some cases, the heterocycle of R$^1$ is a monocyclic 7- to 11-membered heterocycle, 7- to 10-membered monocyclic heterocycle, 7- to 9-membered monocyclic heterocycle, or 7- to 8-membered monocyclic heterocycle. In some cases, the hetero-cycle of R$^1$ is a 5- to 6-membered monocyclic heterocycle or 5- to 9-membered monocyclic heterocycle. In some cases, the heterocycle of R$^1$ is an 8- to 9-membered monocyclic heterocycle. In some cases, the heterocycle of R$^1$ is satu-rated. The monocyclic heterocycle may be optionally sub-stituted as described elsewhere herein.

In some embodiments, for a compound or salt of Formula (I), Formula (II), or Formula (III), the heterocycle of R$^1$ is a 5- to 12-membered bridged heterocycle, 6- to 12-membered bridged heterocycle, 7- to 12-membered bridged hetero-cycle, or 8- to 12-membered bridged heterocycle. In some cases, the heterocycle of R$^1$ is a 5- to 11-membered bridged heterocycle, 5- to 10-membered bridged heterocycle, 5- to 9-membered bridged heterocycle, or 5- to 8-membered bridged heterocycle. In some cases, the heterocycle of R$^1$ is a 6- to 11-membered bridged heterocycle, 6- to 10-mem-bered bridged heterocycle, 6- to 9-membered bridged het-erocycle, or 6- to 8-membered bridged heterocycle. In some cases, the heterocycle of R$^1$ is a bridged 7- to 11-membered heterocycle, 7- to 10-membered bridged heterocycle, 7- to 9-membered bridged heterocycle, or 7- to 8-membered bridged heterocycle. In some cases, the heterocycle of R$^1$ is a 5- to 6-membered bridged heterocycle or 5- to 9-mem-bered bridged heterocycle. In some cases, the heterocycle of R$^1$ is an 8- to 9-membered bridged heterocycle. In some embodiments, the heterocycle of R$^1$ is saturated. The bridged heterocycle may be optionally substituted as described elsewhere herein.

In some embodiments, for a compound or salt of Formula (I), Formula (II), or Formula (III), R$^1$ is a 5- to 9-membered heterocycle, the 5- to 9-membered heterocycle contains at most 1 nitrogen atom. In some embodiments, R$^1$ is selected from optionally substituted 5- to 9-membered heterocycle, each of which is optionally substituted.

In some embodiments, for a compound or salt of Formula (I), Formula (II), or Formula (III), the heterocycle of R$^1$ contains at most 1 nitrogen atom. In some embodiments, the heterocycle of R$^1$ contains at most 1 heteroatom. In some embodiments, the heterocycle of R$^1$ contains at most 2 heteroatom atoms. In some cases, the heteroatom is selected from nitrogen, oxygen, and sulfur. In some cases, the heterocycle is a monocyclic heterocycle or a bridged heterocycle. In some cases, the heterocycle is a monocyclic heterocycle. In some cases, the heterocycle is a bridged heterocycle. In some cases, the heterocycle is selected from In some cases, the heterocycle is selected from In some cases, the bridged heterocycle is selected from The heterocycle may be optionally substituted as described elsewhere herein.

In some embodiments, for a compound or salt of Formula (I), Formula (II), or Formula (III), the spiroheterocycle of R$^1$ contains at most 1 nitrogen atom. In some embodiments, the spiroheterocycle of R$^1$ contains at most 2 heteroatom atoms. In some embodiments, the spiroheterocycle of R$^1$ contains at most 3 heteroatom atoms. In some embodiments, the spiroheterocycle of R$^1$ contains at most 1 heteroatom atom. In some cases, the spiroheterocycle of R$^1$ contains at least 2 heteroatom atoms. In some cases, the spiroheterocycle of R$^1$ contains at least 3 heteroatom atoms. In some cases, the spiroheterocycle of R$^1$ contains at least 4 heteroatom atoms. In some cases, the spiroheterocycle of R$^1$ contains at least 2 nitrogen atoms. In some embodiments, the spiroheterocycle of R$^1$ contains at most 1 heteroatom atom. In some cases, the spiroheterocycle of R$^1$ contains at most 1 sulfur atom. In some cases, the heteroatom is selected from nitrogen, oxygen, and sulfur. In some embodiments, the spiroheterocycle of R$^1$ is selected from In some embodiments, the spiroheterocycle of R$^1$ is selected from The spiroheterocycle may be optionally substituted as described elsewhere herein.

In some embodiments, for a compound or salt of Formula (I), Formula (II), or Formula (III), R$^1$ is selected from optionally substituted 7- to 8-membered spiroheterocycle. In some cases, R$^1$ is selected from optionally substituted 7-membered spiroheterocycle. In some cases, R$^1$ is selected from optionally substituted 8-membered spiroheterocycle.

In some embodiments, for a compound or salt of Formula (I), Formula (II), or Formula (III), the fused heterocycle of R$^1$ is a 6- to 12-membered fused heterocycle, 6- to 12-membered fused heterocycle, 7- to 12-membered fused heterocycle, or 8- to 12-membered fused heterocycle. In some cases, the fused heterocycle of R$^1$ is a 6- to 11-membered fused heterocycle, 6- to 10-membered fused heterocycle, 6- to 9-membered fused heterocycle, or 6- to 8-membered fused heterocycle. In some cases, the fused heterocycle of R$^1$ is a 7- to 11-membered fused heterocycle, 7- to 10-membered fused heterocycle, 7- to 9-membered fused heterocycle, or 7- to 8-membered fused heterocycle. In some cases, the fused heterocycle of R$^1$ is an 8- to 11-membered fused heterocycle. In some cases, the fused heterocycle of R$^1$ is a 6-membered fused heterocycle. The fused heterocycle may be optionally substituted as described elsewhere herein.

In some embodiments, for a compound or salt of Formula (I), Formula (II), or Formula (III), the fused heterocycle of R$^1$ is selected from a 6-, 9-, 10-, 11-, and 12-membered fused heterocycle. In some cases, the fused heterocycle of R$^1$ is selected from a 9- to 12-membered fused heterocycle. In some cases, the fused heterocycle of $R^1$ is selected from a 10- to 12-membered fused heterocycle. The fused heterocycle is optionally substituted with one or more substituents independently selected from halogen, —$OR^{20}$, —$N(R^{20})_2$, —$NO_2$, =O, $C_{1-6}$ aminoalkyl, $C_{1-6}$alkoxy, $C_{1-6}$ hydroxyalkyl, $C_{1-6}$haloalkyl, and $C_{1-6}$alkyl. The fused heterocycle is optionally substituted with one or more substituents independently selected from halogen, —$OR^{20}$, —$N(R^{20})_2$, —$NO_2$, $C_{1-6}$ aminoalkyl, $C_{1-6}$ alkoxy, $C_{1-6}$ hydroxyalkyl, $C_{1-6}$ haloalkyl, and $C_{1-6}$ alkyl.

In some embodiments, for a compound or salt of Formula (I), Formula (II), or Formula (III), the fused heterocycle of $R^1$ contains at most 1 nitrogen atom. In some embodiments, the fused heterocycle of $R^1$ contains at most 1 heteroatom atom. In some cases, the heteroatom is selected from nitrogen, oxygen, and sulfur. In some cases, the fused heterocycle is

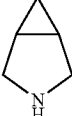

The fused heterocycle may be optionally substituted as described elsewhere herein.

In some embodiments, for a compound or salt of Formula (I), Formula (II), or Formula (III), $R^1$ is selected from $C_6$-$C_7$ carbocycle, 5- to 10-membered heterocycle, 7- to 8-membered spiroheterocycle, and 6-, 9-, 10-, 11-, and 12-membered fused heterocycle, each of which is optionally substituted.

In some embodiments, for a compound of Formula (I), $R^1$ is selected from $C_6$-$C_7$ carbocycle, 5- to 10-membered heterocycle, 7- to 8-membered spiroheterocycle, and 6-, 8- to 12-membered fused heterocycle, each of which is optionally substituted with one or more substituents independently selected from halogen, —$OR^{20}$, —$N(R^{20})_2$, —$NO_2$, =O, $C_{1-6}$ aminoalkyl, $C_{1-6}$alkoxy, $C_{1-6}$ hydroxyalkyl, $C_{1-6}$haloalkyl, and $C_{1-6}$ alkyl.

In some embodiments, for a compound or salt of Formula (I), Formula (II), or Formula (III), $R^1$ is selected from $C_6$-$C_7$ carbocycle, 5- to 10-membered heterocycle, 7- to 8-membered spiroheterocycle, and 6-, 8- to 12-membered fused heterocycle, each of which is optionally substituted with one or more substituents independently selected from halogen, —$OR^{20}$, —$N(R^{20})_2$, —$NO_2$, $C_{1-6}$ aminoalkyl, $C_{1-6}$ alkoxy, $C_{1-6}$ hydroxyalkyl, $C_{1-6}$ haloalkyl, and $C_{1-6}$ alkyl.

In some embodiments, for a compound or salt of Formula (I), Formula (II), or Formula (III), for $R^1$, $R^{20}$ of —$OR^{20}$ and —$N(R^{20})_2$, is selected hydrogen and $C_{1-6}$ alkyl.

In some embodiments, for a compound or salt of Formula (I), Formula (II), or Formula (III), $R^1$ is selected from $C_6$-$C_7$ carbocycle and 5- to 10-membered heterocycle, each of which is optionally substituted. In some cases, the heterocycle contains at most 1 nitrogen atom. In some cases, $R^1$ is selected from $C_6$-$C_7$ carbocycle, each of which is optionally substituted.

In some embodiments, for a compound or salt of Formula (I), Formula (II), or Formula (III), the one or more optional substituents of $R^1$ are independently selected from halogen, —$OR^{20}$, —$N(R^{20})_2$, —$NO_2$, $C_{1-6}$ aminoalkyl, $C_{1-6}$ alkoxy, $C_{1-6}$ hydroxyalkyl, $C_{1-6}$ haloalkyl, —$N(R^{20})C(O)N(R^{20})_2$, and $C_{1-6}$ alkyl.

In some embodiments, for a compound or salt of Formula (I), Formula (II), or Formula (III), one or more optional substituents of $R^1$ are independently selected from halogen, —$OR^{20}$, —$N(R^{20})_2$, —$NO_2$, $C_{1-6}$ aminoalkyl, $C_{1-6}$ alkoxy, $C_{1-6}$ hydroxyalkyl, $C_{1-6}$ haloalkyl, and $C_{1-6}$ alkyl. In some cases, the one or more optional substituents of $R^1$ are independently selected from —$OR^{20}$, —$N(R^{20})_2$, $C_{1-6}$ aminoalkyl, $C_{1-6}$ alkoxy, $C_{1-6}$ hydroxyalkyl, and $C_{1-6}$ alkyl. In some cases, the one or more optional substituents of $R^1$ are independently selected from —$OR^{20}$, —$N(R^{20})_2$, $C_{1-6}$ aminoalkyl, and $C_{1-6}$ hydroxyalkyl. In some cases, the one or more optional substituents of $R^1$ are independently selected from —$OR^{20}$, —$N(R^{20})_2$, $C_{1-6}$ aminoalkyl, $C_{1-6}$ alkyl, and $C_{1-6}$ hydroxyalkyl. In some cases, the one or more optional substituents of $R^1$ are independently selected from —$OR^{20}$, —$N(R^{20})_2$, and $C_{1-6}$ alkyl. In some cases, the one or more optional substituents of $R^1$ are independently selected from —$N(R^{20})C(O)N(R^{20})_2$.

In some embodiments, for a compound or salt of Formula (I), Formula (II), or Formula (III), $R^1$ is selected from $C_3$-$C_{12}$ carbocycle and 5- to 12-membered heterocycle, wherein the 5- to 12-membered heterocycle contains at most 1 nitrogen atom and optionally one or more additional heteroatoms selected from oxygen, boron, and sulfur; or $R^1$ is further selected from 7-, 8-, 10, 11-membered spiro heterocycle and 6-, 9-, 10-, 11-, and 12-membered fused heterocycle wherein the $C_3$-$C_{12}$ carbocycle, 5- to 12-membered heterocycle, 7-, 8-, 10-, 11-membered spiro heterocycle, and 6-, 9-, 10-, 11-, and 12-membered fused heterocycle, are each optionally substituted with one or more substituents independently selected from halogen, —$OR^{20}$, —$SR^{20}$, —$C(O)N(R^{20})_2$, —$N(R^{20})C(O)R^{20}$, —$N(R^{20})C(O)N(R^{20})_2$, —$N(R^{20})_2$, —$C(O)R^{20}$, —$C(O)OR^{20}$, —$OC(O)R^{20}$, —$NO_2$, =O, =$N(R^{20})$, —CN, $C_{1-6}$ aminoalkyl, $C_{1-6}$ alkoxy, $C_{1-6}$ haloalkyl, $C_{1-6}$ alkyl, $C_{2-6}$ alkenyl, and $C_{2-6}$ alkynyl.

In some embodiments, for a compound or salt of Formula (I), Formula (II), or Formula (III), $R^1$ is selected from $C_3$-$C_{12}$ carbocycle and 5- to 12-membered heterocycle, wherein the 5- to 12-membered heterocycle contains at most 1 nitrogen atom and optionally one or more additional heteroatoms selected from oxygen, boron, and sulfur; or $R^1$ is further selected from 7-, 8-, 10, 11-membered spiro heterocycle and 6-, 9-, 10-, 11-, and 12-membered fused heterocycle wherein the $C_3$-$C_{12}$ carbocycle, 5- to 12-membered heterocycle, 7-, 8-, 10-, 11-membered Spiro heterocycle, and 6-, 9-, 10-, 11-, and 12-membered fused heterocycle, are each optionally substituted with one or more substituents independently selected from halogen, —$B(OR^{20})_2$, —$OR^{20}$, —$SR^{20}$, —$N(R^{20})$ $S(O)_2(R^{20})$, $C(O)N(R^{20})_2$, —$N(R^{20})C(O)R^{20}$, —$N(R^{20})C(O)N(R^{20})_2$, —$N(R^{20})_2$, —$C(O)R^{20}$, —$C(O)OR^{20}$, —$OC(O)R^{20}$, —$NO_2$, =O, =S, =$N(R^{20})$, —CN, $C_{1-6}$ aminoalkyl, $C_{1-6}$ alkoxy, $C_{1-6}$ cyanoalkyl, $C_{1-6}$ haloalkyl, $C_{1-6}$ alkyl, $C_{2-6}$ alkenyl, and $C_{2-6}$ alkynyl.

In some embodiments, for a compound or salt of Formula (I), Formula (II), or Formula (III), $R^1$ is selected from 5- to 10-membered heterocycle, 7-, 8-, 10-, 11-membered spiro heterocycle, and 6-, 9-, 10-, 11-, and 12-membered fused heterocycle, and wherein each are optionally substituted with one or more substituents independently selected from halogen, —$N(R^{20})_2$, $C_{1-6}$ alkyl, —$OR^{20}$, —$N(R^{20})C(O)N$ $(R^{20})_2$, —$B(OR^{20})_2$, —$N(R^{20})C(O)N(R^{20})_2$, =O, $C_{1-6}$ hydroxyalkyl, halogen, —$N(R^{20})C(O)R^{20}$, —$N(R^{20})$ $S(O)_2$ $(R^{20})$, and $C_{1-6}$ aminoalkyl.

In some embodiments, for a compound or salt of Formula (I), Formula (II), or Formula (III), $R^1$ is selected from 5- to 10-membered heterocycle, 7-, 8-, 10-, 11-membered spiro heterocycle, and 6-, 9-, 10-, 11-, and 12-membered fused heterocycle, and wherein each are optionally substituted with one or more substituents independently selected from halogen, —N(R$^{20}$)$_2$, C$_{1-6}$ alkyl, —OR$^{20}$, —N(R$^{20}$)C(O)N (R$^{20}$)$_2$, —B(OR$^{20}$)$_2$, C$_{1-6}$ cyanoalkyl, —N(R$^{20}$)C(O) N(R$^{20}$)$_2$, =O, C$_{1-6}$ hydroxyalkyl, halogen. —N(R$^{20}$)C(O) R$^{20}$, —N(R$^{20}$) S(O)$_2$(R$^{20}$), and C$_{1-6}$ aminoalkyl. In some cases, R$^1$ is selected from wherein each is optionally substituted with one or more substituents independently selected from halogen, —N(R$^{20}$)$_2$, C$_{1-6}$ alkyl, —OR$^{20}$, —N(R$^{20}$)C(O)N(R$^{20}$)$_2$, —B(OR$^{20}$)$_2$, C$_{1-6}$ cyanoalkyl, —N(R$^{20}$)C(O)N(R$^{20}$)$_2$, =O, C$_{1-6}$ hydroxyalkyl, halogen, —N(R$^{20}$)C(O)R$^{20}$, —N(R$^{20}$) S(O)$_2$(R$^{20}$), and C$_{1-6}$ aminoalkyl. In some cases, R$^1$ is selected from -continued -continued In some embodiments, for a compound or salt of Formula (I), Formula (II), or Formula (III), $R^1$ is selected from 5- to 10-membered heterocycle, wherein the 5- to 10-membered heterocycle is optionally substituted with one or more substituents independently selected from —OR$^{20}$, —N(R$^{20}$)$_2$, C$_{1-6}$ alkyl, C$_{1-6}$ hydroxyalkyl, C$_{1-6}$ aminoalkyl, —N(R$^{20}$)C(O)N(R$^{20}$)$_2$, —N(R$^{20}$)C(O)R$^{20}$, and —B(OR$^{20}$)$_2$. In some cases, $R^1$ is selected from each of which is optionally substituted with one or more substituents independently selected from —OR$^{20}$, —N(R$^{20}$)$_2$, C$_{1-6}$ alkyl, C$_{1-6}$ hydroxyalkyl, C$_{1-6}$ aminoalkyl, —N(R$^{20}$)C(O)N(R$^{20}$)$_2$, —N(R$^{20}$)C(O)R$^{20}$, and —B(OR$^{20}$)$_2$.

In some embodiments, for a compound of Formula (I), Formula (II), or Formula (III), $R^1$ is selected from

87

88

-continued

In some embodiments, for a compound or salt of Formula (I), Formula (II), or Formula (III), $R^1$ is selected from 5- to 10-membered heterocycle, wherein the 5- to 10-membered heterocycle is optionally substituted with one or more substituents independently selected from —$N(R^{20})_2$, —$OR^{20}$, and $C_{1-6}$ alkyl. In some cases, the 5- to 10-membered heterocycle is optionally substituted with one or more substituents independently selected from —$OR^{20}$, and $C_{1-6}$ alkyl. In some embodiments, for a compound of Formula (I), Formula (II), or Formula (III), $R^1$ is selected from

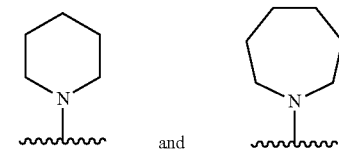

and, each of which is optionally substituted with one or more substituents independently selected from —$OR^{20}$, and $C_{1-6}$ alkyl. In some cases, $R^1$ is selected from

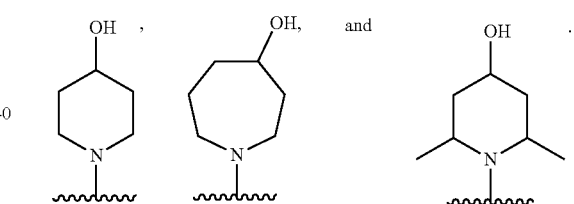

In some embodiments, for a compound or salt of Formula (I), Formula (II), or Formula (III), $R^1$ is selected from -continued

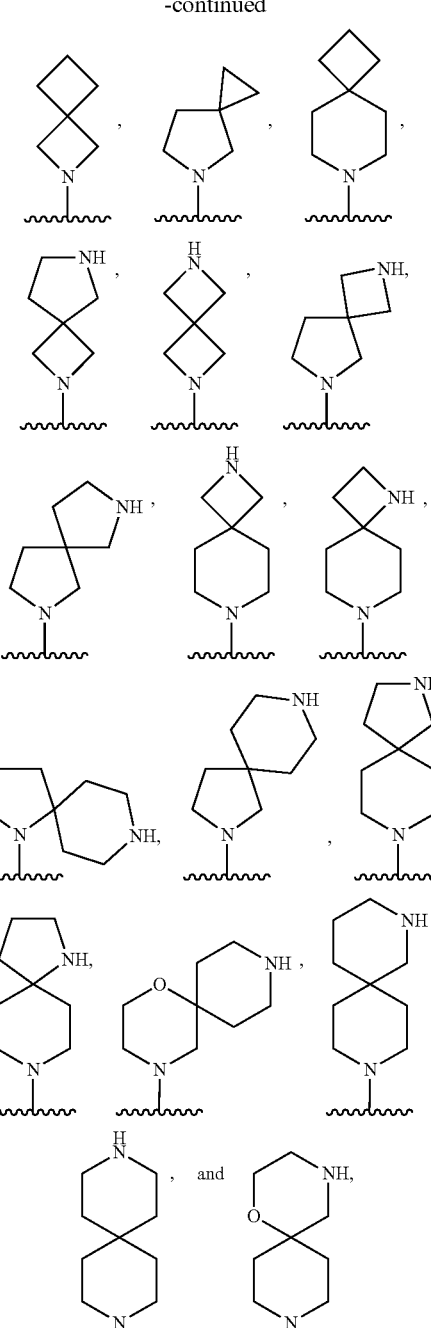

each of which are optionally substituted.

In some embodiments, for a compound or salt of Formula (I), Formula (II), or Formula (III), R¹ is selected from

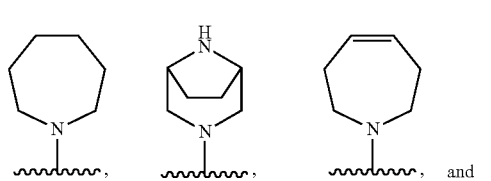

-continued

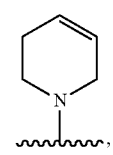

each of which is optionally substituted with one or more substituents independently selected from —OH, —CN, oxo, $C_{1-6}$ cyanoalkyl.

In some embodiments fora compound or salt of Formula (I), Formula (II), or Formula (III), R¹ is selected from

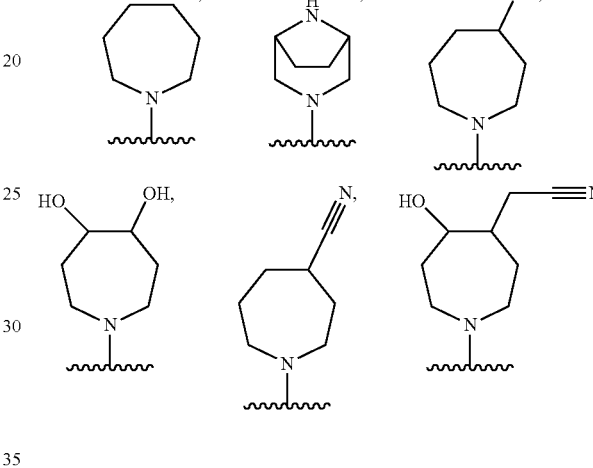

In some embodiments, for a compound or salt of Formula (I), Formula (II), or Formula (III), R¹ is selected from

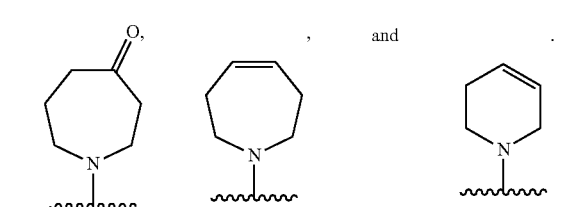

each of which are optionally substituted.

In some embodiments, for a compound or salt of Formula (I), Formula (II), or Formula (III), R¹ is selected from

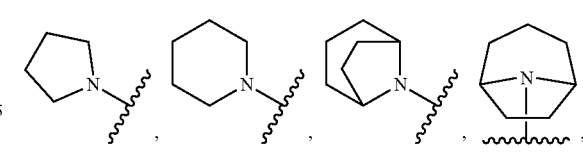

-continued each of which are optionally substituted.

In some embodiments, for a compound or salt of Formula (I), Formula (II), or Formula (III), R¹ is selected from -continued each of which are optionally substituted.

In some embodiments, for a compound or salt of Formula (I), Formula (II), or Formula (III), R¹ is which is optionally substituted.

In some embodiments, for a compound or salt of Formula (I), Formula (II), or Formula (III), R¹ is selected from

93

-continued

94

-continued

-continued

In some embodiments, for a compound or salt of Formula (I), Formula (II), or Formula (III), R¹ is selected from In some cases, R¹ is In some cases, R¹ is In some embodiments, for a compound or salt of Formula (I), Formula (II), or Formula (III), wherein the 5- to 12-membered heterocycle of R¹ is unsaturated and a bridged heterocycle. In some cases, R¹ is selected from an optionally substituted 7- to 8-membered unsaturated and bridged heterocycle. In some cases, R¹ is selected from In some embodiments, for a compound of Formula (I) or Formula (II), R¹ is selected from 5- to 10-membered heterocycle, 7-, 8-, 10-, 11-membered Spiro heterocycle, and 6-, 9-, 10-, 11-, and 12-membered fused heterocycle, and wherein each are optionally substituted with one or more substituents independently selected from halogen, —N(R²⁰)₂, C₁₋₆ alkyl, —OR²⁰, —N(R²⁰)C(O)N(R²⁰)₂, —B(OR²⁰)₂, C₁₋₆ cyanoalkyl, —N(R²⁰)C(O)N(R²⁰)₂, ═O, C₁₋₆ hydroxyalkyl, halogen, —N(R²⁰)C(O)R²⁰, —N(R²⁰)S(O)₂(R²⁰), and C₁₋₆ aminoalkyl; R³ is naphthalene, wherein naphthalene is optionally substituted with one or more substituents independently selected from halogen, —OH, —NH₂, —NO₂, ═O, C₁₋₆ alkyl, C₂₋₆ alkynyl, C₁₋₆ aminoalkyl, C₁₋₆ hydroxyalkyl, and C₁₋₆haloalkyl; R⁴ is selected from hydrogen, halogen or C₁-C₃ alkyl; Y is O; L is independently a C₁-C₄ alkylene; R² is selected from -L-heterocycle, wherein the heterocycle portion is optionally substituted with one or more substituents independently selected from halogen, hydroxy, C₁-C₄ alkyl, C₁-C₄ alkoxy, C₁-C₄ haloalkyl, C₁-C₄ hydroxyalkyl, or —N(R⁵)₂. In some cases, Y—R² is selected from wherein the heterocycle portion is optionally substituted.

In some embodiments, for a compound or salt of Formula (I), Formula (II), or Formula (III), R¹ is selected from an optionally substituted 5- to 12-membered unsaturated heterocycle, wherein the heterocycle has as most one nitrogen atom. In some cases, the 5- to 12-membered unsaturated heterocycle has at least one nitrogen atom. In some cases, the 5- to 12-membered unsaturated heterocycle has at most one nitrogen atom.

In some embodiments, for a compound or salt of Formula (I), Formula (II), or Formula (III), R¹ is selected from 6- to 7-membered heterocycle. In some cases, R¹ is selected from 7-membered heterocycle. In some cases, R¹ is selected from 6-membered heterocycle. In some cases, the 6- to 7-membered heterocycle contains only 1 nitrogen atom and optionally one or more additional heteroatoms selected from oxygen, and sulfur. In some cases, the optionally one or more additional heteroatoms are selected from sulfur. In some cases, the optionally one or more additional heteroatoms are selected from oxygen. In some cases, the 6- to 7-membered heterocycle contains only 1 nitrogen atom and no further additional heteroatoms. In some cases, the 6- to 7-membered heterocycle is a non-aromatic 6- to 7-membered heterocycle. In some cases, the 6- to 7-membered heterocycle of R¹ is bound to Formula (I) via the only 1 nitrogen atom. In some cases, the 6- to 7-membered heterocycle of R¹ is bound to Formula (II) via the only 1 nitrogen atom. In some cases, the 6- to 7-membered heterocycle of R¹ is bound to Formula (III) via the only 1 nitrogen atom. In some cases, $R^1$ is selected from each of which is substituted. In some cases, $R^1$ is selected from each of which is substituted. In some cases, the substituents of $R^1$ are each selected from one or more halogen, —OR$^{20}$, —SR$^{20}$, —N(R$^{20}$)$_2$, —NHCN, —NO$_2$, =O, —CN, C$_{1-6}$ fluoroalkyl, and C$_{2-6}$ alkynyl; and further optionally substituted with one or more substituents independently selected from —C(O)N(R$^{20}$)$_2$, C$_{1-6}$ aminoalkyl, C$_{1-6}$ hydroxyalkyl, C$_{1-6}$ cyanoalkyl, C$_{1-6}$ alkyl, and C$_{2-6}$ alkenyl. In some cases, the substituents of $R^1$ are each selected from one or more halogen, —OR$^{20}$, —N(R$^{20}$)$_2$, —NHCN, =O, —CN, and C$_{2-6}$ alkynyl; and further optionally substituted with one or more substituents independently selected from —C(O)N (R$^{20}$)$_2$, C$_{1-6}$ aminoalkyl, C$_{1-6}$ hydroxyalkyl, C$_{1-6}$ cyanoalkyl, and C$_{1-6}$ alkyl. In some cases, the substituents of $R^1$ are each selected from one or more halogen, —OH, —NHCN, =O, —CN, and C$_{2-6}$ alkynyl; and further optionally substituted with one or more substituents independently selected from C$_{1-6}$ alkyl. In some cases, $R^1$ is selected from -continued In some cases, $R^1$ is selected from each of which is optionally substituted. In some cases, $R^1$ is selected from each of which is optionally substituted. In some cases, $R^1$ is selected from each of which is optionally substituted. In some cases, the one or more optional substituents of $R^1$ are each independently selected from fluorine, —OH, —C(O)NH$_2$, —NH— C(O)—(C$_{1-6}$ alkoxy), —NH—C(O)—(C$_{1-6}$ hydroxyalkyl), —NH$_2$, —NH(CN), =O, —CN, C$_{1-6}$ hydroxyalkyl, C$_{1-6}$ cyanoalkyl, C$_{1-6}$ alkyl, and C$_{2-6}$ alkynyl. In some cases, the one or more optional substituents of $R^1$ are each independently selected from halogen, —OH, —CN, $C_{1-6}$ cyanoalkyl, $C_{1-6}$ alkyl, and $C_{2-6}$ alkynyl. In some cases, the one or more optional substituents of $R^1$ are each independently selected from halogen, —OH, and —CN. In some cases, the one or more optional substituents of $R^1$ are each independently selected from fluorine, —OH, —CN, $C_{1-6}$ cyanoalkyl, $C_{1-6}$ alkyl, oxo, and $C_{2-6}$ alkynyl. In some cases, the one or more optional substituents of $R^1$ are each independently selected from fluorine, —OH, —CN, $C_{1-6}$ cyanoalkyl, $C_{1-6}$ alkyl, and $C_{2-6}$ alkynyl. In some cases, $R^1$ is selected from -continued

101

-continued

102

-continued

In some cases,
R¹ is selected from and 103 104

-continued -continued

In some cases. R¹ is selected from

In some cases, R¹ is selected from

In some cases, $R^1$ is selected from wherein each is optionally substituted with one or more substituents independently selected from halogen, —OH, —NH$_2$, —NO$_2$, C$_{1-6}$ aminoalkyl, C$_{1-6}$ alkoxy, C$_{1-6}$ hydroxy-alkyl, C$_{1-6}$ haloalkyl, and C$_{1-6}$ alkyl. In some cases, $R^1$ is selected from In some embodiments, for a compound or salt of Formula (I), Formula (II), or Formula (III), $R^1$ is selected from an optionally substituted unsaturated 6- to 8-membered heterocycle. In some cases, $R^1$ is selected from an optionally substituted unsaturated 6-membered heterocycle. In some cases, $R^1$ is selected from an optionally substituted unsaturated 7-membered heterocycle. In some cases, the heterocycle has 1 or 2 double bonds. In some cases, the heterocycle has only 1 double bond. In some cases, the heterocycle has only 2 double bonds. In some cases, $R^1$ is selected from wherein each is optionally substituted with one or more substituents independently selected from halogen, —OH, —NH$_2$, —NO$_2$, C$_{1-6}$ aminoalkyl, C$_{1-6}$ alkoxy, C$_{1-6}$ hydroxy-alkyl, C$_{1-6}$ haloalkyl, and C$_{1-6}$ alkyl. In some cases, $R^1$ is selected from In some cases, $R^1$ is selected from wherein each is optionally substituted with one or more substituents independently selected from halogen, —OH, —NH$_2$, —NO$_2$, C$_{1-6}$ aminoalkyl, C$_{1-6}$ alkoxy, C$_{1-6}$ hydroxy-alkyl, C$_{1-6}$ haloalkyl, and C$_{1-6}$ alkyl. In some cases, $R^1$ is selected from 107
-continued 108
-continued In some cases, R¹ is selected from

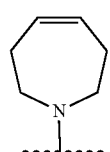

In some cases, R¹ is

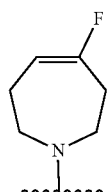

In some cases, R¹ is selected from wherein each is substituted with one or more substituents independently selected from halogen.

In some embodiments, for a compound or salt of Formula (I), Formula (II), or Formula (III), R¹ is selected from an unsaturated 6- to 7-membered heterocycle, wherein the unsaturated 6- to 7-membered heterocycle is substituted with one or more substituents selected from halogen. In some cases, the unsaturated 6- to 7-membered heterocycle is substituted with at least one halogen. In some cases, the unsaturated 6- to 7-membered heterocycle is substituted with at only one halogen. In some cases, the unsaturated 7-membered heterocycle is substituted with one fluorine. In some cases, R¹ is selected from an unsaturated 6-membered heterocycle, substituted with at least one halogen. In some cases, R¹ is selected from an unsaturated 7-membered heterocycle, substituted with at least one halogen. In some cases, R¹ is selected from In some cases, R¹ is selected from In some cases, R is selected from In some cases, R¹ is selected from In some cases, R is selected from In some cases, R¹ is selected from In some cases, $R^1$ is In some cases, $R^1$ is In some cases, $R^1$ is In some embodiments, for a compound or salt of Formula (I), Formula (II), or Formula (III), $R^1$ is selected from an optionally substituted unsaturated 6- to 8-membered heterocycle. In some cases, $R^1$ is selected from an optionally substituted unsaturated 7-membered heterocycle. In some cases, $R^1$ is selected from wherein each is optionally substituted with one or more substituents independently selected from halogen, —OH, —NH$_2$, —NO$_2$, C$_{1-6}$ aminoalkyl, C$_{1-6}$ alkoxy, C$_{1-6}$ hydroxyalkyl, C$_{1-6}$ haloalkyl, and C$_{1-6}$ alkyl. In some cases, $R^1$ is selected from In some embodiments, for a compound or salt of Formula (I), Formula (II), or Formula (III), $R^1$ is selected from an optionally substituted 6-membered heterocycle. In some cases, the 6-membered heterocycle contains only 1 nitrogen atom. In some cases, the 6-membered heterocycle of $R^1$ is bound to Formula (I) via the only 1 nitrogen atom. In some cases, the 6-membered heterocycle of $R^1$ is bound to Formula (II) via the only 1 nitrogen atom. In some cases, the 6-membered heterocycle of $R^1$ is bound to Formula (III) via the only 1 nitrogen atom. In some cases, $R^1$ is selected from any of which is optionally substituted. In some cases, the one or more optional substituents of $R^1$ are each independently selected from halogen, —OR$^{20}$, —N(R$^{20}$)$_2$, =O, —CN, C$_{1-6}$ hydroxyalkyl, C$_{1-6}$ cyanoalkyl, C$_{1-6}$ alkyl, and C$_{2-6}$ alkynyl. In some cases, the one or more optional substituents of $R^1$ are each independently selected from fluorine, —OH, —NH$_2$, —NH(CN), =O, —CN, C$_{1-6}$ hydroxyalkyl, C$_{1-6}$ cyanoalkyl, C$_{1-6}$alkyl, and C$_{2-6}$alkynyl. In some cases, the one or more optional substituents of $R^1$ are each independently selected from fluorine, —OH, —NH$_2$, —NH(CN), =O, —CN, C$_{1-6}$ hydroxyalkyl, C$_{1-6}$ alkyl, and C$_{2-6}$ alkynyl. In some cases, the 6-membered heterocycle is a partially unsaturated 6-membered heterocycle or a saturated 6-membered heterocycle. In some cases, the 6-membered heterocycle is partially unsaturated. In some cases, the 6-membered heterocycle is a saturated 6-membered heterocycle. In some cases, the 6-membered heterocycle is a monocyclic 6-membered heterocycle. In some cases, the 6-membered heterocycle is not a bridged heterocycle. In some cases, $R^1$ is selected from

111

-continued

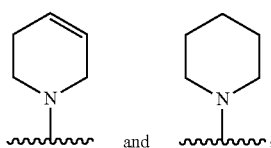 [SMILES: *N1CC=CCC1 ; *N1CCCCC1]

In some embodiments, for a compound of Formula (I), Formula (II), or Formula (III), $R^1$ is selected from an optionally substituted 6-membered unsaturated heterocycle and 6-membered saturated heterocycle.

In some embodiments, for a compound or salt of Formula (I), Formula (II), or Formula (III), $R^1$ is selected from

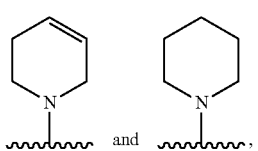 [SMILES: *N1CC=CCC1 ; *N1CCCCC1]

wherein each is optionally substituted with one or more substituents independently selected from halogen, —OH, —NH$_2$, —NO$_2$, $C_{1-6}$ aminoalkyl, $C_{1-6}$ alkoxy, $C_{1-6}$ hydroxyalkyl, $C_{1-6}$haloalkyl, and $C_{1-6}$alkyl.

In some embodiments, for a compound or salt of Formula (I), Formula (II), or Formula (III), $R^1$ is selected from wherein each is optionally substituted with one or more substituents independently selected from halogen, and $C_{1-6}$ haloalkyl.

In some embodiments, for a compound or salt of Formula (I), Formula (II), or Formula (III), $R^1$ is selected from wherein each is optionally substituted two substituents independently selected from halogen, —OH, —NH$_2$, —NO$_2$, $C_{1-6}$ aminoalkyl, $C_{1-6}$ alkoxy, $C_{1-6}$ hydroxyalkyl, $C_{1-6}$haloalkyl, and $C_{1-6}$alkyl.

In some embodiments, for a compound or salt of Formula (I), Formula (II), or Formula (III), $R^1$ is selected from wherein each is optionally substituted with two substituents independently selected from halogen, and $C_{1-6}$ haloalkyl. In some cases, $R^1$ is In some embodiments, for a compound or salt of Formula (I), Formula (II), or Formula (III), $R^1$ is selected from an optionally substituted 6- to 10-membered heterocycle. In some cases, the 6- to 10-membered heterocycle contains at least 1 nitrogen atom. In some cases, $R^1$ is selected from

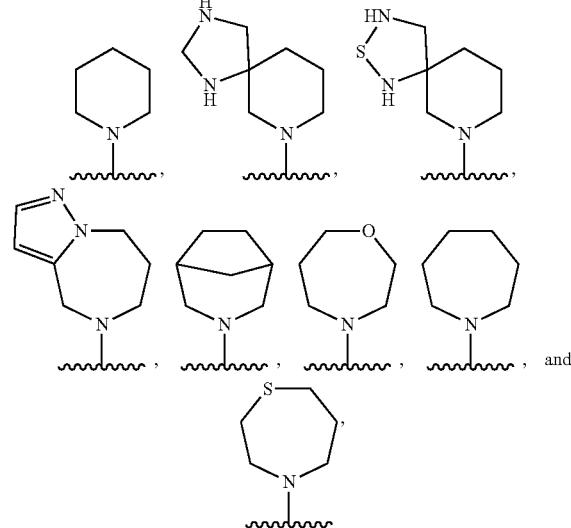

each of which is optionally substituted with one or more substituents independently selected from halogen, =O, —OH, —CN, —NHCN, —C(O)N(R$^{20}$)$_2$, $C_{1-6}$ aminoalkyl, $C_{1-6}$ hydroxyalkyl, $C_{1-6}$ cyanoalkyl, and $C_{1-6}$ alkyl. In some cases, each $R^{20}$ is independently selected from hydrogen; and $C_{1-6}$ alkyl, $C_{3-12}$ carbocycle, and 3- to 12-membered heterocycle, each of which is optionally substituted with one or more substituents independently selected from halogen, —OH, —CN, —NO$_2$, —NH$_2$, —N($C_{1-6}$ alkyl)$_2$, $C_{1-10}$ alkyl, —$C_{1-10}$ haloalkyl, —O—$C_{1-10}$ alkyl, oxo, $C_{3-12}$ carbocycle, and 3- to 12-membered heterocycle. In some cases, $R^1$ is selected from —OH, —CN, —NHCN, —C(O)N(R$^{20}$)$_2$, —C(O) NR$^{20}$OR$^{20}$, C$_{1-6}$ aminoalkyl, C$_{1-6}$ hydroxyalkyl, C$_{1-6}$ cyanoalkyl, and C$_{1-6}$ alkyl. In some cases, R$^1$ is selected from In some cases, R$^1$ is selected from In some cases, R$^1$ is selected from In some cases, R$^1$ is selected from In some embodiments, for a compound or salt of Formula (I), Formula (II), or Formula (III), R$^1$ is selected from an optionally substituted 10-membered heterocycle. In some cases, the 10-membered heterocycle is a bicyclic heterocycle. In some cases, the 10-membered heterocycle is a spiro heterocycle. In some cases, the 10-membered heterocycle is a fused heterocycle. In some cases, the 10-membered heterocycle is a saturated heterocycle. In some cases, the 10-membered heterocycle is a non-aromatic heterocycle. In some cases, the 10-membered heterocycle contains at least 1 nitrogen atom. In some cases, the 10-membered heterocycle contains at least 2 nitrogen atoms. In some cases, the 10-membered heterocycle contains at least 3 nitrogen atoms. In some cases, the 10-membered heterocycle contains at least 1 sulfur atom. In some cases, R$^1$ is selected from each of which is optionally substituted with one or more substituents independently selected from halogen, ═O, In some cases, $R^1$ is selected from which is optionally substituted with one or more substituents independently selected from halogen, $-OR^{20}$, $-SR^{20}$, $-N(R^{20})_2$, $-NO_2$, $=O$, $-CN$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, and $C_{2-6}$ alkynyl.

In some embodiments, for a compound or salt of Formula (I), Formula (II), or Formula (III), $R^1$ is selected from an optionally substituted unsaturated 9- to 11-membered heterocycle. In some cases, $R^1$ is selected from an optionally substituted unsaturated 10-membered heterocycle. In some cases, $R^1$ is selected from an optionally substituted unsaturated 10-membered fused heterocycle. In some cases, $R^1$ is which is optionally substituted. In some cases, the one or more optional substituents are selected from halogen, $-OH$, $-C(O)N(R^{20})_2$, $-N(R^{20})_2$, $-C(O)R^{20}$, $-NO_2$, $=O$, $-CN$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, and $C_{2-6}$ alkynyl. In some cases, $R^1$ is optionally substituted with one or more substituents selected from $-N(R^{20})_2$, $-C(O)R^{20}$, $-NO_2$, $=O$, $-CN$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, and $C_{2-6}$ alkynyl. In some cases, each $R^{20}$ is independently selected from hydrogen; and $C_{1-6}$ alkyl, and $C_{3-12}$ carbocycle, and each of which is optionally substituted with one or more substituents independently selected from halogen, $-OH$, $-CN$, $-NO_2$, $-NH_2$, $C_{1-10}$ alkyl, $-C_{1-10}$ haloalkyl, $-O-C_{1-10}$ alkyl, $C_{2-10}$ alkenyl, $C_{2-10}$ alkynyl, $C_{3-12}$ carbocycle, and 3- to 12-membered heterocycle.

In some embodiments, for a compound or salt of Formula (I), Formula (II), or Formula (III), $R^1$ is selected from a 7- to 11-membered spiro heterocycle. In some cases, $R^1$ is selected from a 10-membered spiro heterocycle. In some cases, the spiro heterocycle has at least 3 nitrogen atoms. In some cases, the spiro heterocycle has at least 1 sulfur atom. In some cases, $R^1$ is selected from and each of which is optionally substituted. In some cases, the one or more optional substituents are independently selected from halogen, $-OH$, $-N(R^{20})_2$, $-NO_2$, $=O$, $-CN$, $-NHCN$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, and $C_{2-6}$ alkynyl. In some cases, $R^1$ is selected from and In some cases, $R^1$ is In some cases, $R^1$ is In some cases, M is selected from O, and $NR^3$. In some cases, M is selected from O. In some cases, M is selected from $NR^3$. In some cases, $R^3$ is selected from $C_{1-6}$ alkyl. In some cases, $R^3$ is selected from $C_{1-2}$ alkyl. In some cases, $R^3$ is selected from methyl.

In some embodiments, for a compound or salt of Formula (I), Formula (II), or Formula (III), $R^1$ is selected from an optionally substituted 8- to 10-membered fused heterocycle. In some cases, the 8- to 10-membered fused heterocycle is a bicyclic heterocycle. In some cases, the 8- to 10-membered fused heterocycle is a saturated heterocycle. In some cases, the 8- to 10-membered fused heterocycle is an unsaturated heterocycle. In some cases, the 8- to 10-membered heterocycle is a non-aromatic heterocycle. In some cases, $R^1$ is selected from an optionally substituted 9-membered fused heterocycle. In some cases, $R^1$ is selected from an optionally substituted 10-membered fused heterocycle. In some cases, the 10-membered fused heterocycle is a bicyclic heterocycle. In some cases, the 10-membered fused heterocycle is a saturated heterocycle. In some cases, the 9-membered heterocycle is a non-aromatic heterocycle. In some cases, the 10-membered heterocycle is a non-aromatic heterocycle. In some cases, the fused heterocycle has one saturated ring and one aromatic ring. In some cases, the fused heterocycle has one saturated ring and one unsaturated ring. In some cases, the fused heterocycle has two saturated rings. In some cases, the 10-membered heterocycle contains at least 1 nitrogen atom. In some cases, the 10-membered heterocycle contains at least 2 nitrogen atoms. In some cases, the 10-membered heterocycle contains at least 3 nitrogen atoms. In some cases, the 9-membered heterocycle contains at least 1 nitrogen atom. In some cases, the 9-membered heterocycle contains at least 2 nitrogen atoms. In some cases, the 9-membered heterocycle contains at least 3 nitrogen atoms. In some cases, $R^1$ is selected from each of which is optionally substituted with one or more substituents. In some cases, $R^1$ is which is optionally substituted with one or more substituents. In some cases, $R^1$ is which is optionally substituted with one or more substituents. In some cases, the one or more optional substituents of $R^1$ are independently selected from halogen, —OH, —S(O)$_2$(R$^{20}$), —S(O)$_2$N(R$^{20}$)$_2$, —S(O)N(R$^{20}$)$_2$, —S(O)R$^{20}$ (=NR$^{20}$), —C(=NR$^{20}$)N(R$^{20}$)$_2$, —C(O)N(R$^{20}$)$_2$, —C(O)NHOR$^{20}$, —N(R$^{20}$)$_2$, —C(O)R$^{20}$, —NO$_2$, =O, —CN, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{1-6}$ alkyl, C$_{2-6}$ alkynyl, and 5- to 12-membered heterocycle, wherein the 5- to 12-membered heterocycle are each optionally substituted independently with one or more R$^{1*}$. In some cases, the one or more optional substituents of $R^1$ are independently selected from halogen, —OH, —S(O)$_2$(R$^{20}$), —S(O)$_2$N(R$^{20}$)$_2$, —S(O)N(R$^{20}$)$_2$, —S(O)R$^{20}$(=NR$^{20}$), —C(O)N(R$^{20}$)$_2$, —C(O)NHOR$^{20}$, —N(R$^{20}$)$_2$, —C(O)R$^{20}$, —NO$_2$, =O, —CN, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{1-6}$ alkyl, and C$_{2-6}$ alkynyl. In some cases, the optional one or more substituents are independently selected from halogen, =O, —OH, —CN, —NHCN, —S(O)$_2$(R$^{20}$), —S(O)$_2$N(R$^{20}$)$_2$, —S(O)N(R$^{20}$)$_2$, —S(O)R$^{20}$(=NR$^{20}$), —C(O)R$^{20}$, —C(O)N(R$^{20}$)$_2$, —C(O)NR$^{20}$OR$^{20}$, C$_{1-6}$ alkyl-N(R$^{20}$)$_2$, C$_{1-6}$ aminoalkyl, C$_{1-6}$ hydroxyalkyl, C$_{1-6}$ cyanoalkyl, and C$_{1-6}$ alkyl. In some cases, the optional one or more substituents are independently selected from halogen, =O, C$_{1-6}$ alkyl-N(R$^{20}$)$_2$, —S(O)$_2$(R$^{20}$), —S(O)N(R$^{20}$)$_2$, —S(O)R$^{20}$(=NR$^{20}$), —C(O)R$^{20}$, —C(O)N(R$^{20}$)$_2$, and —C(O)NR$^{20}$OR$^{20}$. In some cases, the optional one or more substituents are independently selected from halogen, =O, —S(O)$_2$(R$^{20}$), —S(O)N(R$^{20}$)$_2$, —S(O)R$^{20}$(=NR$^{20}$), —C(O)R$^{20}$, —C(O)N(R$^{20}$)$_2$, and —C(O)NR$^{20}$OR$^{20}$. In some cases, the optional one or more substituents are independently selected from —C(O)R$^{20}$, —C(O)N(R$^{20}$)$_2$, and —C(O)NR$^{20}$OR$^{20}$. In some cases, the optional one or more substituents are independently selected from —S(O)$_2$(R$^{20}$), —S(O)$_2$N(R$^{20}$)$_2$, —S(O)N(R$^{20}$)$_2$, —S(O)R$^{20}$(=NR$^{20}$). In some cases, the optional one or more substituents are independently selected from —S(O)N(R$^{20}$)$_2$. In some cases, the optional one or more substituents are independently selected from S(O)$_2$(R$^{20}$). In some cases, the optional one or more substituents are independently selected from S(O)R$^{20}$(=NR$^{20}$). In some cases, the optional one or more substituents are independently selected from —C(O)R$^{20}$. In some cases, the optional one or more substituents are independently selected from —C(O)N(R$^{20}$)$_2$. In some cases, the optional one or more substituents are independently selected from —C(O)NR$^{20}$OR$^{20}$. In some cases, $R^1$ is selected from -continued each of which is further optionally substituted. In some cases, the further one or more optional substituents are selected from halogen, —OH, =O, —CN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, and $C_{2-6}$ alkynyl. In some cases, the further one or more optional substituents are selected from halogen, —CN, $C_2$ alkenyl, and $C_{1-6}$ alkyl. In some cases, the further one or more optional substituents are selected from halogen, and $C_{1-6}$ alkyl. In some cases, the further one or more optional substituents are selected from halogen. In some cases, each $R^{20}$ is independently selected from hydrogen; and $C_{1-6}$ alkyl, $C_{3-12}$ carbocycle, and 3- to 12-membered heterocycle. In some cases, each $R^{20}$ is independently selected from hydrogen; and $C_{1-6}$ alkyl, and 3- to 12-membered heterocycle. In some cases, each $R^{20}$ is independently selected from hydrogen; and $C_{1-6}$ alkyl, and 3- to 12-membered saturated heterocycle. In some cases, each $R^{20}$ is independently selected from 5- to 6-membered saturated heterocycle. In some cases, the heterocycle of $R^{20}$ has at least one nitrogen atom. In some cases, the heterocycle of $R^{20}$ has at least one sulfur atom. In some cases, the heterocycle of $R^{20}$ has at least one oxygen atom. In some cases, the heterocycle of $R^{20}$ contains only 1 heteroatom. In some cases, the heterocycle of $R^{20}$ has at least two heteroatoms. In some cases, the heterocycle of $R^{20}$ contains only 2 heteroatoms. In some cases, the optional one or more substituents of $R^1$ are independently selected from halogen, CN, $C_2$ alkenyl, In some cases, the optional one or more substituents of $R^1$ are independently selected from halogen, In some cases, the optional one or more substituents of $R^1$ are independently selected from

121

-continued

122

-continued

In some cases, the optional one or more substituents of R$^1$ are independently selected from halogen, In some cases, R$^1$ is selected from In some cases, R$^1$ is selected from 123
-continued 124
In some cases, R$^1$ is selected from

25 In some cases. R$^1$ is selected from

50 and

125

-continued

In some cases, the optional one or more substituents of $R^1$ are independently selected from halogen, and $C_{1-6}$ alkyl-N $(R^{20})_2$. In some cases, the optional one or more substituents of $R^1$ are independently selected from halogen, , and

126

In some cases, $R^1$ is selected from

In some cases, each $R^{20}$ is independently selected from hydrogen, $C_{1-6}$ alkyl, and $C_{3-6}$ carbocycle. In some cases, $R^1$ is selected , and In some cases, $R^1$ is selected

127

-continued

128

-continued

In some cases, R$^1$ is selected from which is optionally substituted with one more substituents independently selected from halogen, —OH, —S(O)$_2$(R$^{20}$), —S(O)$_2$N(R$^{21}$)$_2$, —S(O)N(R$^{20}$)$_2$, —S(O)R$^{20}$(=NR$^{20}$), —C(O)N(R$^{20}$)$_2$, —C(=NR$^{20}$)N(R$^{20}$)$_2$, —C(O)OR$^{20}$, —C(O)NHOR$^{20}$, —N(R$^{20}$)$_2$, —C(O)R$^{20}$, —NO$_2$, =O, —CN, C$_{1-6}$ alkyl-N(R$^{20}$)$_2$, C$_{1-6}$ aminoalkyl, C$_{1-6}$ alkoxy, C$_{1-6}$ alkoxyalkyl, C$_{1-6}$ hydroxyalkyl, C$_{1-6}$ cyanoalkyl, C$_{1-6}$ haloalkyl, C$_{1-6}$ alkyl, C$_{2-6}$ alkynyl, 5- to 12-membered heterocycle, wherein the 5- to 12-membered heterocycle is optionally substituted with one or more substituents selected from halogen, —OR$^{20}$, and C$_{1-6}$ alkyl. In some cases, R$^1$ is selected from is optionally substituted with one more substituents independently selected from halogen and C$_{1-6}$ alkyl. In some cases, R$^1$ is selected from

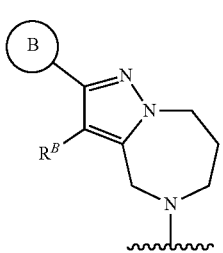

and

In some embodiments, for a compound or salt of Formula (I), Formula (II), or Formula (III), R¹ is selected from a

wherein

is selected from a 5- to 12-membered heterocycle, wherein the 5- to 12-membered heterocycle is optionally substituted independently with one or more R¹*; and R$^B$ is selected from hydrogen, halogen, $C_{1-6}$ alkyl, $C_{1-6}$ haloalkyl, $C_{2-6}$ alkynyl, and —CN. In some cases, R$^B$ is selected from hydrogen, and halogen. In some cases, R$^B$ is chloride. In some case, R$^B$ is hydrogen. In some cases

has at least 1, 2, 3, or 4 heteroatoms. In some cases has at least 1, 2, 3, or 4 nitrogen atoms. In some cases, has at least 1 oxygen atom. In some cases, is a monocyclic heterocycle. In some cases, is a bicyclic heterocycle. In some cases, is selected from an optionally substituted 5-membered heterocycle. In some cases, is selected from an optionally substituted 9-membered heterocycle. In some cases is selected from each of which is optionally substituted with one or more R¹*. In some cases, is selected from

131

-continued

, , and , each of which is optionally substituted with one or more $R^{1*}$. In some cases, each $R^{1*}$ is independently selected from halogen, $-OR^{20}$, $-S(O)_2(R^{20})$, $-S(O)_2N(R^{20})_2$, $-S(O)N(R^{20})_2$, $-S(O)R^{20}(=NR^{20})$, $-NR^{20}S(O)_2R^{20}$, $-C(O)N(R^{20})_2$, $-C(O)NR^{20}OR^{20}$, $-N(R^{20})C(O)R^{20}$, $-N(R^{20})C(O)N(R^{20})_2$, $-N(R^{20})C(O)OR^{20}$, $-N(R^{20})_2$, $-C(O)R^{20}$, $-C(O)OR^{20}$, $-OC(O)R^{20}$, $-OC(O)N(R^{20})_2$, $-NO_2$, $=O$, $=N(R^{20})$, $=NO(R^{20})$, $-CN$, $-NHCN$, $C_{1-6}$ alkyl-N$(R^{20})_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, and $C_{1-6}$ alkyl. In some cases, each $R^{1*}$ is independently selected from halogen, $C_{1-6}$ alkyl-N$(R^{20})_2$, $C_{1-6}$ aminoalkyl, $C_{1-6}$ hydroxyalkyl, $C_{1-6}$ cyanoalkyl, $C_{1-6}$ haloalkyl, and $C_{1-6}$ alkyl. In some cases, each $R^{1*}$ is independently selected from halogen, and $C_{1-6}$ alkyl. In some cases,

B is selected from

In some embodiments, for a compound or salt of Formula (I), Formula (II), Formula (II*), or Formula (III), when $R^1$ is substituted with $-C(O)R^{20}$, $R^{20}$ is selected from a 5- to 12-membered heterocycle, which is optionally substituted. In some cases, $R^1$ is substituted with $-C(O)R^{20}$. In some cases, $R^{20}$ is selected from a 5- to 12-membered unsubstituted heterocycle. In some cases, $R^{20}$ is selected from a 5- to 6-membered heterocycle, which is optionally substituted. In some cases, the heterocycle has at least one nitrogen atom. In some cases, the heterocycle has at least one sulfur atom. In some cases, the heterocycle has at least one oxygen atom. In some cases, the heterocycle has two heteroatoms. In some cases, the heterocycle of $R^{20}$ is selected from each of which is optionally substituted. In some cases, $R^{20}$ is selected from In some cases, the optional substituents are selected from $C_{1-10}$ alkyl, oxo, and $=NH$.

In some embodiments, for a compound or salt of Formula (I), Formula (II), Formula (II*), or Formula (III), each $R^{20}$ is independently selected from hydrogen; and $C_{1-6}$ alkyl, $C_{3-12}$ carbocycle, and 3- to 12-membered heterocycle, each of which is optionally substituted with one or more substituents independently selected from halogen, $-OH$, $-CN$, $-NO_2$, $-NH_2$, $-N(C_{1-6}$ alkyl)$_2$, $C_{1-10}$ alkyl, $-C_{1-10}$ haloalkyl, $-O-C_{1-10}$ alkyl, oxo, and $=NH$. In some cases, each $R^{20}$ is independently selected from hydrogen; and unsubstituted $C_{1-6}$ alkyl, and 3- to 12-membered heterocycle which is optionally substituted with one or more substituents independently selected from halogen, $-OH$, $-CN$, $-NO_2$, $-NH_2$, $-N(C_{1-6}$ alkyl)$_2$, $C_{1-10}$ alkyl, $-C_{1-10}$ haloalkyl, $-O-C_{1-10}$ alkyl, oxo, and $=NH$.

In some embodiments, for a compound or salt of Formula (I), Formula (II), or Formula (III), $R^1$ is an optionally substituted 12- to 15-membered heterocycle. In some cases, $R^1$ is an optionally substituted 12-membered heterocycle. In some cases, $R^1$ is an optionally substituted 13-membered heterocycle. In some cases, $R^1$ is an optionally substituted 14-membered heterocycle. In some cases, $R^1$ is an optionally substituted 15-membered heterocycle. In some cases, the heterocycle of $R^1$ is tricyclic. In some cases, the heterocycle of $R^1$ contains a fused heterocycle. In some cases, the heterocycle of $R^1$ contains a spiro-heterocycle. In some cases, the heterocycle of $R^1$ contains a fused and spiro-heterocycle. In some cases, the heterocycle of $R^1$ is an unsaturated heterocycle. In some cases, the heterocycle of $R^1$ is a non-aromatic heterocycle. In some cases, the heterocycle of $R^1$ has at least one double bond. In some cases, the heterocycle of $R^1$ has at least two double bonds. In some cases, the heterocycle of R[1] has at least 2 heteroatoms. In some cases, the heterocycle of R[1] has at least 3 heteroatoms. In some cases, the heterocycle of R[1] has at least 4 heteroatoms. In some cases, the heterocycle of R[1] has at least 5 heteroatoms. In some cases, the heterocycle of R[1] has at least 6 heteroatoms. In some cases, the heterocycle of R[1] has at least 7 heteroatoms. In some cases, the heteroatoms are selected from oxygen, nitrogen, and sulfur. In some cases, the heterocycle of R[1] has at least 3, 4, or 5 nitrogen atoms, and at least 1 sulfur atom. In some cases, the heterocycle of R[1] has at least 3, 4, or 5 nitrogen atoms, and at least 1 oxygen atom. In some cases, the heterocycle of R[1] has at least 3, 4, or 5 nitrogen atoms. In some cases, the heterocycle of R[1] has at least 3, 4, or 5 nitrogen atoms and no other heteroatoms. In some cases, the heteroatoms are selected from nitrogen and sulfur. In some cases, the heteroatoms are selected from nitrogen and oxygen. In some cases, R[1] is selected from -continued each of which is optionally substituted with one or more substituents. In some cases, R[1] is selected from

135

136

-continued

-continued each of which is optionally substituted with one or more substituents. In some cases, the optional one or more substituents of $R^1$ are independently selected from halogen, —OH, —NHCN, —S(O)$_2$(R$^{20}$), —S(O)$_2$N(R$^{20}$)$_2$, —S(O)N (R$^{20}$)$_2$, —S(O)R$^{20}$(=NR$^{20}$), —C(O)N(R$^{20}$)$_2$, —C(O) NHOR$^{20}$, —N(R$^{20}$)$_2$, —C(O)R$^{20}$, —NO$_2$, =O, =NH, —CN, C$_{1-6}$ aminoalkyl, C$_{1-6}$ alkoxy, C$_{1-6}$ hydroxyalkyl, C$_{1-6}$ cyanoalkyl, C$_{1-6}$haloalkyl, C$_{1-6}$ alkyl, and C$_{2-6}$ alkynyl. In some cases, the optional one or more substituents of $R^1$ are independently selected from halogen, —OH, —NHCN, —S(O)$_2$(R$^{20}$), —S(O)$_2$N(R$^{20}$)$_2$, —S(O)N(R$^{20}$)$_2$, —S(O)R$^{20}$ (=NR$^{20}$), —C(O)N(R$^{20}$)$_2$, —C(O)NHOR$^{20}$, —N(R$^{20}$)$_2$, —C(O)R$^{20}$, —NO$_2$, =O, —CN, C$_{1-6}$ aminoalkyl, C$_{1-6}$ alkoxy, C$_{1-6}$ hydroxyalkyl, C$_{1-6}$ cyanoalkyl, C$_{1-6}$haloalkyl, C$_{1-6}$ alkyl, and C$_{2-6}$ alkynyl. In some cases, the optional one or more substituents of $R^1$ are independently selected from halogen, —OH, C$_{1-6}$ alkyl, and —C(O)N(R$^{20}$)$_2$. In some cases, $R^1$ is selected from 137
-continued 138
-continued In some embodiments, for a compound or salt of Formula (I), Formula (II), or Formula (III), $R^1$ is an optionally substituted 12- to 15-membered heterocycle. In some cases, $R^1$ is

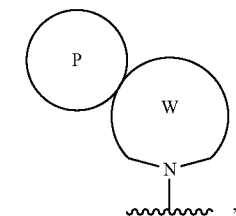

wherein Ring W is an optionally substituted heterocycle and Ring P is an optionally substituted carbocycle or optionally substituted heterocycle, wherein Ring P forms a spirocycle with Ring W. In some cases, Ring W is an optionally substituted fused heterocycle. In some cases, Ring P and Ring W combine to form a heterocycle having at least 12 atoms and most 15 atoms. In some cases, Ring P and Ring W have in total at least 12 atoms and most 15 atoms. In some cases, Ring W is an optionally substituted 10-membered fused heterocycle. In some cases, $R^1$ is wherein Ring P is an optionally substituted carbocycle or optionally substituted heterocycle. In some cases, $R^1$ is In some cases, Ring P is an optionally substituted carbocycle. In some cases, Ring P is an optionally substituted heterocycle. In some cases, Ring P forms an optionally substituted $C_3$-$C_6$ carbocycle or optionally substituted 4- to 6-membered heterocycle. In some cases, Ring P forms an optionally substituted $C_3$ carbocycle. In some cases, Ring P forms an optionally substituted $C_4$ carbocycle. In some cases, Ring P forms an optionally substituted $C_5$ carbocycle. In some cases, Ring P forms an optionally substituted 4-membered heterocycle. In some cases, Ring P forms an optionally substituted 5-membered heterocycle. In some cases, Ring P forms an optionally substituted 5-membered heterocycle. In some cases, Ring P has at least 1, 2, or 3 heteroatoms. In some cases, the heteroatoms are selected from oxygen, nitrogen, and sulfur. In some cases, Ring P has 1 sulfur atom. In some cases, Ring P has 1 nitrogen atom. In some cases, Ring P has 1 oxygen atom. In some cases, the one or more optional substituents of Ring P are independently selected from halogen, —OH, —NHCN, =O, =$NR^{20}$, —CN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, and $C_{2-6}$ alkynyl. In some cases, the one or more optional substituents of Ring P are independently selected from halogen, —OH, =O, =NH, —CN, and $C_{1-6}$ alkyl. In some cases, the one or more optional substituents of Ring W are independently selected from halogen, —OH, —NHCN, —$S(O)_2(R^{20})$, —$S(O)_2N(R^{20})_2$, —$S(O)N(R^{20})_2$, —$S(O)R^{20}$(=$NR^{20}$), —$C(O)N(R^{20})_2$, —$C(O)NHOR^{20}$, —$N(R^{20})_2$, —$C(O)R^{20}$, —$NO_2$, —CN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, and $C_{2-6}$ alkynyl. In some cases, the one or more optional substituents of Ring W are independently selected from halogen, —$S(O)_2(R^{20})$, —$S(O)_2N(R^{20})_2$, —$S(O)N(R^{20})_2$, —$S(O)R^{20}$(=$NR^{20}$), —$C(O)N(R^{20})_2$, —$C(O)NR^{20}OR^{20}$, —$C(O)$NHOR$^{20}$, —$N(R^{20})_2$, —$C(O)R^{20}$, and $C_{1-6}$ alkyl. In some cases, the one or more optional substituents of Ring W are independently selected from —$C(O)R^{20}$. In some cases, Ring P is substituted. In some cases, Ring W is substituted.

In some embodiments, for a compound or salt of Formula (I), Formula (II), or Formula (III), $R^1$ is selected from

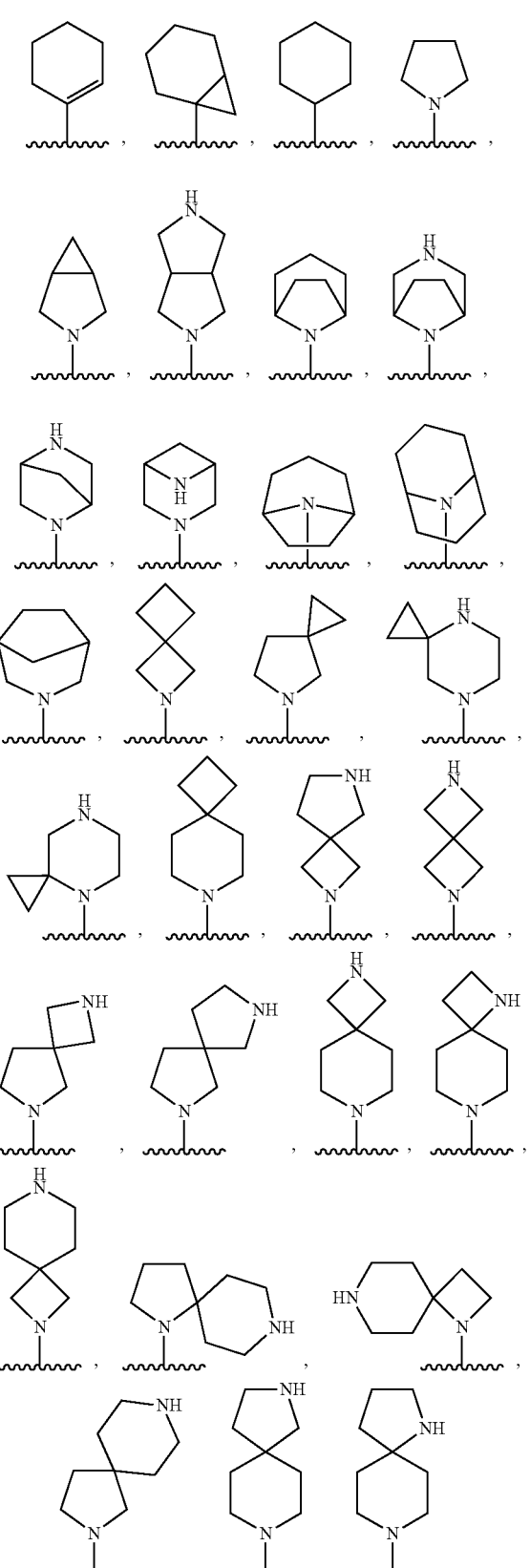

-continued

-continued each of which is optionally substituted with one or more substituents. In some cases, the one or more of the optional substituents are independently selected from halogen, —OH, —N(R$^{20}$)$_2$, —B(OH)$_2$, —C(O)N(R$^{20}$)$_2$, —NHCN, —NO$_2$, C$_{1-6}$ alkoxy, =O, —CN, C$_{1-6}$ alkyl, C$_{2-6}$ alkenyl, C$_{1-6}$ aminoalkyl, C$_{1-6}$ hydroxyalkyl, and C$_{1-6}$ haloalkyl. In some cases, R$^1$ is selected from

143

144

This page consists entirely of chemical structure diagrams arranged in columns, labeled with line numbers 5, 10, 15, 20, 25, 30, 35, 40, 45, 50, 55, 60, 65 along the center.

145

146

147

148

149

-continued

,

,

,

,

,

,

,

150

-continued

,

,

, and

.

In some embodiments, for a compound or salt of Formula (I), Formula (II), or Formula (III), $R^2$ is selected from optionally substituted -L-heterocycle. In some cases, the heterocycle is a bicyclic heterocycle. In some cases, the heterocycle is a monocyclic heterocycle. In some cases, the heterocycle has only 1 nitrogen atom. In some cases, the heterocycle has only 1 nitrogen atom and no other heteroatoms. In some cases, Y—$R^2$ is selected from and

, wherein the heterocycle portion is optionally substituted. In some cases, $R^2$ is selected from and

, wherein the heterocycle portion is optionally substituted. In some cases, Y—R is selected from wherein the heterocycle portion is optionally substituted. In some cases, Y—R$^2$ is selected from wherein the heterocycle portion is optionally substituted. In some cases, the heterocycle is optionally substituted with one or more substituent selected from halogen, hydroxy, C$_1$-C$_3$ alkyl, —N(R$^5$)S(O)$_2$(R$^5$), —OC(O)N(R$^5$)$_2$, oxo, =CH$_2$, =NO—C$_1$-C$_3$ alkyl, —CH$_2$OC(O)heterocycle, —CH$_2$heterocycle, —CH$_2$OC(O)N(R$^5$)$_2$, and —O—C$_1$-C$_3$ alkyl, wherein the alkyl of —O—C$_1$-C$_3$ alkyl is optionally substituted with substituents selected from heterocycle, oxo, and hydroxy. In some cases, Y—R$^2$ is selected from 153
-continued 154
-continued In some cases, Y—R² is selected from In some cases, Y—R² is selected from,

155

156

In some embodiments, for a compound or salt of Formula (I), Formula (II), or Formula (III), $R^2$ is selected from $-L-N(R^{21})_2$. In some cases, each $R^{2'}$ is selected from hydrogen and $C_{1-6}$ alkyl. In some cases, each $R^{21}$ is selected from $C_{1-6}$ alkyl. In some cases, L is independently selected from a substituted $C_1-C_4$ alkylene, and wherein two substituents on the same carbon atom of L come together to form a $C_3-C_6$ carbocycle, wherein the $C_3-C_6$ carbocycle is optionally substituted with one or more substituents selected from halogen. In some cases, L is In some cases, $R^2$ is In some cases, $Y—R^2$ is In some embodiments, for a compound or salt of Formula (I), Formula (II), or Formula (III), each $R^{2'}$ is independently selected from hydrogen. In some cases, each $R^{2'}$ is independently selected from hydrogen and $C_{1-6}$ alkyl. In some cases, each $R^{21}$ is independently selected from $C_{1-6}$ alkyl. In some cases, each $R^{21}$ is independently selected from hydrogen; and $C_{3-12}$ carbocycle, and 3- to 12-membered heterocycle, each of which is optionally substituted with one or more substituents independently selected from halogen, —OH, —CN, —NO₂, —NH₂, —N(C₁₋₆ alkyl)₂, C₁₋₁₀ alkyl, —C₁₋₁₀ haloalkyl, —O—C₁₋₁₀ alkyl, oxo.

In some embodiments, for a compound or salt of Formula (I), Formula (II), or Formula (III), $R^1$ is selected from an optionally substituted 8- to 10-membered fused heterocycle. In some cases, the 8- to 10-membered fused heterocycle is and a bicyclic heterocycle. In some cases, the 8- to 10-membered fused heterocycle is a saturated heterocycle. In some cases, the 8- to 10-membered heterocycle is a non-aromatic heterocycle. In some cases, $R^1$ is selected from an optionally substituted 9-membered fused heterocycle. In some cases, $R^1$ is selected from an optionally substituted 10-membered fused heterocycle. In some cases, the 10-membered fused heterocycle is a bicyclic heterocycle. In some cases, the 10-membered fused heterocycle is a saturated heterocycle. In some cases, the 10-membered heterocycle is a non-aromatic heterocycle. In some cases, the fused heterocycle has one saturated ring and one aromatic ring. In some cases, the fused heterocycle has one saturated ring and one unsaturated ring. In some cases, the fused heterocycle has two saturated rings. In some cases, the 10-membered heterocycle contains at least 1 nitrogen atom. In some cases, the 9-membered heterocycle contains at least 2 nitrogen atoms. In some cases, the 9-membered heterocycle contains at least 3 nitrogen atoms. In some cases, the 10-membered heterocycle contains at least 2 nitrogen atoms. In some cases, the 10-membered heterocycle contains at least 3 nitrogen atoms. In some cases, $R^1$ is selected from each of which is optionally substituted with one or more substituents. In some cases, $R^1$ is selected from each of which is optionally substituted with one or more substituents. In some cases, $R^1$ is which is optionally substituted with one or more substituents. In some cases, the optional one or more substituents are independently selected from halogen, =O, —OH, —CN, —NHCN, —C(O)R$^{20}$, —C(O)N(R$^{20}$)$_2$, —C(O)NR$^{20}$OR$^{20}$, $C_{1-6}$ aminoalkyl, $C_{1-6}$ hydroxyalkyl, $C_{1-6}$ cyanoalkyl, and $C_{1-6}$ alkyl. In some cases, the optional one or more substituents are independently selected from halogen, =O, —C(O) R$^{20}$, —C(O)N(R$^{20}$)$_2$, and —C(O)NR$^{20}$OR$^{20}$. In some cases, the optional one or more substituents are independently selected from —C(O)R$^{20}$, —C(O)N(R$^{20}$)$_2$, and —C(O) NR$^{20}$OR$^{20}$. In some cases, the optional one or more substituents are independently selected from —C(O)R$^{20}$. In some cases, the optional one or more substituents are independently selected from —C(O)N(R$^{20}$)$_2$. In some cases, the optional one or more substituents are independently selected from —C(O)NR$^{20}$OR$^{20}$. In some cases, each R$^{20}$ is independently selected from hydrogen; and $C_{1-6}$ alkyl, $C_{3-12}$ carbocycle, and 3- to 12-membered heterocycle. In some cases, each R$^{20}$ is independently selected from hydrogen; and $C_{1-6}$ alkyl, and 3- to 12-membered heterocycle. In some cases, each R$^{20}$ is independently selected from hydrogen; and $C_{1-6}$ alkyl, and 3- to 12-membered saturated heterocycle. In some cases, the optional one or more substituents of $R^1$ are independently selected from In some cases, $R^1$ is selected from

159

160

In some cases. R$^1$ is selected from

In some cases, R$^1$ is

In some embodiments, for a compound or salt of Formula (I), R$^1$ is selected from an optionally substituted saturated 6- to 7-membered heterocycle. In some cases, R$^1$ is selected from an optionally substituted saturated 6-membered heterocycle. In some cases, R$^1$ is selected from which is optionally substituted. In some cases, the optional one or more substituents are independently selected from halogen, —CN, —NHCN, C$_{1-6}$ cyano-alkyl, and C$_{1-6}$ alkyl. In some cases, the optional one or more substituents are independently selected from —CN, —NHCN, C$_{1-6}$ cyanoalkyl, and C$_{1-6}$ alkyl. In some cases, the optional one or more substituents are independently selected from —CN, —NHCN, C$_{1-6}$ cyanoalkyl, and C$_{1-6}$ alkyl. In some cases, the optional one or more substituents are independently selected from —NHCN, and C$_{1-6}$ alkyl. In some cases, R$^1$ is selected from which is substituted with one or more substituents selected from —NHCN, and $C_{1-6}$ alkyl. In some cases, $R^1$ is selected from In some embodiments, for a compound or salt of Formula (I), $R^1$ is selected from a substituted saturated 6-membered heterocycle, wherein the saturated 6-membered heterocycle is substituted with at least one —NHCN, and optionally one or more $C_{1-6}$ alkyl; B is selected from an optionally substituted 8- to 15-membered fused heterocycle and optionally substituted $C_8$-$C_{15}$ fused carbocycle, each of which is optionally substituted with one or more substituents independently selected from halogen, oxo, —NH$_2$, $C_1$-$C_3$ alkyl, —OH, —C(O)NH$_2$, —NH$_2$, ═O, —CN, $C_{1-6}$ alkoxy, $C_{1-6}$ hydroxyalkyl, and $C_{2-6}$ alkynyl; Ring A is selected from an optionally substituted heterocycle; Y is O; $R^2$ is selected from -L-heterocycle, wherein the heterocycle portion is optionally substituted with one or more substituents independently selected from halogen, hydroxy, $C_1$-$C_4$ alkyl, $C_1$-$C_4$ alkoxy, $C_1$-$C_4$ haloalkyl, $C_1$-$C_4$ hydroxyalkyl, or —N(R$^5$)$_2$; and L is selected from $C_1$-$C_4$ alkylene. In some cases, $R^1$ is selected from In some cases, B is selected from In some cases, B is selected from In some cases, B is In some embodiments, for a compound or salt of Formula (I), Formula (II), or Formula (III), B is an optionally substituted 8- to 10-membered fused carbocycle. In some cases, B is a substituted 8- to 10-membered fused carbocycle. In some cases, B is an unsubstituted 8- to 10-membered fused carbocycle. In some cases, B is an optionally substituted 9-membered fused carbocycle. In some cases, B is a substituted 9-membered fused carbocycle. In some cases, B is which is optionally substituted with one or more substituents. In some cases, B is which is substituted with one or more substituents. In some cases, for B, the one or more substituents are independently selected from halogen, oxo, —NH$_2$, C$_1$-C$_3$ alkyl, —B(OH)$_2$, —OH, —C(O)NH$_2$, —NH$_2$, =O, —CN, C$_{1-6}$ alkoxy, C$_{1-6}$ hydroxyalkyl, and C$_{2-6}$ alkynyl. In some cases, B is substituted with at least one halogen. In some cases, B is substituted with at least one chlorine. In some cases, B is substituted with at least one fluorine. In some cases, B is selected from In some cases, B is which is substituted with one or more substituents selected from halogen and C$_{1-6}$ haloalkyl. In some cases, B is which is substituted with one or more substituents selected from halogen. In some cases, B is selected from In some cases, B is which is substituted with one or more substituents selected from fluorine. In some cases, B is selected from In some cases, B is which is substituted with one or more substituents selected from chlorine. In some cases, B is selected from In some cases, B is a substituted 10-membered fused carbocycle. In some cases, for the 10-membered fused carbocycle of B, the one or more substituents are independently selected from halogen, —NH$_2$, C$_1$-C$_3$ alkyl, —B(OH)$_2$, —OH, —C(O)NH$_2$, —NH$_2$, =O, —CN, C$_{1-6}$ alkoxy, C$_{1-6}$ hydroxyalkyl, and C$_{2-6}$ alkynyl. In some cases, B is selected from In some cases, for the 10-membered fused carbocycle of B, is substituted with at least one halogen. In some cases, B is selected from In some cases, B is an unsubstituted 9- to 10-membered fused carbocycle. In some cases, B is selected and each of which is unsubstituted. In some cases, B is In some cases, B is In some embodiments, for a compound or salt of Formula (I), Formula (II), or Formula (III), the one or more optional substituents of $R^1$ are independently selected from halogen, —OH, —S(O)$_2$(R$^{20}$), —S(O)$_2$N(R$^{20}$)$_2$, —S(O)N(R$^{20}$)$_2$, —S(O)R$^{20}$(=NR$^{20}$), —C(O)N(R$^{20}$)$_2$, —C(=NR$^{20}$) N(R$^{20}$)$_2$, —C(O)NHOR$^{20}$, —N(R$^{20}$)$_2$, —C(O)R$^{20}$, —NO$_2$, =O, —CN, $C_{1-6}$ alkyl-N(R$^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkynyl, 5- to 12-membered heterocycle, wherein the 5- to 12-membered heterocycle is optionally substituted with one or more substituents selected from halogen, and $C_{1-6}$ alkyl.

In some embodiments, for a compound or salt of Formula (I), Formula (II), or Formula (III), $R^1$ is and the one or more optional substituents of $R^1$ are independently selected from halogen, —OH, —S(O)$_2$(R$^{20}$), —S(O)$_2$N(R$^{20}$)$_2$, —S(O)N(R$^{20}$)$_2$, —S(O)R$^{20}$(=NR$^{20}$), —C(O)N(R$^{20}$)$_2$, —C(=NR$^{20}$)N(R$^{20}$)$_2$, —C(O)NHOR$^{20}$, —N(R$^{20}$)$_2$, —C(O)R$^{20}$, —NO$_2$, =O, —CN, $C_{1-6}$ alkyl-N (R$^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkynyl, and optionally substituted 5- to 12-membered heterocycle. In some cases, the one or more optional substituents of $R^1$ are independently selected from halogen, —OH, —S(O)$_2$(R$^{20}$), —S(O)$_2$N(R$^{20}$)$_2$, —S(O)N(R$^{20}$)$_2$, —S(O)R$^{20}$(=NR$^{20}$), —C(O)N(R$^{20}$)$_2$, —C(=NR$^{20}$) N(R$^{20}$)$_2$, —C(O)NHOR$^{20}$, —N(R$^{20}$)$_2$, —C(O)R$^{20}$, —NO$_2$, =O, —CN, $C_{1-6}$ alkyl-N(R$^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkynyl, and optionally substituted 5- to 12-membered heterocycle. In some cases, the one or more optional substituents of $R^1$ are independently selected from halogen, —CN, $C_{2-6}$ alkynyl, —C(=NR$^{20}$)N(R$^{20}$)$_2$, and optionally substituted 5- to 12-membered heterocycle. In some cases, the one or more optional substituents of $R^1$ are independently selected from halogen, —C(=NR$^{20}$)N(R$^{20}$)$_2$, and optionally substituted 5- to 12-membered heterocycle. In some cases, the one or more optional substituents of $R^1$ are independently selected from —C(=NR$^{20}$)N(R$^{20}$)$_2$, and optionally substituted 5- to 12-membered heterocycle. In some cases, the one or more optional substituents of $R^1$ are independently selected from optionally substituted 5- to 12-membered heterocycle. In some cases, the one or more optional substituents of $R^1$ are independently selected from a 5-membered heterocycle and 9-membered heterocycle, each of which is optionally substituted independently with one or more $R^{1*}$. In some cases, $R^1$ is substituted with at least one halogen atom and optionally substituted with one or more substituents are independently selected from —CN, $C_{2-6}$ alkynyl, —C(=NR$^{20}$)N (R$^{20}$)$_2$, and 5- to 12-membered heterocycle, wherein the 5- to 12-membered heterocycle is optionally substituted independently with one or more $R^{1*}$. In some cases, the heterocycle has at least one nitrogen atom. In some cases, the heterocycle has at least one oxygen atom. In some cases, the heterocycle has at least one nitrogen atom and at least one oxygen atom. In some cases, heterocycle has at least two heteroatoms. In some cases, the heterocycle has at least three heteroatoms. In some cases, the heterocycle has at least four heteroatoms. In some cases, the heterocycle of the one or more optional substituents of $R^1$ is selected from each of which is optionally substituted with one or more $R^{1*}$. In some cases, the heterocycle of the one or more optional substituents of $R^1$ is selected from which is optionally substituted with one or more $R^{1*}$. In some cases, each $R^{1*}$ is independently selected from halogen, —$OR^{20}$, —$S(O)_2(R^{21})$, —$S(O)_2N(R^{20})_2$, —S(O)N $(R^{20})_2$, —$S(O)R^{20}(=NR^{20})$, —$NR^{20}S(O)_2R^{20}$, —C(O)N $(R^{20})_2$, —$C(O)NR^{20}OR^{20}$, —$N(R^{20})C(O)R^{20}$, —$N(R^{20})C$ $(O)N(R^{20})_2$, —$N(R^{20})C(O)OR^{20}$, —$N(R^{20})_2$, —$C(O)R^{20}$, —$C(O)OR^{20}$, —$OC(O)R^{20}$, —$OC(O)N(R^{20})_2$, —$NO_2$, =O, =$N(R^{20})$, =$NO(R^{20})$, —CN, —NHCN, $C_{1-6}$ alkyl-N $(R^{20})_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, and $C_{1-6}$ alkyl. In some cases, each $R^{1*}$ is independently selected from halogen, —$OR^{20}$, —$S(O)_2(R^{20})$, —$S(O)_2N(R^{20})_2$, —$S(O)N(R^{20})_2$, —$S(O)R^{20}(=NR^{20})$, —$NR^{20}S(O)_2R^{20}$, —$C(O)N(R^{20})_2$, —$C(O)NR^{20}OR^{20}$, —$N(R^{20})C(O)R^{20}$, —$N(R^{20})C(O)N$ $(R^{20})_2$, —$N(R^{20})C(O)OR^{20}$, —$N(R^{20})_2$, —$C(O)R^{20}$, —$C(O)OR^{20}$, —$OC(O)R^{20}$, —$OC(O)N(R^{20})_2$, —$NO_2$, =O, =$N(R^{20})$, =$NO(R^{20})$, —CN, —NHCN, $C_{1-6}$ alkyl-N $(R^{20})_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, and $C_{1-6}$ alkyl. In some cases, each $R^{1*}$ is independently selected from halogen, $C_{1-6}$ alkyl-N$(R^{20})_2$, $C_{1-6}$ aminoalkyl, $C_{1-6}$ hydroxyalkyl, $C_{1-6}$ cyanoalkyl, $C_{1-6}$ haloalkyl, and $C_{1-6}$ alkyl. In some cases, each $R^{1*}$ is independently selected from halogen, $C_{1-6}$ haloalkyl, and $C_{1-6}$ alkyl. In some cases, each $R^{1*}$ is independently selected from halogen, and $C_{1-6}$ alkyl. In some cases, each $R^{1*}$ is independently selected from halogen. In some cases, each $R^{1*}$ is independently selected from $C_{1-6}$ alkyl. In some cases, each $R^{1*}$ is independently selected from —$OR^{20}$. In some cases, each $R^{1*}$ is independently selected from —OH. In some cases, each $R^{1*}$ is independently selected from —OMe. In some cases, the heterocycle of the one or more optional substituents of $R^1$ is selected from In some embodiments, for a compound or salt of Formula (I), Formula (II), or Formula (III), the one or more optional substituents of $R^1$ are independently selected from —$C(=NR^{20})N(R^{20})_2$, and optionally substituted 5- to 12-membered heterocycle. In some cases, the one or more optional substituents of $R^1$ are independently selected from optionally substituted 5- to 12-membered heterocycle. In some cases, the heterocycle is selected from each of which is optionally substituted with one or more $R^{1*}$. In some cases, the one or more optional substituents of $R^1$ is selected from -continued each of which is optionally substituted. In some cases, $R^1$ is selected In some embodiments, for a compound or salt of Formula (I), Formula (II), or Formula (III), each $R^{1*}$ is independently selected from halogen, $-OR^{20}$, $-S(O)_2(R^{20})$, $-S(O)_2N$ $(R^{20})_2$, $-S(O)N(R^{20})_2$, $-S(O)R^{20}(=NR^{20})$, $-NR^{20}S(O)_2$ $R^{20}$, $-C(O)N(R^{20})_2$, $-C(O)NR^{20}OR^{20}$, $-N(R^{20})C(O)$ $R^{20}$, $-N(R^{20})C(O)N(R^{20})_2$, $-N(R^{20})C(O)OR^{20}$, $-N(R^{20})_2$, $-C(O)R^{20}$, $-C(O)OR^{20}$, $-OC(O)R^{20}$, $-OC$ $(O)N(R^{20})_2$, $-NO_2$, $=O$, $=N(R^{20})$, $=NO(R^{20})$, $-CN$, $-NHCN$, $C_{1-6}$ alkyl-$N(R^{20})_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, and $C_{1-6}$ alkyl. In some cases, each $R^{1*}$ is independently selected from halogen, $-OR^{20}$, $-S(O)_2(R^{20})$, $-S(O)_2N(R^{20})_2$, $-S(O)N(R^{20})_2$, $-S(O)R^{20}(=NR^{20})$, $-NR^{20}S(O)_2R^{20}$, $-C(O)N(R^{20})_2$, $-C(O)NR^{20}OR^{20}$, $-N(R^{20})C(O)R^{20}$, $-N(R^{20})C(O)N(R^{20})_2$, $-N(R^{20})C(O)OR^{20}$, $-N(R^{20})_2$, $-C(O)R^{20}$, $-C(O)OR^{20}$, $-OC(O)R^{20}$, $-OC(O)N(R^{20})_2$, $-NO_2$, $=O$, $=N(R^{20})$, $=NO(R^{20})$, $-CN$, $-NHCN$, $C_{1-6}$ alkyl-$N(R^{20})_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, and $C_{1-6}$ alkyl. In some cases, each $R^{1*}$ is independently selected from halogen, $C_{1-6}$ alkyl-$N(R^{20})_2$, $C_{1-6}$ aminoalkyl, $C_{1-6}$ hydroxyalkyl, $C_{1-6}$ cyanoalkyl, $C_{1-6}$ haloalkyl, and $C_{1-6}$ alkyl. In some cases, each $R^{1*}$ is independently selected from halogen, $C_{1-6}$ haloalkyl, and $C_{1-6}$ alkyl. In some cases, each $R^{1*}$ is independently selected from halogen, and $C_{1-6}$ alkyl. In some cases, each $R^{1*}$ is independently selected from halogen. In some cases, each $R^{1*}$ is independently selected from $C_{1-6}$ alkyl.

In some embodiments, for a compound or salt of Formula (I), Formula (II), or Formula (III), $R^1$ is selected from 5- to 15-membered heterocycle (preferably 8- to 10-membered heterocycle or preferably 10-membered heterocycle), each of which are optionally substituted with one or more substituents independently selected from halogen, oxo, $-C(O)$ $N(R^{20})_2$, $-C(O)NR^{20}OR^{20}$, $-N(R^{20})_2$, $-C(O)R^{20}$, $C(O)$ $OR^{20}$, $-SO_2R^{20}$, $-NHCN$, $C_{1-6}$ cyanoalkyl, $C_{1-6}$ alkyl, $C_{1-6}$ alkyl-$N(R^{20})_2$, $C_{2-6}$ alkynyl, and 5- to 12-membered heterocycle (preferably 5- to 9-membered heterocycle), wherein the 5- to 12-membered heterocycle are each optionally substituted independently with one or more $R^{1*}$; each $R^{1*}$ is independently selected from halogen, $C_{1-6}$ haloalkyl, and $C_{1-6}$ alkyl. In some cases, the 8- to 10-membered heterocycle is bicyclic. In some cases, the 10-membered heterocycle is substituted. In some cases, $R^1$ is selected which is optionally substituted. In some cases, $R^1$ is selected

173

-continued

174

-continued

| 175 | 176 |
|---|---|
| -continued | -continued |

In some cases, R$^1$ is selected

In some cases, R$^1$ is

In some embodiments, for a compound or salt of Formula (I), Formula (II), or Formula (III), R$^1$ is selected from 5- to 15-membered heterocycle (preferably 8- to 10-membered heterocycle or preferably 10-membered heterocycle), each of which are optionally substituted with one or more substituents independently selected from halogen, —C(O)N (R$^{20}$)$_2$, —C(O)NR$^{20}$OR$^{20}$, —N(R$^{20}$)$_2$, —C(O)R$^{20}$, —C(O) OR$^{20}$, —NHCN, C$_{1-6}$ cyanoalkyl, C$_{1-6}$ alkyl, C$_{2-6}$ alkynyl, and 5- to 12-membered heterocycle (preferably 5- to 6-membered heterocycle), wherein the 5- to 12-membered heterocycle are each optionally substituted independently with one or more R$^{1*}$; each R$^{1*}$ is independently selected from halogen, C$_{1-6}$ haloalkyl, and C$_{1-6}$ alkyl. In some cases, the 8- to 10-membered heterocycle is bicyclic. In some cases, the 10-membered heterocycle is substituted. In some cases, R$^1$ is selected

177 each of which is optionally substituted. In some cases, R¹ is selected which is optionally substituted. In some cases, R¹ is selected

178

179

-continued

,

,

, and

.

In some cases, R¹ is selected and

.

In some cases, M is selected from O, and NMe. In some cases, M is O. In some cases, M is NMe. In some cases, $R^2$ is selected from -L-N($R^{21}$)$_2$ and -L-heterocycle, optionally substituted with one or more $R^6$. In some cases, Y—$R^2$ is selected from

,

180

-continued

,

, and

.

In some cases, B is selected from an optionally substituted carbocycle. In some cases, B is selected from and

, each of which is optionally substituted. In some cases, B is selected from

,

,

,

,

,

, and

.

In some cases B is

.

In some cases, B is

In some cases, n is 0.

In some embodiments, for a compound or salt of Formula (I), Formula (II), or Formula (III), $R^1$ is selected from a compound in the Examples section. In some cases, Y is selected from a compound in the Examples section. In some cases, L is selected from a compound in the Examples section. In some cases, $R^2$ is selected from a compound in the Examples section. In some cases, B is selected from a compound in the Examples section. In some cases, M is selected from a compound in the Examples section. In some cases, the optional substituents of the heterocycle for $R^1$ is selected from a compound in the Examples section.

In some embodiments, for a compound or salt of Formula (I), Formula (II), or Formula (III), $R^2$ is -L-N$(R^{21})_2$. In some cases, $R^2$ is -L-OR$^{21}$. In some cases, $R^2$ is heterocycle. In some cases, $R^2$ is $C_1$-$C_6$ alkyl. In some cases, $R^2$ is -L-heterocycle. In some cases, $R^2$ is -L-aryl. In some cases, $R^2$ is -L-heteroaryl. In some cases, $R^2$ is -L-cycloalkyl. In some cases, $R^2$ is -L-N$(R^{21})_2$. In some cases, $R^2$ is -L-NHC(=NH)NH$_2$. In some cases, $R^2$ is -L-C(O)N$(R^{21})_2$. In some cases, $R^2$ is -L-$C_1$-$C_6$ haloalkyl. In some cases, $R^2$ is -L-OR$^{21}$. In some cases, $R^2$ is -L-NR$^{21}$C(O)-aryl. In some cases, $R^2$ is -L-COOH. In some cases, $R^2$ is -L-NR$^{21}$S(O)$_2$(R$^{21}$). In some cases, $R^2$ is -L-S(O)$_2$N$(R^{21})_2$. In some cases, $R^2$ is -L-N$(R^{21})$C(O)(OR$^{21}$). In some cases, $R^2$ is -L-OC(O)N$(R^{21})_2$. In some cases, $R^2$ is or -LC(=O)OC$_1$-$C_6$ alkyl. In some cases, the heterocycle, the aryl portion of -L-NR$^{21}$C(O)-aryl, the heterocycle portion of -L-heterocycle, and the cycloalkyl portion of the -L-cycloalkyl are each optionally substituted with one or more $R^6$, and wherein the aryl portion of the -L- aryl and the heteroaryl portion of the -L-heteroaryl are each optionally substituted with one or more $R^7$. In some cases, when Y is a bond, O, or S. $R^2$ is further selected from hydrogen In some embodiments, Formula (I) or Formula (II) is represented by Formula (II*):

Formula (II*)

or a pharmaceutically acceptable salt thereof wherein:

M is selected from 0, and NR$^3$;

$R^3$ is selected from hydrogen, $C_1$-$C_6$ alkyl, and $C_1$-$C_6$ cyanoalkyl;

$R^1$ is selected from a 7- to 10-membered heterocycle, wherein the 7- to 10-membered heterocycle is optionally substituted with one or more substituents independently selected from halogen, —B(OR$^{20}$)$_2$, —OR$^{20}$, SR$^{20}$, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, —C(O)N(R$^{20}$)$_2$, —C(=NR$^{20}$)N(R$^{20}$)$_2$, —C(O)NR$^{20}$OR$^{20}$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =N(R$^{20}$), =NO(R$^{20}$), —CN, —NHCN, $C_{1-6}$ alkyl-N(R$^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$haloalkyl, $C_{1-6}$ alkyl, $C_{2-6}$ alkenyl, $C_{2-6}$ alkynyl, and 5- to 12-membered heterocycle, wherein the 5- to 12-membered heterocycle is optionally substituted independently with one or more $R^{1*}$;

each $R^{1*}$ is independently selected from halogen, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, —C(O)N(R$^{20}$)$_2$, —C(O)NR$^{20}$OR$^{20}$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =N(R$^{20}$), =NO(R$^{20}$), —CN, —NHCN, $C_{1-6}$ alkyl-N(R$^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, and $C_3$-$C_{12}$ carbocycle;

B is selected from $C_6$-$C_{15}$ carbocycle, wherein the $C_6$-$C_{15}$ carbocycle is optionally substituted with one or more substituents independently selected from halogen, $C_1$-$C_3$ alkyl, —B(OR$^{20}$)$_2$, —OR$^{20}$, —C(O)N(R$^{20}$)$_2$, —N(R$^{20}$)$_2$, =O, —CN, —NHCN, $C_{1-6}$ alkyl-N(R$^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{2-6}$ alkenyl, and $C_{2-6}$ alkynyl;

$R^2$ is selected from -L-heterocycle, wherein the heterocycle of -L-heterocycle is optionally substituted with one or more $R^6$;

L is independently selected from a $C_1$-$C_4$ alkylene, wherein the $C_1$-$C_4$ alkylene is optionally substituted with one or more substituents selected from hydroxy, $C_1$-$C_4$ hydroxyalkyl, $C_1$-$C_4$ alkyl; and wherein optionally two substituents on the same carbon atom of L come together to form a $C_3$-$C_6$ carbocycle;

each $R^{20}$ is independently selected from hydrogen; and $C_{1-6}$ alkyl, $C_{3-6}$ carbocycle, and 3- to 6-membered heterocycle, each of which is optionally substituted with one or more substituents independently selected from halogen, —OH, —CN, —NO$_2$, —NH$_2$, —N($C_{1-6}$ alkyl)$_2$, $C_{1-10}$ alkyl, —$C_{1-10}$ haloalkyl, —O—$C_{1-10}$ alkyl, oxo, =NH, $C_{3-12}$ carbocycle, and 3- to 12-membered heterocycle.

In some embodiments, for a compound or salt of Formula (II*), $R^1$ is selected from an optionally substituted 7- to 10-membered spiro heterocycle and optionally substituted 7- to 10-membered fused heterocycle. In some cases, the heterocycle of $R^1$ has at least one nitrogen atom. In some cases, the at least one nitrogen at of the heterocycle of $R^1$ is bound to Formula (II*). In some cases, $R^1$ is selected from an optionally substituted 10-membered spiro heterocycle and optionally substituted 10-membered fused heterocycle. In some cases, the optional one or more substituents of $R^1$ are independently selected from halogen, —OH, —S(O)$_2$(R$^{20}$), —S(O)$_2$N(R$^{20}$)$_2$, —S(O)N(R$^{20}$)$_2$, —S(O)R$^{20}$(=NR$^{20}$), —C(O)N(R$^{20}$)$_2$, —C(=NR$^{20}$)N(R$^{20}$)$_2$, —C(O)OR$^{20}$, —C(O)NHOR$^{20}$, —N(R$^{20}$)$_2$, —C(O)R$^{20}$, —NO$_2$, =O, —CN, $C_{1-6}$ alkyl-N(R$^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkynyl, 5- to 12-membered heterocycle, wherein the 5- to 12-membered heterocycle is optionally substituted with one or more substituents selected from halogen, and $C_{1-6}$ alkyl. In some cases, $R^1$ is selected from which is substituted with one or more substituents independently selected from halogen, —OH, —S(O)$_2$(R$^{20}$), —S(O)$_2$N(R$^{20}$)$_2$, —S(O)N(R$^{20}$)$_2$, —S(O)R$^{20}$(=NR$^{20}$), —C(O)N(R$^{20}$)$_2$, —C(=NR$^{20}$)N(R$^{20}$)$_2$, —C(O)OR$^{20}$, —C(O)NHOR$^{20}$, —N(R$^{20}$)$_2$, —C(O)R$^{20}$, —NO$_2$, =O, —CN, $C_{1-6}$ alkyl-N(R$^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkynyl, 5- to 12-membered heterocycle, wherein the 5- to 12-membered heterocycle is optionally substituted with one or more substituents selected from halogen, and $C_{1-6}$ alkyl. In some cases, $R^1$ is selected from

184

-continued

185

-continued

186

-continued

In some cases, R¹ is selected and

-continued

In some cases, $R^1$ is

In some cases, M is selected from O. In some cases, M is NCH$_2$CH$_3$. In some cases, M is NMe. In some cases, the heterocycle of $R^2$ is a saturated heterocycle. In some cases, $R^6$ of $R^2$ is independently selected at each occurrence from halogen, =CH$_2$, hydroxy, C$_1$-C$_3$ hydroxyalkyl, C$_1$-C$_3$ alkyl, C$_1$-C$_3$ haloalkyl, C$_1$-C$_3$ alkoxy, cyano, and C$_1$-C$_3$ aminoalkyl. In some cases, L of $R^2$ is selected from C$_1$-C$_4$ alkylene and In some cases, $R^2$ is selected from In some cases, B is selected from an optionally substituted C$_9$-C$_{10}$ fused carbocycle. In some cases, B is selected from each of which is optionally substituted. In some cases, B is optionally substituted with one or more substituents independently selected from halogen, oxo, —NH$_2$, C$_1$-C$_3$ alkyl, —B(OH)$_2$, —OH, —O—C$_1$-C$_3$ haloalkyl, —C(O)NH$_2$, —NH$_2$, =O, —CN, C$_{1-6}$ alkoxy, C$_{1-6}$ hydroxyalkyl, and C$_{2-6}$ alkynyl. In some cases, B is optionally substituted with one or more substituents independently selected from halogen. In some cases, B is In some cases, B is In some cases, B is unsubstituted. In some cases, B is substituted.

In some embodiments, for a compound or salt of Formula (II*), $R^1$ is selected from an optionally substituted 7- to 10-membered spiro heterocycle and optionally substituted 7- to 10-membered fused heterocycle. In some cases, $R^1$ is selected from an optionally substituted 10-membered spiro heterocycle and optionally substituted 10-membered fused heterocycle. In some cases, $R^1$ is selected from an optionally substituted 10-membered spiro heterocycle. In some cases, $R^1$ is selected from an optionally substituted 10-membered fused heterocycle. In some cases, the heterocycle of $R^1$ has at least 3 heteroatoms. In some cases, the optional one or more substituents of $R^1$ are independently selected from halogen, —OH, —S(O)$_2$(R$^{20}$), —S(O)N(R$^{20}$)$_2$, —S(O)$_2$N(R$^{20}$)$_2$, —S(O)N(R$^{20}$)$_2$, —S(O)R$^{20}$(=NR$^{20}$), —C(O)N(R$^{20}$)$_2$, —C(=NR$^{20}$)N(R$^{20}$)$_2$, —C(O)OR$^{20}$, —C(O)NHOR$^{20}$, —N(R$^{20}$)$_2$, —C(O)R$^{20}$, —NO$_2$, =O, —CN, C$_{1-6}$ alkyl-N(R$^{20}$)$_2$, C$_{1-6}$ aminoalkyl, C$_{1-6}$ alkoxy, C$_{1-6}$ alkoxyalkyl, C$_{1-6}$ hydroxyalkyl, C$_{1-6}$ cyanoalkyl, C$_{1-6}$ haloalkyl, C$_{1-6}$ alkyl, C$_{2-6}$ alkynyl, 5- to 12-membered heterocycle, wherein the 5- to 12-membered heterocycle is optionally substituted with one or more substituents selected from halogen, and C$_{1-6}$ alkyl. In some cases, $R^1$ is selected from which is substituted with one or more substituents independently selected from halogen, —OH, —S(O)$_2$(R$^{20}$), —S(O)$_2$N(R$^{21}$)$_2$, —S(O)N(R$^{20}$)$_2$, —S(O)R$^{20}$(=NR$^{20}$), —C(O)N(R$^{20}$)$_2$, —C(=NR$^{20}$)N(R$^{20}$)$_2$, —C(O)OR$^{20}$, —C(O)NHOR$^{20}$, —N(R$^{20}$)$_2$, —C(O)R$^{20}$, —NO$_2$, =O, —CN, C$_{1-6}$ alkyl-N(R$^{20}$)$_2$, C$_{1-6}$ aminoalkyl, C$_{1-6}$ alkoxy, C$_{1-6}$ alkoxyalkyl, C$_{1-6}$ hydroxyalkyl, C$_{1-6}$ cyanoalkyl, C$_{1-6}$ haloalkyl, C$_{1-6}$ alkyl, C$_{2-6}$ alkynyl, 5- to 12-membered heterocycle, wherein the 5- to 12-membered heterocycle is optionally substituted with one or more substituents selected from halogen, and C$_{1-6}$ alkyl. In some cases, $R^1$ is selected from

191

192

-continued

In some cases, $R^1$ is selected from and and

In some cases, $R^1$ is

In some cases, M is selected from O. In some cases, M is NMe. In some cases, the heterocycle of $R^2$ is a saturated heterocycle. In some cases, $R^6$ of $R^2$ is independently selected at each occurrence from halogen, $=CH_2$, hydroxy, $C_1$-$C_3$ hydroxyalkyl, $C_1$-$C_3$ alkyl, $C_1$-$C_3$ haloalkyl, $C_1$-$C_3$ alkoxy, cyano, and $C_1$-$C_3$ aminoalkyl. In some cases, L of $R^2$ is selected from $C_1$-$C_4$ alkylene and In some cases, $R^2$ is selected from , and In some cases, B is selected from an optionally substituted $C_9$-$C_{10}$ fused carbocycle. In some cases, B is selected from , and each of which is optionally substituted. In some cases, B is optionally substituted with one or more substituents independently selected from halogen, oxo, —NH$_2$, $C_1$-$C_3$ alkyl, —B(OH)$_2$, —OH, —O—$C_1$-$C_3$ haloalkyl, —C(O)NH$_2$, —NH$_2$, $=$O, —CN, $C_{1-6}$ alkoxy, $C_{1-6}$ hydroxyalkyl, and $C_{2-6}$ alkynyl. In some cases, B is optionally substituted with one or more substituents independently selected from halogen. In some cases, B is In some cases, B is In some cases, B is unsubstituted. In some cases, B is substituted.

In some embodiments, for a compound or salt of Formula (I), Formula (II), Formula (II*), or Formula (III), the heterocycle or carbocycle of $R^1$ is not substituted by $C_{1-6}$ cyanoalkyl. In some embodiments, for a compound or salt of Formula (I), the heterocycle or carbocycle of $R^1$ is not substituted by $C_{1-6}$ cyanoalkyl. In some embodiments, for a compound or salt of Formula (II), the heterocycle or carbocycle of $R^1$ is not substituted by $C_{1-6}$ cyanoalkyl. In some embodiments, for a compound or salt of Formula (III), the heterocycle or carbocycle of $R^1$ is not substituted by $C_{1-6}$ cyanoalkyl.

In some embodiments, for a compound or salt of Formula (I), Formula (II), Formula (II*), or Formula (III), each $R^{20}$ is independently selected from hydrogen; and $C_{1-6}$ alkyl.

In some embodiments, for a compound or salt of Formula (I), Formula (II), Formula (II*), or Formula (III), is not substituted by $C_{1-6}$ cyanoalkyl.

In some embodiments, for a compound or salt of Formula (I), Formula (II), or Formula (III), $R^1$ is not a piperazine. In some cases, $R^1$ is not a substituted piperazine.

In some embodiments, for a compound of Formula (I), wherein the compound is not a Michael acceptor.

In some embodiments, for a compound of Formula (I), the compound or salt does not include an electrophilic substituent.

In some embodiments, for a compound or salt of Formula (I), Formula (II), Formula (II*), or Formula (III), does not contain an electrophile moiety.

In some embodiments, for a compound or salt of Formula (I), Formula (II), Formula (II*), or Formula (III), does not contain a covalent modifier.

In some embodiments, for a compound or salt of Formula (I), Formula (II), Formula (II*), or Formula (III), the one or more optional substituents of $R^1$ are not electrophiles.

Included in the present disclosure are salts, particularly pharmaceutically acceptable salts, of the compounds described herein. The compounds of the present invention that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion, e.g., a halide such as bromide, chloride, or fluoride, particularly bromide.

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, compounds described herein are intended to include all Z-, E- and tautomeric forms as well.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

The compounds disclosed herein, in some embodiments, are used in different enriched isotopic forms, e.g., enriched in the content of $^2H$, $^3H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, compounds described herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2H$), tritium ($^3H$), iodine-125 ($^{125}I$) or carbon-14 ($^{14}C$). Isotopic substitution with $^2H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$ and $^{125}I$ are all contemplated. All isotopic variations of the compounds of the present invention, whether radioactive or not, are encompassed within the scope of the present invention.

In certain embodiments, the compounds disclosed herein have some or all of the $^1H$ atoms replaced with $^2H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Compounds of the present invention also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

The compounds described herein may in some cases exist as diastereomers, enantiomers, or other stereoisomeric forms. Where absolute stereochemistry is not specified, the compounds presented herein include all diastereomeric, enantiomeric, and epimeric forms as well as the appropriate mixtures thereof. Separation of stereoisomers may be performed by chromatography or by forming diastereomers and separating by recrystallization, or chromatography, or any combination thereof. (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis.

The methods and compositions described herein include the use of amorphous forms as well as crystalline forms (also known as polymorphs). The compounds described herein may be in the form of pharmaceutically acceptable salts. As well, in some embodiments, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In certain embodiments, compounds or salts of the compounds may be prodrugs, e.g., wherein a hydroxyl in the parent compound is presented as an ester or a carbonate, or carboxylic acid present in the parent compound is presented as an ester. The term "prodrug" is intended to encompass compounds which, under physiologic conditions, are converted into pharmaceutical agents of the present disclosure. One method for making a prodrug is to include one or more selected moieties which are hydrolyzed under physiologic conditions to reveal the desired molecule. In other embodiments, the prodrug is converted by an enzymatic activity of the host animal such as specific target cells in the host animal. For example, esters or carbonates (e.g., esters or carbonates of alcohols or carboxylic acids and esters of phosphonic acids) are preferred prodrugs of the present disclosure.

Prodrug forms of the herein described compounds, wherein the prodrug is metabolized in vivo to produce a compound as set forth herein are included within the scope of the claims. In some cases, some of the herein-described compounds may be a prodrug for another derivative or active compound.

Prodrugs are often useful because, in some situations, they may be easier to administer than the parent drug. They may, for instance, be bioavailable by oral administration whereas the parent is not. Prodrugs may help enhance the cell permeability of a compound relative to the parent drug. The prodrug may also have improved solubility in pharmaceutical compositions over the parent drug. Prodrugs may be designed as reversible drug derivatives, for use as modifiers to enhance drug transport to site-specific tissues or to increase drug residence inside of a cell.

In some embodiments, the design of a prodrug increases the lipophilicity of the pharmaceutical agent. In some embodiments, the design of a prodrug increases the effective water solubility. See, e.g., Fedorak et al., *Am. J. Physiol.*, 269:G210-218 (1995); McLoed et al., *Gastroenterol*, 106: 405-413 (1994); Hochhaus et al., *Biomed. Chrom.*, 6:283-286 (1992); J. Larsen and H. Bundgaard, *Int. J. Pharmaceutics*, 37, 87 (1987); J. Larsen et al., *Int. J. Pharmaceutics*, 47, 103 (1988); Sinkula et al., *J. Pharm. Sci.*, 64:181-210 (1975); T. Higuchi and V. Stella, *Pro-drugs as Novel Delivery Systems*, Vol. 14 of the A.C.S. Symposium Series; and Edward B. Roche, *Bioreversible Carriers in Drug Design*, American Pharmaceutical Association and Pergamon Press, 1987, all incorporated herein for such disclosure). According to another embodiment, the present disclosure provides methods of producing the above-defined compounds. The compounds may be synthesized using conventional techniques. Advantageously, these compounds are conveniently synthesized from readily available starting materials.

Synthetic chemistry transformations and methodologies useful in synthesizing the compounds described herein are known in the art and include, for example, those described in R. Larock, *Comprehensive Organic Transformations*

(1989); T. W. Greene and P. G. M. Wuts, *Protective Groups in Organic Synthesis,* 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995).

Pharmaceutical Formulations

Provided herein, in certain embodiments, are compositions comprising a therapeutically effective amount of any compound or salt of any one of Formulas (I), (II), (II*), and (III) (also referred to herein as "a pharmaceutical agent").

Pharmaceutical compositions may be formulated using one or more physiologically acceptable carriers including excipients and auxiliaries which facilitate processing of the pharmaceutical agent into preparations which are used pharmaceutically. Proper formulation is dependent upon the route of administration chosen. A summary of pharmaceutical compositions is found, for example, in Remington: The Science and Practice of Pharmacy, Nineteenth Ed (Easton, Pa., Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999).

The compositions and methods of the present disclosure may be utilized to treat an individual in need thereof. In certain embodiments, the individual is a mammal such as a human, or a non-human mammal. When administered to an animal, such as a human, the composition or the pharmaceutical agent, is preferably administered as a pharmaceutical composition comprising, for example, a pharmaceutical agent and a pharmaceutically acceptable carrier or excipient. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration, e.g., routes, such as injection or implantation, that circumvent transport or diffusion through an epithelial barrier, the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule, granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable excipient can contain physiologically acceptable agents that act, for example, to stabilize, increase solubility or to increase the absorption of a compound such as a pharmaceutical agent. Such physiologically acceptable agents include, for example, carbohydrates, such as glucose, sucrose or dextrans, antioxidants, such as ascorbic acid or glutathione, chelating agents, low molecular weight proteins or other stabilizers or excipients.

The choice of a pharmaceutically acceptable excipient, including a physiologically acceptable agent, depends, for example, on the route of administration of the composition. The preparation or pharmaceutical composition can be a self emulsifying drug delivery system or a self microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

A pharmaceutical composition (preparation) can be administered to a subject by any of a number of routes of administration including, for example, orally, for example, drenches as in aqueous or non-aqueous solutions or suspensions, tablets, capsules, including sprinkle capsules and gelatin capsules, boluses, powders, granules, pastes for application to the tongue; absorption through the oral mucosa, e.g., sublingually; anally, rectally or vaginally, for example, as a pessary, cream or foam; parenterally, including intramuscularly, intravenously, subcutaneously or intrathecally as, for example, a sterile solution or suspension; nasally; intraperitoneally; subcutaneously; transdermally, for example, as a patch applied to the skin; and topically, for example, as a cream, ointment or spray applied to the skin, or as an eye drop. The compound may also be formulated for inhalation. In certain embodiments, a compound may be simply dissolved or suspended in sterile water.

A pharmaceutical composition may be a sterile aqueous or non-aqueous solution, suspension or emulsion, e.g., a microemulsion. The excipients described herein are examples and are in no way limiting. An effective amount or therapeutically effective amount refers to an amount of the one or more pharmaceutical agents administered to a subject, either as a single dose or as part of a series of doses, which is effective to produce a desired therapeutic effect.

Subjects may generally be monitored for therapeutic effectiveness using assays and methods suitable for the condition being treated, which assays will be familiar to those having ordinary skill in the art and are described herein. Pharmacokinetics of a pharmaceutical agent, or one or more metabolites thereof, that is administered to a subject may be monitored by determining the level of the pharmaceutical agent or metabolite in a biological fluid, for example, in the blood, blood fraction, e.g., serum, and/or in the urine, and/or other biological sample or biological tissue from the subject. Any method practiced in the art and described herein to detect the agent may be used to measure the level of the pharmaceutical agent or metabolite during a treatment course.

The dose of a pharmaceutical agent described herein for treating a disease or disorder may depend upon the subject's condition, that is, stage of the disease, severity of symptoms caused by the disease, general health status, as well as age, gender, and weight, and other factors apparent to a person skilled in the medical art. Pharmaceutical compositions may be administered in a manner appropriate to the disease to be treated as determined by persons skilled in the medical arts. In addition to the factors described herein and above related to use of pharmaceutical agent for treating a disease or disorder, suitable duration and frequency of administration of the pharmaceutical agent may also be determined or adjusted by such factors as the condition of the patient, the type and severity of the patient's disease, the particular form of the active ingredient, and the method of administration. Optimal doses of an agent may generally be determined using experimental models and/or clinical trials. The optimal dose may depend upon the body mass, weight, or blood volume of the subject. The use of the minimum dose that is sufficient to provide effective therapy is usually preferred. Design and execution of pre-clinical and clinical studies for a pharmaceutical agent, including when administered for prophylactic benefit, described herein are well within the skill of a person skilled in the relevant art. When two or more pharmaceutical agents are administered to treat a disease or disorder, the optimal dose of each pharmaceutical agent may be different, such as less than when either agent is administered alone as a single agent therapy. In certain particular embodiments, two pharmaceutical agents in combination may act synergistically or additively, and either agent may be used in a lesser amount than if administered alone. An amount of a pharmaceutical agent that may be administered per day may be, for example, between about 0.01 mg/kg and 100 mg/kg, e.g., between about 0.1 to 1 mg/kg, between about 1 to 10 mg/kg, between about 10-50 mg/kg, between about 50-100 mg/kg body weight. In other embodiments, the amount of a pharmaceutical agent that may be administered per day is between about 0.01 mg/kg and 1000 mg/kg, between about 100-500 mg/kg, or between about 500-1000 mg/kg body weight. The optimal dose, per day or per course of treatment, may be different for the disease or disorder to be treated and may also vary with the administrative route and therapeutic regimen.

Pharmaceutical compositions comprising a pharmaceutical agent can be formulated in a manner appropriate for the delivery method by using techniques routinely practiced in the art. The composition may be in the form of a solid, e.g., tablet, capsule, semi-solid, e.g., gel, liquid, or gas, e.g., aerosol. In other embodiments, the pharmaceutical composition is administered as a bolus infusion.

Pharmaceutical acceptable excipients are well known in the pharmaceutical art and described, for example, in Rowe et al., Handbook of Pharmaceutical Excipients: A Comprehensive Guide to Uses, Properties, and Safety, 5$^{th}$ Ed., 2006, and in Remington: The Science and Practice of Pharmacy (Gennaro, 21$^{st}$ Ed. Mack Pub. Co., Easton, PA (2005)). Exemplary pharmaceutically acceptable excipients include sterile saline and phosphate buffered saline at physiological pH. Preservatives, stabilizers, dyes, buffers, and the like may be provided in the pharmaceutical composition. In addition, antioxidants and suspending agents may also be used. In general, the type of excipient is selected based on the mode of administration, as well as the chemical composition of the active ingredient(s). Alternatively, compositions described herein may be formulated as a lyophilizate. A composition described herein may be lyophilized or otherwise formulated as a lyophilized product using one or more appropriate excipient solutions for solubilizing and/or diluting the pharmaceutical agent(s) of the composition upon administration. In other embodiments, the pharmaceutical agent may be encapsulated within liposomes using technology known and practiced in the art. In certain particular embodiments, a pharmaceutical agent is not formulated within liposomes for application to a stent that is used for treating highly, though not totally, occluded arteries. Pharmaceutical compositions may be formulated for any appropriate manner of administration described herein and in the art.

A pharmaceutical composition, e.g., for oral administration or for injection, infusion, subcutaneous delivery, intramuscular delivery, intraperitoneal delivery or other method, may be in the form of a liquid. A liquid pharmaceutical composition may include, for example, one or more of the following: a sterile diluent such as water, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral composition can be enclosed in ampoules, disposable syringes or multiple dose vials made of glass or plastic. The use of physiological saline is preferred, and an injectable pharmaceutical composition is preferably sterile. In another embodiment, for treatment of an ophthalmological condition or disease, a liquid pharmaceutical composition may be applied to the eye in the form of eye drops. A liquid pharmaceutical composition may be delivered orally.

For oral formulations, at least one of the pharmaceutical agents described herein can be used alone or in combination with appropriate additives to make tablets, powders, granules or capsules, and if desired, with diluents, buffering agents, moistening agents, preservatives, coloring agents, and flavoring agents. The pharmaceutical agents may be formulated with a buffering agent to provide for protection of the compound from low pH of the gastric environment and/or an enteric coating. A pharmaceutical agent included in a pharmaceutical composition may be formulated for oral delivery with a flavoring agent, e.g., in a liquid, solid or semi-solid formulation and/or with an enteric coating.

A pharmaceutical composition comprising any one of the pharmaceutical agents described herein may be formulated for sustained or slow release, also called timed release or controlled release. Such compositions may generally be prepared using well known technology and administered by, for example, oral, rectal, intradermal, or subcutaneous implantation, or by implantation at the desired target site. Sustained-release formulations may contain the compound dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of pharmaceutical agent contained within a sustained release formulation depends upon the site of implantation, the rate and expected duration of release, and the nature of the condition, disease or disorder to be treated or prevented.

In certain embodiments, the pharmaceutical compositions comprising a pharmaceutical agent are formulated for transdermal, intradermal, or topical administration. The compositions can be administered using a syringe, bandage, transdermal patch, insert, or syringe-like applicator, as a powder/talc or other solid, liquid, spray, aerosol, ointment, foam, cream, gel, paste. This preferably is in the form of a controlled release formulation or sustained release formulation administered topically or injected directly into the skin adjacent to or within the area to be treated, e.g., intradermally or subcutaneously. The active compositions can also be delivered via iontophoresis. Preservatives can be used to prevent the growth of fungi and other microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetypyridinium chloride, chlorobutanol, phenol, phenylethyl alcohol, thimerosal, and combinations thereof.

Pharmaceutical compositions comprising a pharmaceutical agent can be formulated as emulsions for topical application. An emulsion contains one liquid distributed in the body of a second liquid. The emulsion may be an oil-in-water emulsion or a water-in-oil emulsion. Either or both of the oil phase and the aqueous phase may contain one or more surfactants, emulsifiers, emulsion stabilizers, buffers, and other excipients. The oil phase may contain other oily pharmaceutically approved excipients. Suitable surfactants include, but are not limited to, anionic surfactants, non-ionic surfactants, cationic surfactants, and amphoteric surfactants. Compositions for topical application may also include at least one suitable suspending agent, antioxidant, chelating agent, emollient, or humectant.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. Liquid sprays may be delivered from pressurized packs, for example, via a specially shaped closure. Oil-in-water emulsions can also be used in the compositions, patches, bandages and articles. These systems are semisolid emulsions, micro-emulsions, or foam emulsion systems.

In some embodiments, the pharmaceutical agent described herein can be formulated as in inhalant. Inhaled methods can deliver medication directly to the airway. The pharmaceutical agent can be formulated as aerosols, microspheres, liposomes, or nanoparticles. The pharmaceutical agent can be formulated with solvents, gases, nitrates, or any combinations thereof. Compositions described herein are optionally formulated for delivery as a liquid aerosol or inhalable dry powder. Liquid aerosol formulations are optionally nebulized predominantly into particle sizes that can be delivered to the terminal and respiratory bronchioles. Liquid aerosol and inhalable dry powder formulations are preferably delivered throughout the endobronchial tree to the terminal bronchioles and eventually to the parenchymal tissue.

Aerosolized formulations described herein are optionally delivered using an aerosol forming device, such as a jet, vibrating porous plate or ultrasonic nebulizer, preferably selected to allow the formation of aerosol particles having with a mass medium average diameter predominantly between 1 to 5μ. Further, the formulation preferably has balanced osmolarity ionic strength and chloride concentration, and the smallest aerosolizable volume able to deliver effective dose of the pharmaceutical agent. Additionally, the aerosolized formulation preferably does not impair negatively the functionality of the airways and does not cause undesirable side effects.

Aerosolization devices suitable for administration of aerosol formulations described herein include, for example, jet, vibrating porous plate, ultrasonic nebulizers and energized dry powder inhalers, that are able to nebulize the formulation into aerosol particle size predominantly in the size range from 1-5μ. Predominantly in this application means that at least 70% but preferably more than 90% of all generated aerosol particles are within 1-5μ range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AeroNeb™ and AeroDose™ vibrating porous plate nebulizers (AeroGen, Inc., Sunnyvale, California), Sidestream® nebulizers (Medic-Aid Ltd., West Sussex, England), Pan LC® and Pari LC Star® jet nebulizers (Pari Respiratory Equipment, Inc., Richmond, Virginia), and Aerosonic™ (DeVilbiss Medizinische Produkte (Deutschland) GmbH, Heiden, Germany) and UltraAire® (Omron Healthcare, Inc., Vernon Hills, Illinois) ultrasonic nebulizers.

In some embodiments, the pharmaceutical agent(s) can be formulated with oleaginous bases or ointments to form a semisolid composition with a desired shape. In addition to the pharmaceutical agent, these semisolid compositions can contain dissolved and/or suspended bactericidal agents, preservatives and/or a buffer system. A petrolatum component that may be included may be any paraffin ranging in viscosity from mineral oil that incorporates isobutylene, colloidal silica, or stearate salts to paraffin waxes. Absorption bases can be used with an oleaginous system. Additives may include cholesterol, lanolin (lanolin derivatives, beeswax, fatty alcohols, wool wax alcohols, low HLB (hydrophobel-lipophobe balance) emulsifiers, and assorted ionic and non-ionic surfactants, singularly or in combination.

Controlled or sustained release transdermal or topical formulations can be achieved by the addition of time-release additives, such as polymeric structures, matrices, that are available in the art. For example, the compositions may be administered through use of hot-melt extrusion articles, such as bioadhesive hot-melt extruded film. The formulation can comprise a cross-linked polycarboxylic acid polymer formulation. A cross-linking agent may be present in an amount that provides adequate adhesion to allow the system to remain attached to target epithelial or endothelial cell surfaces for a sufficient time to allow the desired release of the compound.

An insert, transdermal patch, bandage or article can comprise a mixture or coating of polymers that provide release of the pharmaceutical agents at a constant rate over a prolonged period of time. In some embodiments, the article, transdermal patch or insert comprises water-soluble pore forming agents, such as polyethylene glycol (PEG) that can be mixed with water insoluble polymers to increase the durability of the insert and to prolong the release of the active ingredients.

Transdermal devices (inserts, patches, bandages) may also comprise a water insoluble polymer. Rate controlling polymers may be useful for administration to sites where pH change can be used to effect release. These rate controlling polymers can be applied using a continuous coating film during the process of spraying and drying with the active compound. In one embodiment, the coating formulation is used to coat pellets comprising the active ingredients that are compressed to form a solid, biodegradable insert.

A polymer formulation can also be utilized to provide controlled or sustained release. Bioadhesive polymers described in the art may be used. By way of example, a sustained-release gel and the compound may be incorporated in a polymeric matrix, such as a hydrophobic polymer matrix. Examples of a polymeric matrix include a microparticle. The microparticles can be microspheres, and the core may be of a different material than the polymeric shell. Alternatively, the polymer may be cast as a thin slab or film, a powder produced by grinding or other standard techniques, or a gel such as a hydrogel. The polymer can also be in the form of a coating or part of a bandage, stent, catheter, vascular graft, or other device to facilitate delivery of the pharmaceutical agent. The matrices can be formed by solvent evaporation, spray drying, solvent extraction and other methods known to those skilled in the art.

Kits with unit doses of one or more of the agents described herein, usually in oral or injectable doses, are provided. Such kits may include a container containing the unit dose, an informational package insert describing the use and attendant benefits of the drugs in treating disease, and optionally an appliance or device for delivery of the composition.

Methods of Treatment

In an aspect, the present disclosure provides compounds that inhibit KRas G12 mutants. In some cases, the method may inhibit KRas G12 mutants activity in a cell. In some cases, inhibiting KRas G12 mutants activity in a cell may include contacting the cell in which inhibition of KRas G12 mutants activity is desired with an effective amount of a compound of Formula (I), Formula (II), Formula (II*), Formula (III), or pharmaceutical compositions containing the compound or pharmaceutically acceptable salt thereof. In some cases, the contacting is in vitro. In some cases, the contacting is in vivo. As used herein, the term "contacting" refers to the bringing together of indicated moieties in an in vitro system or an in vivo system. For example, "contacting" a KRas G12D and/or other G12 mutants with a compound provided herein includes the administration of a compound provided herein to an individual or patient, such as a human, having KRas G12D and/or other G12 mutants, as well as, for example, introducing a compound provided herein into a sample containing a cellular or purified preparation containing the KRas G12D and/or other G12 mutants. In some cases, a cell in which inhibition of KRas G12D and/or other G12 mutants activity is desired is contacted with an effective amount of a compound of Formula (I) or Formula (II) or Formula (II*) or Formula (III) or pharmaceutically acceptable salt thereof to negatively modulate the activity of KRas G12D and/or other G12 mutants. In some cases, by negatively modulating the activity of KRas G12D and/or other G12 mutants, the methods described herein are designed to inhibit undesired cellular proliferation resulting from enhanced KRas G12D and/or other G12 mutants activity within the cell. The cells may be contacted in a single dose or multiple doses in accordance with a particular treatment regimen to effect the desired negative modulation of KRas G12D and/or other G12 mutants. The ability of compounds to bind KRas G12D and/or other G12 mutants may be monitored in vitro using well known methods.

In some embodiments, the inhibitory activity of exemplary compounds in cells may be monitored, for example, by measuring the inhibition of KRas G12D and/or other G12 mutants activity of the amount of phosphorylated ERK.

In another aspect, methods of treating cancer in a patient in need thereof, comprising administering to said patient a therapeutically effective amount of a compound of Formula (I), Formula (II), Formula (II*), Formula (III), or a pharmaceutically acceptable salt thereof, or a pharmaceutical composition comprising the compound or pharmaceutically acceptable salt thereof are provided. The compositions and methods provided herein may be used for the treatment of a KRas G12D and/or other G12 mutants-associated cancer in a patient in need thereof, comprising administering to the patient a therapeutically effective amount of a compound of Formula (I), Formula (II), Formula (II*), Formula (III), a pharmaceutically acceptable salt any one thereof, or a pharmaceutical composition comprising the compound or pharmaceutically acceptable salt thereof are provided. In some cases, the KRas G12D and/or other G12 mutants associated cancer is lung cancer. The compositions and methods provided herein may be used for the treatment of a wide variety of cancers including tumors such as lung, prostate, breast, brain, skin, cervical carcinomas, testicular carcinomas, etc. More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. In some cases, the cancer is non-small cell lung cancer, small cell lung cancer, colorectal cancer, rectal cancer or pancreatic cancer. In some cases, the cancer is non-small cell lung cancer. In some cases, the concentration and route of administration to the patient will vary depending on the cancer to be treated. The compounds, pharmaceutically acceptable salts thereof and pharmaceutical compositions comprising such compounds and salts also may be co-administered with other anti-neoplastic compounds, e.g., chemotherapy, or used in combination with other treatments, such as radiation or surgical intervention, either as an adjuvant prior to surgery or post-operatively.

Also provided herein is a compound of Formula (I), Formula (II), Formula (II*), Formula (III), or a pharmaceutically acceptable salt thereof, or a pharmaceutical composition thereof as defined herein for use in therapy.

Also provided herein is a compound of Formula (I), Formula (II), Formula (II*), Formula (III), or a pharmaceutically acceptable salt thereof, or a pharmaceutical composition thereof as defined herein for use in the treatment of cancer.

Also provided herein is a compound of Formula (I), Formula (II), Formula (II*), Formula (III), or a pharmaceutically acceptable salt thereof, or a pharmaceutical composition thereof for use in the inhibition of KRas G12D and/or other G12 mutants.

Also provided herein is a compound of Formula (I), Formula (II), Formula (III), or a pharmaceutically acceptable salt thereof, or a pharmaceutical composition thereof as defined herein, for use in the treatment of a KRas G12D and/or other G12 mutants-associated disease or disorder.

Also provided herein is the use of a compound of Formula (I), Formula (II), Formula (II*), Formula (III), or a pharmaceutically acceptable salt thereof, as defined herein in the manufacture of a medicament for the treatment of cancer.

Also provided herein is a use of a compound of Formula (I), Formula (II), Formula (II*), Formula (III), or a pharmaceutically acceptable salt thereof, as defined herein in the manufacture of a medicament for the inhibition of activity of KRas G12D and/or other G12 mutants.

Also provided herein is the use of a compound of Formula (I), Formula (II), Formula (III), or a pharmaceutically acceptable salt thereof, as defined herein, in the manufacture of a medicament for the treatment of a KRas G12D and/or other G12 mutants-associated disease or disorder.

In another aspect, the present disclosure provides a method for treating cancer in a patient in need thereof, the method comprising (a) determining that cancer is associated with a KRas G12D mutation and/or other G12 mutants (e.g., a KRas G12D and/or other G12 mutants-associated cancer) (e.g., as determined using a regulatory agency-approved, e.g., FDA-approved, assay or kit); and (b) administering to the patient a therapeutically effective amount of a compound of Formula (I), Formula (II), Formula (II*), Formula (III), or a pharmaceutically acceptable salt thereof, or a pharmaceutical composition thereof.

The compounds described herein can be used in the preparation of medicaments for the prevention or treatment of diseases or conditions. In addition, a method for treating any of the diseases or conditions described herein in a subject in need of such treatment, involves administration of pharmaceutical compositions containing at least one compound described herein, or a pharmaceutically acceptable salt, pharmaceutically acceptable prodrug, or pharmaceutically acceptable solvate thereof, in therapeutically effective amounts to said subject.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be determined in a manner recognized in the field according to the particular circumstances surrounding the case, including, e.g., the specific agent being administered, the route of administration, the condition being treated, and the subject or host being treated. In general, however, doses employed for adult human treatment will typically be in the range of about 0.02-about 5000 mg per day, in some embodiments, about 1-about 1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers.

Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and ED$_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the ED$_{50}$ with minimal toxicity. The dosage may vary within this range depending upon the dosage form employed and the route of administration utilized.

In certain embodiments, the invention provides a method of treating or preventing a disease, state or condition in a patient in need thereof comprising administering to the patient an effective amount of a compound of any one of embodiments of the invention or a pharmaceutically acceptable salt thereof. The disease, state or condition may be selected from a group as described elsewhere herein.

Bifunctional Compounds

In some embodiments, compounds herein can adopt to selectively eliminate an over activated KRas signaling which is induced by KRas mutations by directly binding with the mutated KRas protein, either by stabilizing its GDP bound form (the inactive form) or by blocking the interaction between GTP bound form and its downstream target protein. In some embodiments, another way is to hijack the protein degradation mechanism in a cell and leverage E3 ligases' (like VHL, CRBN or IAPs) substrate specificity through a bi-functional molecule called Proteolysis targeting chimera (PROTAC) (Winter G E, Buckley D L, Paulk J, Roberts J M, Souza A, Dhe-Paganon S, Bradner J E. DRUG DEVELOPMENT. Phthalimide conjugation as a strategy for in vivo target protein degradation. Science. 2015 Jun. 19; 348 (6241): 1376-81), which can bind with both mutated KRas protein and E3 ligase, create interactions between those two proteins and induce KRas degradation.

Disclosed herein is a bifunctional compound composed of a target protein (i.e., KRAS G12D)-binding moiety and an E3 ubiquitin ligase-binding moiety, which may induce proteasome-mediated degradation of selected proteins. In some embodiments, the bifunctional compound comprises a target protein (i.e., KRAS G12D)-binding moiety and an E3 ubiquitin ligase-binding moiety known in the art. In some embodiments, disclosed herein is the use of the compound disclosed herein in the preparation of degrading a target protein compound by using chemical modification of the compound disclosed herein. In some cases, the target protein-binding moiety is derived from a compound of Formula (I), Formula (II), Formula (II*), or Formula (III).

Preparation of Compounds

The compounds of the present disclosure can generally be prepared in a number of ways well known to those skilled in the art of organic synthesis. By way of example, compounds of the present disclosure can be synthesized using the methods described herein, together with synthetic methods known in the art of synthetic organic chemistry, or variations thereof as appreciated by those skilled in the art. The compounds of the present disclosure may be prepared as described in the schemes and examples described elsewhere herein.

The following examples further illustrate the invention but, of course, should not be construed as in any way limiting its scope

EXAMPLES

The following synthetic schemes are provided for purposes of illustration, not limitation. The following examples illustrate the various methods of making compounds described herein. It is understood that one skilled in the art may be able to make these compounds by similar methods or by combining other methods known to one skilled in the art. It is also understood that one skilled in the art would be able to make, in a similar manner as described below by using the appropriate starting materials and modifying the synthetic route as needed. In general, starting materials and reagents can be obtained from commercial vendors or synthesized according to sources known to those skilled in the art or prepared as described herein.

The present disclosure provides processes for preparing the compounds described herein (described in greater detail below).

General Schemes

Scheme IA

IA-a

IA-b

IA-c

IA-d

I

211

Treatment of $R_1$ with methyl 2,4-dichloro-6-methylpyrimidine-5-carboxylate in the presence of a base such as DIEA in DCM can afford IA-a, which can be deprotonated with LDA or LiHMDS at −78° C. in THF. IA-b can be formed by addition of a solution of a ketone in THF at −78° C. and the reaction is quenched at −78° C. Ester IA-b can be reduced by DIBAL or LiAlH$_4$ to diol IA-c, which can be cyclized into IA-d via Mitsunobu reaction or in the presence of BuLi and TsCl in THF at −78° C. Compound I can be prepared via Pd mediated coupling reactions or in the presence of a base such as NaH or LiHMDS.

Scheme IB

IB-a

IB-b

IB-c

IB-d

IB-e

212

-continued

I

Ethyl 4-chloro-6-methyl-2-(methylthio)pyrimidine-5-carboxylate can be deprotonated with LDA or LiHMDS at −78° C. in THF. IB-a can be formed by addition of a solution of a ketone in THF at −78° C. and the reaction is quenched at −78° C. Ester IB-a can be reduced by DIBAL or LiAlH$_4$ to diol IB-b, which can be cyclized into IB-c via Mitsunobu reaction or in the presence of BuLi and TsCl in THF at −78° C. Treatment of R1 with IB-c can afford IB-d in the presence of a base such as DIEA in DCM can afford IB-d, which can be oxidized to sulfone IB-e. Compound I can be prepared via Pd mediated coupling reactions or in the presence of a base such as NaH or LiHMDS.

Scheme IIA

IIA-a

IIA-b

IIA-c

IIA-d

-continued

IIA-e

II

Treatment of t-Butyl-sulfinimade and a ketone in the presence of Ti(OEt)$_4$ can afford IIA-a. A solution of IIA-a in THF can be added to a solution of IA-a, deprotonated with LDA or LiHMDS at −78° C. in THF, and the reaction can be quenched at −78° C. to afford IIA-b. Ester IIA-b can be reduced by DIBAL or LiAlH$_4$ to IIA-c, which can be cyclized into IIA-d via a sequence of removal of sufinimade under HCl, chorination of OH and cyclization in the presence of a base such as NaOH (ref. Garcia, D.; Moreno, B.; Soler, T.; Foubelo, F.; Yus, M. Tetrahedron Lett. 2009, 50, 4710). R$_3$ of IIA-e can be introduced via reductive amination or alkylation. Compound II can be prepared via Pd mediated coupling reactions or in the presence of a base such as NaH or LiHMDS.

Scheme IIB

IIA-a ⟶

IIB-a

IIB-b

IIB-c

-continued

IIB-d

IIB-e

IIB-f

II

Ethyl 4-chloro-6-methyl-2-(methylthio)pyrimidine-5-carboxylate can be deprotonated with LDA or LiHMDS at −78° C. in THF. IIB-a can be formed by addition of a solution of IIA-a in THF at −78° C. and the reaction is quenched at −78° C. Ester IIB-a can be reduced by DIBAL or LiAlH$_4$ to diol IIB-b, which can be cyclized into IIB-c as described in Scheme IIA above. R$_3$ of IIB-d can be introduced via reductive amination or alkylation. Treatment of R1 with IIB-d can afford IIB-e in the presence of a base such as DIEA in DCM. IIB-e can be oxidized to sulfoxide IIB-f, which can be converted to II in the presence of a base such as NaH or LiHMDS.

Example 1: Exemplary Synthesis of 4'-(azepan-1-yl)-4-chloro-2'-(((2R,7aS)-2-fluorotetrahydro-1H-pyrrolizin-7a(5H)-yl)methoxy)-2,3,5',8'-tetrahydrospiro[indene-1,7'-pyrano[4,3-d]pyrimidine] (Compound 1)

1a

-continued

1b

1c

1d

1

Step 1: To a solution of methyl 2,4-dichloro-6-methylpy-rimidine-5-carboxylate (1.0 g, 4.52 mmol, 1.0 eq) in ACN (7 mL) was added DIPEA (1.17 g, 9.05 mmol, 2.0 eq) and azepane (449 mg, 4.52 mmol, 1.0 eq) at 20° C. Then the reaction was stirred at 20° C. for 2 hrs. TLC showed that the reaction was completed. The reaction was concentrated under vacuum. The residue was poured into water (20 mL). The aqueous phase was extracted with EtOAc (5 mL*2). The combined organic layers were washed with brine (10 mL), dried over $Na_2SO_4$, filtered and concentrated under vacuum. The residue was purified by column chromatography on silica gel (PE:EtOAc=10:1) to give compound 1a (1.1 g, 3.88 mmol, 85.7% yield) as a yellow solid. $^1H$ NMR (400 MHz, $CDCl_3$) δ 3.88 (s, 3H), 3.49-3.52 (m, 4H), 2.36 (s, 3H), 1.75-1.85 (m, 4H), 1.50-1.60 (m, 4H).

Step 2: To a solution of LDA (2 M, 2.11 mL, 1.2 eq) in THF (30 mL) was added compound 1a (1.0 g, 3.52 mmol, 1.0 eq) at –60° C. The mixture was stirred at –60° C. for 30 mins. 4-Chloro-2,3-dihydro-TH-inden-1-one (587 mg, 3.52 mmol, 1.0 eq) was added at –60° C. The mixture was stirred at –60° C. for 1 hr. The reaction mixture was quenched by addition HCl (5%, 50 mL) at 0° C., and then extracted with EtOAc (20 mL*2). The combined organic layers were washed with brine (20 mL), dried over $Na_2SO_4$, filtered, and concentrated under reduced pressure. The residue was puri-fied by column chromatography on silica gel (PE:EtOAc=5: 1) to give compound 1b (0.5 g, 1.20 mmol, 33.9% yield) as a yellow solid. LCMS calcld for $C_{22}H_{25}Cl_2N_3O_3$ $(M+H)^+$ m/z=450.1; found 450.1. $^1H$ NMR (400 MHz, $CDCl_3$) (7.22 (d, J=8.0 Hz, 1H), 7.13 (t, J=7.6 Hz, 1H), 7.03 (d, J=7.6 Hz, 1H), 6.06 (s, 1H), 3.69 (s, 3H), 3.47-3.54 (m, 4H), 3.08-3.11 (m, 2H), 2.76-2.99 (m, 2H), 2.22-2.26 (m, 2H), 1.70-1.80 (m, 4H), 1.45-1.60 (m, 4H).

Step 3: To a solution of compound 1b (490 mg, 1.09 mmol, 1.0 eq) in DCM (5 mL) was added DIBAL-H (1 M, 3.26 mL, 3.0 eq) at 0° C. Then the reaction was stirred at 0° C. for 1 hr. The reaction mixture was quenched by $H_2O$ (20 ml) at 25° C. The mixture was extracted with DCM (10 mL*2). The combined organic layers were washed with brine (15 mL), dried over $Na_2SO_4$, filtered, and concentrated under reduced pressure. The residue was purified by column chromatography on silica gel (PE/EtOAc=80/1 to 8/1 to give compound 1c (200 mg, 474 umol, 43.5% yield) as white solid. LCMS calcld for $C_{21}H_{25}Cl_2N_3O_2$ $(M+H)^+$ m/z=422.1; found 422.1. $^1H$ NMR (400 MHz, $CD_3OD$) (7.25 (d, J=8.0 Hz, 1H), 7.19 (t, J=7.6 Hz, 1H), 7.09 (d, J=7.6 Hz, 1H), 4.40-4.44 (m, 1H), 4.29-4.32 (m, 1H), 3.78-3.81 (m, 4H), 3.25-3.26 (m, 1H), 2.96-3.03 (m, 2H), 2.84-2.88 (m, 1H), 2.56-2.59 (m, 1H), 2.01-2.04 (m, 1H), 1.75-1.90 (m, 4H), 1.55-1.65 (m, 4H).

Step 4: To a solution of compound 1c (200 mg, 474 umol, 1 eq) in THF (10 mL) was added $PPh_3$ (149 mg, 568 umol, 1.2 eq) and DIAD (115 mg, 568 umol, 1.2 eq) at 0° C. under $N_2$. Then the reaction was stirred at 0° C. for 2 hrs under $N_2$. LCMS showed the reaction was completed. The reaction mixture was concentrated under reduced pressure. The resi-due was purified by column chromatography on silica gel (PE:EtOAc=20:1) to give compound 1d (100 mg, 247 umol, 52.2% yield) as a yellow solid. $C_{21}H_{23}Cl_2N_3O$ $(M+H)^+$ m/z=404.1; found 404.1. $^1H$ NMR (400 MHz, $CDCl_3$) δ 7.31 (d, J=8.0 Hz, 1H), 7.17 (t, J=7.6 Hz, 1H), 7.12 (d, J=7.6 Hz, 1H), 4.65-4.71 (m, 1H), 4.51-4.53 (m, 1H), 3.50-3.65 (m, 4H), 3.07-3.17 (m, 3H), 2.96-3.00 (m, 1H), 2.36-2.38 (m, 1H), 2.15-2.20 (m, 1H), 1.70-1.75 (m, 4H), 1.50-1.65 (m, 4H).

Step 5: To a solution of ((2R,7aS)-2-fluorotetrahydro-1H-pyrrolizin-7a(5H)-yl)methanol (37.8 mg, 237 umol, 1.2 eq) in THF (2 mL) was added NaH (15.8 mg, 396 umol, 60% purity, 2.0 eq) at 0° C. The reaction was stirred at 0° C. for 30 min. Then a solution of compound 1d (80 mg, 198 umol, 1.0 eq) in THF (0.5 mL) was added to the above solution at 0° C. The reaction was continued to stir at 60° C. for 8 hrs. LC-MS showed 11% of starting material remained and 52.9% of desired compound was detected. The reaction was quenched with $H_2O$ (10 mL) at 0° C. The aqueous phase was extracted with EtOAc (5 mL*2). The combined organic phase was washed with brine (5 mL), dried over $Na_2SO_4$, filtered, and concentrated under vacuum. The residue was purified by prep-TLC ($SiO_2$, DCM:MeOH=6:1) to give 4'-(azepan-1-yl)-4-chloro-2'-(((2R,7aS)-2-fluorotetrahydro-1H-pyrrolizin-7a(5H)-yl)methoxy)-2,3,5',8'-tetrahydrospiro[indene-1,7'-pyrano[4,3-d]pyrimidine](compound 1, 11.0 mg, 20.8 umol, 10.5% yield) as yellow solid. $C_{29}H_{36}ClFN_4O_2$ (M+H)$^+$ m/z=526.25; found 527.2. $^1$H NMR (400 MHz, CDCl$_3$) δ 7.10 (d, J=8.0 Hz, 1H), 6.90-7.00 (m, 2H), 5.00-5.40 (m, 1H), 4.50-4.53 (m, 1H), 4.32-4.36 (m, 1H), 3.93-3.95 (m, 1H), 3.79-3.81 (m, 1H), 3.38-3.41 (m, 4H), 3.05-3.15 (m, 2H), 2.90-3.00 (m, 2H), 2.85-2.87 (m, 1H), 2.70-2.80 (m, 2H), 2.15-2.25 (m, 1H), 1.95-2.10 (m, 4H), 1.50-1.80 (m, 6H), 1.30-1.50 (m, 6H).

Example 2. Exemplary Synthesis of 4'-((1R,5S)-3,8-diazabicyclo[3.2.1]octan-3-yl)-4-chloro-2'-(((2R,7aS)-2-fluorotetrahydro-1H-pyrrolizin-7a(5H)-yl)methoxy)-2,3,5',8'-tetrahydrospiro[indene-1,7'-pyrano[4,3-d]pyrimidine](Compound 2)

-continued

2c

2d

2e

2a

2b

2

Step 1. Synthesis of tert-butyl 3-(2-chloro-5-methoxycarbonyl-6-methyl-pyrimidin-4-yl)-3,8-diaza-bicyclo[3.2.1]octane-8-carboxylate (2a). To a solution of methyl 2,4-dichloro-6-methyl-pyrimidine-5-carboxylate (200.0 mg, 0.9 mmol) in MeCN (4 mL) was added a mixture of DIEA (233.88 mg, 1.81 mmol) and tert-butyl 3,8-diazabicyclo[3.2.1]octane-3-carboxylate (192.08 mg, 0.9 mmol) in DMF (1 mL) at 0° C. The reaction mixture was stirred at 0° C. for 30 min under Ar. The solution was diluted with EtOAc (5 ml) and washed with $H_2O$ (5 ml×3) and brine (5 ml). The organic phase was dried over $Na_2SO_4$ and concentrated. The residue was purified by silica gel chromatography (eluting with EtOAc:PE=1:7) to give tert-butyl 3-(2-chloro-5-methoxycarbonyl-6-methyl-pyrimidin-4-yl)-3,8-diaza-bicyclo[3.2.1]octane-8-carboxylate (2a, 280 mg, 0.71 mmol, 78% yield) as a white solid. LCMS (ESI): m/z calcld for $C_{18}H_{25}ClN_4O_4{}^+H$: 397.87, found: 397.2.

Step 2. Synthesis of tert-butyl 3-[2-[[(2R,8S)-2-fluoro-1,2,3,5,6,7-hexahydropyrrolizin-8-yl]methoxy]-5-methoxycarbonyl-6-methyl-pyrimidin-4-yl]-3,8-diazabicyclo[3.2.1]octane-8-carboxylate (2b). To a degassed solution of tert-butyl 3-(2-chloro-5-methoxycarbonyl-6-methyl-pyrimidin-4-yl)-3,8-diaza-bicyclo[3.2.1]octane-8-carboxylate (2a, 400.0 mg, 1.01 mmol) in toluene (15 mL) were added [(2R,8S)-2-fluoro-1,2,3,5,6,7-hexahydropyrrolizin-8-yl]methanol (332.67 mg, 2.09 mmol), Ruphos (97.5 mg, 0.21 mmol), $Pd_2(dba)_3$ (95.71 mg, 0.1 mmol) and $Cs_2CO_3$ (851.06 mg, 2.61 mmol). The degassed mixture was stirred at 110° C. for 16 h under Ar. The reaction mixture was concentrated under reduced pressure to give crude product which was purified by silica gel chromatography column (EtOAc:PE=1:1 to DCM:MeOH=10:1) to obtain tert-butyl 3-[2-[[(2R,8S)-2-fluoro-1,2,3,5,6,7-hexahydropyrrolizin-8-yl]methoxy]-5-methoxycarbonyl-6-methyl-pyrimidin-4-yl]-3,8-diazabicyclo[3.2.1]octane-8-carboxylate (2b, 460 mg, 0.88 mmol, 88% yield) as a sticky brown solid. LCMS (ESI): m/z calcld for $C_{26}H_{38}FN_5O_5{}^+H$: 520.2, found: 520.2.

Step 3. Synthesis of tert-butyl 3-[6-[(4-chloro-1-hydroxy-indan-1-yl)methyl]-2-[[(2R,8S)-2-fluoro-1,2,3,5,6,7-hexahydropyrrolizin-8-yl]methoxy]-5-methoxycarbonyl-pyrimidin-4-yl]-3,8-diazabicyclo[3.2.1]octane-8-carboxylate (2c). To a solution of tert-butyl 3-[5-methoxycarbonyl-6-methyl-2-[[(2R,8S)-2-fluoro-1,2,3,5,6,7-hexahydropyrrolizin-8-yl]methoxy]pyrimidin-4-yl]-3,8-diazabicyclo[3.2.1]octane-8-carboxylate (2b, 150.0 mg, 0.29 mmol) in THF (15 mL) at −70° C. was added LDA (0.72 mL, 1.44 mmol, 2 mol/L in THF) dropwise. The reaction mixture was stirred between −70° C. to −20° C. for 1.5 h under Ar. Then a solution of 4-chloroindan-1-one (240.47 mg, 1.44 mmol) in THF (3 mL) was added dropwise to the above resulting solution at −70° C. The reaction mixture was stirred between −70° C. to 0° C. for 3 h under Ar. The reaction mixture was quenched by aqueous $NH_4Cl$ solution at −50° C., and extracted with EtOAc, washed with brine, dried over anhydrous $Na_2SO_4$, filtered and concentrated under vacuo to give the crude product which was purified on prep-TLC (DCM:MeOH=10:1) to give tert-butyl 3-[6-[(4-chloro-1-hydroxy-indan-1-yl)methyl]-2-[[(2R,8S)-2-fluoro-1,2,3,5,6,7-hexahydropyrrolizin-8-yl]methoxy]-5-methoxycarbonyl-pyrimidin-4-yl]-3,8-diazabicyclo[3.2.1]octane-8-carboxylate (2c, 75 mg, 0.11 mmol, 38% yield) as a light yellow sticky solid. LCMS (ESI): m/z calcld for $C_{35}H_{45}ClFN_5O_6{}^+H$: 686.1, found: 686.2.

Step 4. Synthesis of tert-butyl 3-[6-[(4-chloro-1-hydroxy-indan-1-yl)methyl]-2-[[(2R,8S)-2-fluoro-1,2,3,5,6,7-hexahydropyrrolizin-8-yl]methoxy]-5-(hydroxymethyl)pyrimidin-4-yl]-3,8-diazabicyclo[3.2.1]octane-8-carboxylate (2d).

To a degassed solution of tert-butyl 3-[6-[(4-chloro-1-hydroxy-indan-1-yl)methyl]-5-methoxycarbonyl-2-[[(2R,8S)-2-fluoro-1,2,3,5,6,7-hexahydropyrrolizin-8-yl]methoxy]pyrimidin-4-yl]-3,8-diazabicyclo[3.2.1]octane-8-carboxylate (2c, 120.0 mg, 0.17 mmol) in anhydrous THF (8 mL) at −70° C. was added dropwise DIBAL-H (2.91 mL, 4.37 mmol) at −70° C. The mixture was warmed to 0° C. naturally and stirred for 16 h under Ar. The reaction mixture was quenched by aqueous $NH_4Cl$ solution at 0° C., and extracted with EtOAc, washed with brine, dried over anhydrous $Na_2SO_4$, filtered and concentrated under vacuo to give crude product which was purified on Pre-TLC (DCM:MeOH=10:1) to give tert-butyl 3-[6-[(4-chloro-1-hydroxy-indan-1-yl)methyl]-2-[[(2R,8S)-2-fluoro-1,2,3,5,6,7-hexahydropyrrolizin-8-yl]methoxy]-5-(hydroxymethyl)pyrimidin-4-yl]-3,8-diazabicyclo[3.2.1]octane-8-carboxylate (2d, 60 mg, 0.091 mmol, 52.1% yield) as a colorless sticky solid. LCMS (ESI): m/z calcld for $C_{34}H_{45}ClFN_5O_5{}^+H$: 658.3, found: 658.3.

Step 5. Synthesis of tert-butyl 3-[4'-chloro-2-[[(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]-3,8-diazabicyclo[3.2.1]octane-8-carboxylate (2e). To a degassed mixture of tert-butyl 3-[6-[(4-chloro-1-hydroxy-indan-1-yl)methyl]-2-[[(2R,8S)-2-fluoro-1,2,3,5,6,7-hexahydropyrrolizin-8-yl]methoxy]-5-(hydroxymethyl)pyrimidin-4-yl]-3,8-diazabicyclo[3.2.1]octane-8-carboxylate (2d, 70.0 mg, 0.11 mmol) and DIPEA (0.04 mL, 0.23 mmol) in anhydrous THF (5 mL) at 0° C. was added MsCl (60.92 mg, 0.53 mmol) dropwise. The degassed mixture was warmed to 10° C. and stirred for 16 h under Ar. The mixture was quenched by aqueous $NaHCO_3$ solution and extracted with EtOAc, washed with water and brine. The organics was dried over anhydrous $Na_2SO_4$, filtered and concentrated under vacuo. The residue was purified by Pre-TLC (DCM:MeOH=15:1) to give crude product (2e, 65 mg) as a sticky brown solid. LCMS (ESI): m/z calcld for $C_{34}H_{43}ClFN_5O_4{}^+H$: 640.3, found: 640.2.

Step 6. Synthesis of 4'-((1R,5S)-3,8-diazabicyclo[3.2.1]octan-3-yl)-4-chloro-2'-(((2R,7aS)-2-fluorotetrahydro-1H-pyrrolizin-7a(5H)-yl)methoxy)-2,3,5',8'-tetrahydrospiro[indene-1,7'-pyrano[4,3-d]pyrimidine](2). To a solution of tert-butyl 3-[4'-chloro-2-[[(2R,8S)-2-fluoro-1,2,3,5,6,7-hexahydro-pyrrolizin-8-yl]methoxy]spiro[5,8-dihydropyrano[4,3-d]pyrimidine-7,1'-indane]-4-yl]-3,8-diazabicyclo[3.2.1]octane-8-carboxylate (64.0 mg, 0.1 mmol) in DCM (1.5 mL) was added TFA (2.95 mL, 39.77 mmol). The mixture was stirred at rt. for 20 min. The mixture was concentrated under vacuo to afford the crude product which was purified by Prep-HPLC (eluted with $CH_3CN$ in $H_2O$ (0.1% TFA) from 5.0% to 95%). Then the preparation solution is treated with 1N hydrochloric acid to replace TFA to give 4'-chloro-4-(3,8-diazabicyclo[3.2.1]octan-3-yl)-2-[[(2R,8S)-2-fluoro-1,2,3,5,6,7-hexahydropyrrolizin-8-yl]methoxy]spiro[5,8-dihydropyrano[4,3-d]pyrimidine-7,1'-indane];dihydrochloride (12.32 mg, 0.0141 mmol, 14% yield) as a white solid. LCMS (ESI): m/z calcld for $C_{29}H_{35}ClFN_5O_2{+}H$: 540.2, found: 540.2. $^1H$ NMR (400 MHz, $CD_3OD$) δ 7.37 (m, 3H), 5.59 (dd, J=52.0, 13.6 Hz, 1H), 5.07 (d, J=13.9 Hz, 1H), 4.69-4.35 (m, 3H), 4.35-4.06 (m, 3H), 3.90 (m, 6H), 3.42 (s, 2H), 3.26-3.07 (m, 2H), 3.00 (s, 1H), 2.88-1.99 (m, 12H).

221

Example 3. Exemplary Synthesis of (4'-[(1R,5S)-3,
8-diazabicyclo[3.2.1]octan-3-yl]-2'-[[(2R,8S)-2-
fluoro-1,2,3,5,6,7-hexahydropyrrolizin-8-yl]
methoxy]spiro[2H-indeno[1,2-c]pyrazole-4,7'-5,8-
dihydropyrano[4,3-d]pyrimidine](Compound 3)

3a

3f

3b     3c

3g

3d

3h

2a

3

3e

Step 1. Synthesis of 4-hydrazono-2,4-dihydroindeno[1,2-
c]pyrazole (3a). To a solution of indane-1,3-dione (5.00 g,
34.2 mmol, 1.0 eq) in THF (50 mL) was added DMF-DMA
(4.15 g, 34.9 mmol, 1.02 eq) dropwise. The resulting mix-
ture was stirred at room temperature for 1 h. TLC showed
SM was consumed. The mixture was concentrated in vacuo
to afford crude 2-(dimethylaminomethylene)indane-1,3-dione (3a. 6.87 g, 34.1 mmol, crude) as a black solid, which was used in next step directly without further purification. LCMS calcld for $C_{12}H_{12}NO_2$ (M+H)$^+$ m/z=202.1; found: 202.1.

Step 2. Synthesis of 4-hydrazono-2,4-dihydroindeno[1,2-c]pyrazole (3b). To a solution of 2-(dimethylaminomethylene)indane-1,3-dione (3a, 6.87 g, 34.1 mmol, crude) in AcOH (10.0 mL) was added hydrazine hydrate (10.0 mL, 205 mmol, 5.0 eq) drop wise. Then the mixture was stirred at 90° C. for 16 h and the solvent was removed in vacuo. The residue was suspended in water (30 mL), and the solid was collected by filtration, washed with water (90 mL) and aq. NaHCO₃ (90 mL), and dried in vacuo to afford 4-hydrazono-2,4-dihydroindeno[1,2-c]pyrazole (3b, 5.23 g, 30.7 mmol, 89.9% yield over two steps) as a yellow solid. LCMS calcld for $C_{10}H_9N_4$(M+H) m/z=185.0; found: 185.0.

Step 3. Synthesis of 2H-indeno[1,2-c]pyrazol-4-one (3c). A solution of NaIO₄ (9.59 g, 44.8 mmol, 2.0 eq) in water (100 mL) and EtOAc (100 mL) was stirred at room temperature for 5 min. Then 2,4-dihydroindeno[1,2-c]pyrazol-4-yldiazene (3b, 4.13 g, 22.4 mmol) was added, the resulting mixture was stirred at room temperature for 2 h. The mixture was extracted with EtOAc (100 mL*3), the combined organic phase was concentrated and purified by flash chromatography (silica gel, eluted with EtOAc in PE 0 to 30%) to give the 2H-indeno[1,2-c]pyrazol-4-one (3c, 1.74 g, 10.2 mmol, 45.6% yield) as a white solid. LCMS calcld for $C_{10}H_7N_2O$ (M+H) m/z=171.0; found: 171.0.

Step 4. Synthesis of 2-(2-trimethylsilylethoxymethyl)indeno[1,2-c]pyrazol-4-one (3d). To a solution of 2H-indeno[1,2-c]pyrazol-4-one (800 mg, 4.70 mmol, 1.0 eq) in DMF (12 mL) was added NaH (3c, 169 mg, 7.05 mmol, 1.5 eq) at 0° C., the mixture was stirred at the same temperature for 30 min, then SEMCl (1.17 g, 7.05 mmol, 1.5 eq) was added. The resulting mixture was allowed to warm to room temperature and stirred for 1 h. The reaction was quenched with NH₄Cl (aq) and extracted with EtOAc (50 mL*3), the combined organic phase was concentrated and purified by flash chromatography (silica gel, eluted with EtOAc in PE 0 to 25%) to give a mixture of 2-(2-trimethylsilylethoxymethyl)indeno[1,2-c]pyrazol-4-one and its regioisomer (not shown) (3d, 1.38 g, 4.60 mmol, 97% yield) as a yellow solid. LCMS calcld for $C_{16}H_{21}N_2O_2Si$ (M+H) m/z=301.1; found: 301.0.

Step 5. Synthesis of tert-butyl (1S,5R)-3-[2-chloro-6-[[4-hydroxy-2-(2-trimethylsilylethoxymethyl)indeno[1,2-c]pyrazol-4-yl]methyl]-5-methoxycarbonyl-pyrimidin-4-yl]-3,8-diazabicyclo[3.2.1]octane-8-carboxylate (3e). To a solution of tert-butyl rac-(1S,5R)-3-(2-chloro-5-methoxycarbonyl-6-methyl-pyrimidin-4-yl)-3,8-diazabicyclo[3.2.1]octane-8-carboxylate (2a, 800 mg, 2.02 mmol, 1.0 eq) in dry THF (6 mL) was added LDA (1.21 mL, 2.42 mmol, 1.2 eq, 2M in THF/n-heptane) dropwise at −70° C. under N₂, the mixture was stirred at the same temperature for 0.5 h, then 2-(2-trimethylsilylethoxymethyl)indeno[1,2-c]pyrazol-4-one (3d, 667 mg, 2.22 mmol, 1.1 eq) in dry THF (6 mL) was added drop wise. The mixture was stirred at the same temperature for 1 h and then quenched with NH₄Cl (aq.). The residue was extracted with EtOAc (20 mL*3) and the organic phase was concentrated in vacuum. The residue was purified by flash chromatography (silica gel, Eluant with EtOAc in PE 0 to 50%) to afford tert-butyl (1S,5R)-3-[2-chloro-6-[[4-hydroxy-2-(2-trimethylsilylethoxymethyl)indeno[1,2-c]pyrazol-4-yl]methyl]-5-methoxycarbonyl-pyrimidin-4-yl]-3,8-diazabicyclo[3.2.1]octane-8-carboxylate (3e, 1.20 g, 1.72 mmol, 85.4% yield) as a white solid. LCMS calcld for $C_{34}H_{46}ClN_6O_6Si$ (M+H)$^+$ m/z=697.3; found: 697.5.

Step 6. Synthesis of 4'-((1R,5S)-3,8-diazabicyclo[3.2.1] octan-3-yl)-2'-(((2R,7aS)-2-fluorotetrahydro-1H-pyrrolizin-7a(5H)-yl)methoxy)-5',8'-dihydro-2H-spiro[indeno[1,2-c] pyrazole-4,7'-pyrano[4,3-d]pyrimidine](3f). To a solution of tert-butyl (1R,5S)-3-[2-chloro-6-[[4-hydroxy-2-(2-trimethylsilylethoxymethyl)indeno[1,2-c]pyrazol-4-yl]methyl]-5-methoxycarbonyl-pyrimidin-4-yl]-3,8-diazabicyclo[3.2.1] octane-8-carboxylate (3e, 670 mg, 0.960 mmol, 1.0 eq) in dry DCM (5 mL) was added DIBAL-H (2.56 mL, 3.84 mmol, 4.0 eq, 1.5 M in toluene) at 0° C. under N₂, the resulting mixture was stirred at same temperature for 1 h and then quenched with H₂O. The mixture was extracted with EtOAc (50 mL*3) and the organic phase was concentrated and purified by flash column chromatography (silica gel, eluting EtOAc in PE 0 to 50%). The desired fractions were concentrated to dryness in vacuo to afford tert-butyl (1R, 5S)-3-[2-chloro-5-(hydroxymethyl)-6-[[4-hydroxy-2-(2-trimethylsilylethoxymethyl)indeno[1,2-c]pyrazol-4-yl] methyl]pyrimidin-4-yl]-3,8-diazabicyclo[3.2.1]octane-8-carboxylate (3f, 320 mg, 0.478 mmol, 49.8% yield). LCMS calcld for $C_{33}H_{46}ClN_6O_5Si$ (M+H)$^+$ m/z=669.3; found: 669.2.

Step 7. Synthesis of tert-butyl (1R,5S)-3-[2-chloro-2'-(2-trimethylsilylethoxymethyl)spiro[5,8-dihydropyrano[4,3-d] pyrimidine-7,4'-indeno[1,2-c]pyrazole]-4-yl]-3,8-diazabicyclo[3.2.1]octane-8-carboxylate (3g). To a solution of tert-butyl (1R,5S)-3-[2-chloro-5-(hydroxymethyl)-6-[[4-hydroxy-2-(2-trimethylsilylethoxymethyl)indeno[1,2-c] pyrazol-4-yl]methyl]pyrimidin-4-yl]-3,8-diazabicyclo [3.2.1]octane-8-carboxylate (3f, 67.0 mg, 0.100 mmol, 1.0 eq) in dry THF (1.50 mL) was added n-BuLi (0.042 mL, 0.11 mmol, 1.05 eq, 2.5 M in THF) under N₂ at −78° C., then stirred for 1 h. A solution of TsCl (21.0 mg, 0.110 mmol, 1.05 eq) in dry THF (1.50 mL) was added slowly, the mixture was allowed warm to 0° C. and stirred for 30 min, then it was cooled to −78° C. and n-BuLi (0.042 mL, 0.11 mmol, 1.05 eq, 2.5 M in THF) was added. After it was stirred at the same temperature for 10 min, the mixture was allowed to warm to room temperature and stirred for 1 h. Then it was quenched by the addition of H₂O (2 mL) and extracted with EtOAc (10 mL*3), the organic phase was concentrated and purified by flash column chromatography (silica gel, eluting EtOAc in PE 0 to 25%). The desired fractions were concentrated to dryness in vacuo to afford tert-butyl (1R,5S)-3-[2-chloro-2'-(2-trimethylsilylethoxymethyl)spiro[5,8-dihydropyrano[4,3-d]pyrimidine-7,4'-indeno[1,2-c]pyrazole]-4-yl]-3,8-diazabicyclo[3.2.1]octane-8-carboxylate (3 g, 49.0 mg, 0.0752 mmol, 75.2% yield) as a yellow oil. LCMS calcld for $C_{33}H_{44}ClN_6O_4Si$ (M+H)$^+$ m/z=651.3; found: 651.3.

Step 8. Synthesis of tert-butyl (1R,5S)-3-[2-[[(2R,8S)-2-fluoro-1,2,3,5,6,7-hexahydropyrrolizin-8-yl]methoxy]-2'-(2-trimethylsilylethoxymethyl)spiro[5,8-dihydropyrano[4,3-d]pyrimidine-7,4'-indeno[1,2-c]pyrazole]-4-yl]-3,8-diazabicyclo[3.2.1]octane-8-carboxylate (3h). A mixture of [(2R,8S)-2-fluoro-1,2,3,5,6,7-hexahydropyrrolizin-8-yl] methanol (35.9 mg, 0.230 mmol, 3.0 eq), Pd₂(dba)₃ (6.89 mg, 0.0100 mmol, 0.1 eq), Ruphos (7.02 mg, 0.0200 mmol, 0.2 eq), Cs₂CO₃ (738 mg, 0.230 mmol, 3.0 eq) and tert-butyl (1R,5S)-3-[2-chloro-2'-(2-trimethylsilylethoxymethyl)spiro [5,8-dihydropyrano[4,3-d]pyrimidine-7,4'-indeno[1,2-c] pyrazole]-4-yl]-3,8-diazabicyclo[3.2.1]octane-8-carboxylate (3 g, 49.0 mg, 0.0800 mmol, 1.0 eq) in Toluene (3 mL) was charged with N₂ for 3 times. The resulting mixture was heated to 110° C. for 16 h. The resulting solution was cooled to rt and filtered, and then the filtrate was concentrated and purified by flash column chromatography (silica gel, eluting MeOH in DCM 0 to 10%). The desired fractions were concentrated to dryness in vacuo to afford tert-butyl (1R, 5S)-3-[2-[[rac-(2R,8S)-2-fluoro-1,2,3,5,6,7-hexahydropyr-rolizin-8-yl]methoxy]-2'-(2-trimethylsilylethoxymethyl) spiro[5,8-dihydropyrano[4,3-d]pyrimidine-7,4'-indeno[1,2-c]pyrazole]-4-yl]-3,8-diazabicyclo[3.2.1]octane-8-carboxylate (3h, 51.0 mg, 0.0659 mmol, 87.6% yield) as a yellow solid. LCMS calcld for $C_{41}H_{57}FN_7O_5Si(M+H)^+$ m/z=774.4; found: 774.6.

Step 9. Synthesis of 4'-((1R,5S)-3,8-diazabicyclo[3.2.1]octan-3-yl)-2'-(((2R,7aS)-2-fluorotetrahydro-1H-pyrrolizin-7a(5H)-yl)methoxy)-5',8'-dihydro-2H-spiro[indeno[1,2-c]pyrazole-4,7'-pyrano[4,3-d]pyrimidine](3). To a solution of tert-butyl rac-(1R,5S)-3-[2-[[rac-(2R,8S)-2-fluoro-1,2,3,5,6,7-hexahydropyrrolizin-8-yl]methoxy]-2'-(2-trimethylsily-lethoxymethyl)spiro[5,8-dihydropyrano[4,3-d]pyrimidine-7,4'-indeno[1,2-c]pyrazole]-4-yl]-3,8-diazabicyclo[3.2.1]octane-8-carboxylate (51.0 mg, 0.0700 mmol, 1.0 eq) in MeCN (1 mL) was added HCl in dioxane (1.00 mL, 4.00 mmol, 4 M). The resulting mixture was stirred at room temperature for 5 h. The solvent was removed by $N_2$ and the residue was purified by Prep-HPLC on a C18 column (5 uM, 50×150 mm) with mobile phase: $H_2O$ (0.1% $NH_4HCO_3$)/MeOH at flow rate: 35 mL/min to afford 4'-[(1R,5S)-3,8-diazabicyclo[3.2.1]octan-3-yl]-2'-[(2R,8S)-2-fluoro-1,2,3,5,6,7-hexahydropyrrolizin-8-yl]methoxy]spiro[2H-indeno[1,2-c]pyrazole-4,7'-5,8-dihydropyrano[4,3-d]pyrimidine] (7.28 mg, 0.0134 mmol, 20.3% yield) as a yellow solid. LCMS calcld for $C_{30}H_{35}FN_7O_2$ $(M+H)^+$ m/z=544.3; found: 544.5. $^1$H NMR (400 MHz, CD$_3$OD) δ 7.63 (d, J=7.2 Hz, 1H), 7.53 (d, J=7.6 Hz, 1H), 7.40-7.47 (m, 2H), 7.36 (t, J=7.2 Hz, 1H), 5.28 (d, J=52.0 Hz, 1H), 4.97 (d, J=13.6 Hz, 1H), 4.79-4.82 (m, 1H), 4.03-4.21 (m, 3H), 3.73 (d, J=12.4 Hz, 1H), 3.59 (s, 2H), 3.50 (d, J=17.6 Hz, 1H), 3.40 (d, J=12.8 Hz, 1H), 3.11-3.26 (m, 4H), 2.95-3.05 (m, 1H), 2.63 (d, J=17.6 Hz, 1H), 1.78-2.13 (m, 10H).

Compound 4. 1-[7'-bromo-2-[[(2R,8S)-2-fluoro-1,2,3,5,6,7-hexahydropyrrolizin-8-yl]methoxy]spiro[5,8-dihydropyrano[4,3-d]pyrimidine-7,1'-tetralin]-4-1]azepan-4-ol Compound 4 was prepared similar to that of Ex. 1 as a dihydrochloride salt. LCMS calcld for $C_{30}H_{38}BrFN_4O_3$ $(M+H)^+$ m/z=601.2; found: 601.2. $^1$H NMR (400 MHz, CD$_3$OD) δ 7.65-7.57 (m, 1H), 7.41-7.32 (m, 1H), 7.13-7.04

(m, 1H), 5.69-5.20 (m, 1H), 5.09-5.00 (m, 1H), 4.85-4.72 (m, 3H), 4.04-3.78 (m, 8H), 3.51-3.39 (m, 1H), 3.19-3.98 (m, 2H), 2.86-2.58 (m, 4H), 2.50-2.41 (m, 1H), 2.41-1.67 (m, 13H).

Compound 5. 4-(azepan-1-yl)-5'-bromo-2-[[(2R, 8S)-2-fluoro-1,2,3,5,6,7-hexahydropyrrolizin-8-yl] methoxy]spiro[5,8-dihydropyrano[4,3-d]pyrimidine-7,1'-tetralin]

Compound 5 was prepared similar to that of Ex. 1 as a TFA salt. LCMS (ESI): m/z calcld for $C_{30}H_{38}BrFN_4O_2{}^+H$: 587.2, found: 587.2. $^1$H NMR (400 MHz, CD$_3$OD) δ 7.55 (d, J=7.6 Hz, 1H), 7.50 (d, J=6.9 Hz, 1H), 7.14 (t, J=7.2 Hz, 1H), 5.59 (d, J=51.6 Hz, 1H), 4.99 (d, J=12.0 Hz, 1H), 4.74 (d, J=14.8 Hz, 3H), 3.89 (dd, J=38.2, 24.9 Hz, 6H), 3.54-3.37 (m, 1H), 3.17 (dd, J=18.1, 6.4 Hz, 1H), 3.06 (d, J=18.2 Hz, 1H), 2.92 (d, J=17.4 Hz, 1H), 2.81-2.73 (m, 1H), 2.64 (d, J=19.6 Hz, 2H), 2.45 (s, 1H), 2.35 (s, 2H), 2.19 (d, J=16.4 Hz, 3H), 2.06-1.81 (m, 6H), 1.65 (d, J=28.8 Hz, 4H).

Compound 6. 1-[4'-chloro-2-[[rac-(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]azepan-4-ol Compound 6 was prepared similar to that of Ex. 1 as a dihydrochloride salt. LCMS (ESI): m/z calcld for $C_{29}H_{37}ClFN_4O_3{}^+H$: 543.4, found: 543.4. H NMR (400 MHz, CD$_3$OD) δ 7.37 (d, J=8.8 Hz, 1H), 7.32-7.22 (m, 2H), 5.59 (d, J=51.4 Hz, 1H), 4.94-4.89 (m, 1H), 4.82-4.72 (m, 2H), 4.64 (dd, J=14.9, 5.4 Hz, 1H), 4.09-3.73 (m, 8H),

227

3.52-3.41 (m, 1H), 3.20-3.07 (m, 3H), 3.05-2.94 (m, 1H), 2.77-2.58 (m, 3H), 2.49-2.29 (m, 5H), 2.27-2.07 (m, 3H), 1.97-1.74 (m, 4H).

Compound 7 & compound 8. 4-(azepan-1-yl)-2-[[(2R,8S)-2-fluoro-1,2,3,5,6,7-hexahydropyrrolizin-8-yl]methoxy]spiro[5,8-dihydropyrano[4,3-d]pyrimidine-7,4'-tetralin]-6'-ol, isomer 1 & 2 isomer 1 & 2

Compound 7 and compound 8 were prepared similar to that of Ex. 1 separated by reverse phase HPLC. LCMS (ESI): m/z calcld for $C_{30}H_{39}FN_4O_3$ $^+$H: 523.1, found: 523.1. $^1$H NMR (400 MHz, CD$_3$OD, isomer 1, compound 7) δ 6.96 (d, J=8.3 Hz, 1H), 6.79 (d, J=2.3 Hz, 1H), 6.67 (dd, J=8.3, 2.4 Hz, 1H), 5.29 (d, J=54.4 Hz, 1H), 4.81 (d, 1H), 4.58 (d, 1H), 4.17 (d, 1H), 4.08 (d, 1H), 3.65 (t, 4H), 3.30-3.13 (m, 3H), 3.01 (dd, 2H), 2.94-2.82 (m, 1H), 2.74 (qd, 2H), 2.26 (ddd, 2H), 2.13-1.93 (m, 6H), 1.91-1.71 (m, 6H), 1.59 (d, J=3.3 Hz, 4H). $^1$H NMR (400 MHz, CD$_3$OD, isomer 2, compound 8) δ 6.94 (d, J=8.3 Hz, 1H), 6.77 (d, J=2.3 Hz, 1H), 6.65 (dd, J=8.3, 2.4 Hz, 1H), 5.27 (d, J=54.4 Hz, 1H), 4.79 (d, J=14.2 Hz, 1H), 4.56 (d, J=14.1 Hz, 1H), 4.15 (d, J=10.4 Hz, 1H), 4.06 (d, J=10.4 Hz, 1H), 3.72-3.56 (m, 4H), 3.29-3.13 (m, 3H), 3.04-2.94 (m, 2H), 2.85 (d, J=17.8 Hz, 1H), 2.80-2.63 (m, 2H), 2.32-1.77 (m, 14H), 1.65-1.51 (m, 4H).

Compound 9. 4-(azepan-1-yl)-7'-chloro-2-[[rac-(2R,8S)-2-fluoro-1,2,3,5,6,7-hexahydropyrrolizin-8-yl]methoxy]spiro[5,8-dihydropyrano[4,3-d]primidine-7,3'-indane]-4'-ol Compound 9 was prepared similar to that of Ex. 1 as a TFA salt. LCMS m/z calcld for $C_{29}H_{36}ClFN_4O_3$$^+$H: 543.1,

228 found: 543.2. $^1$H NMR (400 MHz, CD$_3$OD) δ 7.13 (d, J=8.6 Hz, 1H), 6.66 (d, J=8.6 Hz, 1H), 5.57 (d, J=51.3 Hz, 1H), 4.75 (d, J=14.1 Hz, 1H), 4.70-4.50 (m, 3H), 4.00-3.74 (m, 5H), 3.75-3.63 (m, 2H), 3.52-3.44 (m, 1H), 3.38-3.34 (m, 1H), 3.09-2.96 (m, 2H), 2.90-2.86 (m, 1H), 2.71-2.63 (m, 1H), 2.62-2.56 (m, 1H), 2.45-2.31 (m, 4H), 2.27-2.13 (m, 2H), 2.00-1.75 (m, 4H), 1.69-1.48 (m, 4H). $^{19}$F NMR (377 MHz, CD$_3$OD) δ −174.17.

Compound 10. 5'-bromo-4-(3,8-diazabicyclo[3.2.1]octan-3-yl)-2-[[(2R,8S)-2-fluoro-1,2,3,5,6,7-hexahydropyrrolizin-8-yl]methoxy]spiro[5,8-dihydropyrano[4,3-d]pyrimidine-7,1'-tetralin]

Compound 10 was prepared similar to that of Ex. 2 as a dihydrochloride salt. LCMS (ESI): m/z calcld for $C_{30}H_{37}BrFN_5O_2$$^+$H: 598.2, found: 598.2. [1]H NMR (400 MHz, CD$_3$OD) δ 7.57 (d, J=7.9 Hz, 1H), 7.52 (d, J=7.8 Hz, 1H), 7.17 (t, J=7.8 Hz, 1H), 5.62 (d, J=52.1 Hz, 1H), 5.01 (dd, 1H), 4.86 (s, 2H), 4.73 (s, 1H), 4.70 (s, 1H), 4.40 (t, 1H), 4.25 (s, 2H), 4.04-3.84 (m, 4H), 3.73 (d, 1H), 3.47 (td, 1H), 3.24 (dd, 1H), 3.15 (d, 1H), 2.94 (d, 1H), 2.87-2.75 (m, 2H), 2.74-2.59 (m, 2H), 2.53 (d, 1H), 2.39 (dd, 2H), 2.27 (s, 2H), 2.15 (s, 5H), 2.03 (t, 1H), 1.88 (s, 1H).

Compound 11. 1-[7'-fluoro-2-[[(2R,8S)-2-fluoro-1,2,3,5,6,7-hexahydropyrrolizin-8-yl]methoxy]spiro[5,8-dihydropyrano[4,3-d]pyrimidine-7,1'-tetralin]-4-yl]azepan-4-ol;dihydrochloride Compound 11 was prepared similar to that of Ex. 1 as a dihydrochloride salt. LCMS m/z calcld for $C_{30}H_{38}F2N_4O_3{}^+H$ 541.2, found 541.2. $^1H$ NMR (400 MHz, $CD_3OD$) δ 7.22-7.12 (m, 2H), 6.98 (dd, J=9.7, 7.1 Hz, 1H), 5.59 (d, J=51.7 Hz, 1H), 5.04 (d, J=14.2 Hz, 1H), 4.77 (d, J=9.4 Hz, 3H), 4.07-3.72 (m, 8H), 3.47 (s, 1H), 3.09 (dt, J=34.3, 14.2 Hz, 2H), 2.83 (s, 2H), 2.61 (s, 2H), 2.45 (s, 1H), 2.35 (s, 2H), 2.15 (d, 6H), 1.89 (dd, 6H).

Compound 12. 4-(azepan-1-yl)-2-[[(2R,8S)-2-fluoro-1,2,3,5,6,7-hexahydropyrrolizin-8-yl]methoxy]spiro[5,8-dihydropyrano[4,3-d]pyrimidine-7,1'-tetralin]

Compound 12 was prepared similarly to that of Ex. 1 as a dihydrochloride salt. LCMS (ESI): m/z calcld for $C_{30}H_{39}FN_4O_2{}^+H$; 507.2, found; 507.2. $^1H$ NMR (400 MHz, $CD_3OD$) δ 7.32 (d, J=7.7 Hz, 1H), 7.13 (d, J=7.4 Hz, 1H), 7.07 (t, J=7.0 Hz, 2H), 5.49 (d, J=51.3 Hz, 1H), 4.90-4.84 (m, 1H), 4.69-4.62 (m, 2H), 4.62-4.53 (m, 1H), 3.92-3.72 (m, 6H), 3.40-3.31 (m, 1H), 3.12-3.00 (m, 1H), 2.95-2.89 (m, 1H), 2.82-2.69 (m, 2H), 2.63-2.55 (m, 1H), 2.54-2.48 (m, 1H), 2.41-2.31 (m, 1H), 2.30-2.19 (m, 2H), 2.14-2.06 (m, 2H), 2.00-1.91 (m, 2H), 1.84-1.45 (m, 10H).

Example 4. Exemplary Synthesis of 1-[7'-amino-2-[[(2R,8S)-2-fluoro-1,2,3,5,6,7-hexahydropyrrolizin-8-yl]methoxy]spiro[5,8-dihydropyrano[4,3-d]pyrimidine-7,1'-tetralin]-4-yl]azepan-4-ol (Compound 13)

Compound 4

-continued

13a

Compound 13

Step 1. Synthesis of 1-[7'-(benzhydrylideneamino)-2-[[(2R,8S)-2-fluoro-1,2,3,5,6,7-hexahydropyrrolizin-8-yl]methoxy]spiro[5,8-dihydropyrano[4,3-d]pyrimidine-7,1'-tetralin]-4-yl]azepan-4-ol (13a). The solution of $Pd_2dba_3$ (4.57 mg, 0.0 mmol), diphenylmethanimine (18.08 mg, 0.1 mmol), t-BuONa (9.58 mg, 0.1 mmol), BINAP (2.11 mg, 0.01 mmol) and 1-[7'-bromo-2-[[(2R,8S)-2-fluoro-1,2,3,5,6,7-hexahydropyrrolizin-8-yl]methoxy]spiro[5,8-dihydropyrano[4,3-d]pyrimidine-7,1'-tetralin]-4-yl]azepan-4-ol (4, 30. mg, 0.05 mmol) in Toluene (2 mL) was stirred at 100° C. under $N_2$ for 6 h. The mixture was concentrated and purified by prep-HPLC (eluted with $CH_3CN$ in $H_2O$ (0.1% NH4HCO3) from 5% to 95%) to obtain 1-[7'-(benzhydrylideneamino)-2-[[(2R,8S)-2-fluoro-1,2,3,5,6,7-hexahydropyrrolizin-8-yl]methoxy]spiro[5,8-dihydropyrano[4,3-d]pyrimidine-7,1'-tetralin]-4-yl]azepan-4-ol (13a, 10 mg, 0.014 mmol, 29% yield) as a brown solid. LCMS calcld for $C_{43}H_{48}FN_5O_3$ (M+H)$^+$ m/z=702.8; found; 702.4.

Step 2. Synthesis of 1-[7'-amino-2-[[(2R,8S)-2-fluoro-1,2,3,5,6,7-hexahydropyrrolizin-8-yl]methoxy]spiro[5,8-dihydropyrano[4,3-d]pyrimidine-7,1'-tetralin]-4-yl]azepan-4-ol (13). The solution of $NH_2NHOH \cdot HCl$ (2.97 mg, 0.04 mmol), AcONa (3.5 mg, 0.04 mmol) and 1-[7'-(benzhydrylideneamino)-2-[[(2R,8S)-2-fluoro-1,2,3,5,6,7-hexahydropyrrolizin-8-yl]methoxy]spiro[5,8-dihydropyrano[4,3-d]pyrimidine-7,1'-tetralin]-4-yl]azepan-4-ol (13a, 10. mg, 0.01 mmol) in Methanol (1 mL) was stirred at 25° C. under $N_2$ for 16 h. The reaction was concentrated to get the crude, which was then purified by prep-HPLC (eluted with $CH_3CN$ in $H_2O$ (0.1% TFA) from 5% to 95%), then exchanged with HCl before lyophilization to give 1-[7'-amino-2-[[(2R,8S)-2-fluoro-1,2,3,5,6,7-hexahydropyrrolizin-8-yl]methoxy]

spiro[5,8-dihydropyrano[4,3-d]pyrimidine-7,1'-tetralin]-4-yl]azepan-4-ol;dihydrochloride (13, 2.43 mg, 0.0037 mmol, 26.3% yield) as yellow solid. LCMS calcld for $C_{30}H_{40}FN_5O_3$ (M+H)$^+$ m/z=538.3; found; 538.3. $^1$H NMR (400 MHz, CD$_3$OD) δ 7.60-7.50 (m, 1H), 7.40-7.21 (m, 2H), 5.69-5.50 (m, 1H), 5.08-4.98 (m, 1H), 4.85-4.65 (m, 4H), 4.05-3.70 (m, 8H), 3.51-3.39 (m, 1H), 3.17-3.06 (m, 2H), 2.95-2.85 (m, 2H), 2.77-2.58 (m, 2H), 2.50-2.00 (m, 9H), 1.96-1.73 (m, 4H).

Compound 14. 2-[[(2S,8R)-2-fluoro-1,2,3,5,6,7-hexahydropyrrolizin-8-yl]methoxy]-4-(4-hydroxyazepan-1-yl)spiro[5,8-dihydropyrano[4,3-d]pyrimidine-7,4'-tetralin]-6'-ol Compound 14 was prepared similarly to that of Ex. 1 as a formic acid salt. LCMS (ESI): m/z calcld for $C_{30}H_{39}FN_4O_4$+H; 539.1; found 539.1. $^1$H NMR (400 MHz, CD$_3$OD) δ 8.51 (s, 1H), 6.95 (d, J=8.2 Hz, 1H), 6.79-6.72 (m, 1H), 6.66 (dd, J=8.3, 2.4 Hz, 1H), 5.39 (d, J=53.6 Hz, 1H), 4.82-4.76 (m, 1H), 4.64-4.54 (m, 1H), 4.30 (dd, J=10.9, 2.7 Hz, 1H), 4.25-4.16 (m, 1H), 3.91-3.51 (m, 6H), 3.49-3.39 (m, 2H), 3.23-3.10 (m, 1H), 3.00 (d, J=17.6 Hz, 1H), 2.86 (d, J=17.8 Hz, 1H), 2.80-2.65 (m, 2H), 2.54-2.21 (m, 3H), 2.21-1.87 (m, 8H), 1.88-1.56 (m, 5H). $^{19}$F NMR (377 MHz, CD$_3$OD) δ –173.75.

Compound 15. 1-[5'-chloro-2-[[(2R,8S)-2-fluoro-1,2,3,5,6,7-hexahydropyrrolizin-8-yl]methoxy]spiro[5,8-dihydropyrano[4,3-d]pyrimidine-7,1'-tetralin]-4-yl]azepan-4-ol Compound 15 was prepared similarly to that of Ex. 1 as a formic acid salt. LCMS (ESI): m/z calcld for $C_{30}H_{38}ClFN_4O_3$+H: 557.1; found: 557.1. $^1$H NMR (400 MHz, DMSO) δ 7.37 (t, J=6.7 Hz, 2H), 7.21 (t, J=7.9 Hz, 1H), 5.25 (d, J=54.5 Hz, 1H), 4.78 (t, 1H), 4.55 (d, 1H), 4.02-3.90 (m, 1H), 3.85 (dd, 1H), 3.66 (s, 3H), 3.13-2.66 (m, 10H), 2.11-1.41 (m, 16H).

Example 5. Exemplary Synthesis of 1-(4-chloro-2'-(((2R,7aS)-2-fluorotetrahydro-1H-pyrrolizin-7a(5H)-yl)methoxy)-2,3,5',8'-tetrahydrospiro[indene-1,7'-pyrano[4,3-d]pyrimidin]-4'-yl)azepane-4-carbonitrile (Compound 16)

Compound 6

16a

Compound 16

Step 1. Preparation of 1-(4-chloro-2'-(((2R,7aS)-2-fluoro-tetrahydro-1H-pyrrolizin-7a(5H)-yl) methoxy)-2,3,5',8'-tetrahydrospiro[indene-1,7'-pyrano[4,3-d]pyrimidin]-4'-yl)
azepan-4-yl methanesulfonate (16a). The mixture of 1-[4'-chloro-2-[[rac-(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]azepan-4-ol;dihydrochloride (15.0 mg, 0.02 mmol), methanesulfonyl chloride (0.02 mL, 0.29 mmol) and N,N-diethylethanamine (0.05 mL, 0.37 mmol) in DCM (1 mL) was stirred at 25° C. for 30 min. The mixture was concentrated to afford a crude product which was purified on silica gel column eluted with EtOAc in PE from 5% to 50% to afford 1-[4'-chloro-2-[[rac-(2R,8S)-2-fluoro-1,2,3,5,6,7-hexa-hydropyrrolizin-8-yl]methoxy]spiro[5,8-dihydropy-rano[4,3-d]pyrimidine-7,1'-indane]-4-yl]azepan-4-yl]meth-anesulfonate (16a, 15 mg, 0.0241 mmol, 99.2% yield) as yellow sticky solid. LCMS calcld for $C_{30}H_{38}ClFN_4O_5S$ $(M+H)^+$ m/z=621.3, found; 621.3.

Step 2. Preparation of 1-(4-chloro-2'-(((2R,7aS)-2-fluoro-tetrahydro-1H-pyrrolizin-7a (5H)-yl)methoxy)-2,3,5',8'-tet-rahydrospiro[indene-1,7'-pyrano[4,3-d]pyrimidin]-4'-yl) azepane-4-carbonitrile (16). The mixture of [1-[4'-chloro-2-[[rac-(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]azepan-4-yl]methanesulfonate (65.0 mg, 0.1 mmol), 18-crown-6 (27.66 mg, 0.1 mmol) and NaCN (51.29 mg, 1.05 mmol) in DMF (1 mL) was stirred at 25° C. for 16 h. The mixture was diluted with EtOAc (2 mL), washed with water (1 mL) and brine (1 ml), dried over $Na_2SO_4$, concentrated. The crude product was purified by prep-HPLC (eluted with $CH_3CN$ in $H_2O$ (0.1% FA)) from 5.0% to 95% to afford 1-[4'-chloro-2-[[rac-(2R,8S)-2-fluoro-1,2,3,5,6,7-hexahy-dropyrrolizin-8-yl]methoxy]spiro[5,8-dihydropyrano[4,3-d] pyrimidine-7,1'-indane]-4-yl]azepane-4-carbonitrile;formic acid (16, 11.79 mg, 0.0193 mmol, 18.43% yield) as white solid. LCMS calcld for $C_{30}H_{36}ClFN_5O_2$ $(M+H)^+$ m/z=552.2, found: 552.2. $^1H$ NMR (400 MHz, $CD_3OD$) δ 8.57 (s, 1H), 7.31-7.10 (m, 3H), 5.34 (d, J=54.1 Hz, 1H), 4.73-4.55 (m, 2H), 4.26-4.17 (m, 2H), 3.83-3.62 (m, 3H), 3.58-3.34 (m, 4H), 3.14-2.89 (m, 6H), 2.40-1.91 (m, 14H).

Compound 17. 1-(7-chloro-2'-(((2R,7aS)-2-fluoro-tetrahydro-1H-pyrrolizin-7a(5H)-yl)methoxy)-3,4,5',8'-tetrahydro-2H-spiro[naphthalene-1,7'-pyrano[4,3-d]pyrimidin]-4'-yl)azepan-4-ol Compound 17 was prepared similarly to that of Ex. 1 as a formic acid salt. LCMS calcld for $C_{30}H_{38}ClFN_4O_3$ $(M+H)^+$ m/z=557.2, found: 557.2. $^1H$ NMR (400 MHz, $CD_3OD$) δ 8.52 (s, 1H), 7.31 (d, J=2.3 Hz, 1H), 7.21-7.16

(m, 1H), 7.12 (dd, J=8.2, 3.4 Hz, 1H), 5.33 (d, J=53.3 Hz, 1H), 4.65-4.60 (m, 1H), 4.24-4.14 (m, 2H), 3.74-3.55 (m, 6H), 3.15-3.03 (m, 1H), 2.94-2.87 (m, 2H), 2.94-2.89 (m, 2H), 2.88-2.79 (m, 2H), 2.29-2.15 (m, 1H), 2.12-1.92 (m, 8H), 1.91-1.63 (m, 6H).

Compound 18. 4'-chloro-2-[[(2R,8S)-2-fluoro-1,2,3,5,6,7-hexahydropyrrolizin-8-yl]methoxy]-4-(2,3,6,7-tetrahydroazepin-1-yl)spiro[5,8-dihydropyrano[4,3-d]pyrimidine-7,1'-indane]

Compound 18 was prepared similarly to that of Ex. 1 as a TFA salt. LCMS (ESI): m/z calcld for $C_{29}H_{34}ClFN_4O_2^+H$: 525.06, found: 525.2. H NMR (400 MHz, $CDCl_3$) δ 7.27-7.22 (m, 1H), 7.12-7.02 (m, 2H), 7.03-6.99 (s, 1H), 5.67 (s, 2H), 5.49 (d, J=53.2 Hz, 1H), 5.04-4.91 (m, 1H), 4.66-4.39 (m, 2H), 4.31-4.19 (m, 1H), 4.17-4.03 (m, 2H), 3.81-3.63 (m, 4H), 3.47-3.36 (m, 2H), 3.31-3.23 (m, 2H), 3.11-3.01 (m, 2H), 2.94-2.78 (m, 2H), 2.38-2.13 (m, 12H).

Example 6. Exemplary Synthesis of 1-[4'-chloro-2-[[rac-(2R,8S)-2-fluoro-1,2,3,5,6,7-hexahydropyr-rolizin-8-yl]methoxy]spiro[5,8-dihydropyrano[4,3-d] pyrimidine-7,1'-indane]-4-yl]azepan-4-one (Compound 21) and 2-(1-(4-chloro-2'-(((2R,7aS)-2-fluorotetrahydro-1H-pyrrolizin-7a(5H)-yl)methoxy)-2,3,5',8'-tetrahydrospiro[indene-1,7'-pyrano[4,3-d] pyrimidin]-4'-yl)azepan-4-yl)acetonitrile (Compound 19)

Compound 6 ⟶

Compound 21

235

-continued

19a

Compound 19

Step 1. Synthesis of 1-[4'-chloro-2-[[rac-(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]azepan-4-one (21). The mixture of 1-[4'-chloro-2-[[rac-(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]azepan-4-ol (6, 20.0 mg, 0.040 mmol) and DMP (23.43 mg, 0.060 mmol) was stirred at 25° C. for 30 min. The mixture was concentrated and purified by Prep-HPLC eluted with CH₃CN in H₂O (0.1% FA) from 5.0% to 95% to afford 1-[4'-chloro-2-[[rac-(2R,8S)-2-fluoro-1,2,3,5,6,7-hexahydropyrrolizin-8-yl]methoxy]spiro [5,8-dihydropyrano[4,3-d]pyrimidine-7,1'-indane]-4-yl]azepan-4-one; formic acid (21, 1.8 mg, 0.003 mmol, 8.0% yield) as sticky solid. LCMS calcld for C₂₉H₃₅ClFN₄O₃ (M+H)⁺ m/z=541.1, found: 541.1. ¹H NMR (400 MHz, CD₃OD) δ 8.43 (s, 1H), 7.33 (d, J=7.6 Hz, 1H), 7.20 (t, J=7.6 Hz, 1H), 7.07 (dd, J=7.6, 1.9 Hz, 1H), 5.49 (d, J=51.8 Hz, 1H), 4.73 (d, J=14.6 Hz, 1H), 4.48 (d, J=14.6 Hz, 1H), 4.42 (d, J=11.6 Hz, 1H), 4.35 (d, J=11.6 Hz, 1H), 3.95 (t, J=6.1 Hz, 2H), 3.89-3.65 (m, 5H), 3.17-3.05 (m, 2H), 3.03-2.88 (m, 4H), 2.81-2.73 (m, 2H), 2.62-2.34 (m, 5H), 2.33-2.16 (m, 5H).

Step 2. Synthesis of 2-(1-(4-chloro-2'-(((2R,7aS)-2-fluorotetrahydro-1H-pyrrolizin-7a(5H)-yl)methoxy)-2,3,5',8'-tetrahydrospiro[indene-1,7'-pyrano[4,3-d]pyrimidin]-4'-yl)azepan-4-ylidene)acetonitrile (19a). To a mixture of 1-[4'-chloro-2-[[rac-(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]azepan-4-one (21, 20.0 mg, 0.04 mmol) and 2-diethoxyphosphorylacetonitrile (6.55 mg, 0.04 mmol) in dried THF (1 mL) was added sodium hydride (1.77 mg, 0.07 mmol) at 25° C. under argon. The mixture was stirred at rt for 1 h. The mixture was diluted with EtOAc (10 mL), washed with water (5 mL) and brine (1 ml), dried over Na₂SO₄, concentrated. The crude product was purified by Prep-TLC to afford 2-[1-[4'-chloro-2-[[(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]azepan-4-ylidene]acetonitrile (19a, 10 mg, 0.018 mmol, 48.0% yield) as yellow sticky solid. LCMS calcld for C₃₁H₃₅ClFN₅O₂ (M+H)⁺ m/z=564.1, found: 564.1.

Step 3. Preparation of 2-(1-(4-chloro-2'-(((2R,7aS)-2-fluorotetrahydro-1H-pyrrolizin-7a(5H)-yl)methoxy)-2,3,5',8'-tetrahydrospiro[indene-1,7'-pyrano[4,3-d]pyrimidin]-4'-yl)azepan-4-yl)acetonitrile (19). The suspension of 2-[1-[4'-chloro-2-[[(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]azepan-4-ylidene]acetonitrile (10.0 mg, 0.02 mmol) and Pd—C (0.19 mg, 0.0018 mmol) in methanol (1 mL) was purged with H₂ three times. The mixture was stirred under H₂ (1 atm) at 25° C. for 16 h. The mixture was filtered and concentrated to afford a crude product which was purified by Prep-HPLC eluted with (eluted with CH₃CN in H₂O (0.1% FA) from 5.0% to 95%) to obtain 2-[1-[4'-chloro-2-[[(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]azepan-4-yl]acetonitrile;formic acid (19, 2.24 mg, 0.0034 mmol, 18.9% yield) as white sticky solid. LCMS calcld for C₃₁H₃₈ClFN₅O₂ (M+H)⁺ m/z=566.2, found: 566.2. ¹H NMR (400 MHz, CD₃OD) δ 8.47 (s, 1H), 7.41-7.08 (m, 3H), 5.45 (d, J=51.1 Hz, 1H), 4.78-4.23 (m, 4H), 3.96-3.33 (m, 7H), 3.26-3.21 (m, 1H), 3.16-2.88 (m, 4H), 2.59-2.33 (m, 5H), 2.28-1.60 (m, 12H).

Example 7. Exemplary Synthesis of 4-(azepan-1-yl)-2-[[(2R,8S)-2-fluoro-1,2,3,5,6,7-hexahydropyrrolizin-8-yl]methoxy]spiro[5,8-dihydropyrano[4,3-d]pyrimidine-7,4'-tetralin]-6'-carbonitrile (Compound 20)

20a

237

-continued

Compound 20

The solution of 4-(azepan-1-yl)-7'-bromo-2-[[(2R,8S)-2-fluoro-1,2,3,5,6,7-hexahydropyrrolizin-8-yl]methoxy]spiro[5,8-dihydropyrano[4,3-d]pyrimidine-7,1'-tetralin](20a, prepared similarly to that of Ex. 1, 30. mg, 0.05 mmol), K$_2$CO$_3$ (21.24 mg, 0.15 mmol), Zn(CN)$_2$ (18.05 mg, 0.15 mmol) and Xphos G3 Pd (4.69 mg, 0.01 mmol) in 1,4-Dioxane (1 mL) and Water (0.2 mL) was stirred at 100° C. under N$_2$ for 6 h. The reaction mixture was concentrated to get the crude product, which was then purified by prep-HPLC (eluted with CH$_3$CN in H$_2$O (0.1% FA) from 5% to 95%) to give 4-(azepan-1-yl)-2-[[(2R,8S)-2-fluoro-1,2,3,5,6,7-hexahydropyrrolizin-8-yl]methoxy]spiro[5,8-dihydro-pyrano[4,3-d]pyrimidine-7,4'-tetralin]-6'-carbonitrile;formic acid (20, 3.2 mg, 0.0042 mmol, 8.2% yield) as yellow solid. LCMS calcld for C$_{31}$H$_{38}$FN$_5$O$_2$ (M+H)$^+$ m/z=532.3; found: 532.3. $^1$H NMR (400 MHz, CD$_3$OD) δ 8.51 (s, 1H), 7.72-7.64 (m, 1H), 7.58-7.49 (m, 1H), 7.38-7.26 (m, 1H), 5.47-5.26 (m, 1H), 4.93-4.76 (m, 1H), 4.68-4.52 (m, 1H), 4.33-4.14 (m, 2H), 3.75-3.60 (m, 4H), 3.53-3.33 (m, 3H), 3.19-3.07 (m, 1H), 3.03-2.75 (m, 4H), 2.48-1.90 (m, 9H), 1.87-1.72 (m, 5H), 1.69-1.51 (m, 4H).

Example 8. Exemplary Synthesis of syn-1-[4'-chloro-2-[[(2R,8S)-2-fluoro-1,2,3,5,6,7-hexahydro-pyrrolizin-8-yl]methoxy]spiro[5,8-dihydropyrano[4,3-d]pyrimidine-7,1'-indane]-4-yl]azepane-4,5-diol (Compound 22)

Compound 18

238

-continued

Compound 22

To a mixture of 4'-chloro-2-[[rac-(2R,8S)-2-fluoro-1,2,3,5,6,7-hexahydropyrrolizin-8-yl]methoxy]-4-(2,3,6,7-tetra-hydroazepin-1-yl)spiro[5,8-dihydropyrano[4,3-d]pyrimidine-7,1'-indane](18, 50.0 mg, 0.1 mmol) in acetone (0.3 mL) and water (0.1 mL) were added K$_2$O$_5$O$_4$·2H$_2$O (70.17 mg, 0.19 mmol) and NMO (22.31 mg, 0.19 mmol) at 25° C. Then the mixture was stirred at 40° C. for 16 h. The solution was quenched with Na$_2$SO$_3$ aqueous solution, extracted with EtOAc (3 ml), and concentrated. The residue was purified by prep-HPLC eluting with CH$_3$CN in H$_2$O (0.1% TFA) from 5.0% to 95% to give syn-1-[4'-chloro-2-[[rac-(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]azepane-4,5-diol;2,2,2-trifluoroacetic acid (22, 4.71 mg, 0.0065 mmol, 6.8% yield) as a sticky solid. LCMS calcld for C$_{31}$H$_{37}$ClF$_4$N$_4$O$_6$ (M+H)$^+$ m/z=559.24, found: 559.5. $^1$H NMR (400 MHz, CD$_3$OD) δ 7.40-7.38 (dd, J=7.2, 0.8 Hz, 1H), 7.29-7.25 (t, J=7.6 Hz, 1H), 7.29-7.23 (dd, J=7.6 Hz, 1.2 Hz, 1H), 5.67 (s, 2H), 5.60 (d, J=52 Hz, 1H), 4.93-4.65 (m, 4H), 4.00-3.70 (m, 9H), 3.52-3.46 (m, 1H), 3.18-3.06 (m, 2H), 3.02-2.96 (m, 1H), 2.88 (m, 1H), 2.75-2.65 (m, 1H), 2.62-2.62 (m, 1H), 2.50-2.12 (m, 8H), 2.03-1.90 (m, 2H).

Example 9. Exemplary Synthesis of (3R)-1-(4-chloro-2'-(((2R,7aS)-2-fluorotetrahydro-1H-pyr-rolizin-7a(5H)-yl)methoxy)-2,3,5',8'-tetrahydrospiro[indene-1,7'-pyrano[4,3-d]pyrimidin]-4'-yl)-3-methylpiperidin-3-ol (Compound 23)

-continued

23a

23b

23c

23d

-continued

R = S(O)Me,
——SO₂Me

23e

Compound 23

Step 1. Synthesis of ethyl 4-chloro-6-((4-chloro-1-hy-droxy-2,3-dihydro-1H-inden-1-yl)methyl)-2-(methylthio) pyrimidine-5-carboxylate (23a). To a solution of LiHMDS (1 M, 24.3 mL, 2.0 eq) in THF (10 mL) was added a solution of Ethyl 4-chloro-6-methyl-2-(methylthio)pyrimidine-5-car-boxylate (3.0 g, 12.2 mmol, 1.0 eq) in THF (10 mL) at −60° C. Then the reaction was stirred at −60° C. for 30 minutes. After 30 minutes, 4-chloro-2,3-dihydro-1H-inden-1-one (2.03 g, 12.2 mmol, 1.0 eq) in THF (10 mL) was added to the mixture at −60° C. Then the reaction was stirred at −60° C. for 1 hr. LCMS showed that the reaction was completed. The residue was poured into water (50 mL). The aqueous phase was extracted with EtOAc (20 mL*2). The combined organic layers were washed with brine (20 mL), dried over Na₂SO₄, filtered and concentrated under vacuum. The resi-due was purified by column chromatography on silica gel (PE:EtOAc=80:1 to 30:1) to give ethyl 4-chloro-6-((4-chloro-1-hydroxy-2,3-dihydro-1H-inden-1-yl)methyl)-2-(methylthio)pyrimidine-5-carboxylate (23a) (3.5 g, 8.47 mmol, 69.64% yield) as a light-yellow oil. ¹H NMR (400 MHz, CDCl₃) δ 7.24-7.25 (m, 1H), 7.17 (t, J=7.6 Hz, 1H), 7.06-7.08 (m, 1H), 5.29 (s, 1H), 4.31-4.38 (m, 2H), 3.23-3.26 (m, 1H), 3.07-3.11 (m, 1H), 3.06-3.07 (m, 1H), 2.81-2.87 (m, 1H), 2.59 (s, 3H), 2.31-2.37 (m, 3H), 2.12-2.20 (m, 1H), 1.33 (t, J=7.2 Hz, 3H).

Step 2. Synthesis of 4-chloro-1-((6-chloro-5-(hydroxym-ethyl)-2-(methylthio)pyrimidin-4-yl)methyl)-2,3-dihydro-1H-inden-1-ol (23b). To a solution of compound 23a (3.4 g, 8.23 mmol, 1.0 eq) in DCM (35 mL) was added DIBAL-H (1 M, 24.68 Ml, 3.0 eq) at 0° C. The mixture was stirred at 0° C. for 1 hr. LCMS indicated the reaction was completed. The reaction mixture was quenched by water (50 mL) at 0° C., and then extracted with DCM (20 mL*2). The combined organic layers were washed with brine (20 mL), dried over Na$_2$SO$_4$, filtered and concentrated under reduced pressure. The residue was purified by column chromatography on silica gel (PE:EtOAc=100:1 to 30:1) to give compound 23b (2.0 g, 5.39 mmol, 65.48% yield) as a yellow solid. $^1$H NMR (400 MHz, CDCl$_3$) δ 7.26-7.28 (m, 1H), 7.16 (t, J=8.0 Hz, 1H), 7.03-7.05 (m, 1H), 4.62-4.73 (in, 2H), 3.34-3.38 (m, 1H), 3.13-3.16 (m, 1H), 3.03-3.06 (m, 1H), 2.89-2.95 (m, 1H), 2.53 (s, 3H), 2.50-2.52 (m, 1H), 2.07-2.12 (m, 1H).

Step 3. Synthesis of 4,4'-dichloro-2'-(methylthio)-2,3,5', 8'-tetrahydrospiro[indene-1,7'-pyrano[4,3-d]pyrimidine] (23c). To a solution of compound 23b (1.7 g, 4.58 mmol, 1.0 eq) in THF (20 mL) was added DIAD (1.39 g, 6.87 mmol, 1.34 mL, 1.5 eq) and PPh$_3$ (1.8 g, 6.87 mmol, 1.5 eq) at 25° C. Then the reaction was stirred at 25° C. for 10 minutes. LC-MS showed the starting material was consumed completely. The reaction mixture was concentrated under reduced pressure to give a residue. The residue was purified by column chromatography on silica gel (PE/EtOAc=100/1 to 80/1 to give compound 23c (1.07 g, 3.03 mmol, 66.15% yield) as off-white solid. $^1$H NMR (400 MHz, CDCl$_3$) δ 7.30-7.32 (m, 1H), 7.16 (t, J=8.0 Hz, 1H), 6.94-6.96 (m, 1H), 4.72-4.76 (m, 1H), 4.56-4.60 (m, 1H), 3.13-3.19 (m, H), 3.10 (s, 2H), 2.95-2.96 (m, 1H), 2.58 (s, 3H), 2.36-2.40 (m, 1H), 2.11-2.16 (m, 1H).

Step 4. Synthesis of (3R)-1-(4'-chloro-2-methylsulfanyl-spiro[5,8-dihydropyrano[4,3-d]pyrimidine-7,1'-indane]-4-yl)-3-methyl-piperidin-3-ol (23d). A solution of 4,4'-dichloro-2-methylsulfanyl-spiro[5,8-dihydropyrano[4,3-d]pyrimidine-7,1'-indane](80. mg, 0.23 mmol) in DMF (0.3 mL) was added (3R)-3-methylpiperidin-3-ol;hydrochloride (37.77 mg, 0.25 mmol) and DIPEA (87.8 mg, 0.68 mmol) at room temperature. The mixture was stirred at 100° C. for 1 h. The solution was diluted with EtOAc (5 ml), then washed with water (2 mlx3), dried over Na2SO4 and concentrated. The residue was purified with prep-TLC (eluting with EtOAc ether in petroleum from 10% to 90%) to give (3R)-1-(4'-chloro-2-methylsulfanyl-spiro[5,8-dihydropyrano[4,3-d]pyrimidine-7,1'-indane]-4-yl)-3-methyl-piperidin-3-ol (23d, 80 mg, 0.185 mmol, 81.8% yield). LCMS calcld for C$_{22}$H$_{26}$ClN$_3$O$_2$S (M+H)$^+$ m/z=432.98, found: 432.1.

Step 5. Synthesis of 23e. A mixture of (3R)-1-(4'-chloro-2-methylsulfanyl-spiro[5,8-dihydropyrano[4,3-d]pyrimidine-7,1'-indane]-4-yl)-3-methyl-piperidin-3-ol (23d, 80. mg, 0.19 mmol) in THF (0.4 mL) and Water (0.4 mL) was added oxone (68.31 mg, 0.22 mmol) at 25° C. for 1 h. The reaction was quenched with Na$_2$SO$_3$ aqueous solution and diluted with EtOAc (3 ml). The organic layer was washed with water (3 mlx3), dried and concentrated to give 90 mg of 23e as a 5:1 ratio of mixture of sulfoxide and sulfone based on LCMS. LCMS calcld for C$_{22}$H$_{26}$ClN$_3$O$_4$S (M+H)$^+$ m/z=448.98, 464.98, found: 448.1, 464.1.

Step 6. Synthesis of (3R)-1-(4-chloro-2'-(((2R,7aS)-2-fluorotetrahydro-1H-pyrrolizin-7a(5H)-yl)methoxy)-2,3,5', 8'-tetrahydrospiro[indene-1,7'-pyrano[4,3-d]pyrimidin]-4'-yl)-3-methylpiperidin-3-ol (23). A mixture of [(2R,8S)-2-fluoro-1,2,3,5,6,7-hexahydropyrrolizin-8-yl]methanol (177.69 mg, 1.12 mmol) in DMSO (0.3 mL) was added NaH (44.64 mg, 1.12 mmol) at 25° C. for 0.5 h. Then a mixture sulfone and sulfoxide of 23e in DMSO (0.3 mL) was added to the reaction at 25° C. and stirred for 1 h. Acetic acid was added dropwise until pH=7. The crude mixture was purified by prep-HPLC (eluting with CH$_3$CN (0.1% TFA) in H2O from 5% to 95%) to give (3R)-1-[4'-chloro-2-[[(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]-3- methyl-piperidin-3-ol;2,2,2-trifluoroacetic acid (46.03 mg, 0.0695 mmol, 31.13% yield) as a white solid. LCMS calcld for C$_{29}$H$_{36}$ClFN$_4$O$_3$ (M+H)$^+$ m/z=543.07, found: 543.1. $^1$H NMR (400 MHz, CD$_3$OD) δ 7.38 (d, J=7.6 Hz, 1H), 7.28-7.20 (m, 2H), 5.60 (d, J=52 Hz, 1H), 4.99-4.96 (m, 1H), 4.78-4.50 (m, 4H), 4.35-4.278 (m, 1H), 4.01-3.75 (m, 4H), 3.52-3.46 (m, 1H), 3.40-3.31 (m, 1H), 3.25-3.07 (m, 3H), 3.02-2.96 (m, 1H), 2.77-2.58 (m, 2H), 2.49-2.26 (m, 6H), 2.03-1.94 (m, 1H), 1.82-1.71 (m, 3H), 1.24 (s, 3H).

Compound 24. 9-[4'-chloro-2-[[(2R,8S)-2-fluoro-1, 2,3,5,6,7-hexahydropyrrolizin-8-yl]methoxy]spiro[5, 8-dihydropyrano[4,3-d]pyrimidine-7,1'-indane]-4-yl]-1,3,9-triazaspiro[4.5]decane-2,4-dione Compound 24 was prepared similarly to that of Ex. 9. LCMS calcld for C$_{30}$H$_{34}$ClFN$_6$O$_4$ (M+H)$^+$ m/z=597.09, found: 597.5. $^1$H NMR (400 MHz, CD$_3$OD) δ 7.34-7.27 (m, 1H), 7.20 (t, J=7.7 Hz, 1H), 7.14-7.04 (m, 1H), 5.28 (d, J=54.2 Hz, 1H), 4.75-4.58 (m, 1H), 4.53-4.40 (m, 1H), 4.23-4.03 (m, 2H), 4.01-3.66 (m, 2H), 3.43-3.35 (m, 1H), 3.26-3.05 (m, 5H), 3.04-2.89 (m, 4H), 2.43-2.05 (m, 6H), 2.00-1.78 (m, 6H).

Compound 25. 4-(azepan-1-yl)-2-[[(2R,8S)-2-fluoro-1,2,3,5,6,7-hexahydropyrrolizin-8-yl] methoxy]spiro[5,8-dihydropyrano[4,3-d]pyrimidine-7,4'-isochromane]

Compound 25 was prepared similarly to that of Ex. 1 as a formic acid salt. LCMS (ESI): m/z calcld for C$_{29}$H$_{37}$FN$_4$O$_3$(M+H)$^+$: 509.2, found: 509.2. $^1$H NMR (400 MHz, CD$_3$OD) δ 7.41-7.36 (m, 1H), 7.30-7.18 (m, 2H), 7.09

(d, J=7.5 Hz, 1H), 5.39-5.22 (m, 1H), 4.80 (m, 3H), 4.70 (d, J=14.2 Hz, 1H), 4.64-4.52 (m, 1H), 4.23-4.07 (m, 2H), 3.96-3.86 (m, 2H), 3.68-3.61 (m, 4H), 3.30-3.17 (m, 2H), 3.08-2.99 (m, 1H), 2.96-2.89 (m, 2H), 2.37-1.77 (m, 10H), 1.65-1.54 (m, 4H).

Example 10. Exemplary Synthesis of 2'-amino-4-(azepan-1-yl)-2-[[rac-(2R,8S)-2-fluoro-1,2,3,5,6,7-hexahydropyrrolizin-8-yl]methoxy]spiro[5,8-dihy-dropyrano[4,3-d]pyrimidine-7,4'-6,7-dihydro-5H-benzothiophene]-3'-carbonitrile (Compound 26)

1a

26a

26b

26c

-continued

26d

26e

Compound 26

Step 1. Synthesis of methyl 4-(azepan-1-yl)-2-chloro-6-[(2-ethoxy-1-hydroxy-cyclohex-2-en-1-yl)methyl]pyrimi-dine-5-carboxylate (26a). A mixture of methyl 4-(azepan-1-yl)-2-chloro-6-methyl-pyrimidine-5-carboxylate (1a, 1.0 g, 3.52 mmol) and LDA (2.11 mL, 4.23 mmol) in THF (10 mL) was stirred at −78° C. for 1 h. Then, a solution of 2-ethoxy-cyclohex-2-en-1-one (543 mg, 3.88 mmol) and CeCl3 (956 mg, 3.88 mmol), stirred for 4 h in THF (5 mL), was added at −78° C. The mixture was stirred at −78° C. for 1 h. LCMS showed 42% of product and 35% of 1a remained. The mixture was quenched with aq. NH4Cl (5 mL) at −78° C., extracted with EtOAc (5 mL×3), dried, and concentrated. The crude product was purified by flash chromatography (H2O:CH3CN=90:10 to 50:50) to give methyl 4-(azepan-1-yl)-2-chloro-6-[(2-ethoxy-1-hydroxy-cyclohex-2-en-1-yl) methyl]pyrimidine-5-carboxylate (26a, 800 mg, 1.89 mmol, 53.5% yield) was obtained as a yellow sticky oil. LCMS calcld for $C_{21}H_{30}ClN_3O_4$ (M+H)$^+$ m/z=424.2, found: 424.2.

Step 2. Synthesis of 1-[[6-(azepan-1-yl)-2-chloro-5-(hy-droxymethyl)pyrimidine-4-yl]methyl]-2-ethoxy-cyclohex-2-en-1-ol (26b). A suspension of LAH (177 mg, 4.67 mmol) and lithium chloride (198 mg, 4.67 mmol) in 2-Methyltet-rahydrofuran (6 mL) was stirred at room temperature for 20 min. Then methyl 4-(azepan-1-yl)-2-chloro-6-[(2-ethoxy-1-hydroxy-cyclohex-2-en-1-yl)methyl]pyrimidine-5-carboxy-late (26a, 660. mg, 1.56 mmol) was added at 0° C. portion wise. The mixture was stirred at 0° C. for 10 min. The mixture was quenched with NH4Cl (0.5 mL) at 25° C., extracted with EtOAC (10×3 mL), dried over Na2SO4, concentrated.

The crude product was purified by silica gel chromatography (eluted with EtOAc in PE from 10% to 30%) to give 1-[[6-(azepan-1-yl)-2-chloro-5-(hydroxymethyl)pyrimidin-4-yl]methyl]-2-ethoxy-cyclohex-2-en-1-ol (26b, 230 mg, 0.581 mmol, 37.3% yield) as a yellow solid. LCMS calcld for C20H30ClN3O3 (M+H)+ m/z=396.1, found: 396.1.

Step 3. Synthesis of 4-(azepan-1-yl)-2-chloro-1'-ethoxy-spiro[5,8-dihydropyrano[4,3-d]pyrimidine-7,6'-cyclohexene](26c). To a solution of 1-[[6-(azepan-1-yl)-2-chloro-5-(hydroxymethyl)pyrimidin-4-yl]methyl]-2-ethoxy-cyclohex-2-en-1-ol (26b, 230 mg, 0.58 mmol) in THF (2 mL) was added n-Butyllithium (0.35 mL, 0.87 mmol) at −78° C. stirred for 0.5 h. then the TSCl (166 mg, 0.87 mmol) in THF (2 mL) was added at −78° C. and the mixture was warmed to −10° C. stirred for 1 h under Ar. Then the temperature was cooled down to −78° C. and the second batch of n-Butyllithium (0.35 mL, 0.87 mmol) was added, after addition the reaction temperature was allowed to rise to 20° C. and stirred for 1.5 h. The mixture was quenched with NH4Cl (1 mL) at −78° C., extracted with EtOAC (10×3 mL), dried over Na2SO4, concentrated. The crude product was purified by silica gel chromatography (eluted with EtOAc in PE from 1% to 20%) to give 4-(azepan-1-yl)-2-chloro-1'-ethoxy-spiro[5,8-dihydropyrano[4,3-d]pyrimidine-7,6'-cyclohexene](26c, 130 mg, 0.344 mmol, 59.2% yield) as a yellow solid. LCMS calcld for C20H28ClN3O2 (M+H)+ m/z=378.1, found: 378.1.

Step 4. Synthesis of 4-(azepan-1-yl)-1'-ethoxy-2-[[(2R,8S)-2-fluoro-1,2,3,5,6,7-hexahydropyrrolizin-8-yl]methoxy]spiro[5,8-dihydropyrano[4,3-d]pyrimidine-7,6'-cyclohexene](26d). The mixture of NaH (31.8 mg, 0.79 mmol) and [(2R,8S)-2-fluoro-1,2,3,5,6,7-hexahydropyrrolizin-8-yl]methanol (126 mg, 0.79 mmol) in DMSO (1 mL) was stirred at 0° C. for 0.5 h. Then a solution of 4-(azepan-1-yl)-2-chloro-1'-ethoxy-spiro[5,8-dihydropyrano[4,3-d]pyrimidine-7,6'-cyclohexene](26c, 100. mg, 0.26 mmol) in DMSO (0.5 mL) was added at 0° C. and the mixture was stirred at 50° C. for 4 h. The mixture was quenched with H2O (10 mL) at 0° C., extracted with EtOAC (5×3 mL), dried over Na2SO4, concentrated. The crude product was purified by silica gel chromatography (eluted with EtOAc in PE from 10% to 30%) to give 4-(azepan-1-yl)-1'-ethoxy-2-[[(2R,8S)-2-fluoro-1,2,3,5,6,7-hexahydropyrrolizin-8-yl]methoxy]spiro[5,8-dihydropyrano[4,3-d]pyrimidine-7,6'-cyclohexene] as a yellow solid (26d, 80 mg, 0.1598 mmol, 60.387% yield) was obtained as yellow solid. LCMS calcld for C28H41FN4O3 (M+H)+ m/z=501.2, found: 501.6.

Step 5. Synthesis of 4-(azepan-1-yl)-2-[[(2R,8S)-2-fluoro-1,2,3,5,6,7-hexahydropyrrolizin-8-yl]methoxy]spiro[5,8-dihydropyrano[4,3-d]pyrimidine-7,2'-cyclohexane]-1'-one (26e). The mixture of 4-(azepan-1-yl)-1'-ethoxy-2-[[rac-(2R,8S)-2-fluoro-1,2,3,5,6,7-hexahydropyrrolizin-8-yl]methoxy]spiro[5,8-dihydropyrano[4,3-d]pyrimidine-7,6'-cyclohexene](80. mg, 0.16 mmol) and HCl/Dioxane (1. mL, 4. mmol) in Water (0.2 mL) was stirred at 25° C. the mixture was stirred at 25° C. for 10 min. After concentration, the crude product was purified by Prep-TLC (DCM:MeOH=5: 1). LCMS (ESI): m/z calcld for C26H37FN4O3 (M+H)+ m/z=472.2, found: 473.2.

Step 6. Synthesis of 2'-amino-4-(azepan-1-yl)-2-[[(2R, 8S)-2-fluoro-1,2,3,5,6,7-hexahydropyrrolizin-8-yl]methoxy]spiro[5,8-dihydropyrano[4,3-d]pyrimidine-7,4'-6, 7-dihydro-5H-benzothiophene]-3'-carbonitrile (Compound 26). The mixture of 4-(azepan-1-yl)-2-[[(2R,8S)-2-fluoro-1,2,3,5,6,7-hexahydropyrrolizin-8-yl]methoxy]spiro[5,8-dihydropyrano[4,3-d]pyrimidine-7,2'-cyclohexane]-1'-one (26e, 68. mg, 0.14 mmol) and propanedinitrile (9.5 mg, 0.14 mmol) and octathiocane (36.9 mg, 0.14 mmol) and morpholine (25 mg, 0.29 mmol) in Ethanol (0.5 mL) was stirred at 65° C., the mixture was stirred at 65° C. under argon for 7 h. The mixture was filtered and concentrated. The crude product was purified by Prep-HPLC (eluted with CH3CN in H2O (0.1% TFA) from 5.0% to 95%) to give 2'-amino-4-(azepan-1-yl)-2-[[(2R,8S)-2-fluoro-1,2,3,5,6,7-hexahydropyrrolizin-8-yl]methoxy]spiro[5,8-dihydropyrano[4,3-d]pyrimidine-7,4'-6,7-dihydro-5H-benzothiophene]-3'-carbonitrile;2,2,2-trifluoroacetic acid (26, 2.9 mg, 0.003 mmol, 2.1% yield) as a yellow sticky solid. LCMS (ESI): m/z calcld for C29H39FN6O2S (M+H)+ m/z=553.2, found: 553.2.

Compound 23A and 23B. (3R)-1-[(7*)-4'-chloro-2-[[(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]-3-methyl-piperidin-3-ol (23A and 23B)

23A & 23B

Compound 23 was purified on an DAICELCHIRALCEL®AD (250*25 mm 10 mm) column on a Waters SFC 150 system (Mobile Phase A: Supercritical CO2, Mobile Phase B: IPA (+0.1% 7.0 mol/l Ammonia in MeOH); A:B: 60:40; Flow: 70 ml/min) to give faster eluting P1 (3R)-1-[(7*)-4'-chloro-2-[[(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]-3-methyl-piperidin-3-ol (23A) and slower eluting P2 (23B). Compound 23A: 1H NMR (400 MHz, CD3OD) δ 7.351-7.332 (m, 1H), 7.235-7.916 (m, 1H), 7.121-7.103 (m, 1H), 5.399-5.256 (m, 1H), 4.749 (d, J=14 Hz, 1H), 4.459 (d, J=14 Hz, 1H), 4.228-4.119 (m, 2H), 3.665-3.627 (m, 1H), 3.422-3.349 (m, 2H), 3.284-3.231 (m, 4H), 3.165-2.927 (m, 5H), 2.443-1.867 (m, 10H), 1.768-1.626 (m, 2H), 1.189 (s, 3H). Compound 23B: 1H NMR (400 MHz, CD3OD) δ 7.227-7.207 (m, 1H), 7.116-7.077 (m, 1H), 7.041-7.022 (m, 1H), 5.291-5.155 (m, 1H), 4.557-4.406 (m, 2H), 4.150-4.017 (m, 2H), 3.607-3.544 (m, 1H), 3.380-3.347 (m, 1H), 3.297-3.255 (m, 1H), 3.164-2.929 (m, 6H), 2.884-2.802 (m, 3H), 2.305-2.026 (m, 5H), 1.950-1.73 (m, 5H), 1.646-1.482 (m, 2H), 1.090 (s, 3H).

Compound 24A. (5*)-9-[(7*)-4'-chloro-2-[[(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]-1,3,9-triazaspiro[4.5]decane-2,4-dione Compound 24 was purified on an DAICELCHIRALCEL®AD (250*25 mm 10 um) column on a Waters SFC 150 system (Mobile Phase A: Supercritical CO₂, Mobile Phase B: IPA (+0.1% 7.0 mol/l Ammonia in MeOH); A:B: 60:40; Flow: 70 ml/min) to give 3 peaks and the fastest eluting P1 was assigned to compound 24A.

Example 11. Exemplary Synthesis of 5-[(7S)-4'-chloro-2-[[(2R,8S)-2-fluoro-1,2,3,5,6,7-hexahydro-pyrrolizin-8-yl]methoxy]spiro[5,8-dihydropyrano[4,3-d]pyrimidine-7,1'-indane]-4-yl]-N,N-dimethyl-4,6,7,8-tetrahydropyrazolo[1,5-a][1,4]diazepine-2-carboxamide (compound 27A) and 5-[(7R)-4'-chloro-2-[[(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]-N,N-dimethyl-4,6,7,8-tetrahydropyrazolo[1,5-a][1,4]diazepine-2-carboxamide (Compound 27B)

Compound 27A was obtained from 27A-a similarly to that of compound 27B as a formic acid salt. The absolute configuration of 27A was assigned based on a small molecule crystal structure. LCMS calcld for C₃₃H₃₉ClFN₇O₄ (M+H)⁺ m/z=636.3, found: 636.3. ¹H NMR (400 MHz, CD₃OD) δ 8.51 (s, 1H), 7.38-7.20 (m, 2H), 7.08-7.00 (m, 1H), 6.53 (s, 1H), 5.46-5.26 (m, 1H), 4.78-4.68 (m, 3H), 4.59-4.46 (m, 3H), 4.26-4.03 (m, 3H), 3.87-3.76 (m, 1H), 3.52-3.31 (m, 7H), 3.18-2.88 (m, 8H), 2.46-1.90 (m, 10H).

Compound 27B 5-[(7R)-4'-chloro-2-[[(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]-N,N-dimethyl-4,6,7,8-tetrahydropyrazolo[1,5-a][1,4]diazepine-2-carboxamide -continued 27c 27d

27B

Compound 23c was purified on an DAICELCHIRALCEL®AD (25*250 mm, 10 um) column on a Waters SFC 150 system (Mobile Phase A: Supercritical CO₂. Mobile Phase B: IPA (+0.2% 7.0 mol/l Ammonia in MeOH); A:B:60:40; Flow: 100 ml/min) to give 2 peaks and the fastest eluting P1 was assigned to compound 27A-a and the second one P2 was assigned as 27B-a. 27B-a absolute configuration was assigned based on 27A-a single crystal structure.

Step 1. 27B-a (140. mg, 0.4 mmol), N,N-dimethyl-5,6,7, 8-tetrahydro-4H-pyrazolo[1,5-a][1,4]diazepine-2-carbox-amide;hydrochloride (165.07 mg, 0.79 mmol) and DIEA (0.21 mL, 1.19 mmol) in DMF (2 mL) was stirred at 100° C. for 2 h. The mixture was concentrated. The crude product was purified by flash chromatography (eluted with CH₃CN in H₂O from 5.0% to 95%) to get 5-[(7S)-4'-chloro-2-methylsulfanyl-spiro[5,8-dihydropyrano[4,3-d]pyrimidine-7,1'-indane]-4-yl]-N,N-dimethyl-4,6,7,8-tetrahydropyrazolo [1,5-a][1,4]diazepine-2-carboxamide 27b (173 mg, 0.3295 mmol, 83.14% yield) as yellow solid. LCMS calcld for C₂₆H₂₉ClN₆O₂S (M+H)⁺ m/z=525.1, found: 525.1. ¹H NMR (400 MHz, CDCl₃) δ 7.37-7.27 (m, 2H), 7.02 (d, J=7.1 Hz, 1H), 6.49 (s, 1H), 4.69-4.39 (m, 7H), 3.78-3.65 (m, 1H), 3.35 (s, 3H), 3.23-3.11 (m, 3H), 3.09 (s, 3H), 2.99-2.92 (m, 1H), 2.52 (s, 3H), 2.41-2.13 (m, 4H).

Step 2. To a solution of 27b (170. mg, 0.32 mmol) in THF (2 mL) was added a solution of oxone (129.38 mg, 0.42 mmol) in Water (1 mL) at 0° C., then the mixture was stirred at 25° C. for 1 h. The mixture was added water (10 mL) and extracted with EtOAc (10 mL×3), washed with a solution of Na₂SO₃ (5 mL), brine (5 ml), dried over Na₂SO₄, concentrated. The crude product was used directly for the next step. The crude product of N,N-dimethyl-5-[(7S)-4'-chloro-2-methylsulfinyl-spiro[5,8-dihydropyrano[4,3-d]pyrimidine-7,1'-indane]-4-yl]-4,6,7,8-tetrahydropyrazolo[1,5-a][1,4]di-azepine-2-carboxamide 27c (135 mg, 0.2495 mmol, 77.07% yield) and N,N-dimethyl-5-[(7S)-4'-chloro-2-methylsulfo-nyl-spiro[5,8-dihydropyrano[4,3-d]pyrimidine-7,1'-indane]-4-yl]-4,6,7,8-tetrahydropyrazolo[1,5-a][1,4]diazepine-2-carboxamide 27d (35 mg, 0.0628 mmol, 19.41% yield) was obtained as yellow solid. LCMS calcld for 27c C₂₆H₂₉ClN₆O₃S (M+H)⁺ m/z=541.1, found: 541.1, 21% of product 3-1. LCMS calcld for 27d C₂₆H₂₉ClN₆O₄S (M+H)⁺ m/z=557.1, found: 557.1.

Step 3. To a solution of [(2R,8S)-2-fluoro-1,2,3,5,6,7-hexahydropyrrolizin-8-yl]methanol (88.27 mg, 0.55 mmol) in DMF (0.5 mL) was added NaH (22.18 mg, 0.55 mmol) at 25° C. The mixture was stirred at 25° C. for 15 min. A solution of N, N-dimethyl-5-[(7S)-4'-chloro-2-methylsulfi-nyl-spiro[5,8-dihydropyrano[4,3-d]pyrimidine-7,1'-indane]-4-yl]-4,6,7,8-tetrahydropyrazolo[1,5-a][1,4]diazepine-2-carboxamide 27c (100. mg, 0.18 mmol) and N,N-dimethyl-5-[(7S)-4'-chloro-2-methylsulfonyl-spiro[5,8-dihydropyrano[4,3-d]pyrimidine-7,1'-indane]-4-yl]-4,6,7,8-tetrahydropyrazolo[1,5-a][1,4]diazepine-2-carboxamide 27d (20. mg, 0.04 mmol) in DMF (0.5 mL) was added the above solution at 25° C. The mixture was stirred at 25° C. for 15 min. Acetic acid (0.03 mL, 0.55 mmol) was added the reaction mixture to quench the reaction. The crude product was purified by Prep-HPLC (eluted with CH$_3$CN in H$_2$O (0.1% FA) from 5.0% to 95%) to get 5-[(7S)-4'-chloro-2-[[(2R,8S)-2-fluoro-1,2,3,5,6,7-hexahydropyrrolizin-8-yl] methoxy]spiro[5,8-dihydropyrano[4,3-d]pyrimidine-7,1'-indane]-4-yl]-N,N-dimethyl-4,6,7,8-tetrahydropyrazolo[1,5-a][1,4]diazepine-2-carboxamide;formic acid 27B (67.2 mg, 0.1052 mmol, 56.92% yield) was obtained as white solid. LCMS calcld for C$_{33}$H$_{39}$ClFN$_7$O$_3$ (M+H)$^+$ m/z=636.2, found: 636.2. $^1$H NMR (400 MHz, CD$_3$OD) δ 8.52 (s, 1H), 7.33 (d, J=7.9 Hz, 1H), 7.24 (t, J=7.7 Hz, 1H), 7.04 (d, J=7.4 Hz, 1H), 6.53 (s, 1H), 5.42-5.24 (m, 1H), 4.77-4.68 (m, 3H), 4.57-4.48 (m, 3H), 4.23-4.10 (m, 2H), 4.09-3.76 (m, 2H), 3.45-3.34 (m, 2H), 3.31-3.29 (m, 4H), 3.16-2.89 (m, 8H), 2.43-1.90 (m, 10H).

Example 12. Exemplary Synthesis of (7S)-4-(aze-pan-1-yl)-4'-chloro-2-[[(2R,8S)-2-fluoro-1,2,3,5,6,7-hexahydropyrrolizin-8-yl]methoxy]-6-methyl-spiro[5,8-dihydropyrido[4,3-d]pyrimidine-7,1'-indane] (28A)

28A-a 28A-b

-continued 28A-c 28A-d 28A-e

Compound 28A

Step 1. Synthesis of methyl 4-(azepan-1-yl)-6-(((S)-1-(((R)-tert-butylsulfinyl)amino)-4-chloro-2,3-dihydro-1H-inden-1-yl)methyl)-2-chloropyrimidine-5-carboxylate (28A-b). To a solution of LDA (1 M, 4.49 mL) in THF (3 mL) was added compound 1a (0.85 g, 3.00 mmol) at −65° C. After the mixture was stirred at −65° C. for 30 minutes, (R)—N-(4-chloro-2,3-dihydro-1H-inden-1-ylidene)-2-methylpropane-2-sulfinamide (28A-a, Kobayashi, Jun-ichi; et al. *Bioorganic & Medicinal Chemistry* (2021), 30, 115903) (808 mg, 3.00 mmol) was added to the mixture at −65° C. The mixture was stirred at −65° C. for 1 hr. TLC indicated ~50% of 1a was remained and one major new spot with larger polarity was detected. The reaction mixture was poured into water (50 mL), the aqueous phase was extracted with EtOAc (20 mL×2). The combined organic layers were washed with brine (20 mL), dried over Na₂SO₄, filtered, and concentrated under reduced pressure. The residue was purified by column chromatography on silica gel (PE: EtOAc=80:1 to 10:1) to give methyl 4-(azepan-1-yl)-6-(((S)-1-(((R)-tert-butylsulfinyl)amino)-4-chloro-2,3-dihydro-1H-inden-1-yl)methyl)-2-chloropyrimidine-5-carboxylate as a single diastereomer (28A-b, 0.65 g, 1.17 mmol, 39.20% yield) as an off-white solid. ¹H NMR (400 MHz, CDCl₃) δ 7.23-7.25 (m, 1H), 7.12-7.16 (m, 1H), 6.96-6.98 (m, 1H), 6.88 (s, 1H), 3.72 (s, 3H), 3.51-3.56 (m, 2H), 3.42-3.45 (m, 2H), 3.00-3.03 (m, 1H), 2.85-2.95 (m, 4H), 2.66-2.72 (m, 1H), 2.28-2.33 (m, 1H), 1.80 (s, 4H), 1.49-1.56 (m, 4H), 1.29 (s, 9H). Chiral analysis of compound 28A-b (Chiralpak AD-3, 50×4.6 mm I.D., 3 um): 99.66%. The absolute configuration of 28A-b was assigned based on the single crystal structure of (R)-28A-d (HCl salt, not shown, prepared from (S)-28A-a).

Step 2. Synthesis of (R)—N—((S)-1-((6-(azepan-1-yl)-2-chloro-5-(hydroxymethyl)pyrimidin-4-yl)methyl)-4-chloro-2,3-dihydro-1H-inden-1-yl)-2-methylpropane-2-sulfinamide (28A-c). To a solution of compound 28A-b (0.55 g, 994 umol) in DCM (10 mL) was added DIBAL-H (1 M, 2.98 mL) at 0° C. Then the reaction was stirred at 0° C. for 1 hr. The reaction mixture was quenched by ice water (20 mL) at 25° C. The aqueous phase was extracted with DCM (10 mL×2). The combined organic layers were washed with brine (20 mL), dried over Na₂SO₄, filtered, and concentrated under reduced pressure. The residue was purified by prep-TLC (SiO₂, PE/EtOAc=3:1) to give compound 28A-c (0.4 g, 761.13 umol, 76.60% yield) as off-white solid. ¹H NMR: (400 MHz, CDCl₃) δ 7.24 (s, 1H), 7.12-7.16 (m 1H), 7.01-7.03 (m 1H), 4.23-4.34 (m, 2H), 3.70-3.74 (m, 4H), 3.08-3.19 (m, 3H), 2.93-2.95 (m, 1H), 2.72-2.76 (m, 1H), 2.31-2.37 (m, 1H), 1.75-1.82 (m, 4H), 1.55-1.61 (m, 4H), 1.26 (s, 9H).

Step 3. Synthesis of (S)-4'-(azepan-1-yl)-2',4-dichloro-2,3,5',8'-tetrahydro-6'H-spiro[indene-1,7'-pyrido[4,3-d]pyrimidine](28A-d). To a solution of compound 28A-c (0.2 g, 4.58 mmol) in HCl/dioxane (4 M, 2 mL) at 0° C. The mixture was stirred at 0° C. for 3 hrs. The reaction mixture was adjusted pH to 8 by NaHCO₃ and extracted with EtOAc (5 mL×2). The combined organic layers were washed with brine (5 mL), dried over Na₂SO₄, filtered, and concentrated under reduced pressure to give a residue. To a mixture of the residue in CHCl₃ (1.5 mL) was added SOCl₂ (154 mg, 1.29 mmol, 93.86 uL) at 0° C., and the mixture was stirred at 50° C. for 2 hrs. The reaction mixture was concentrated under reduced pressure to give a residue. To a mixture of the residue in THF (1.5 mL) was added NaOH (5M, 12 mL) at 25° C. and the mixture was stirred at 25° C. for 1 hr. LC-MS showed the starting material was consumed completely. The mixture was extracted with EtOAc (5 mL×2). The combined organic layers were washed with brine (10 mL), dried over Na₂SO₄, filtered, and concentrated under reduced pressure to give a residue. The residue was purified by prep-TLC (PE/EtOAc=1:1) to give compound 28A-d (0.1 g, 248 umol, 65% yield) as a light-yellow solid. ¹H NMR: (400 MHz, CDCl₃) δ 7.25-7.27 (m, 1H), 7.13-7.17 (m, 1H), 7.04-7.06 (m, 1H), 3.99-4.03 (m, 1H), 3.85-3.89 (m, 1H), 3.62-3.65 (m, 4H), 3.07-3.13 (m, 1H), 2.97-3.01 (m, 3H), 2.16-2.24 (m, 2H), 1.80 (s, 4H), 1.68 (m, 8H).

Step 4. Synthesis of (S)-4'-(azepan-1-yl)-2',4-dichloro-6'-methyl-2,3,5',8'-tetrahydro-6'H-spiro[indene-1,7'-pyrido[4,3-d]pyrimidine](28A-e). To a solution of compound 28A-d (95 mg, 236 umol) in DMF (1 mL) was added NaH (9.42 mg, 235.53 umol, 60% purity) and iodomethane (33.4 mg, 236 umol, 14.7 uL) at 25° C. Then the reaction was stirred at 25° C. for 2 hrs. LC-MS showed the starting material was consumed completely. The reaction mixture was quenched by water (5 mL), and then extracted with EtOAc (3 mL×2). The combined organic layers were washed with brine (5 mL), dried over Na₂SO₄, filtered, and concentrated under reduced pressure. The residue was purified by prep-TLC (PE/EtOAc=1:1) to give compound 28A-e (40 mg, 96 umol, 41% yield) as light-yellow solid.

Step 5. Synthesis of (7S)-4-(azepan-1-yl)-4'-chloro-2-[[(2R,8S)-2-fluoro-1,2,3,5,6,7-hexahydropyrrolizin-8-yl]methoxy]-6-methyl-spiro[5,8-dihydropyrido[4,3-d]pyrimidine-7,1'-indane](28A). To a solution of compound 28A-e (17 mg, 40.73 umol) and ((2R,7aS)-2-fluorotetrahydro-1H-pyrrolizin-7a(5H)-yl)methanol (12.97 mg, 81.46 umol) in toluene (0.2 mL) was added Cs₂CO₃ (39.81 mg, 122.19 umol) and RuPhos Pd G3 (3.41 mg, 4.07 umol) at 20° C. Then the reaction was stirred at 100° C. for 5 hrs. LC-MS showed the starting material was consumed completely. The residue was purified by prep-HPLC (column: Waters Xbridge Prep OBD C18 150*40 mm*10 um; mobile phase: [water (NH₄HCO₃)-ACN]; B %: 60%-80%, 8 min) to give compound 28A (1.4 mg, 2.59 umol, 6.4% yield) as an off-white solid. ¹H NMR (400 MHz, CD₃OD) δ 7.29-7.3 (m, 1H), 7.26-7.28 (m, 1H), 7.17-7.24 (m, 1H), 5.21-5.34 (m, 1H), 4.14-4.17 (m, 1H), 4.03-4.06 (m, 1H), 3.72-3.81 (m, 6H), 3.15-3.21 (m, 3H), 2.98 (m, 3H), 2.80-2.88 (m, 2H), 2.37-2.45 (m, 1H), 2.25-2.30 (m, 1H), 2.17 (m, 3H), 2.15-2.25 (m, 1H), 2.10-2.05 (m, 1H), 1.88 (m, 2H), 1.64-1.65 (m, 6H), 1.28 (m, 4H).

Example 13. Exemplary Synthesis of [1-[4'-chloro-2-[[(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]-3-piperidyl]cyanamide (29)

29a

-continued

Compound 29

To the mixture of 1-[4'-chloro-2-[[(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]piperidin-3-amine (29a, prepared similarly to that of Ex. 11) (60 mg, 0.11 mmol) and Et$_3$N (0.08 mL, 0.57 mmol) in DCM (0.4 mL) at 0° C. was added carbononitridic bromide (13 mg, 0.12 mmol) in DCM (0.2 mL) and stirred at 0° C. for 0.5 h. The mixture was taken into water (10 mL), which was extracted with DCM (3×5 mL). The organic layers were washed with brine (10 ml), dried over Na$_2$SO$_4$, and concentrated. The crude was purified by prep-HPLC (eluted with CH$_3$CN in H$_2$O (0.1% FA) from 5.0% to 95%) to give [1-[4'-chloro-2-[[(2R,8S)-2-fluoro-1,2,3,5,6,7-hexahydro-pyrrolizin-8-yl]methoxy]spiro[5,8-dihydropyrano[4,3-d]pyrimidine-7,1'-indane]-4-yl]-3-piperidyl]cyanamide; formic acid (29, 15.24 mg, 0.0264 mmol, 23.23% yield) as a white solid. LCMS calcld for C$_{29}$H$_{34}$ClFN$_6$O$_2$ (M+H)$^+$ m/z=553.1, found: 553.1. $^1$H NMR (400 MHz, CD$_3$OD) δ 8.52 (s, 1H), 7.32 (dd, J=7.5, 3.1 Hz, 1H), 7.20 (dd, J=14.7, 7.5 Hz, 1H), 7.13-7.09 (m, 1H), 5.44-5.23 (m, 1H), 4.78-4.69 (m, 1H), 4.61-4.53 (m, 2H), 4.52-4.39 (m, 1H), 4.28-4.15 (m, 2H), 4.02-3.95 (m, 1H), 3.57-3.46 (m, 1H), 3.42-3.34 (m, 2H), 3.25-2.93 (m, 7H), 2.45-1.83 (m, 10H), 1.69-1.54 (m, 2H).

Compound 30. 9-[6'-hydroxy-2-[[rac-(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]-1,3,9-triazaspiro[4.5]decane-2,4-dione Compound 30 was prepared similarly to that of Ex. 9 as a TFA salt. LCMS calcld for C$_{30}$H$_{35}$FN$_6$O$_5$ (M+H)$^+$ m/z=579.3, found: 579.1. $^1$H NMR (400 MHz, CD$_3$OD) δ 7.15-7.08 (m, 1H), 6.80-6.72 (m, 1H), 6.62-6.56 (m, 1H), 5.66-5.48 (m, 1H), 4.70-4.51 (m, 4H), 4.26-3.98 (m, 2H), 3.94-3.84 (m, 2H), 3.78-3.66 (m, 1H), 3.53-3.37 (m, 3H), 3.04-2.97 (m, 2H), 2.82-2.54 (m, 3H), 2.46-2.28 (m, 4H), 2.25-2.08 (m, 4H), 2.00-1.79 (m, 3H).

Compound 31. N-methoxy-5-[(7S)-4'-chloro-2-[[(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]-4,6,7,8-tetrahydropyrazolo[1,5-a][1,4]diazepine-2-carboxamide Compound 31 was prepared from 27B-a similarly to that of Ex. 11 as a formic acid salt. LCMS calcld for C$_{32}$H$_{37}$ClFN$_7$O$_4$ (M+H)$^+$ m/z=638.2 found: 638.2. $^1$H NMR (400 MHz, CD$_3$OD) δ 8.52 (s, 1H), 7.37-7.26 (m, 2H), 7.02 (d, J=7.3 Hz, 1H), 6.61 (s, 1H), 5.39-5.20 (m, 1H), 4.76-4.67 (m, 3H), 4.56-4.46 (m, 3H), 4.10 (d, J=17.1 Hz, 2H), 3.78 (s, 3H), 3.26-3.19 (m, 2H), 3.16-2.80 (m, 6H), 2.49-1.78 (m, 12H)

Compound 32. N-methoxy-5-[4'-chloro-2-[[(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]-4,6,7,8-tetrahydropyrazolo[1,5-a][1,4]diazepine-2-carboxamide Compound 32 was prepared similarly to that of Ex. 9 as a TFA salt. LCMS calcld for $C_{33}H_{40}FN_7O_4$ $(M+H)^+$ m/z=618.3, found: 618.2. $^1H$ NMR (400 MHz, $CD_3OD$) δ 7.14 (d, J=8.3 Hz, 1H), 6.77 (dd, J=8.1, 2.4 Hz, 1H), 6.64 (d, J=1.6 Hz, 1H), 6.54 (t, J=2.6 Hz, 1H), 5.69-5.51 (m, 1H), 4.96-4.90 (m, 2H), 4.86-4.74 (m, 2H), 4.68-4.57 (m, 1H), 4.55-4.46 (m, 3H), 4.07-3.83 (m, 5H), 3.55-3.42 (m, 1H), 3.38-3.35 (m, 3H), 3.15-2.90 (m, 6H), 2.82-2.57 (m, 3H), 2.52-2.31 (m, 4H), 2.28-2.04 (m, 4H).

Compound 33. (3aR,6aS)-5-[(7S)-4'-chloro-2-[[(2R, 8S)-2-fluoro-1,2,3,5,6,7-hexahydropyrrolizin-8-yl] methoxy]spiro[5,8-dihydropyrano[4,3-d]pyrimidine-7,1'-indane]-4-yl]-3a,4,6,6a-tetrahydropyrrolo[3,4-c] pyrrole-1,3-dione Compound 33 was prepared from 27B-a similarly to that of Ex. 11 as a TFA salt. LCMS calcld for $C_{29}H_{31}ClFN_5O_4$ $(M+H)^+$ m/z=568.2, found: 568.1. $^1H$ NMR (400 MHz, $CD_3OD$) δ 7.36 (dd, J=7.9, 0.7 Hz, 1H), 7.23 (t, J=7.7 Hz, 1H), 7.10 (d, J=7.5 Hz, 1H), 5.69-5.50 (m, 1H), 4.86-4.81 (m, 1H), 4.69-4.52 (m, 3H), 4.34 (d, J=12.9 Hz, 1H), 4.22 (d, J=12.9 Hz, 1H), 4.03-3.87 (m, 3H), 3.83-3.70 (m, 2H), 3.58-3.45 (m, 3H), 3.19-3.09 (m, 1H), 3.05-2.91 (m, 3H), 2.75-2.57 (m, 2H), 2.48-2.31 (m, 4H), 2.27-2.17 (m, 2H).

Compound 34. [5-[(7S)-4'-chloro-2-[[(2R,8S)-2-fluoro-1,2,3,5,6,7-hexahydropyrrolizin-8-yl] methoxy]spiro[5,8-dihydropyrano[4,3-d]pyrimidine-7,1'-indane]-4-yl]-4,6,7,8-tetrahydropyrazolo[1,5-a] [1,4]diazepin-2-yl]-pyrrolidin-1-yl-methanone Compound 34 was prepared from 27B-a similarly to that of Ex. 11 as a formic acid salt. LCMS calcld for $C_{30}H_{34}ClFN_6O_4$ $(M+H)^+$ m/z=597.09, found: 597.5. $^1H$ NMR (400 MHz, $CD_3OD$) δ 7.34-m7.27 (m, 1H), (t, J=7.7 Hz, 1H), 7.14-7.04 (m, 1H), 5.28 (d, J=54.2 Hz, 1H), 4.75-4.58 (m, 2H), 4.53-4.40 (m, 2H), 4.23-4.03 (m, 2H), 4.01-3.66 (m, 2H), 3.43-3.35 (m, 1H), 3.26-3.05 (m, 5H), 3.04-2.89 (m, 4H), 2.43-2.05 (m, 6H), 2.00-1.78 (m, 6H).

Compound 35. 5-[(7S)-4'-chloro-2-[[(2R,8S)-2-fluoro-1,2,3,5,6,7-hexahydropyrrolizin-8-yl] methoxy]spiro[5,8-dihydropyrano[4,3-d]pyrimidine-7,1'-indane]-4-yl]-N-isopropyl-4,6,7,8-tetrahydropyrazolo[1,5-a][1,4]diazepine-2-carboxamide Compound 35 was prepared from 27B-a similarly to that of Ex. 11 as a formic acid salt. LCMS calcld for $C_{30}H_{34}ClFN_6O_4$ $(M+H)^+$ m/z=597.09, found: 597.5. $^1H$ NMR (400 MHz, $CD_3OD$) δ 7.34-7.27 (m, 1H), 7.20 (t, J=7.7 Hz, 1H), 7.14-7.04 (m, 1H), 5.28 (d, J=54.2 Hz, 1H), 4.75-4.58 (m, 1H), 4.53-4.40 (m, 1H), 4.23-4.03 (m, 3H), 4.01-3.66 (m, 3H), 3.43-3.35 (m, 1H), 3.26-3.05 (m, 5H), 3.04-2.89 (m, 4H), 2.43-2.05 (m, 6H), 2.00-1.78 (m, 6H).

Compound 36. 3-chloro-5-[(7S)-4'-chloro-2-[[(2R, 8S)-2-fluoro-1,2,3,5,6,7-hexahydropyrrolizin-8-yl] methoxy]spiro[5,8-dihydropyrano[4,3-d]pyrimidine-7,1'-indane]-4-yl]-N,N-dimethyl-4,6,7,8-tetrahydropyrazolo[1,5-a][1,4]diazepine-2-carboxamide

259

Compound 36 was prepared from 27B-a similarly to that of Ex. 11 as a formic acid salt. LCMS calcld for $C_{33}H_{38}Cl_2FN_7O_3$ $(M+H)^+$ m/z=670.5, found: 670.5. $^1H$ NMR (400 MHz, $CD_3OD$) δ 8.52 (s, 1H), 7.32 (d, J=7.1 Hz, 1H), 7.20 (t, J=7.8 Hz, 1H), 7.11 (d, J=7.1 Hz, 1H), 5.40-5.20 (m, 1H), 4.82-4.76 (m, 3H), 4.59 (d, J=14.3 Hz, 1H), 4.46-4.39 (m, 2H), 4.14-4.05 (m, 2H), 3.90-3.80 (m, 2H), 3.26-3.20 (m, 2H), 3.15-3.04 (m, 8H), 3.01-2.96 (m, 2H), 2.47-1.77 (m, 12H).

Compound 37. 5-[(7S)-4'-chloro-2-[[(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]-N-hydroxy-N-methyl-4,6,7,8-tetrahydropyrazolo[1,5-a][1,4]diazepine-2-carboxamide Compound 37 was prepared from 27B-a similarly to that of Ex. 11 as a formic acid salt. LCMS calcld for $C_{32}H_{38}ClFN_7O_4$ $(M+H)^+$ m/z=639.1, found: 638.3. $^1H$ NMR (400 MHz, $CD_3OD$) δ 7.36 (d, J=7.9 Hz, 1H), 7.26 (s, 1H), 7.08 (d, J=7.5 Hz, 1H), 6.82 (s, 1H), 5.30 (d, J=52.8 Hz, 1H), 4.81-4.68 (m, 3H), 4.55 (d, J=13.8 Hz, 3H), 4.13 (d, J=10.2 Hz, 1H), 4.03 (s, 2H), 3.87 (s, 1H), 3.44 (s, 2H), 3.29 (s, 2H), 3.22 (s, 1H), 3.17-2.91 (m, 5H), 2.40 (dd, J=10.5, 7.1 Hz, 1H), 2.31-2.07 (m, 6H), 1.98 (dd, J=17.8, 6.1 Hz, 2H), 1.88 (s, 1H).

Compound 38. morpholino-[5-[(7S)-4'-chloro-2-[[(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]-4,6,7,8-tetrahydropyrazolo[1,5-a][1,4]diazepin-2-yl]methanone;2,2,2-trifluoroacetic acid

260

Compound 38 was prepared from 27B-a similarly to that of Ex. 11 as a TFA salt. LCMS calcld for $C_{35}H_{41}ClFN_7O_4$ $(M+H)^+$ m/z=678.2, found: 678.2. $^1H$ NMR (400 MHz, $CD_3OD$) δ 7.37 (d, J=7.6 Hz, 1H), 7.29-7.25 (m, 1H), 7.11 (d, J=6.4 Hz, 1H), 6.66 (s, 1H), 5.58 (d, J 51.6 Hz, 1H), 5.01-4.99 (m, 3H), 4.63-4.52 (m, 5H), 4.12-4.01 (m, 3H), 3.94-3.83 (m, 4H), 3.77-3.68 (m, 6H), 3.47-3.45 (m, 1H), 3.13-3.94 (m, 4H), 2.70-2.14 (m, 10H)

Example 14. 5-[7'-hydroxy-6-methyl-2-[[(2R,8S)-2-fluoro-1,2,3,5,6,7-hexahydropyrrolizin-8-yl]methoxy]spiro[5,8-dihydropyrido[4,3-d]pyrimidine-7,1'-tetralin]-4-yl]-N,N-dimethyl-4,6,7,8-tetrahydropyrazolo[1,5-a][1,4]diazepine-2-carboxamide (Compound 39)

39a

39b

39c

39d

39e

261

-continued

39f

39g

39h

39i

39j

262

-continued

39k

39l

Compound 39

Step 1. To a solution of 7-hydroxytetralin-1-one (30000. mg, 184.97 mmol) in DMF (200 mL) was added $K_2CO_3$ (51128.92 mg, 369.94 mmol) at rt, then BnBr (34798.63 mg, 203.47 mmol) was added. The mixture was stirred at rt for 16 h. Then the mixture was extracted with $EtOAc/H_2O$. The combined organic layer was washed with brine, dried over $Na_2SO_4$ and concentrated. The obtained solid is triturated in MeOH and then filtered. The filtrate was purified by flash column chromatography (silica gel, eluting with EtOAc in PE) to afford 7-benzyloxytetralin-1-one (39a) (41760 mg, 166 mmol, 89.48% yield) as a yellow solid. LCMS calculated for $C_{17}H_{17}O_2$ $(M+H)^+$ m/z=253.1; found: 253.2. $^1$H NMR (400 MHz, DMSO) δ 7.18-7.49 (m, 8H), 5.14 (s, 2H), 2.87 (t, J=5.6 Hz, 2H), 2.57 (t, J=6.4 Hz, 2H), 1.96-2.07 (m, 2H).

Step 2. 7-benzyloxytetralin-1-one (39a) (4320. mg, 17.12 mmol), (S)-2-methylpropane-2-sulfinamide (2905.23 mg, 23.97 mmol) and Ti(IV) ethoxide (10. mL, 51.37 mmol) were mixed and stirred under argon at rt. The reaction vessel was placed into the microwave reactor and heated to 100° C. for 120 min. The mixture was quenched with potassium sodium tartrate tetrahydrate (aq, 250 mL), filtered, extract with EtOAc and purified by flash column chromatography (silica gel, eluting with 10% to 30% EtOAc/PE) to afford (NE,S)—N-(7-benzyloxytetralin-1-ylidene)-2-methyl-pro-pane-2-sulfinamide (39b) (3300 mg, 9.28 mmol, 54.22% yield) as a brown oil. LCMS calculated for $C_{21}H_{26}NO_2S$ $(M+H)^+$ m/z=356.17; found: 356.3.

Step 3. To a solution of EtOAc (2478.55 mg, 28.13 mmol) in THF (16 mL) was added LDA (5.60 mL, 11.25 mmol) portion wise at −70° C. under Ar, the mixture was stirred at −70° C. for 1 h, then another 1 equiv LDA was added and the reaction stirred for an additional 1 hr at −70° C., and (NE,S)—N-(7-benzyloxytetralin-1-ylidene)-2-methyl-pro-pane-2-sulfinamide (39b) (2000. mg, 5.63 mmol) in THF (8 mL) was added drop wise at −70° C. The resulting mixture was stirred at −70° C. for 2 h, The reaction was heated naturally and overnight. The reaction mixture was quenched with $NH_4Cl$(aq.) at −70° C., and then extracted with EtOAc. The organic layer was washed with water and brine, dried over $Na_2SO_4$, concentrated and purified by flash column chromatography (silica gel, eluting with 0% to 6% MeOH/DCM) to afford ethyl 2-[7-benzyloxy-1-[[(S)-tert-butylsulfi-nyl]amino]tetralin-1-yl]acetate (39c) (1200 mg, 2.71 mmol, 48.08% yield). LCMS calculated for $C_{25}H_{33}NNaO_4S+$ $(M+Na)+$ m/z=466.20; found: 466.4.

Step 4. The mixture of ethyl 2-[7-benzyloxy-1-[[(S)-tert-butylsulfinyl]amino]tetralin-1-yl]acetate (39c) (1200. mg, 2.71 mmol) and HCl in dioxane (5. mL, 20. mmol) in Ethanol (10 mL) was stirred at rt for 1 h. The reaction mixture was concentrated to afford crude ethyl 2-(1-amino-7-benzyloxy-tetralin-1-yl)acetate (39d) (918 mg, 2.7045 mmol, 100% yield). LCMS calculated for $C_{21}H_{26}NO_3$ $(M+H)+$ m/z=340.19; found: 323.4.

Step 5. A mixture of ethyl 2-(1-amino-7-benzyloxy-tetra-lin-1-yl)acetate (39d) (918. mg, 2.7 mmol), ethyl prop-2-enoate (812.33 mg, 8.11 mmol), TEA (1.13 mL, 8.11 mmol) and CuO (43.03 mg, 0.54 mmol) was dissolved in Ethanol (9 mL). The vial was sealed, and this mixture was then stirred for 16 h at 85° C. The crude reaction mixture was filtered and purified by Prep-HPLC (FA) to afford ethyl 3-[[7-benzyloxy-1-(2-ethoxy-2-oxo-ethyl)tetralin-1-yl] amino]propanoate (39e) (620 mg, 1.4106 mmol, 52.2% yield) as a colorless oil. LCMS calculated for $C_{26}H_{34}NO_5$ $(M+H)^+$ m/z=440.24; found: 440.5.

Step 6. To a solution of ethyl 3-[[7-benzyloxy-1-(2-ethoxy-2-oxo-ethyl)tetralin-1-yl]amino]propanoate (39e) (620. mg, 1.41 mmol) in Ethanol (6 mL) was added paraformaldehyde (253.9 mg, 8.46 mmol). Then the mixture was stirred at rt for 1 h under $N_2$, and $NaBH_3CN$ (265.92 mg, 4.23 mmol) was added. The resulting mixture was stirred at rt overnight. The reaction mixture was quenched with water, and then extracted with EtOAc. The organic layer was washed with brine, dried over $Na_2SO_4$, concentrated and purified by flash column chromatography (silica gel, eluting with 0% to 25% EtOAc/PE) to afford ethyl 3-[[7-benzyloxy-1-(2-ethoxy-2-oxo-ethyl)tetralin-1-yl]-methyl-amino]propanoate (39f) (540 mg, 1.1906 mmol, 84.4% yield) as a colorless oil. LCMS calculated for $C_{27}H_{36}NO_5$ $(M+H)^+$ m/z=454.26; found: 454.5.

Step 7. To a solution of ethyl 3-[[7-benzyloxy-1-(2-ethoxy-2-oxo-ethyl)tetralin-1-yl]-methyl-amino]propanoate (39f) (440. mg, 0.97 mmol) in THF (6 mL) was added LIHMDS (2.91 mL, 2.91 mmol) portion wise at −70° C. under $N_2$. Then the mixture was stirred at −70° C. for 1 h. The reaction mixture was quenched with aqueous $NH_4Cl$ at −70° C. The mixture was extracted with EtOAc, washed with brine, dried over $Na_2SO_4$, concentrated and purified by flash column chromatography (silica gel, eluting with 0% to 15% EtOAc/PE) to afford ethyl 7'-benzyloxy-1-methyl-4-oxo-spiro[piperidine-6,1'-tetralin]-3-carboxylate (39g) (154 mg, 0.3779 mmol, 39.0% yield) as a colorless oil. LCMS calculated for $C_{25}H_{30}NO_4$ $(M+H)+$ m/z=408.22; found: 408.4.

Step 8. To a solution of ethyl 7'-benzyloxy-1-methyl-4-oxo-spiro[piperidine-6,1'-tetralin]-3-carboxylate (39g) (279. mg, 0.68 mmol) in ethanol (3 mL) was added thiourea (67.75 mg, 0.89 mmol) and ethoxysodium (139.77 mg, 2.05 mmol). Then the mixture was stirred at 80° C. for 16 h. The reaction mixture was concentrated, diluted with EtOAc. 1M HCl was added to adjust pH=6. The mixture was washed with water and brine, dried over $Na_2SO_4$, concentrated and purified by flash column chromatography (silica gel, eluting with 2% to 8% MeOH/DCM) to afford 7'-benzyloxy-6-methyl-2-sulfanyl-spiro[5,8-dihydropyrido[4,3-d]pyrimi-dine-7,1'-tetralin]-4-ol (39h) (250 mg, 0.5959 mmol, 87.0% yield) as a yellow gel. LCMS calculated for $C_{24}H_{26}N_3O_2S$ $(M+H)+$ m/z=420.18; found: 420.4.

Step 9. To a solution of 7'-benzyloxy-6-methyl-2-sulfa-nyl-spiro[5,8-dihydropyrido[4,3-d]pyrimidine-7,1'-tetralin]-4-ol (39h) (250. mg, 0.6 mmol) in water (5 mL) was added 2-chloroacetic acid (506.81 mg, 5.36 mmol). Then the mixture was stirred at 100° C. overnight under $N_2$. The mixture was filtered. The pH of the aqueous layer was adjusted to 8 by adding an aqueous solution of $NaHCO_3$ aqueous. The resulting precipitate was filtered, and dried in vacuo to afford 7'-benzyloxy-6-methyl-spiro[5,8-dihydro-pyrido[4,3-d]pyrimidine-7,1'-tetralin]-2,4-diol (39i) (224 mg, 0.5552 mmol, 93.2% yield) as a white solid. LCMS calculated for $C_{24}H_{26}N_3O_3$ $(M+H)^+$ m/z=404.20; found: 404.4.

Step 10. The mixture of 7'-benzyloxy-6-methyl-spiro[5, 8-dihydropyrido[4,3-d]pyrimidine-7,1'-tetralin]-2,4-diol (39i) (224. mg, 0.56 mmol) in $POCl_3$ (3. mL, 32.19 mmol) was stirred at 100° C. for 16 h. The reaction mixture was concentrated, extracted with EtOAc, washed with brine (10 mL), dried over $Na_2SO_4$, concentrated and purified by flash column chromatography (silica gel, eluting with 0% to 30% EtOAc/PE) to afford 7'-benzyloxy-2,4-dichloro-6-methyl-spiro[5,8-dihydropyrido[4,3-d]pyrimidine-7,1'-tetralin](39j) (28 mg, 0.064 mmol, 11% yield) as a white solid. LCMS calculated for $C_{24}H_{24}Cl_2N_3O$ $(M+H)+$ m/z=440.13, 442.13; found: 440.4, 442.4.

Step 11. The mixture of 7'-benzyloxy-2,4-dichloro-6-methyl-spiro[5,8-dihydropyrido[4,3-d]pyrimidine-7,1'-tetralin](39j) (28. mg, 0.06 mmol), N,N-dimethyl-5,6,7,8-tetrahydro-4H-pyrazolo[1,5-a][1,4]diazepine-2-carboxamide;hydrochloride (18.67 mg, 0.08 mmol) and DIEA (16.44 mg, 0.13 mmol) in DMF (1 mL) was stirred at rt for 24 h. The reaction mixture was diluted with water, extracted with EtOAc, washed with brine, dried over Na₂SO₄, concentrated and purified by flash column chromatography (silica gel, eluting with 3% to 7% MeOH/DCM) to afford 5-(7'-benzyloxy-2-chloro-6-methyl-spiro[5,8-dihydropyrido[4,3-d]pyrimidine-7,1'-tetralin]-4-yl)-N,N-dimethyl-4,6,7,8-tetrahydropyrazolo[1,5-a][1,4]diazepine-2-carboxamide (39k) (25 mg, 0.041 mmol, 64% yield) as a white solid. LCMS calculated for $C_{34}H_{39}ClN_7O_2$ (M+H)⁺ m/z=612.29; found: 612.4.

Step 12. The mixture of 5-(7'-benzyloxy-2-chloro-6-methyl-spiro[5,8-dihydropyrido[4,3-d]pyrimidine-7,1'-tetralin]-4-yl)-N,N-dimethyl-4,6,7,8-tetrahydropyrazolo[1,5-a][1,4]diazepine-2-carboxamide (39k) (25. mg, 0.04 mmol), [(2R,8S)-2-fluoro-1,2,3,5,6,7-hexahydropyrrolizin-8-yl]methanol (8.45 mg, 0.05 mmol), Cs₂CO₃ (33.28 mg, 0.1 mmol), Pd₂dba₃ (3.74 mg, 0. mmol) and RuPhos (3.81 mg, 0.01 mmol) in toluene (1.5 mL) was stirred at 110° C. for 10 h under N₂. The reaction mixture was cooled to room temperature and the solvent was removed under reduced pressure. The mixture was purified by flash column chromatography (silica gel, eluting with 0% to 10% MeOH/DCM) to afford 5-[7'-benzyloxy-6-methyl-2-[[(2R,8S)-2-fluoro-1,2,3,5,6,7-hexahydropyrrolizin-8-yl]methoxy]spiro[5,8-dihydropyrido[4,3-d]pyrimidine-7,1'-tetralin]-4-yl]-N,N-dimethyl-4,6,7,8-tetrahydropyrazolo[1,5-a][1,4]diazepine-2-carboxamide (39l) (25 mg, 0.034 mmol, 83% yield) as a white solid. LCMS calculated for $C_{42}H_{52}FN_8O_3$ (M+H)⁺ m/z=735.42; found: 735.8.

Step 13. The mixture of 5-[7'-benzyloxy-6-methyl-2-[[(2R,8S)-2-fluoro-1,2,3,5,6,7-hexahydropyrrolizin-8-yl]methoxy]spiro[5,8-dihydropyrido[4,3-d]pyrimidine-7,1'-tetralin]-4-yl]-N,N-dimethyl-4,6,7,8-tetrahydropyrazolo[1,5-a][1,4]diazepine-2-carboxamide (39l) (25. mg, 0.03 mmol) and Pd/C (7.82 mg, 0.01 mmol) in MeOH (1 mL) was stirred at rt for 2 h under H₂. The reaction mixture was filtered, concentrated and purified by prep-HPLC (0.1% NH₄HCO₃) to afford 5-[7'-hydroxy-6-methyl-2-[[(2R,8S)-2-fluoro-1,2,3,5,6,7-hexahydropyrrolizin-8-yl]methoxy]spiro[5,8-dihydropyrido[4,3-d]pyrimidine-7,1'-tetralin]-4-yl]-N,N-dimethyl-4,6,7,8-tetrahydropyrazolo[1,5-a][1,4]diazepine-2-carboxamide (Compound 39) (7.84 mg, 0.0122 mmol, 35.7% yield) as a white solid. LCMS calculated for $C_{35}H_{46}FN_8O_3$ (M+H)⁺ m/z=645.37; found: 645.7. ¹H NMR (400 MHz, CD₃OD) δ 6.92 (dd, J=7.6, 5.6 Hz, 2H), 6.58-6.64 (m, 2H), 5.26 (d, J=54.4 Hz, 1H), 4.79-4.89 (m, 2H), 4.42-4.59 (m, 2H), 3.92-4.14 (m, 4H), 3.76 (dd, J=34.0, 14.8 Hz, 2H), 3.32 (s, 3H), 3.14-3.27 (m, 3H), 3.06 (s, 3H), 2.87-3.03 (m, 3H), 2.65 (dd, J=9.6, 4.0 Hz, 2H), 2.12-2.36 (m, 3H), 2.14 (s, 3H), 1.67-2.10 (m, 9H).

Compound 39A and 39B. 5-[(7S)-2-[[(2R,8S)-2-fluoro-1,2,3,5,6,7-hexahydropyrrolizin-8-yl]methoxy]-7'-hydroxy-6-methyl-spiro[5,8-dihydropyrido[4,3-d]pyrimidine-7,1'-tetralin]-4-yl]-N,N-dimethyl-4,6,7,8-tetrahydropyrazolo[1,5-a][1,4]diazepine-2-carboxamide (39A) and 5-[(7R)-2-[[(2R,8S)-2-fluoro-1,2,3,5,6,7-hexahydropyrrolizin-8-yl]methoxy]-7'-hydroxy-6-methyl-spiro[5,8-dihydropyrido[4,3-d]pyrimidine-7,1'-tetralin]-4-yl]-N,N-dimethyl-4,6,7,8-tetrahydropyrazolo[1,5-a][1,4]diazepine-2-carboxamide (39B)

39A

39B

Compound 39 was purified on an DAICELCHIRAL-CEL® AD (250*25 mm 10 um) column on a Waters SFC 150 system (Mobile Phase A: Supercritical CO₂, Mobile Phase B: MeOH (0.2% NH₃ (7M in MeOH)); A:B: 65:35; Flow: 100 ml/min) to give faster eluting P1 (39A) and slower eluting P2 (39B).

Compound 40. 5-[8'-chloro-7'-hydroxy-2-[[(2R,8S)-2-fluoro-1,2,3,5,6,7-hexahydropyrrolizin-8-yl]methoxy]spiro[5,8-dihydropyrano[4,3-d]pyrimidine-7,1'-tetralin]-4-yl]-N,N-dimethyl-4,6,7,8-tetrahydropyrazolo[1,5-a][1,4]diazepine-2-carboxamide Compound 40 was prepared similarly to that of Ex. 9 as a white solid. LCMS calculated for $C_{34}H_{42}ClFN_7O_4$ (M+H)$^+$ m/z=666.3; found: 666.5/668.5. $^1$H NMR (400 MHz, CD$_3$OD) δ 6.94 (d, J=8.4 Hz, 1H), 6.83 (d, J=8.4 Hz, 1H), 6.64 (d, J=2.4 Hz, 1H), 5.32 (d, J=54.4 Hz, 1H), 5.02 (d, J=14.0 Hz, 1H), 4.90 (s, 2H), 4.69 (d, J=14.4 Hz, 1H), 4.44-4.53 (m, 2H), 4.00-4.20 (m, 3H), 3.84-3.92 (m, 1H), 3.58 (d, J=18.0 Hz, 1H), 3.34 (d, J=18.0 Hz, 1H), 3.27 (s, 3H), 3.06 (s, 3H), 3.01-3.11 (m, 1H), 2.75-2.83 (m, 3H), 1.87-2.40 (m, 13H), 1.68-1.80 (m, 1H).

Example 15. Exemplary Synthesis of 5-[6'-(difluoromethoxy)-2-[[rac-(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]-N,N-dimethyl-4,6,7,8-tetrahydropyrazolo[1,5-a][1,4]diazepine-2-carboxamide (41)

Compound 32

-continued

Compound 41

To a solution of 5-[6'-hydroxy-2-[[rac-(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]-N,N-dimethyl-4,6,7,8-tetrahydropyrazolo[1,5-a][1,4]diazepine-2-carboxamide;2,2,2-trifluoroacetic acid (32) (15. mg, 0.02 mmol) in MeCN (0.3 mL) were added 1-[[bromo(difluoro)methyl]-ethoxy-phosphoryl]oxyethane (8.21 mg, 0.03 mmol) and KF (2.38 mg, 0.04 mmol) at 25° C. The mixture was stirred at 25° C. for 12 h. The crude product was purified by Prep-HPLC (eluted with CH$_3$CN in H$_2$O (0.1% TFA) from 5.0% to 95%) to afford 5-[6'-(difluoromethoxy)-2-[[rac-(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]-N,N-dimethyl-4,6,7,8-tetrahydropyrazolo[1,5-a][1,4]diazepine-2-carboxamide;2,2,2-trifluoroacetic acid (41) (5.4 mg, 0.0055 mmol, 27% yield) as white solid. LCMS calcld for $C_{34}H_{40}F_3N_7O_4$ (M+H)$^+$ m/z=668.3, found: 668.2. $^1$H NMR (400 MHz, CD$_3$OD) δ 7.59-7.26 (m, 1H), 7.12 (d, J=8.1 Hz, 1H), 6.75 (dd, J=8.1, 2.4 Hz, 1H), 6.61 (s, 1H), 6.54 (s, 1H), 5.78-5.57 (m, 1H), 4.81-4.69 (m, 4H), 4.67-4.23 (m, 6H), 4.05-3.89 (m, 3H), 3.33 (s, 3H), 3.12-2.88 (m, 8H), 2.81-2.68 (m, 2H), 2.64-2.47 (m, 3H), 2.45-2.29 (m, 2H), 2.21-2.06 (m, 3H).

Compound 42. 5-[(7S)-4'-chloro-2-[[(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]-N,N,3-trimethyl-4,6,7,8-tetrahydropyrazolo[1,5-a][1,4]diazepine-2-carboxamide Compound 42 was prepared from 27B-a similarly to that of Ex. 11 as a TFA salt. LCMS calcld for $C_{34}H_{42}ClFN_7O_3$ (M+H)$^+$ m/z=650.3, found: 650.3. $^1H$ NMR (400 MHz, CD$_3$OD) δ 7.36 (dd, J=7.9, 0.8 Hz, 1H), 7.24 (t, J=7.7 Hz, 1H), 7.14 (d, J=7.4 Hz, 1H), 5.60 (d, J=50.7 Hz, 1H), 4.87 (s, 2H), 4.72 (dd, J=86.4, 14.4 Hz, 2H), 4.52 (s, 2H), 4.41 (dd, J=6.6, 3.3 Hz, 2H), 4.00-3.83 (m, 5H), 3.47 (td, J=11.1, 5.4 Hz, 1H), 3.21-2.91 (m, 10H), 2.85-2.53 (m, 2H), 2.49-2.09 (m, 11H).

Compound 43. 5-[5'-chloro-7'-hydroxy-2-[[rac-(2R, 8S)-2-fluoro-1,2,3,5,6,7-hexahydropyrrolizin-8-yl] methoxy]spiro[5,8-dihydropyrano[4,3-d]pyrimidine-7,1'-tetralin]-4-yl]-N,N-dimethyl-4,6,7,8-tetrahydropyrazolo[1,5-a][1,4]diazepine-2-carboxamide (43)

Compound 43 was prepared similarly to that of Ex. 9 as a white solid. LCMS calculated for $C_{34}H_{42}ClFN_7O_4$ (M+H)$^+$ m/z=666.3; found: 666.3/668.3. $^1H$ NMR (400 MHz, CD$_3$OD) δ 6.80 (d, J=2.4 Hz, 1H), 6.70 (d, J=2.4 Hz, 1H), 6.55 (d, J=2.0 Hz, 1H), 5.37 (d, J=53.6 Hz, 1H), 4.77-4.80 (m, 2H), 4.60-4.61 (m, 1H), 4.55-4.57 (m, 1H), 4.45-4.51 (m, 2H), 4.14-4.26 (m, 2H), 3.91-3.99 (m, 2H), 3.35-3.51 (m, 3H), 3.30 (s, 3H), 3.10-3.19 (m, 1H), 3.07 (s, 3H), 2.99 (d, J=18.0 Hz, 1H), 2.91 (d, J=18.0 Hz, 1H), 2.66-2.83 (m, 2H), 2.26-2.45 (m, 2H), 2.16-2.25 (m, 1H), 2.05-2.15 (m, 5H), 1.90-2.03 (m, 3H), 1.70-1.84 (m, 1H).

Compound 44. [(3R)-1-[(7S)-4'-chloro-2-[[(2R)-2-fluoro-1,2,3,5,6,7-hexahydropyrrolizin-8-yl] methoxy]spiro[5,8-dihydropyrano[4,3-d]pyrimidine-7,1'-indane]-4-yl]azepan-3-yl]cyanamide Compound 44 was prepared similarly to that of Ex. 11 and Ex. 13 as a TFA salt. LCMS calcld for $C_{30}H_{36}ClFN_6O_2$ (M+H)$^+$ m/z=567.1, found 567.2.

Compound 45. [3-chloro-5-[(7S)-4'-chloro-2-[[(2R, 8S)-2-fluoro-1,2,3,5,6,7-hexahydropyrrolizin-8-yl] methoxy]spiro[5,8-dihydropyrano[4,3-d]pyrimidine-7,1'-indane]-4-yl]-4,6,7,8-tetrahydropyrazolo[1,5-a][1,4]diazepin-2-yl]-morpholino-methanone Compound 45 was prepared from 27B-a similar to that of Ex. 11. LCMS calcld for $C_{35}H_{41}Cl_2FN_7O_4$ (M+H)$^+$ m/z=712.3, found. 712.2. $^1H$ NMR (400 MHz, CD$_3$OD) δ 7.36 (d, J=7.4 Hz, 1H), 7.24 (t, J=7.7 Hz, 1H), 7.13 (d, J=7.4 Hz, 1H), 5.60 (d, J=51.9 Hz, 1H), 4.94-4.74 (m, 3H), 4.62 (d, J=14.5 Hz, 1H), 4.45-4.44 (m, 2H), 4.42-4.31 (m, 2H), 4.03-3.81 (m, 6H), 3.77 (s, 3H), 3.69 (s, 3H), 3.46 (td, J=11.1, 5.9 Hz, 1H), 3.21-2.92 (m, 4H), 2.81-2.53 (m, 2H), 2.52-2.12 (m, 9H).

Compound 46A and 46B. [(3R)-1-[(7*)-4'-chloro-2-[[(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]-3-methyl-3-piperidyl]cyanamide;2,2,2-trifluoroacetic acid Compound 46A and 46B were prepared similarly to that of Ex. 13. The solution was purified by prep-HPLC (eluting with CH$_3$CN in H$_2$O (0.1% TFA) from 5% to 95%) to give faster eluting P1 (46A). $^1H$ NMR (400 MHz, CD$_3$OD) δ

7.372-7.333 (m, 1H), 7.281-7.162 (m, 2H), 5.597 (d, J=50.8 Hz, 1H), 4.767-4.541 (m, 4H), 4.146-3.764 (m, 5H), 3.535-3.405 (m, 1H), 3.289-2.944 (m, 6H), 2.770-2.557 (m, 2H), 2.487-2.203 (m, 6H), 1.971-1.676 (m, 4H), 1.332 (s, 3H) and slower eluting P2 (46B). ¹H NMR (400 MHz, CD₃OD) δ 7.357-7.322 (m, 1H), 7.244-7.069 (m, 2H), 5.574 (d, J=52 Hz, 1H), 4.635-4.440 (m, 4H), 4.151-3.969 (m, 2H), 3.909-3.809 (m, 3H), 3.496-3.382 (m, 1H), 3.184-2.912 (m, 6H), 2.738-2.534 (m, 2H), 2.455-2.135 (m, 6H), 2.031-1.592 (m, 4H), 1.293 (s, 3H).

Compound 47. 3-chloro-5-[(7S)-4'-chloro-2-[[1-(morpholinomethyl)cyclopropyl]methoxy]spiro[5,8-dihydropyrano[4,3-d]pyrimidine-7,1'-indane]-4-yl]-N,N-dimethyl-4,6,7,8-tetrahydropyrazolo[1,5-a][1,4]diazepine-2-carboxamide Compound 47 was prepared from 27B-a similarly to that of Ex. 11 as a formic acid salt. LCMS calcld for C₃₃H₃₈Cl₂FN₇O₃ (M+H)⁺ m/z=670.4, found: 670.4. ¹H NMR (400 MHz, CD₃OD) δ 8.45 (s, 1H), 7.32 (d, J=7.1 Hz, 1H), 7.20 (t, J=7.7 Hz, 1H), 7.12 (d, J=6.9 Hz, 1H), 4.78 (d, J=10.8 Hz, 3H), 4.59 (d, J=14.2 Hz, 1H), 4.43 (d, J=4.3 Hz, 2H), 4.26-4.14 (m, 2H), 3.85 (d, J=5.7 Hz, 2H), 3.67 (t, J=4.4 Hz, 4H), 3.10 (t, J=8.1 Hz, 7H), 3.02-2.85 (m, 3H), 2.56 (d, J=36.2 Hz, 6H), 2.39 (ddd, J=12.1, 7.8, 4.1 Hz, 1H), 2.23 (dd, J=12.1, 6.8 Hz, 3H), 0.66 (s, 2H), 0.50 (s, 2H).

Compound 48. 5-[4'-(difluoromethoxy)-2-[[rac-(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]-N,N-dimethyl-4,6,7,8-tetrahydropyrazolo[1,5-a][1,4]diazepine-2-carboxamide Compound 48 was prepared similarly to that of Ex. 9 as a formic acid salt. LCMS calcld for C₃₄H₄₀F₃N₇O₄ (M+H)⁺ m/z=668.4, found: 668.4. ¹H NMR (400 MHz, DMSO) δ 7.53-7.30 (m, 2H), 7.28-7.14 (m, 1H), 7.11-6.90 (m, 1H), 6.53 (s, 1H), 5.56 (d, J=52.8 Hz, 1H), 4.73 (d, J=14.5 Hz, 3H), 4.45 (dd, J=30.2, 13.4 Hz, 5H), 4.11-3.72 (m, 6H), 3.25 (s, 6H), 3.11-2.54 (m, 8H), 2.26-1.84 (m, 6H). ¹⁹F NMR (377 MHz, CDCl₃) δ −80.44 (dd, J=129.9, 23.5 Hz), −171.65 (d, J=32.3 Hz).

Example 16. Exemplary Synthesis of [3-chloro-5-[(7S)-4'-chloro-2-[[(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]-4,6,7,8-tetrahydropyrazolo[1,5-a][1,4]diazepin-2-yl]-piperazin-1-yl-methanone (49)

49a

49b

Compound 49

Step 1. A solution of [(2R,8S)-2-fluoro-1,2,3,5,6,7-hexa-hydropyrrolizin-8-yl]methanol (55.23 mg, 0.35 mmol) in DMSO (1 mL) was added sodium hydride (20.82 mg, 0.52 mmol) at 25° C. for 0.5 h. After 0.5 h, a solution of [ethyl 3-chloro-5-[(7S)-4'-chloro-2-methylsulfinyl-spiro[5,8-dihy-dropyrano[4,3-d]pyrimidine-7,1'-indane]-4-yl]-4,6,7,8-tet-rahydropyrazolo[1,5-a][1,4]diazepine-2-carboxylate (49a, prepared similarly to that of 27d of Ex. 11) (100. mg, 0.17 mmol) in DMSO (1 mL) was added to above solution at 25° C. for 0.5 h. The mixture was poured into the mixture of NH₄Cl (10 mL) and iced water (10 mL), extracted with DCM/MeOH (10:1)(10*3 mL), dried over Na₂SO₄, concen-trated. Water was added (10 mL) to the residue and the resulting precipitate was filtered, and dried under vacuum to afford 3-chloro-5-[(7S)-4'-chloro-2-[[(2R,8R)-2-fluoro-1,2, 3,5,6,7-hexahydropyrrolizin-8-yl]methyl]spiro[5,8-dihydro-pyrano[4,3-d]pyrimidine-7,1'-indane]-4-yl]-4,6,7,8-tetrahy-dropyrazolo[1,5-a][1,4]diazepine-2-carboxylic acid (49b) (50 mg, 0.0717 mmol, 41.34% yield) was obtained as a white solid Step 2. To a solution of 3-chloro-5-[(7S)-4'-chloro-2-[[(2R,8S)-2-fluoro-1,2,3,5,6,7-hexahydropyrrolizin-8-yl]methoxy]spiro[5,8-dihydropyrano[4,3-d]pyrimidine-7,1'-in-dane]-4-yl]-4,6,7,8-tetrahydropyrazolo[1,5-a][1,4]diazepine-2-carboxylic acid (49b) (40. mg, 0.06 mmol) and DIEA (24.1 mg, 0.19 mmol) in DCM (3 mL) was added HATU (30.79 uL, 0.12 mmol) at 0° C. The mixture was stirred at 25° C. for 10 min. Then, Piperazine (53.54 mg, 0.62 mmol) was added at 0° C. The mixture was stirred at 25° C. for 2 h. The mixture was concentrated to afford a crude product. The crude product was purified by Prep-HPLC. [3-chloro-5-[(7S)-4'-chloro-2-[[(2R,8S)-2-fluoro-1, 2,3,5,6,7-hexahydropyrrolizin-8-yl]methoxy]spiro[5,8-di-hydropyrano[4,3-d]pyrimidine-7,1'-indane]-4-yl]-4,6,7,8-tetrahydropyrazolo[1,5-a][1,4]diazepin-2-yl]-piperazin-1-yl-methanone (49) (11 mg, 0.0135 mmol, 21.68% yield) was obtained as white solid. LCMS calcld for C₃₅H₄₂Cl₂FN₈O₃ (M+H)⁺ m/z=711.3, found: 711.3. ¹H NMR (400 MHz, CD₃OD) δ 7.32 (d, J=7.8 Hz, 1H), 7.54-7.52 (m, 1H), 7.11 (d, J=7.8 Hz, 1H), 5.36-5.19 (m, 1H), 4.82-4.74 (m, 2H), 4.58 (d, J=14.2 Hz, 1H), 4.44-4.41 (m, 2H), 4.10-4.01 (m, 2H), 3.85 (brs, 2H), 3.71 (brs, 2H), 3.56 (brs, 2H), 3.20-3.05 (m, 3H), 3.00-2.92 (m, 4H), 2.90-2.84 (m, 3H), 2.80 (brs, 2H), 2.42-2.31 (m, 1H), 2.25-2.17 (m, 5H), 2.12-1.86 (m, 5H). ¹⁹F NMR (377 MHz, CD₃OD) δ −173.42 (s).

Compound 50. [3-chloro-5-[(7S)-4'-chloro-2-[[(2R, 8S)-2-fluoro-1,2,3,5,6,7-hexahydropyrrolizin-8-yl] methoxy]spiro[5,8-dihydropyrano[4,3-d]pyrimidine-7,1'-indane]-4-yl]-4,6,7,8-tetrahydropyrazolo[1,5-a] [1,4]diazepin-2-yl]-(4-methylpiperazin-1-yl) methanone Compound 50 was prepared similarly to that of Ex. 16. LCMS calcld for C₃₆H₄₄Cl₂FN₈O₃ (M+H)⁺ m/z=725.3, found: 725.3. ¹H NMR (400 MHz, CD₃OD) δ 7.32 (d, J=8.0 Hz, 1H), 7.20 (m, 1H), 7.11 (d, J=8.0 Hz, 1H), 5.35-5.22 (m, 1H), 4.88-4.74 (m, 3H), 4.58 (d, J=14.3 Hz, 1H), 4.43-4.41 (m, 2H), 4.75 (d, J=4.0 Hz, 1H), 3.85 (brs, 2H), 3.75 (brs, 2H), 3.63 (brs, 2H), 3.20-3.04 (m, 3H), 3.02-2.88 (m, 4H), 2.51 (brs, 2H), 2.44 (brs, 2H), 2.40-2.35 (m, 1H), 2.32 (s, 3H), 2.29-2.17 (m, 5H), 2.12-1.82 (m, 6H). ¹⁹F NMR (377 MHz, CD₃OD) δ −173.41 (s).

Compound 51A and 51B. (5R)-9-[(7*)-5'-chloro-2-[[(2R,8S)-2-fluoro-1,2,3,5,6,7-hexahydropyrrolizin-8-yl]methoxy]-7'-hydroxy-spiro[5,8-dihydropyrano[4,3-d]pyrimidine-7,1'-tetralin]-4-yl]-1,3,9-triazaspiro[4.5]decane-2,4-dione Compound 51A and 51B were prepared similarly to that of Ex. 9. The mixture was purified by Prep-HPLC on a C18 column (5 uM, 50×150 mm) with mobile phase: H₂O (0.1% NH₄HCO₃)/MeCN at flow rate: 35 mL/min to afford to give faster eluting P1 (51A): ¹H NMR (400 MHz, CD₃OD) δ 6.78 (d, J=2.4 Hz, 1H), 6.73 (d, J=2.4 Hz, 1H), 5.29 (d, J=54.4 Hz, 1H), 4.78-4.82 (m, 2H), 4.12 (s, 2H), 4.07 (d, J=13.2 Hz, 1H), 3.68 (d, J=13.2 Hz, 1H), 3.37 (d, J=13.2 Hz, 1H), 3.15-3.28 (m, 4H), 3.01 (s, 1H), 2.95 (d, J=11.2 Hz, 1H), 2.62-2.83 (m, 3H), 2.03-2.36 (m, 7H), 1.78-1.98 (m, 7H); and slower eluting P2 (51B): ¹H NMR (400 MHz, CD₃OD) δ 6.78 (d, J=2.4 Hz, 1H), 6.76 (d, J=2.8 Hz, 1H), 5.32 (d, J=53.6 Hz, 1H), 4.79-4.81 (m, 2H), 4.13-4.21 (m, 2H), 4.03 (d, J=13.2 Hz, 1H), 3.76 (d, J=13.6 Hz, 1H), 3.35 (d, J=6.0 Hz, 1H), 2.99-3.14 (m, 4H), 2.96 (d, J=8.4 Hz, 1H), 2.62-2.83 (m, 4H), 1.83-2.21 (m, 14H). Benzyl (R)-2,4-dioxo-1,3,7-triazaspiro[4.5]decane-7-carboxylate (P2) was separated on a CHRALCEL OZ-3 column from a racemic mixture. The faster eluting P1 was determined as an S enantiomer by a single crystal structure. Removal of Cbz from P2 under hydrogenation conditions afforded (R)-1,3, 7-triazaspiro[4.5]decane-2,4-dione, which was used to pre-pare compounds 51A and 51B.

Example 17. Exemplary Synthesis of [3-chloro-5-[(7S)-4'-chloro-2-[[(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]-4,6,7,8-tetrahydropyrazolo[1,5-a][1,4]diazepin-2-yl]-(1-imino-1-oxo-1,4-thiazinan-4-yl)methanone (52)

49b ⟶

52a

Compound 52

Step 1. To a solution of 3-chloro-5-[(7S)-4'-chloro-2-[[(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]-4,6,7,8-tetrahydropyrazolo[1,5-a][1,4]diazepine-2-carboxylic acid (49b) (50. mg, 0.08 mmol) and DIEA (30.12 mg, 0.23 mmol) in DMF (3 mL) was added HATU (59.09 mg, 0.16 mmol) at 0° C. The mixture was stirred at 25° C. for 10 min. Then, thiomorpholine (16.03 mg, 0.16 mmol) was added at 0° C. The mixture was stirred at 25° C. for 2 h. The reaction mixture was diluted with water (20 mL), lots of white solid emerged. The mixture was filtered, and the crude product was recrystallized from EtOAc/PE/MeOH (2 mL/2 mL/0.5 mL) to afford [3-chloro-5-[(7S)-4'-chloro-2-[[(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]-4,6,7,8-tetrahydropyrazolo[1,5-a][1,4]diazepin-2-yl]-thiomorpholino-methanone (52a) (35 mg, 0.031 mmol, 40% yield).

Step 2. The mixture of [3-chloro-5-[(7S)-4'-chloro-2-[[(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]-4,6,7,8-tetrahydropyrazolo[1,5-a][1,4]diazepin-2-yl]-thiomorpholino-methanone (52a) (25. mg, 0.03 mmol), Iodobenzene Diacetate (23.21 mg, 0.07 mmol) and Ammonium acetate (4.23 mg, 0.05 mmol) in Methanol (3 mL) was stirred at 25° C. for 2 h. The mixture was quenched with $H_2O$ (10 mL) and $Na_2SO_3$ (2 mL) at 25° C., extracted with DCM/MeOH (10/1) (5*3 mL), dried over $Na_2SO_4$ and concentrated. The crude product was purified by Prep-HPLC to afford [3-chloro-5-[(7S)-4'-chloro-2-[[(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]-4,6,7,8-tetrahydropyrazolo[1,5-a][1,4]diazepin-2-yl]-(1-imino-1-oxo-1,4-thiazinan-4-yl)methanone (52) (3 mg, 0.0037 mmol, 11% yield). LCMS calcld for $C_{35}H_{42}Cl_2FN_8O_4S$ $(M+H)^+$ m/z=759.2, found: 759.3. $^1H$ NMR (400 MHz, $CD_3OD$) δ 7.32 (d, J=8.0 Hz, 1H), 7.22-7.18 (m, 1H), 7.11 (d, J=8.0 Hz, 1H), 5.37-5.18 (m, 2H), 4.81-4.75 (m, 2H), 4.58 (d, J=14.3 Hz, 2H), 4.48-4.41 (m, 2H), 4.38-4.18 (m, 2H), 4.12-3.92 (m, 4H), 3.89-3.81 (m, 2H), 3.25-3.05 (m, 6H), 3.05-2.88 (m, 4H), 2.35-1.88 (m, 11H). $^{19}F$ NMR (376 MHz, $CD_3OD$) δ −173.40 (s).

Example 18. 3-chloro-5-[(7S)-2-[[(2R,8S)-2-fluoro-1,2,3,5,6,7-hexahydropyrrolizin-8-yl]methoxy]-6-methyl-spiro[5,8-dihydropyrido[4,3-d]pyrimidine-7,1'-indane]-4-yl]-N,N-dimethyl-4,6,7,8-tetrahydropyrazolo[1,5-a][1,4]diazepine-2-carboxamide (53)

28A-a ⟶

53a

53b

53c

53d

-continued

*53e*

*53f*

*53g*

*53h*

*53i*

-continued compound 53

Step 1. To a solution of Ethyl Acetate (10.89 mL, 111.2 mmol) in THF (80 mL) was added LDA (55.60 mL, 111.20 mmol) drop wise at –70° C. under $N_2$. Then the mixture was stirred at –70° C. for 3 h, and triisopropoxytitanium (IV) chloride (118.61 mL, 118.61 mmol) was added drop wise at same temperature and stirred for 30 min, then (R,E)-N-(4-chloro-2,3-dihydro-1H-inden-1-ylidene)-2-methylpropane-2-sulfinamide (28A-a) (10.00 g, 37.07 mmol) was added drop wise. The resulting mixture was stirred further 3 h at –70° C. Then quenched with $NH_4Cl$ solution and extracted with EtOAc. The organic layer was washed with water and brine, dried over $Na_2SO_4$, concentrated and purified by flash column chromatography (silica gel, eluting with 0% to 50% EtOAc/PE) to afford the product ethyl 2-[(1S)-1-[[(R)-tert-butylsulfinyl]amino]-4-chloro-indan-1-yl]acetate (53a) (7.90 g, 22.10 mmol, 59.55% yield) as yellow solid. LCMS calculated for $C_{17}H_{24}ClNO_3SNa$ $(M+Na)^+$ m/z=380.11, 382.10; found: 380.3, 382.3.

Step 2. To the mixture of ethyl 2-[(1S)-1-[[(R)-tert-bu-tylsulfinyl]amino]-4-chloro-indan-1-yl]acetate (53a) (7.90 g, 22.07 mmol) in Ethanol (70 mL) was added the solution of HCl/dioxane (22.07 mL, 88.29 mmol) and the mixture was stirred at room temperature for 1 h. The solvent was removed by concentration to afford crude ethyl 2-[(1S)-1-amino-4-chloro-indan-1-yl]acetate hydrochloride (53b) (6.40 g, 22.1 mmol, 99.92% yield), which was used directly in the next step. LCMS calculated for $C_{13}H_{18}ClNO_2$ $(M+H)^+$ m/z=290.07, 292.07; found: 151.1, 152.1.

Step 3. The mixture of ethyl 2-[(1S)-1-amino-4-chloro-indan-1-yl]acetate;hydrochloride (53b) (6.40 g, 22.05 mmol), ethyl prop-2-enoate (15.46 g, 154.38 mmol), $Et_3N$ (9.23 mL, 66.16 mmol) and CuO (0.35 g, 4.41 mmol) in Ethanol (50 mL) was heated to 85° C. in a seal tube. The crude reaction mixture was filtered, and filtrate was concentrated in vacuo to give the crude product, which was purified by flash column chromatography (silica gel, eluting with 0% to 50% PE/EtOAc) to afford ethyl 3-[[(1S)-4-chloro-1-(2-ethoxy-2-oxo-ethyl)indan-1-yl]amino]propanoate (53c) (7.30 g, 20.6 mmol, 93.54% yield) as a colorless oil. LCMS calculated for $C_{18}H_{25}ClNO_4$ $(M+H)^+$ m/z=354.15, 356.14; found: 354.3, 356.3.

Step 4. The mixture of ethyl 3-[[(1S)-4-chloro-1-(2-ethoxy-2-oxo-ethyl)indan-1-yl]amino]propanoate (53c) (2.00 g, 5.65 mmol), Paraformaldehyde (2.04 g, 67.83 mmol) and $NaBH_3CN$ (1.07 g, 16.96 mmol) in Ethanol (20 mL) was stirred at 25° C. for 16 h. The reaction mixture was quenched with water, and then extracted with EtOAc. The organic layer was washed with brine, dried over $Na_2SO_4$, concentrated and purified by flash column chromatography (silica gel, eluting with 0% to 20% EtOAc/PE) to afford ethyl 3-[[(1S)-4-chloro-1-(2-ethoxy-2-oxo-ethyl)indan-1-yl]-methyl-amino]propanoate (53d) (1.90 g, 5.16 mmol, 91.38% yield) as a yellow oil. LCMS calculated for $C_{19}H_{27}ClNO_4$ $(M+H)^+$ m/z=368.16, 370.16; found: 368.3, 370.3.

Step 5. To a solution of ethyl 3-[[(1S)-4-chloro-1-(2-ethoxy-2-oxo-ethyl)indan-1-yl]-methyl-amino]propanoate (53d) (1.10 g, 2.99 mmol) in THF (11 mL) was added [bis(trimethylsilyl)amino]potassium (8.97 mL, 8.97 mmol) dropwise at −70° C. under $N_2$. The mixture was stirred at same temperature for 2 h. The reaction mixture was quenched with $NH_4Cl$ at −70° C., and then extracted with EtOAc. The organic layer was washed with water and brine, dried over $Na_2SO_4$, concentrated, and purified by flash column chromatography (silica gel, eluting with 0% to 20% EtOAc/PE) to afford ethyl (1S)-4-chloro-1'-methyl-4'-oxo-spiro[indane-1,6'-piperidine]-3'-carboxylate (53e) (860 mg, 2.67 mmol, 89.37% yield) as a yellow oil. LCMS calculated for $C_{17}H_{21}ClNO_3$ $(M+H)^+$ m/z=322.12, 324.12; found: 322.3, 324.3.

Step 6. To a solution of ethyl (1S)-4-chloro-1'-methyl-4'-oxo-spiro[indane-1,6'-piperidine]-3'-carboxylate (53e) (860.00 mg, 2.67 mmol) in Ethanol (10 mL) was added Thiourea (406.86 mg, 5.34 mmol) and $C_2H_5ONa$ (545.58 mg, 8.02 mmol). Then the mixture was stirred at 80° C. under $N_2$ for 12 h. The reaction mixture was concentrated, then adjust pH to 6 with hydrochloric acid (1N), precipitate the solid, filter and dry the filter cake to afford (7S)-4'-chloro-6-methyl-2-sulfanyl-spiro[5,8-dihydropyrido[4,3-d]pyrimidine-7,1'-indane]-4-ol (53f) (890.00 mg, 2.67 mmol, 99.76% yield) as brown solid. LCMS calculated for $C_{16}H_{17}ClN_3OS$ $(M+H)^+$ m/z=334.08, 336.07; found: 334.2, 334.2.

Step 7. To a solution of (7S)-4'-chloro-6-methyl-2-sulfanyl-spiro[5,8-dihydropyrido[4,3-d]pyrimidine-7,1'-indane]-4-ol (53f) (890.0 mg, 2.67 mmol) in Water (10 mL) was added Chloroacetic Acid (1.26 g, 13.33 mmol) under $N_2$. Then the mixture was stirred at 100° C. for 16 h. Upon completion, the reaction was filtered, and the pH of the filtrate was adjusted to 8 with $NaHCO_3$ saturated aqueous. The solid was collected by filtration and dried to afford (7S)-4'-chloro-6-methyl-spiro[5,8-dihydropyrido[4,3-d]pyrimidine-7,1'-indane]-2,4-diol (53g) (614 mg, 1.93 mmol, 72.48% yield) as a brown solid. LCMS calculated for $C_{16}H_{17}ClN_3O_2$ $(M+H)^+$ m/z=318.10, 320.10; found: 318.2, 320.3.

Step 8. The mixture of (7S)-4'-chloro-6-methyl-spiro[5,8-dihydropyrido[4,3-d]pyrimidine-7,1'-indane]-2,4-diol (53g) (590.0 mg, 1.86 mmol) in Phosphorus Oxychloride (4 mL, 42.91 mmol) was stirred at 100° C. for 5 h. LCMS showed SM was consumed, then concentrated, diluted with DCM and purified by flash column chromatography (silica gel, eluting with 0% to 100% EtOAc in PE). Then concentrated and diluted with EtOAc, washed with $NaHCO_3$ aqueous and brine, dried over $Na_2SO_4$ and concentrated to afford (7S)-2,4,4'-trichloro-6-methyl-spiro[5,8-dihydropyrido[4,3-d]pyrimidine-7,1'-indane](53h) (432.0 mg, 1.22 mmol, 65.60% yield) as a yellow solid. LCMS calculated for $C_{16}H_{15}Cl_3N_3$ $(M+H)^+$ m/z=354.04, 356.03; found: 354.1, 356.1.

Step 9. The mixture of (7S)-2,4,4'-trichloro-6-methyl-spiro[5,8-dihydropyrido[4,3-d]pyrimidine-7,1'-indane] (53h) (150.0 mg, 0.42 mmol), 3-chloro-N,N-dimethyl-5,6, 7,8-tetrahydro-4H-pyrazolo[1,5-a][1,4]diazepine-2-carboxamide;hydrochloride (118.07 mg, 0.42 mmol) and DIEA (109 mg, 0.85 mmol) in DMF (2 mL) was stirred at room temperature for 30 h. The reaction mixture was diluted with water, extracted with EtOAc, washed with brine, dried over $Na_2SO_4$, concentrated and purified by flash column chromatography (silica gel, eluting with 3% to 7% MeOH/DCM) to afford 3-chloro-5-[(7S)-2,4'-dichloro-6-methyl-spiro[5,8-dihydropyrido[4,3-d]pyrimidine-7,1'-indane]-4-yl]-N,N-dimethyl-4,6,7,8-tetrahydropyrazolo[1,5-a][1,4]diazepine-2-carboxamide (53i) (120.0 mg, 0.2139 mmol, 50.58% yield) as a white solid. LCMS calculated for $C_{26}H_{29}Cl_3N_7O$ $(M+H)^+$ m/z=560.15, 562.15; found: 560.3, 562.3.

Step 10. The mixture of 3-chloro-5-[(7S)-2,4'-dichloro-6-methyl-spiro[5,8-dihydropyrido[4,3-d]pyrimidine-7,1'-indane]-4-yl]-N,N-dimethyl-4,6,7,8-tetrahydropyrazolo[1,5-a][1,4]diazepine-2-carboxamide (53i) (20.0 mg, 0.036 mmol), [(2R,8S)-2-fluoro-1,2,3,5,6,7-hexahydropyrrolizin-8-yl]methanol (7.38 mg, 0.046 mmol), $Cs_2CO_3$ (29.06 mg, 0.089 mmol), $Pd_2dba_3$ (3.27 mg, 0.004 mmol) and Ruphos (3.33 mg, 0.007 mmol) in Toluene (1 mL) was stirred at 110° C. for 10 h under $N_2$. The reaction mixture was cooled to room temperature and the solvent was removed under reduced pressure. The mixture was purified by flash column chromatography (silica gel, eluting with 0% to 12% MeOH/DCM) followed by prep-HPLC (0.1% $NH_4HCO_3$) to afford 3-chloro-5-[(7S)-2-[[(2R,8S)-2-fluoro-1,2,3,5,6,7-hexahydropyrrolizin-8-yl]methoxy]-6-methyl-spiro[5,8-dihydropyrido[4,3-d]pyrimidine-7,1'-indane]-4-yl]-N,N-dimethyl-4,6,7,8-tetrahydropyrazolo[1,5-a][1,4]diazepine-2-carboxamide (53) (9.78 mg, 0.015 mmol, 42.25% yield) as a white solid. LCMS calculated for $C_{34}H_{43}ClFN_8O_2$ $(M+H)^+$ m/z=649.32; found: 649.3. $^1H$ NMR (400 MHz, $CD_3OD$) δ 7.13-7.34 (m, 4H), 5.26 (d, J=54.4 Hz, 1H), 4.75-4.83 (m, 2H), 4.36-4.54 (m, 2H), 3.97-4.09 (m, 3H), 3.68-3.93 (m, 3H), 3.11-3.28 (m, 3H), 3.10 (s, 3H), 3.08 (s, 3H), 2.80-3.05 (m, 5H), 2.21-2.47 (m, 3H), 2.19 (s, 3H), 1.80-2.18 (m, 7H).

Compound 54. 3-chloro-N,N-dimethyl-5-[rac-(7S)-4'-chloro-2-[(6-methylene-2,3,5,7-tetrahydro-1H-pyrrolizin-8-yl)methoxy]spiro[5,8-dihydropyrano[4,3-d]pyrimidine-7,1'-indane]-4-yl]-4,6,7,8-tetrahydropyrazolo[1,5-a][1,4]diazepine-2-carboxamide Compound 54 was prepared from 27B-a similarly to that of Ex. 11 as a formic acid salt. LCMS calcld for $C_{34}H_4OCl_2N_7O_3$ (M+H)$^+$ m/z=664.3, found: 664.5/666.5. $^1$H NMR (400 MHz, CD$_3$OD) δ 7.32 (d, J=7.9 Hz, 1H), 7.20 (t, J=7.7 Hz, 1H), 7.10 (d, J=7.4 Hz, 1H), 5.34-5.20 (m, 2H), 4.83-4.71 (m, 3H), 4.59 (d, J=14.4 Hz, 1H), 4.48-4.32 (m, 4H), 4.28 (d, J=14.5 Hz, 1H), 3.94-3.75 (m, 3H), 3.74-3.64 (m, 1H), 3.23-3.04 (m, 8H), 3.04-2.89 (m, 4H), 2.73 (d, J=15.9 Hz, 1H), 2.45-2.28 (m, 2H), 2.28-2.00 (m, 6H).

Example 19. Exemplary Synthesis of 3-chloro-5-((S)-4-chloro-2'-(((2R,7aS)-2-fluorotetrahydro-1H-pyrrolizin-7a(5H)-yl)methoxy)-6'-methyl-2,3,5',8'-tetrahydro-6'H-spiro[indene-1,7'-pyrido[4,3-d]pyrimidin]-4'-yl)-N,N-dimethyl-5,6,7,8-tetrahydro-4H-pyrazolo[1,5-a][1,4]diazepine-2-carboxamide (55)

53i compound 55

To a solution of [(2R,8S)-2-fluoro-1,2,3,5,6,7-hexahydro-pyrrolizin-8-yl]methanol (76.63 mg, 0.48 mmol) in THF (1 mL) was added NaH (16.05 mg, 0.4 mmol) at 0° C. under N$_2$. The mixture was stirred at rt for 1 h, and then 3-chloro-5-[(7S)-2,4'-dichloro-6-methyl-spiro[5,8-dihydropyrido[4,3-d]pyrimidine-7,1'-indane]-4-yl]-N,N-dimethyl-4,6,7,8-tetrahydropyrazolo[1,5-a][1,4]diazepine-2-carboxamide (53i) (90.0 mg, 0.16 mmol) was added. The resulting mixture was stirred at 70° C. for 16 h. The reaction mixture was quenched with 1M HCl in MeOH, concentrated, purified by flash column chromatography (silica gel, eluting with 0% to 15% MeOH/DCM), and then purified by prep-HPLC (0.1% NH$_4$HCO$_3$) to afford 3-chloro-5-[(7S)-4'-chloro-2-[[(2R, 8S)-2-fluoro-1,2,3,5,6,7-hexahydropyrrolizin-8-yl] methoxy]-6-methyl-spiro[5,8-dihydropyrido[4,3-d]pyrimidine-7,1'-indane]-4-yl]-N,N-dimethyl-4,6,7,8-tetrahydropyrazolo[1,5-a][1,4]diazepine-2-carboxamide (55) (44.52 mg, 0.0635 mmol, 39.55% yield) as a white solid. LCMS calculated for $C_{34}H_{42}Cl_2FN_8O_2$ (M+H)$^+$ m/z=683.28, 685.28; found: 683.4, 685.4. $^1$H NMR (400 MHz, CD$_3$OD) δ 7.23-7.34 (m, 2H), 7.17 (dd, J=7.2, 1.6 Hz, 1H), 5.27 (d, J=54.0 Hz, 1H), 4.75-4.83 (m, 2H), 4.36-4.53 (m, 2H), 3.95-4.11 (m, 3H), 3.67-3.94 (m, 3H), 3.14-3.27 (m, 3H), 3.10 (s, 3H), 3.08 (s, 3H), 2.91-3.06 (m, 3H), 2.83-2.91 (m, 2H), 2.23-2.51 (m, 3H), 2.20 (s, 4H), 1.81-2.19 (m, 7H).

Compound 56. [3-chloro-5-[(7R)-4'-chloro-2-[[(2R, 8S)-2-fluoro-1,2,3,5,6,7-hexahydropyrrolizin-8-yl]methoxy]spiro[5,8-dihydropyrano[4,3-d]pyrimidine-7,1'-indane]-4-yl]-4,6,7,8-tetrahydropyrazolo[1,5-a][1,4]diazepin-2-yl]-(1,1-dioxo-1,4-thiazinan-4-yl)methanone (56)

Compound 56 was prepared similarly to that of Ex. 16. LCMS calcld for $C_{35}H_4OCl_2FN_7O_5S$ (M+H)$^+$ m/z=760.2, found: 760.5.

Example 20. Exemplary Synthesis of 1-[3-chloro-5-[(7S)-4'-chloro-2-[[(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]-4,6,7,8-tetrahydropyrazolo[1,5-a][1,4]diazepin-2-yl]-N,N-dimethyl-methanamine (57)

57a

-continued

57b

57c

57d

Compound 57

Step 1. To a solution of (7S)-4,4'-dichloro-2-methylsulfanyl-spiro[5,8-dihydropyrano[4,3-d]pyrimidine-7,1'-indane](27B-a P2) (300. mg, 0.85 mmol) in NMP (8 mL) were added ethyl 3-chloro-5,6,7,8-tetrahydro-4H-pyrazolo[1,5-a][1,4]diazepine-2-carboxylate (517.36 mg, 2.12 mmol) and DIPEA (329.26 mg, 2.55 mmol) at 25° C. The mixture was stirred at 100° C. for 16 h. The mixture was diluted with EtOAC (60 mL), washed with water (30*3 mL) and brine (30 ml), dried over $Na_2SO_4$, concentrated. The crude product was purified by flash chromatography (eluted with EtOAc in PE from 0% to 50%) to afford ethyl 3-chloro-5-[rac-(7S)-4'-chloro-2-methylsulfanyl-spiro[5,8-dihydropyrano[4,3-d]pyrimidine-7,1'-indane]-4-yl]-4,6,7,8-tetrahydropyrazolo[1,5-a][1,4]diazepine-2-carboxylate (57a) (300 mg, 0.535 mmol, 63.03%) yield as a pale white solid. LCMS calcld for $C_{26}H_{27}Cl_2N_5O_3S$ $(M+H)^+$ m/z=560.1, found: 560.2.

Step 2. To a solution of ethyl 3-chloro-5-[(7S)-4'-chloro-2-methylsulfanyl-spiro[5,8-dihydropyrano[4,3-d]pyrimidine-7,1'-indane]-4-yl]-4,6,7,8-tetrahydropyrazolo[1,5-a][1,4]diazepine-2-carboxylate (57a) (65. mg, 0.12 mmol) in DCM (1 mL) was added diisobutylaluminium hydride (0.23 mL, 0.23 mmol) at −78° C. The mixture was stirred at −78° C. for 1 h. IPA (1 mL) and water (1 mL) were added at −78° C., and the reaction mixture was allow back to rt and stirred for 1 h. The mixture was diluted with DCM (20 mL) and filtered. The solution was washed with brine (20 mL), dried over $Na_2SO_4$, concentrated to provide the crude product 3-chloro-5-[(7S)-4'-chloro-2-methylsulfanyl-spiro[5,8-dihydropyrano[4,3-d]pyrimidine-7,1'-indane]-4-yl]-4,6,7,8-tetrahydropyrazolo[1,5-a][1,4]diazepine-2-carbaldehyde (57b) (53 mg, 0.10 mmol, 88.5% yield), which was used directly in the next step. LCMS calcld for $C_{24}H_{23}Cl_2N_5O_2S$ $(M+H)^+$ m/z=516.1 found: 516.2.

Step 3. To a solution of 3-chloro-5-[(7S)-4'-chloro-2-methylsulfanyl-spiro[5,8-dihydropyrano[4,3-d]pyrimidine-7,1'-indane]-4-yl]-4,6,7,8-tetrahydropyrazolo[1,5-a][1,4]diazepine-2-carbaldehyde (57b) (60. mg, 0.12 mmol) in DCM (2 mL) was added Dimethylamine (0.35 mL, 0.35 mmol) at 25° C. The mixture was stirred at 25° C. for 1 h. Then Sodium triacetoxyborohydride (73.91 mg, 0.35 mmol) and AcOH (0.7 mg, 0.01 mmol) was added the reaction. The mixture was stirred at 25° C. for 1 h. The mixture was quenched with $H_2O$ (20 mL) at 25° C., extracted with DCM (20 mL×3), dried over Na2SO4, concentrated. The crude product was purified by Prep-HPLC (eluted with $CH_3CN$ in $H_2O$ (0.1% $NH_4HCO_3$) from 5.0% to 95%) to give 1-[3-chloro-5-[(7S)-4'-chloro-2-methylsulfanyl-spiro[5,8-dihydropyrano[4,3-d]pyrimidine-7,1'-indane]-4-yl]-4,6,7,8-tetrahydropyrazolo[1,5-a][1,4]diazepin-2-yl]-N,N-dimethyl-methanamine (57c) (34 mg, 0.0623 mmol, 53.6% yield) as a white solid. LCMS calcld for $C_{26}H_{30}Cl_2N_6OS$ $(M+H)^+$ m/z=545.2 found: 545.1.

Step 4. To a solution of 1-[3-chloro-5-[(7S)-4'-chloro-2-methylsulfanyl-spiro[5,8-dihydropyrano[4,3-d]pyrimidine-7,1'-indane]-4-yl]-4,6,7,8-tetrahydropyrazolo[1,5-a][1,4]diazepin-2-yl]-N,N-dimethyl-methanamine (57c) (40. mg, 0.07 mmol) in THF (2 mL) was added a solution of oxone (45.08 mg, 0.15 mmol) in Water (1 mL) at 0° C. Then the mixture was stirred at 25° C. for 3 h. The mixture was added water (30 mL) and extracted with EtOAC (40 mL×3), washed with a solution of $Na_2SO_3$ (20 mL), brine (50 ml), dried over $Na_2SO_4$, concentrated in vacuum to give the crude product. The aqueous layer was adjusted to pH=9 with the $NaHCO_3$ solution. The mixture was extracted with EtOAC (40 mL×3), dried over $Na_2SO_4$, concentrated in vacuum to give the crude product 1-[3-chloro-5-[(7S)-4'-chloro-2-methylsulfinyl-spiro[5,8-dihydropyrano[4,3-d]pyrimidine-7,1'-indane]-4-yl]-4,6,7,8-tetrahydropyrazolo[1,5-a][1,4]diazepin-2-yl]-N,N-dimethyl-methanamine (57d) (37 mg, 0.0659 mmol, 89.86% yield) as a white solid. LCMS calcld for $C_{26}H_{30}Cl_2N_6O_2S$ $(M+H)^+$ m/z=561.2, found: 561.1.

Step 5. To a solution of [(2R,8S)-2-fluoro-1,2,3,5,6,7-hexahydropyrrolizin-8-yl]methanol (26.22 mg, 0.16 mmol) in DMF (1 mL) was added NaH (5.27 mg, 0.13 mmol) at 25° C. The mixture was stirred at 25° C. for 15 min. A solution of 1-[3-chloro-5-[(7S)-4'-chloro-2-methylsulfinyl-spiro[5,8-dihydropyrano[4,3-d]pyrimidine-7,1'-indane]-4-yl]-4,6,7,8-tetrahydropyrazolo[1,5-a][1,4]diazepin-2-yl]-N,N-dim-ethyl-methanamine (57d) (37. mg, 0.07 mmol) in DMF (0.5 mL) was added and the mixture was stirred at 25° C. for 1 h. Acetic acid (0.01 mL, 0.13 mmol) was added the reaction mixture. The crude product was purified by Prep-HPLC (FA) to afford 1-[3-chloro-5-[(7S)-4'-chloro-2-[[(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]-4,6,7,8-tetrahydropyrazolo[1,5-a][1,4]diazepin-2-yl]-N,N-dimethyl-methanamine;formic acid (57) (24.13 mg, 0.034 mmol, 51.60% yield) as a white solid. LCMS calcld for $C_{33}H_{40}Cl_2FN_7O_2$ $(M+H)^+$ m/z=656.26, found: 656.3. $^1H$ NMR (400 MHz, CD$_3$OD) δ 8.46 (s, 1H), 7.32 (d, J=7.8 Hz, 1H), 7.20 (t, J=7.7 Hz, 1H), 7.11 (d, J=7.4 Hz, 1H), 5.46 (d, J=52.5 Hz, 1H), 4.79 (d, J=12.4 Hz, 4H), 4.59 (d, J=14.4 Hz, 1H), 4.45 (d, J=5.2 Hz, 2H), 4.34 (s, 2H), 3.93 (s, 2H), 3.87 (s, 2H), 3.79-3.48 (m, 3H), 3.28-3.20 (m, 1H), 3.09 (dt, J=21.4, 6.8 Hz, 1H), 3.03-2.86 (m, 3H), 2.63 (s, 6H), 2.58-2.32 (m, 3H), 2.29-2.13 (m, 6H), 2.04 (s, 1H).

Compound 58. (5R)-9-[(7S)-4'-chloro-2-[[(2R,8S)-2-fluoro-1,2,3,5,6,7-hexahydropyrrolizin-8-yl]methoxy]-6-methyl-spiro[5,8-dihydropyrido[4,3-d]pyrimidine-7,1'-indane]-4-yl]-1,3,9-triazaspiro[4.5]decane-2,4-dione Compound 58 was prepared similarly to that of Ex. 19. LCMS calculated for $C_{31}H_{38}ClFN_7O_3$ $(M+H)^+$ m/z=610.27, 611.27; found: 610.3, 611.3. $^1H$ NMR (400 MHz, CD$_3$OD): δ 7.23-7.32 (m, 2H), 7.17 (dd, J=6.9, 1.5 Hz, 1H), 5.26 (dd, J=55.4, 3.3 Hz, 1H), 4.10 (q, J=10.4 Hz, 2H), 3.95 (q, J=13.5 Hz, 2H), 3.70 (q, J=14.8 Hz, 2H), 3.39 (d, J=13.2 Hz, 1H), 3.13-3.26 (m, 3H), 2.93-3.12 (m, 4H), 2.89 (s, 2H), 2.40-2.51 (m, 1H), 2.21-2.32 (m, 1H), 2.19 (s, 3H), 2.06-2.18 (m, 3H), 1.81-2.02 (m, 7H). $^{19}F$ NMR (376 MHz, CD$_3$OD): δ −173.76 (s).

Intermediate 1. Synthesis of 3-chloro-N,N-dim-ethyl-5,6,7,8-tetrahydro-4H-pyrazolo[1,5-a][1,4]diazepine-2-carboxamide (Int-1)

Int-1a

Int-1b

Int-1c

Int-1d

-continued

Int-1e

Int-1f

Int-1

Step 1. Synthesis of 2-nitro-N-prop-2-ynyl-benzenesulfo-namide (Int-1a). A solution of prop-2-yn-1-amine (1.87 mL, 29.15 mmol) and N,N-Diisopropylethylamine (10.15 mL, 58.3 mmol) in DCM (100 mL) was cooled to 0° C. 2-ni-trobenzenesulfonyl chloride (6460. mg, 29.15 mmol) was added portion wise. Upon complete addition, the solution was allowed to warm to room temperature and was further stirred for 1 hr. The mixture was washed with water and brine, dried over Na$_2$SO$_4$, concentrated. The crude product was purified by silica gel chromatography (eluted with EtOAc in petroleum ether from 20% to 50%) to afford 2-nitro-N-prop-2-ynyl-benzenesulfonamide (Int-1a, 5984 mg, 24.9 mmol, 85.45% yield) as a yellow solid. LCMS calculated for C$_9$H$_9$N$_2$O$_4$S (M+H)$^+$ m/z=241.0, found: 241.0.

Step 2. Synthesis of N-(3-chloropropyl)-2-nitro-N-prop-2-ynyl-benzenesulfonamide (Int-1b). To a mixture of 2-ni-tro-N-prop-2-ynyl-benzenesulfonamide (Int-1a, 20. g, 83.25 mmol) and K2CO3 (33.37 g, 241.43 mmol) in Acetone (200 mL) was added neat 1-Bromo-3-Chloropropane (41.16 mL, 416.25 mmol) dropwise. Upon complete addition, the reac-tion mixture was stirred at 25° C. overnight. The mixture was diluted with EtOAC (300 mL), washed with water (100 mL) and brine (20 ml), dried over Na2SO4, concentrated. The mixture was concentrated, then washed with water and brine, dried over Na$_2$SO$_4$, concentrated. The crude product form 4 batches on the same scale were combined and purified by silica gel chromatography (eluted with EtOAc in petroleum ether from 10% to 90%) to give N-(3-chloropro-pyl)-2-nitro-N-prop-2-ynyl-benzenesulfonamide (Int-1b, 87.00 g, 275 mmol, 82.48% yield) as a yellow solid. LCMS calcld for Cl$_2$H$_{14}$ClN$_2$O$_4$S (M+H)$^+$ m/z=317.0, found: 317.0.

Step 3. Synthesis of ethyl 5-(2-nitrophenyl)sulfonyl-4,6,7,8-tetrahydropyrazolo[1,5-a][1,4]diazepine-2-carboxylate (Int-1c). To solution of N-(3-chloropropyl)-2-nitro-N-prop-2-ynyl-benzenesulfonamide (Int-1b, 10 g, 31.57 mmol) and ethyl 2-diazoacetate (5403.14 mg, 47.35 mmol) in Chlo-robenzene (80 mL) was added N,N-Diisopropylethylamine (5.5 mL, 31.57 mmol) at 140° C. for 1.5 hours. Upon complete addition, cesium carbonate (12.31 g, 37.88 mmol) was added and again heated to 140° C. for 30 minutes. The solvent was concentrated, and the mixture was extracted with EtOAC, washed with brine, dried over Na$_2$SO$_4$, con-centrated. The crude product was purified by silica gel chromatography (eluted with EtOAc in petroleum ether from 20% to 90%), then triturated in EtOAc to afford ethyl 5-(2-nitrophenyl)sulfonyl-4,6,7,8-tetrahydropyrazolo[1,5-a] [1,4]diazepine-2-carboxylate (Int-1c, 5.80 g, 14.7 mmol, 46.58% yield) as a yellow solid. LCMS calcld for C$_{16}$H$_{19}$N$_4$O$_6$S (M+H)$^+$ m/z=395.1, found: 395.0.

Step 4. Synthesis of ethyl 5-(2-nitrophenyl)sulfonyl-4,6,7,8-tetrahydropyrazolo[1,5-a][1,4]diazepine-2-carboxylate (Int-1d). To a solution of ethyl 5-(2-nitrophenyl)sulfonyl-4,6,7,8-tetrahydropyrazolo[1,5-a][1,4]diazepine-2-carboxy-late (Int-1c, 12.6 g, 31.95 mmol) in THF (100 mL) and Methanol (25 mL) a was added 1M LiOH in water (128 mL, 127.79 mmol) at 25° C. The mixture was stirred at 55° C. for 2 h. The mixture was acidified with HCl (1 mol/L in H$_2$O) to pH=6 and the crude product was triturated in water and filtered. 5-(2-nitrophenyl)sulfonyl-4,6,7,8-tetrahydropyra-zolo[1,5-a][1,4]diazepine-2-carboxylic acid (Int-1d, 11.5 g, 31.1 mmol, 97.28% yield) was obtained as a yellow solid. LCMS calcld for C$_{14}$H$_{14}$N$_4$O$_6$S (M+H)$^+$ m/z=367.1, found: 367.0.

Step 5. Synthesis of N,N-dimethyl-5-(2-nitrophenyl) sulfonyl-4,6,7,8-tetrahydropyrazolo[1,5-a][1,4]diazepine-2-carboxamide (Int-1e). To a solution of 5-(2-nitrophenyl) sulfonyl-4,6,7,8-tetrahydropyrazolo[1,5-a][1,4]diazepine-2-carboxylic acid (Int-1d, 9.60 g, 26.2 mmol), DIEA (18.26 mL, 104.82 mmol) and HATU (14.946 g, 39.31 mmol) in DMF (90 mL) was added 2M N-methylmethanamine in THF (20 mL) at 30° C. The mixture was stirred at 30° C. for 2 h. The mixture was diluted with DCM (300×2 mL), washed with water (400 mL) and brine (400×2 mL), dried over Na$_2$SO$_4$ and concentrated to afford a crude product N,N-dimethyl-5-(2-nitrophenyl)sulfonyl-4,6,7,8-tetrahydro-pyrazolo[1,5-a][1,4]diazepine-2-carboxamide (Int-1e, 10.1 g, 24.4 mmol, 93.07% yield) as a yellow oil. LCMS calcld for C$_{16}$H$_{20}$N$_4$O$_3$S (M+H)$^+$ m/z=394.1, found: 394.2.

Step 6. Synthesis of 3-chloro-N,N-dimethyl-5-(2-nitrop-henyl)sulfonyl-4,6,7,8-tetrahydropyrazolo[1,5-a][1,4]diaz-epine-2-carboxamide (Int-1f). To a solution of N,N-dim-ethyl-5-(2-nitrophenyl)sulfonyl-4,6,7,8-tetrahydropyrazolo [1,5-a][1,4]diazepine-2-carboxamide (Int-1e, 10.1 g, 25.67 mmol) in DMF (100 mL) was added N-Chlorosuccinimide (3.428 g, 25.67 mmol) at 0° C. under argon. The mixture was stirred at 45° C. for 1 h. The mixture was concentrated to afford a crude product. The crude product was triturated in water and filtered to afford 3-chloro-N,N-dimethyl-5-(2-nitrophenyl)sulfonyl-4,6,7,8-tetrahydropyrazolo[1,5-a][1,4]diazepine-2-carboxamide (Int-1f, 10.2 g, 23.4 mmol, 91.00% yield) as a crude yellow solid. LCMS calcld for $C_{16}H_{17}ClN_4O_6S$ (M+H)$^+$ m/z=428.1, found: 428.0.

Step 7. Synthesis of 3-chloro-N,N-dimethyl-5,6,7,8-tetra-hydro-4H-pyrazolo[1,5-a][1,4]diazepine-2-carboxamide(Intermediate 1). To a solution of 3-chloro-N,N-dimethyl-5-(2-nitrophenyl)sulfonyl-4,6,7,8-tetrahydropyrazolo[1,5-a][1,4]diazepine-2-carboxamide (Int-1f, 10.2 g, 23.84 mmol), 4-methoxybenzenethiol (8.8 mL, 71.52 mmol) and $CS_2CO_3$ (31.067 g, 95.36 mmol) in MeCN (100 mL). The mixture was stirred at 25° C. for 2 h. The mixture was concentrated and the crude product was purified by silica gel chromatography (eluted with MeOH in DCM from 3% to 10%) to afford 3-chloro-N,N-dimethyl-5,6,7,8-tetrahydro-4H-pyrazolo[1,5-a][1,4]diazepine-2-carboxamide (Int-1, 3.20 g, 13.2 mmol, 55.30% yield) as a yellow solid. LCMS calcld for $C_{10}H_{15}ClN_4O$ (M+H)$^+$ m/z=243.1, found: 243.0.

Intermediate 2. Synthesis of 2-methylsulfanyl-5,6,7,8-tetrahydro-4H-pyrazolo[1,5-a][1,4]diazepine (Int-2)

Int-2a

Int-2b

Int-2c

Int-2d

Int-2e

Int-2f

-continued

Int-2g

Int-2h

Int-2i

Int-2

Step 1. Synthesis of 1,1-dimethoxy-4,4-bis(methylsulfa-nyl)but-3-en-2-one (Int-2a). To a solution of sodium hydride (6.77 g, 169.31 mmol) in THF (100 mL) was added Carbon Disulfide (5.1 mL, 84.65 mmol) at 0'° C. The mixture was stirred at 25° C. for 10 min. Then, a solution of 1,1-dimethoxypropan-2-one (10 g, 84.65 mmol) in THF (30 mL) was added at 0° C. The mixture was stirred at 25° C. for 2 h. Then, a solution of Methyl Iodide (6.35 mL, 101.58 mmol) in THF (30 mL) was added at 0° C. The mixture was stirred at 25° C. for 2 h. The mixture was poured into $NaHCO_3$ (70 mL) and iced water (70 mL), extracted with EtOAC (100*3 mL), dried over $Na_2SO_4$, concentrated. The crude product was purified by flash chromatography (eluted with EtOAc in petroleum ether from 0% to 20%) to afford 1,1-dimethoxy-4,4-bis(methylsulfanyl)but-3-en-2-one (Int-2a, 6.00 g, 27.0 mmol, 31.88% yield) as a pale-yellow oil.

Step 2. Synthesis of 5-(dimethoxymethyl)-3-methylsulfa-nyl-1H-pyrazole (Int-2b). To a solution of 1,1-dimethoxy-4,4-bis(methylsulfanyl)but-3-en-2-one (Int-2a, 11 g, 49.48 mmol) in Ethanol (210 mL) was added hydrazine;hydrate (10.11 g, 197.91 mmol) and the reaction mixture was stirred at 25° C. for 16 h. The mixture was poured into iced water (100 mL), extracted with EtOAC (100*3 mL), dried over $Na_2SO_4$, concentrated. The crude product was purified by flash chromatography (eluted with EtOAc in petroleum ether from 0% to 50%) to afford 5-(dimethoxymethyl)-3-methyl-sulfanyl-1H-pyrazole (Int-2b, 6.00 g, 31.9 mmol, 64.42% yield) as a pale-yellow oil.

Step 3. Synthesis of 3-methylsulfanyl-1H-pyrazole-5-car-baldehyde (Int-2c). To a solution of 5-(dimethoxymethyl)-3-methylsulfanyl-1H-pyrazole (Int-2b, 2.6 g, 13.81 mmol) in Acetone (30 mL) and Water (10 mL) was added p-Tolu-enesulfonic acid (1189.16 mg, 6.91 mmol) at 25° C. The mixture was stirred at 50° C. for 2 h. The mixture was poured into the mixture of $NH_4Cl$ (30 mL) and iced water (30 mL). The mixture was filtered, and the filter cake was evaporated. The solid was dissolved with MeOH (20 mL) and filtered. The filter was dried under vacuum to give 3-methylsulfanyl-1H-pyrazole-5-carbaldehyde (Int-2c, 1.8 g, 12.3 mmol, 89.19% yield) was obtained as a pale-yellow solid. LCMS calcld for $C_5H_6N_2OS$ (M+H)$^+$ m/z=143.0, found: 143.2.

Step 4. Synthesis of 3-[(E)-(3-methylsulfanyl-1H-pyrazol-5-yl)methyleneamino]propan-1-ol (Int-2d). The solution of 3-methylsulfanyl-1H-pyrazole-5-carbaldehyde (Int-2c, 1.1 g, 7.74 mmol) and 3-aminopropan-1-ol (639.21 mg, 8.51 mmol) in Ethanol (10 mL) was stirred at 80° C. for 16 h. The mixture was concentrated to afford a crude product which was used directly in the next step. 3-[(E)-(3-methylsulfanyl-1H-pyrazol-5-yl)methyleneamino]propan-1-ol (Int-2d, 1.7 g, 3.23 mmol, 41.80% yield) was obtained as crude yellow oil. LCMS calcld for $C_8H_{13}N_3O$ S (M−H)$^−$ m/z=199.1, found: 199.1.

Step 5. Synthesis of 3-[(3-methylsulfanyl-1H-pyrazol-5-yl)methylamino]propan-1-ol (Int-2e). To a solution of 3-[(E)-(3-methylsulfanyl-1H-pyrazol-5-yl)methyleneamino]propan-1-ol (Int-2d, 1.7 g, 8.53 mmol) in Methanol (30 mL) was added Sodium triacetoxyborohydride (3.62 g, 17.06 mmol) at 0° C. The mixture was stirred at 25° C. for 6 h. The mixture was concentrated, and the crude product was purified by C18 flash chromatography (eluted with ACN in water from 0% to 7%) to give 3-[(3-methylsulfanyl-1H-pyrazol-5-yl)methylamino]propan-1-ol (Int-2e, 1.5 g, 7.45 mmol, 87.35% yield). LCMS calcld for $C_8H_{15}N_3O$ S (M+H)$^+$ m/z=202.2, found: 202.2.

Step 6. Synthesis of tert-butyl N-(3-hydroxypropyl)-N-[(3-methylsulfanyl-1H-pyrazol-5-yl)methyl]carbamate (Int-2f). To a solution of 3-[(3-methylsulfanyl-1H-pyrazol-5-yl)methylamino]propan-1-ol (Int-2e, 100 mg, 0.5 mmol) and Et$_3$N (0.14 mL, 0.99 mmol) in DCM (3 mL) was added Boc$_2$O (0.14 mL, 0.6 mmol) at 0° C. The mixture was stirred at 25° C. for 2 h. The mixture was diluted with DCM (10 mL) and filtered. The solution was washed with water (10 mL) and brine (10 mL), dried over Na$_2$SO$_4$, concentrated. The crude product was purified by Prep-TLC (eluted with EtOAc 100%) to give tert-butyl N-(3-hydroxypropyl)-N-[(3-methylsulfanyl-1H-pyrazol-5-yl)methyl]carbamate (Int-2f, 50 mg, 0.15 mmol, 30% yield) as a colorless viscous semi-solid. LCMS calcld for $C_{13}H_{24}N_3O_3S$ (M+H)$^+$ m/z=302.1, found: 302.1.

Step 7. Synthesis of 3-[tert-butoxycarbonyl-[(3-methylsulfanyl-1H-pyrazol-5-yl)methyl]amino]propyl methanesulfonate (Int-2g). To a solution of tert-butyl N-(3-hydroxypropyl)-N-[(3-methylsulfanyl-1H-pyrazol-5-yl)methyl] carbamate (Int-2f, 50 mg, 0.17 mmol) and in DCM (2 mL) was added MsCl (28.5 mg, 0.25 mmol) at 0° C. The mixture was stirred at 25° C. for 2 h. The mixture was quenched with H$_2$O (20 mL), extracted with DCM (10*2 mL), dried over Na$_2$SO$_4$, concentrated. The crude product was purified by Prep-TLC (eluted with EtOAc in petroleum ether 50%) to give 3-[tert-butoxycarbonyl-[(3-methylsulfanyl-1H-pyrazol-5-yl)methyl]amino]propyl methanesulfonate (Int-2g, 27 mg, 0.069 mmol, 42% yield) as a colorless viscous semi-solid. LCMS calcld for $C_{14}H_{25}N_3O_5S_2$ (M+Na)$^+$ m/z=402.1, found: 402.0.

Step 8. Synthesis of tert-butyl 2-methylsulfanyl-4,6,7,8-tetrahydropyrazolo[1,5-a][1,4]diazepine-5-carboxylate (Int-2h). To a solution of 3-[tert-butoxycarbonyl-[(3-methylsulfanyl-1H-pyrazol-5-yl)methyl]amino]propyl methanesulfonate (Int-2g, 200 mg, 0.53 mmol) in THF (20 mL) was added sodium hydride (63.24 mg, 1.58 mmol) at 0°

C. under N$_2$. The mixture was stirred at 25° C. for 3 h. The mixture was quenched with the mixture of NH$_4$Cl (20 mL) and iced water (20 mL), extracted with EtOAC (20*3 mL), dried over Na$_2$SO$_4$, concentrated. The crude product was purified by flash chromatography (eluted with EtOAc in petroleum ether from 0% to 35%) to give tert-butyl 2-methylsulfanyl-4,6,7,8-tetrahydropyrazolo[1,5-a][1,4]diazepine-5-carboxylate (Int-2h, 50 mg, 0.176 mmol, 33.5% yield) as a yellow oil. LCMS calcld for $C_{13}H_{21}N_3O_2$ (M+H)$^+$ m/z=284.2, found: 284.2.

Step 9. Synthesis of 2-methylsulfanyl-5,6,7,8-tetrahydro-4H-pyrazolo[1,5-a][1,4]diazepine (Intermediate 2). To a solution of tert-butyl 2-methylsulfanyl-4,6,7,8-tetrahydropyrazolo[1,5-a][1,4]diazepine-5-carboxylate (Int-2h, 40 mg, 0.14 mmol) in DCM (2 mL) was added TFA (0.5 mL, 6.53 mmol) at 0° C. The mixture was stirred at 25° C. for 1 h. The mixture was transferred dropwise onto a saturated aqueous solution of NaHCO$_3$ (20 mL), extracted with DCM (3×10 mL), dried over Na$_2$SO$_4$, concentrated. the crude product was purified by Prep-TLC (eluted with MeOH in DCM of 10%) to give 2-methylsulfanyl-5,6,7,8-tetrahydro-4H-pyrazolo[1,5-a][1,4]diazepine (Intermediate 2, 8 mg, 0.044 mmol, 31% yield) a yellow oil. LCMS calcld for $C_8H_{13}N_3S$ (M+H)$^+$ m/z=184.1, found: 184.2.

Compound 59. 1-[3-chloro-5-[(7S)-4'-chloro-2-[[(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]-4,6,7,8-tetrahydropyrazolo[1,5-a][1,4]diazepin-2-yl]-N-methyl-methanamine Compound 59 was prepared similarly to that of Ex. 20. LCMS calcld for $C_{33}H_{40}Cl_2FN_7O_2$ (M+H)$^+$ m/z=642.59, found: 642.3. $^1$H NMR (DMSO-d6, 400 Hz): δ 7.39 (d, J=8.4 Hz, 1H), 7.25 (t, J=7.6 Hz, 1H), 7.15 (d, J=7.2 Hz, 1H), 5.32-5.19 (m, 1H), 4.76-4.70 (m, 3H), 4.50-4.47 (m, 1H), 4.32-4.32 (m, 2H), 3.93 (d, J=10.4 Hz, 1H), 3.84 (d, J=10.4 Hz, 1H), 3.75-3.74 (m, 3H), 3.51 (s, 3H), 3.07-3.04 (m, 3H), 3.00-2.97 (m, 2H), 2.93-2.90 (m, 3H), 2.84-2.79 (m, 1H), 2.33-2.30 (m, 2H), 2.25 (s, 3H), 2.17-2.10 (m, 1H), 2.09-2.01 (m, 3H), 1.99-1.98 (m, 1H), 1.93-1.91 (m, 1H).

Compound 60. (5R)-9-[(7S)-2-[[(2R,8S)-2-fluoro-1, 2,3,5,6,7-hexahydropyrrolizin-8-yl]methoxy]-6-methyl-spiro[5,8-dihydropyrido[4,3-d]pyrimidine-7, 1'-indane]-4-yl]-1,3,9-triazaspiro[4.5]decane-2,4-dione Compound 60 was prepared similarly to that of Ex. 19. LCMS calculated for $C_{31}H_{39}FN_7O_3$ (M+H)$^+$ m/z=576.31; found: 576.3. $^1$H NMR (400 MHz, CD$_3$OD) δ 7.17-7.30 (m, 4H), 5.32 (d, J=53.6 Hz, 1H), 4.21, 4.13 (d, J=10.8 Hz, 2H), 3.99 (d, J=13.2 Hz, 1H), 3.91 (d, J=12.8 Hz, 1H), 3.75, 3.66 (d, J=14.8 Hz, 2H), 3.40 (d, J=13.2 Hz, 1H), 3.24-3.36 (m, 3H), 2.93-3.11 (m, 6H), 2.22-2.47 (m, 3H), 2.19 (s, 3H), 1.83-2.17 (m, 9H).

Compound 61. 3-chloro-5-[(7S)-4',7'-difluoro-2-[[(2R,8S)-2-fluoro-1,2,3,5,6,7-hexahydropyrrolizin-8-yl]methoxy]-6-methyl-spiro[5,8-dihydropyrido[4,3-d]pyrimidine-7,1'-indane]-4-yl]-N,N-dimethyl-4,6,7,8-tetrahydropyrazolo[1,5-a][1,4]diazepine-2-carboxamide Compound 61 was prepared similarly to that of Ex. 18. LCMS calculated for $C_{34}H_{41}ClF_3N_8O_2$ (M+H)$^+$ m/z=685.3; found: 685.3. $^1$H NMR (400 MHz, CD$_3$OD) δ 7.04 (td, J=8.8, 3.6 Hz, 1H), 6.97 (td, J=9.2, 4.0 Hz, 1H), 5.27 (d, J=54.0 Hz, 1H), 4.80 (d, J=6.8 Hz, 2H), 4.35-4.51 (m, 2H), 4.01, 4.07 (d, J=10.8 Hz, 2H), 3.99-4.10 (m, 1H), 3.83-3.92 (m, 1H), 3.65, 3.79 (d, J=14.8 Hz, 2H), 3.14-3.25 (m, 3H), 3.05-3.12 (m, 1H), 3.10 (s, 3H), 3.08 (s, 3H), 2.92-3.02 (m, 2H), 2.87 (d, J=18.0 Hz, 1H), 2.30-2.58 (m, 3H), 2.28 (s, 3H), 2.03-2.23 (m, 4H), 1.82-2.00 (m, 4H).

Compound 62. (7S)-4'-chloro-2-[[(2R,8S)-2-fluoro-1,2,3,5,6,7-hexahydropyrrolizin-8-yl]methoxy]-4-(2-methylsulfonyl-4,6,7,8-tetrahydropyrazolo[1,5-a][1, 4]diazepin-5-yl)spiro[5,8-dihydropyrano[4,3-d]pyrimidine-7,1'-indane]

Compound 62 was prepared similarly to that of Ex. 11 using intermediate 2. LCMS calcld for $C_{31}H_{36}ClFN_6O_4S$ (M+H)$^+$ m/z=643.2, found: 643.3. $^1$H NMR (400 MHz, CDCl$_3$) δ 7.34 (d, J=7.6 Hz, 1H), 7.26-7.23 (m, 1H), 6.97 (d, J=7.6 Hz, 1H), 6.67 (brs, 1H), 5.31 (d, J=53.2 Hz, 1H), 4.68-4.32 (m, 6H), 4.11-4.04 (m, 3H), 3.69-3.63 (m, 1H), 3.43-3.08 (m, 8H), 3.06-2.85 (m, 3H), 2.40-2.14 (m, 6H), 2.07-1.89 (m, 4H). $^{19}$F NMR (377 MHz, CDCl$_3$) δ −172.99 (s).

Compound 63. 3-chloro-5-[(7S)-7'-fluoro-2-[[(2R, 8S)-2-fluoro-1,2,3,5,6,7-hexahydropyrrolizin-8-yl] methoxy]-6-methyl-spiro[5,8-dihydropyrido[4,3-d] pyrimidine-7,1'-indane]-4-yl]-N,N-dimethyl-4,6,7,8-tetrahydrpopyrazolo[1,5-a][1,4]diazepine-2-carboxamide Compound 63 was prepared similarly to that of Ex. 18. LCMS calculated for $C_{34}H_{42}ClF_2N_8O_2$ $(M+H)^+$ m/z=667.31, 668.31; found: 667.2, 668.2. $^1H$ NMR (400 MHz, $CD_3OD$) δ=7.31 (td, J=7.9, 5.1, 1H), 7.09 (d, J=7.5, 1H), 6.93 (dd, J=10.1, 8.4, 1H), 5.26 (d, J=54.6, 1H), 4.75-4.81 (m, 2H), 4.35-4.52 (m, 2H), 3.96-4.09 (m, 3H), 3.83-3.92 (m, 1H), 3.73 (d, J=14.6, 2H), 3.11-3.28 (m, 4H), 3.10 (s, 3H), 3.08 (s, 3H), 2.93-3.07 (m, 3H), 2.85 (d, J=18.0, 1H), 2.48 (dt, J=13.2, 8.6, 1H), 2.29-2.43 (m, 1H), 2.26 (s, 3H), 2.02-2.23 (m, 4H), 1.79-2.00 (m, 4H). $^{19}F$ NMR (376 MHz, $CD_3OD$) δ=−120.88 (s), −173.46 (s).

Example 21. Exemplary Synthesis of 3-chloro-5-[(7S)-2-[[(2R,8S)-2-fluoro-1,2,3,5,6,7-hexahydropy-rrolizin-8-yl]methoxy]-6-methyl-spiro[5,8-dihydro-pyrido[4,3-d]pyrimidine-7,1'-tetralin]-4-yl]-N,N-dimethyl-4,6,7,8-tetrahydropyrazolo[1,5-a][1,4]diazepine-2-carboxamide (Compound 64)

-continued

64e

64f

64g

64h

64a

64b

64c

64d

Int-1

64i

-continued

64j compound 64

Step 1. Synthesis of (NE,R)-2-methyl-N-tetralin-1-ylidene-propane-2-sulfinamide (64a). A mixture of (R)-2-methylpropane-2-sulfinamide (24.87 g, 205.21 mmol) and tetraethoxytitanium (42.95 mL, 205.21 mmol) in Toluene (100 mL) was stirred and heated to 90° C. Then the tetralin-1-one (10. g, 68.4 mmol) was added to mixture dropwise and stirred for 5 h. The mixture was quenched with Potassium sodium tartrate tetrahydrate (aq, 600 mL), filtered and extract with ethyl acetate and purified by flash column chromatography (silica gel, eluting with 10% to 30% EtOAc/PE) to afford (NE,R)-2-methyl-N-tetralin-1-ylidene-propane-2-sulfinamide (64a, 13.60 g, 54.5 mmol, 79.73% yield) as a brown oil. LCMS calculated for $C_{14}H_{20}NOS$ (M+H)+ m/z=250.1; found: 250.1.

Step 2. Synthesis of ethyl 2-[(1S)-1-[[(R)-tert-butylsulfinyl]amino]tetralin-1-yl]acetate (64b). To a solution of Diisopropylamine (16.49 mL, 117.34 mmol) in THF (230 mL) was added butyllithium (44.8 mL, 112 mmol) portion wise at 0° C. under $N_2$. Then the mixture was stirred at 0° C. for 0.5 h then cooled to −70° C. to which was added EtOAc (10.44 mL, 106.67 mmol). The solution was stirred for 1 h upon which was added triisopropoxytitanium(IV) chloride (213.34 mL, 213.34 mmol) at −70° C. and stirred for 30 min, then (NE,R)-2-methyl-N-tetralin-1-ylidene-propane-2-sulfinamide (64a, 13.3 g, 53.33 mmol) in THF (34 mL) was added drop wise at −70° C. The resulting mixture was stirred at −70° C. for 2 h. Then quenched with $NH_4Cl$ at −70° C., extracted with EtOAc. The organic layer was washed with water and brine, dried over $Na_2SO_4$, concentrated and purified by flash column chromatography (silica gel, eluting with 5% to 34% EtOAc/PE) to afford ethyl 2-[(1S)-1-[[(R)-tert-butylsulfinyl]amino]tetralin-1-yl]acetate (64b, 15.43 g, 45.7 mmol, 85.74% yield) as a yellow oil. LCMS calculated for $C_{18}H_{28}NO_3S$ (M+H)+ m/z=338.18, found: 338.3.

Step 3. Synthesis of ethyl 2-[(1S)-1-amino-7-fluoro-indan-1-yl]acetate (64c). The mixture of ethyl 2-[(1S)-1-[[(S)-tert-butylsulfinyl]amino]tetralin-1-yl]acetate (64b, 2.37 g, 7.02 mmol) and HCL/dioxane (7.02 mL, 28.09 mmol) in Ethanol (8 mL) was stirred at rt for 1 h. Aqueous ammonia was added to the reaction mixture until pH adjusted to 9, then the reaction mixture was extracted with EtOAc, The crude reaction mixture was purified by Prep-HPLC to afford crude ethyl 2-[(1S)-1-amino-7-fluoro-indan-1-yl]acetate (64c) as a brown oil. LCMS calculated for $C_{14}H_{19}NO_2$ (M+H)+ m/z=217.2; found: 217.1.

Step 4. Synthesis of ethyl 3-[[(1S)-1-(2-ethoxy-2-oxo-ethyl)tetralin-1-yl]amino]propanoate (64d). A mixture of ethyl 2-[(1S)-1-aminotetralin-1-yl]acetate (64c, 1.55 g, 6.64 mmol), ethyl prop-2-enoate (4.66 g, 46.5 mmol), $Et_3N$ (2.78 mL, 19.93 mmol) and CuO (0.11 g, 1.33 mmol) was dissolved in Ethanol (20 mL). The vial was sealed, and this mixture was then stirred for 8 h at 85° C. The crude reaction mixture was filtered and purified by flash column chromatography (silica gel, eluting with 0% to 50% PE/EA) to afford ethyl 3-[[(1S)-1-(2-ethoxy-2-oxo-ethyl)tetralin-1-yl]amino]propanoate (64d, 2000 mg, 6.00 mmol, 90.29% yield) as a light-yellow oil. LCMS calculated for $C_{19}H_{28}NO_4$ (M+H)+ m/z=334.2; found: 334.2.

Step 5. Synthesis of ethyl 3-[methyl-[(1S)-1-(2-ethoxy-2-oxo-ethyl)tetralin-1-yl]amino]propanoate (64e). To a solution of ethyl 3-[[(1S)-1-(2-ethoxy-2-oxo-ethyl)tetralin-1-yl]amino]propanoate (64d, 2 g, 6 mmol) in Ethanol (80 mL) was added Paraformaldehyde (1.08 g, 35.99 mmol) and $CH_3BNNa$ (1.13 g, 18 mmol). Then the mixture was stirred at 25° C. for 16 h, the reaction mixture was quenched with water, and then extracted with EtOAc. The organic layer was washed with brine, dried over $Na_2SO_4$, concentrated and purified by flash column chromatography (silica gel, eluting with 0% to 20% EtOAc/PE) to afford ethyl 3-[methyl-[(1S)-1-(2-ethoxy-2-oxo-ethyl)tetralin-1-yl]amino]propanoate (64e, 1680 mg, 4.84 mmol, 80.61% yield) as a colorless oil. LCMS calculated for $C_{20}H_{30}NO_4$ (M+H)+ m/z=348.2; found: 348.2.

Step 6. Synthesis of ethyl (6S)-1-methyl-4-oxo-spiro[piperidine-6,1'-tetralin]-3-carboxylate (64f). To a solution of [bis(trimethylsilyl)amino]potassium (14.5 mL) in THF (8 mL) was added ethyl 3-[methyl-[(1S)-1-(2-ethoxy-2-oxo-ethyl)tetralin-1-yl]amino]propanoate (64e, 1.68 g, 4.84 mmol) portion wise at −70° C. under $N_2$. Then the mixture was stirred at −70° C. for 2 h. The reaction mixture was quenched with $NH_4Cl$ at −70° C., and then extracted with EtOAc. The organic layer was washed with water and brine, dried over $Na_2SO_4$, concentrated, and purified by flash column chromatography (silica gel, eluting with 0% to 20% EtOAc/PE) to afford ethyl (6S)-1-methyl-4-oxo-spiro[piperidine-6,1'-tetralin]-3-carboxylate (64f, 1300 mg, 4.31 mmol, 89.21% yield) as a yellow oil. LCMS calculated for $C_{18}H_{23}NO_3$ (M+H)+ m/z=302.2; found: 302.3.

Step 7. Synthesis of (7S)-6-methyl-2-sulfanyl-spiro[5,8-dihydropyrido[4,3-d]pyrimidine-7,1'-tetralin]-4-ol (64g). To a solution of ethyl (6S)-1-methyl-4-oxo-spiro[piperidine-6,1'-tetralin]-3-carboxylate (64f, 1300 mg, 4.31 mmol) in Ethanol (10 mL) was added Thiourea (656.69 mg, 8.63 mmol) and $C_2H_5ONa$ (880.6 mg, 12.94 mmol). Then the mixture was stirred at 80° C. under $N_2$ for 12 h. The reaction mixture was concentrated, then pH was adjusted to 6 with hydrochloric acid (1N), the resulting precipitate was filtered to afford (7S)-6-methyl-2-sulfanyl-spiro[5,8-dihydropyrido[4,3-d]pyrimidine-7,1'-tetralin]-4-ol (64 g, 1000 mg, 3.19 mmol, 73.97% yield) as yellow solid. LCMS calculated for $C_{17}H_{19}N_3O$ S (M+H)$^+$ m/z=314.13; found: 314.0.

Step 8. Synthesis of (7S)-6-methylspiro[5,8-dihydro-pyrido[4,3-d]pyrimidine-7,1'-tetralin]-2,4-diol (64h). To a solution of (7S)-6-methyl-2-sulfanyl-spiro[5,8-dihydro-pyrido[4,3-d]pyrimidine-7,1'-tetralin]-4-ol (64 g, 1 g, 3.19 mmol) in Water (12 mL) was added Chloroacetic Acid (1.51 g, 15.95 mmol) under $N_2$. Then the mixture was stirred at 100° C. for 16 h. The reaction was filtered, and the pH of the filtrate was adjusted to 8 with NaHCO$_3$. The solid was collected by filtration and dried to afford (7S)-6-methylspiro[5,8-dihydropyrido[4,3-d]pyrimidine-7,1'-tetralin]-2,4-diol (64h, 913 mg, 3.07 mmol, 96.23% yield) as a white solid. LCMS calculated for $C_{17}H_{20}N_3O_2$ (M+H)$^+$ m/z=298.15; found: 298.1.

Step 9. Synthesis of (7S)-2,4-dichloro-6-methyl-spiro[5,8-dihydropyrido[4,3-d]pyrimidine-7,1'-tetralin](64i). The mixture of (7S)-6-methylspiro[5,8-dihydropyrido[4,3-d]pyrimidine-7,1'-tetralin]-2,4-diol (64h, 300 mg, 1.01 mmol) in POCl$_3$ (3.21 mL, 35.02 mmol) was stirred at 100° C. for 4.5 h. The reaction was concentrated and purified by flash column chromatography (silica gel, eluting with 0% to 100% EtOAc/PE) to afford (7S)-2,4-dichloro-6-methyl-spiro[5,8-dihydropyrido[4,3-d]pyrimidine-7,1'-tetralin](64i, 360 mg, 0.808 mmol, 80.07% yield) as an orange solid. LCMS calculated for $C_{17}H_{18}C_2N_3$ (M+H)$^+$ m/z=334.1, 336.1; found: 334.0/336.0.

Step 10. Synthesis of -chloro-5-[(7S)-2-chloro-6-methyl-spiro[5,8-dihydropyrido[4,3-d]pyrimidine-7,1'-tetralin]-4-yl]-N,N-dimethyl-4,6,7,8-tetrahydropyrazolo[1,5-a][1,4]diazepine-2-carboxamide (64j). To a solution of (7S)-2,4-dichloro-6-methyl-spiro[5,8-dihydropyrido[4,3-d]pyrimidine-7,1'-tetralin](64i, 3 g, 8.98 mmol) in DMSO (30 mL). 3-chloro-N,N-dimethyl-5,6,7,8-tetrahydro-4H-pyrazolo[1,5-a][1,4]diazepine-2-carboxamide (Int-1, 2724 mg, 11.22 mmol) and DIEA (4.69 mL, 26.93 mmol) were added. The reaction was stirred at 20° C. over weekends. Then the mixture was filtered and purified by Prep-HPLC on a C18 column (5 uM, 50×150 mm) with mobile phase: H$_2$O (0.1% NH$_4$HCO$_3$)/MeCN at flow rate: 65 mL/min to afford 3-chloro-5-[(7S)-2-chloro-6-methyl-spiro[5,8-dihydro-pyrido[4,3-d]pyrimidine-7,1'-tetralin]-4-yl]-N,N-dimethyl-4,6,7,8-tetrahydropyrazolo[1,5-a][1,4]diazepine-2-carbox-amide (64j, 3525 mg, 6.52 mmol, 72.66% yield) as a white solid. LCMS calculated for $C_{27}H_{31}Cl_2N_7O$ (M+H)$^+$ m/z=540.20, 542.20; found: 540.1, 542.1.

Step 11. Synthesis of 3-chloro-5-[(7S)-2-[[(2R,8S)-2-fluoro-1,2,3,5,6,7-hexahydropyrrolizin-8-yl]methoxy]-6-methyl-spiro[5,8-dihydropyrido[4,3-d]pyrimidine-7,1'-te-tralin]-4-yl]-N,N-dimethyl-4,6,7,8-tetrahydropyrazolo[1,5-a][1,4]diazepine-2-carboxamide (Compound 64). To a solution of [(2R,8S)-2-fluoro-1,2,3,5,6,7-hexahydropyr-rolizin-8-yl]methanol (3.4 g, 21.36 mmol) in DMSO (70 mL) was added sodium hydride (854.27 mg, 21.36 mmol). The reaction was stirred at rt for 40 min. Then 3-chloro-5-[(7S)-2-chloro-6-methyl-spiro[5,8-dihydropyrido[4,3-d]py-rimidine-7,1'-tetralin]-4-yl]-N,N-dimethyl-4,6,7,8-tetrahydropyrazolo[1,5-a][1,4]diazepine-2-carboxamide (64j, 2600 mg, 4.81 mmol) was added and the reaction was stirred at 40° C. for 1.5 h. The reaction mixture was cooled to rt and diluted with H$_2$O. It was extracted with EtOAc (50 mL*6) and concentrated to get crude product. The reaction was purified with pre-HPLC on a C18 column with a mobile phase (H$_2$O—NH$_4$HCO$_3$/ACN) to afford 3-chloro-5-[(7S)-2-[[(2R,8S)-2-fluoro-1,2,3,5,6,7-hexahydropyrrolizin-8-yl]methoxy]-6-methyl-spiro[5,8-dihydropyrido[4,3-d]pyrimi-dine-7,1'-tetralin]-4-yl]-N,N-dimethyl-4,6,7,8-tetrahydropyrazolo[1,5-a][1,4]diazepine-2-carboxamide (Compound 64, 2.3 g, 3.451 mmol, 67.33% yield). LCMS calculated for $C_{35}H_{45}ClFN_8O_2$ (M+H)$^+$ m/z=663.33; found: 663.4 $^1$H NMR (400 MHz, CD$_3$OD) δ 7.49 (d, J=7.6 Hz, 1H), 7.04-7.24 (m, 3H), 5.27 (d, J=53.6 Hz, 1H), 4.89-4.74 (m, 2H), 4.33-4.53 (m, 2H), 4.16-3.81 (m, 5H), 3.72-3.62 (m, 1H), 3.26-2.88 (m, 12H), 2.81-2.68 (m, 2H), 2.45-2.32 (m, 1H), 2.30-2.04 (m, 7H), 2.02-1.75 (m, 7H).

Compound 64B. 3-chloro-5-[(7R)-2-[[(2R,8S)-2-fluoro-1,2,3,5,6,7-hexahydropyrrolizin-8-yl]methoxy]-6-methyl-spiro[5,8-dihydropyrido[4,3-d]pyrimidine-7,1'-tetralin]-4-yl]-N,N-dimethyl-4,6,7,8-tetrahydropyrazolo[1,5-a][1,4]diazepine-2-carboxamide Compound 64B was isolated as minor isomer from example 21 on Regis (R,R)Whelk-O1 (250*25 mm 10 um) column on a Waters SFC 150 system (Mobile Phase A: Supercritical CO$_2$, Mobile Phase B: CO$_2$/EtOH[0.5% NH$_3$ (7M in MeOH)]=70/30; Flow: 100 ml/min) to give faster eluting P1 (64) and slower eluting P2 (64B). LCMS calculated for $C_{35}H_{45}ClFN_8O_2$ (M+H)$^+$ m/z=663.33; found: 663.3. $^1$H NMR (400 MHz, CD$_3$OD) δ 7.49 (d, J=7.6 Hz, 1H), 7.04-7.25 (m, 3H), 5.25 (d, J=54.8 Hz, 1H), 4.75, 4.90 (d, J=16.8 Hz, 2H), 4.36-4.56 (m, 2H), 3.81-4.15 (m, 5H), 3.67 (d, J=14.8 Hz, 1H), 2.89-3.28 (m, 12H), 2.69-2.80 (m, 2H), 2.32-2.49 (m, 1H), 2.03-2.31 (m, 7H), 1.71-2.03 (m, 7H).

Compound 65. 3-chloro-5-[(7S)-4'-fluoro-2-[[(2R, 8S)-2-fluoro-1,2,3,5,6,7-hexahydropyrrolizin-8-yl] methoxy]-6-methyl-spiro[5,8-dihydropyrido[4,3-d] pyrimidine-7,1'-indane]-4-yl]-N,N-dimethyl-4,6,7,8-tetrahydropyrazolo[1,5-a][1,4]diazepine-2-carboxamide Compound 65 was prepared similarly to that of Ex. 18. LCMS calculated for $C_{34}H_{42}ClF_2N_8O_2$ (M+H)$^+$ m/z=667.31; found: 667.3. $^1$H NMR (400 MHz, CD$_3$OD) δ 7.29 (td, J=8.0, 5.2 Hz, 1H), 7.05 (d, J=7.6 Hz, 1H), 6.99 (t, J=8.8 Hz, 1H), 5.26 (d, J=54.8 Hz, 1H), 4.73-4.83 (m, 2H), 4.34-4.53 (m, 2H), 3.96-4.10 (m, 3H), 3.66-3.94 (m, 3H), 3.13-3.26 (m, 3H), 3.10 (s, 3H), 3.08 (s, 3H), 2.83-3.06 (m, 5H), 2.24-2.52 (m, 3H), 2.20 (s, 3H), 1.79-2.19 (m, 7H).

Compound 66. (5R)-9-[(7S)-7'-fluoro-2-[[(2R,8S)-2-fluoro-1,2,3,5,6,7-hexahydropyrrolizin-8-yl] methoxy]-6-methyl-spiro[5,8-dihydropyrido[4,3-d] pyrimidine-7,1'-indane]-4-yl]-1,3,9-triazaspiro[4.5] decane-2,4-dione Compound 66 was prepare similarly to that of Ex. 19. LCMS calculated for $C_{31}H_{38}F_2N_7O_3$ (M+H)$^+$ m/z=594.29; found: 594.4. $^1$H NMR (400 MHz, CD$_3$OD) δ 7.25-7.40 (m, 1H), 7.10 (d, J=7.6 Hz, 1H), 6.89-6.99 (m, 1H), 5.26 (d, J=52.4 Hz, 1H), 3.86-4.18 (m, 4H), 3.65 (d, J=14.8 Hz, 2H), 2.93-3.37 (m, 9H), 2.82-2.91 (m, 1H), 2.42-2.55 (m, 1H), 1.80-2.32 (m, 14H).

Compound 67. (5R)-9-[(7S)-4',7'-difluoro-2-[[(2R, 8S)-2-fluoro-1,2,3,5,6,7-hexahydropyrrolizin-8-yl] methoxy]-6-methyl-spiro[5,8-dihydropyrido[4,3-d] pyrimidine-7,1'-indane]-4-yl]-1,3,9-triazaspiro[4.5] decane-2,4-dione Compound 67 was prepared similarly to that of Ex. 19. LCMS calculated for $C_{31}H_{37}F3N_7O_3$ (M+H)$^+$ m/z=612.3; found: 612.3. $^1$H NMR (400 MHz, CD$_3$OD) δ 7.05 (td, J=8.8, 3.6 Hz, 1H), 6.98 (td, J=9.2, 4.0 Hz, 1H), 5.23 (d, J=52.4 Hz, 1H), 4.05, 4.13 (d, J=10.4 Hz, 2H), 4.03 (d, J=13.2 Hz, 1H), 3.92 (d, J=13.2 Hz, 1H), 3.62, 3.68 (d, J=14.8 Hz, 2H), 3.34 (d, J=13.63 Hz, 1H), 3.08-3.23 (m, 5H), 2.94-3.07 (m, 3H), 2.88 (d, J=18.0 Hz, 1H), 2.48-2.58 (m, 1H), 2.26 (s, 3H), 2.19-2.31 (m, 1H), 2.03-2.18 (m, 3H), 1.82-2.00 (m, 7H).

Compound 68. (5R)-9-[(7S)-4'-fluoro-2-[[(2R,8S)-2-fluoro-1,2,3,5,6,7-hexahydropyrrolizin-8-yl] methoxy]-6-methyl-spiro[5,8-dihydropyrido[4,3-d] pyrimidine-7,1'-indane]-4-yl]-1,3,9-triazaspiro[4.5] decane-2,4-dione Compound 68 was prepared similarly to that of Ex. 19. LCMS calculated for $C_{31}H_{38}F2N_7O_3$ (M+H)$^+$ m/z=594.29; found: 594.3. $^1$H NMR (400 MHz, CD$_3$OD) δ 7.21-7.39 (m, 1H), 6.92-7.11 (m, 2H), 5.26 (d, J=53.6 Hz, 1H), 3.87-4.19 (m, 4H), 3.70 (d, J=14.8 Hz, 2H), 3.39 (d, J=13.2 Hz, 1H), 2.88-3.26 (m, 9H), 2.42-2.54 (m, 1H), 2.04-2.30 (m, 7H), 1.81-2.01 (m, 7H).

Compound 69. 3-chloro-5-[(7S)-7'-chloro-2-[[(2R, 8S)-2-fluoro-1,2,3,5,6,7-hexahydropyrrolizin-8-yl] methoxy]-6-methyl-spiro[5,8-dihydropyrido[4,3-d] pyrimidine-7,1'-indane]-4-yl]-N,N-dimethyl-4,6,7,8-tetrahydropyrazolo[1,5-a][1,4]diazepine-2-carboxamide Compound 69 was prepared similarly to that of Ex. 19. LCMS calculated for $C_{34}H_{42}Cl_2FN_8O_2$ $(M+H)^+$ m/z=683.28, 685.28; found: 683.2, 685.2. $^1H$ NMR (400 MHz, CD$_3$OD) δ 7.16-7.29 (m, 3H), 5.26 (d, J=54.7 Hz, 1H), 4.77, 4.87 (d, J=16.6 Hz, 2H), 4.34-4.54 (m, 2H), 4.02-4.11 (m, 1H), 3.98, 4.07 (d, J=10.5 Hz, 2H), 3.84-3.92 (m, 1H), 3.65, 3.83 (d, J=14.4 Hz, 2H), 3.10-3.30 (m, 4H), 3.09 (d, J=6.7 Hz, 6H), 2.88-3.05 (m, 3H), 2.67 (d, J=17.8 Hz, 1H), 2.33-2.53 (m, 2H), 2.00-2.34 (m, 4H), 2.22 (s, 3H), 1.78-1.98 (m, 4H).

Compound 70. (5R)-9-[(7S)-7'-chloro-2-[[(2R,8S)-2-fluoro-1,2,3,5,6,7-hexahydropyrrolizin-8-yl] methoxy]-6-methyl-spiro[5,8-dihydropyrido[4,3-d] pyrimidine-7,1'-indane]-4-yl]-1,3,9-triazaspiro[4.5] decane-2,4-dione Compound 70 was prepared similarly to that of Ex. 19. LCMS calculated for $C_{31}H_{38}ClFN_7O_3$ $(M+H)^+$ m/z=610.27, 611.27; found: 610.3, 611.3. $^1H$ NMR (400 MHz, DMSO) δ 10.77 (s, 1H), 8.68 (s, 1H), 7.15-7.32 (m, 3H), 5.23 (d, J=54.0 Hz, 1H), 3.80-3.94 (m, 4H), 3.75 (d, J=15.2 Hz, 1H), 3.46 (d, J=14.4 Hz, 1H), 3.01-3.15 (m, 4H), 2.91-3.01 (m, 3H), 2.74-2.86 (m, 2H), 2.65 (d, J=17.6 Hz, 1H), 2.32-2.44 (m, 1H), 2.11 (s, 3H), 1.85-2.08 (m, 5H), 1.66-1.85 (m, 6H).

Compound 71. (5R)-9-[(7S)-2-[[(2R,8S)-2-fluoro-1, 2,3,5,6,7-hexahydropyrrolizin-8-yl]methoxy]-6-methyl-spiro[5,8-dihydropyrido[4,3-d]pyrimidine-7, 1'-tetralin]-4-yl]-1,3,9-triazaspiro[4.5]decane-2,4-dione Compound 71 was prepared similarly to that of Ex. 19. LCMS calculated for $C_{32}H_{41}FN_7O_3$ $(M+H)^+$ m/z=590.32; found: 590.3. $^1H$ NMR (400 MHz, CD$_3$OD) δ 7.45-7.57 (m, 1H), 7.05-7.26 (m, 3H), 5.23 (d, J=52.0 Hz, 1H), 3.90-4.19 (m, 4H), 3.73 (d, J=15.0 Hz, 2H), 3.38 (d, J=13.2 Hz, 1H), 2.89-3.24 (m, 7H), 2.71-2.80 (m, 2H), 1.75-2.29 (m, 17H).

Compound 72. 5-[(7S)-2-[[(2R,8S)-2-fluoro-1,2,3,5, 6,7-hexahydropyrrolizin-8-yl]methoxy]-6-methyl-spiro[5,8-dihydropyrido[4,3-d]pyrimidine-7,1'-tetra-lin]-4-yl]-N,N-dimethyl-4,6,7,8-tetrahydropyrazolo [1,5-a][1,4]diazepine-2-carboxamide Compound 72 was prepared similarly to that of Ex. 19. LCMS calculated for $C_{35}H_{46}FN_8O_2$ $(M+H)^+$ m/z=629.37; found: 629.3. $^1H$ NMR (400 MHz, DMSO) δ 7.45 (d, J=7.6 Hz, 1H), 7.20 (t, J=7.6 Hz, 1H), 7.13 (td, J=7.6, 1.2 Hz, 1H), 7.07 (d, J=6.4 Hz, 1H), 6.51 (s, 1H), 5.24 (d, J=54.0 Hz, 1H), 4.79, 4.72 (d, J=16.4 Hz, 2H), 4.47 (t, J=5.2 Hz, 2H), 3.77-4.00 (m, 4H), 3.61-3.73 (m, 2H), 3.24 (s, 3H), 2.96-3.10 (m, 3H), 2.93 (s, 3H), 2.66-2.90 (m, 5H), 2.03-2.22 (m, 2H), 2.00 (s, 3H), 1.59-1.98 (m, 10H).

Example 22. Exemplary Synthesis of 5-[5-[(7S)-7'-fluoro-2-[[(2R,8S)-2-fluoro-1,2,3,5,6,7-hexahydro-pyrrolizin-8-yl]methoxy]-6-methyl-spiro[5,8-dihy-dropyrido[4,3-d]pyrimidine-7,1'-indane]-4-yl]-4,6,7,8-tetrahydropyrazolo[1,5-a][1,4]diazepin-2-yl]-3-methyl-1,2,4-oxadiazole Compound 73

Int-1c

73a

73b

73c

-continued

Compound 73

Step 1. Synthesis of 3-methyl-5-(5,6,7,8-tetrahydro-4H-pyrazolo[1,5-a][1,4]diazepin-2-yl)-1,2,4-oxadiazole (73a). To a solution of N-hydroxyacetamidine (375.66 mg, 5.07 mmol) and 3 Å molecular sieves in THF (5 mL) were added NaH (76.06 mg, 3.17 mmol), The mixture was stirred at R.T. for 15 min. ethyl 5-(2-nitrophenyl)sulfonyl-4,6,7,8-tetrahy-dropyrazolo[1,5-a][1,4]diazepine-2-carboxylate (Int-1c, 500 mg, 1.27 mmol) was added to the mixture. The mixture was stirred at 25° C. for 3 h. The mixture was filtered over celite and concentrated. The crude product was purified by flash chromatography (eluted with $CH_3CN$ in $H_2O$ from 5.0% to 95%) to afford the desired product 3-methyl-5-(5,6,7,8-tetrahydro-4H-pyrazolo[1,5-a][1,4]diazepin-2-yl)-1,2,4-oxadiazole (73a, 230 mg, 1.05 mmol, 82.75% yield) as a yellow solid. LCMS calculated for $C_{10}H_{13}N_5O$ $(M+H)^+$ m/z=220.1, found: 220.1.

Step 2. Synthesis of 5-[5-[(7S)-2-chloro-7'-fluoro-6-methyl-spiro[5,8-dihydropyrido[4,3-d]pyrimidine-7,1'-in-dane]-4-yl]-4,6,7,8-tetrahydropyrazolo[1,5-a][1,4]diazepin-2-yl]-3-methyl-1,2,4-oxadiazole (73c). The mixture of (7S)-2,4-dichloro-7'-fluoro-6-methyl-spiro[5,8-dihydropyrido[4,3-d]pyrimidine-7,1'-indane](73b, prepared similarly as 64i, 50 mg, 0.15 mmol), 3-methyl-5-(5,6,7,8-tetrahydro-4H-pyrazolo[1,5-a][1,4]diazepin-2-yl)-1,2,4-oxadiazole (73a, 34.03 mg, 0.16 mmol) and DIEA (0.05 mL, 0.3 mmol) in DMSO (1 mL) was stirred at rt for 68 h. The reaction mixture was diluted with water, extracted with EtOAc, washed with brine, dried over $Na_2SO_4$, concentrated and purified by prep-HPLC (0.1% $NH_4HCO_3$) to afford to afford 5-[5-[(7S)-2-chloro-7'-fluoro-6-methyl-spiro[5,8-dihydro-pyrido[4,3-d]pyrimidine-7,1'-indane]-4-yl]-4,6,7,8-tetrahy-dropyrazolo[1,5-a][1,4]diazepin-2-yl]-3-methyl-1,2,4-oxa-diazole (73c, 50 mg, 0.0960 mmol, 64.92% yield) as a white solid. LCMS calculated for $C_{26}H_{27}ClFN_8O$ $(M+H)^+$ m/z=521.20, 523.19; found: 521.1, 523.1.

Step 3. Synthesis of 5-[5-[(7S)-7'-fluoro-2-[[(2R,8S)-2-fluoro-1,2,3,5,6,7-hexahydropyrrolizin-8-yl]methoxy]-6-methyl-spiro[5,8-dihydropyrido[4,3-d]pyrimidine-7,1'-in-dane]-4-yl]-4,6,7,8-tetrahydropyrazolo[1,5-a][1,4]diazepin-2-yl]-3-methyl-1,2,4-oxadiazole (Compound 73). To a solution of [(2R,8S)-2-fluoro-1,2,3,5,6,7-hexahydropyr-rolizin-8-yl]methanol (152.79 mg, 0.96 mmol) in DMSO (3 mL) was added NaH (38.39 mg, 0.96 mmol) under $N_2$ and stirred 20 min, then the mixture was added 5-[5-[(7S)-2-chloro-7'-fluoro-6-methyl-spiro[5,8-dihydropyrido[4,3-d]pyrimidine-7,1'-indane]-4-yl]-4,6,7,8-tetrahydropyrazolo[1, 5-a][1,4]diazepin-2-yl]-3-methyl-1,2,4-oxadiazole (73c, 50 mg, 0.1 mmol) and stirred at 40° C. for 1 h, The reaction mixture was quenched with water, and extracted with EtOAc, washed with brine, dried over $Na_2SO_4$, concentrated and purified by flash column chromatography (silica gel, eluting with 3% to 12% MeOH/DCM) and purified by prep-HPLC (0.1% $NH_4HCO_3$) to afford 5-[5-[(7S)-7'-fluoro-2-[[(2R,8S)-2-fluoro-1,2,3,5,6,7-hexahydropyr-rolizin-8-yl]methoxy]-6-methyl-spiro[5,8-dihydropyrido[4,3-d]pyrimidine-7,1'-indane]-4-yl]-4,6,7,8-tetrahydropyrazolo[1,5-a][1,4]diazepin-2-yl]-3-methyl-1,2,4-oxadiazole (Compound 73, 32 mg, 0.0487 mmol, 50.76% yield) as a white solid. LCMS calculated for $C_{34}H_{40}F_2N_9O_2$ (M+H)$^+$ m/z=644.33, 645.33; found: 644.3, 645.3. $^1$H NMR (400 MHz, CD$_3$OD) δ=7.27-7.35 (m, 1H), 7.10 (d, J=7.6, 1H), 6.99 (s, 1H), 6.91-6.97 (m, 1H), 5.24 (d, J=53.1, 1H), 4.50-4.66 (m, 4H), 3.97-4.11 (m, 4H), 3.64-3.76 (m, 2H), 3.05-3.22 (m, 5H), 2.91-3.04 (m, 2H), 2.83 (d, J=18.0, 1H), 2.45-2.56 (m, 1H), 2.41 (s, 3H), 2.18-2.35 (m, 5H), 2.09-2.18 (m, 2H), 2.00-2.08 (m, 1H), 1.75-1.99 (m, 4H).

Compound 74. 5-[5-[(7S)-2-[[(2R,8S)-2-fluoro-1,2,3,5,6,7-hexahydropyrrolizin-8-yl]methoxy]-6-methyl-spiro[5,8-dihydropyrido[4,3-d]pyrimidine-7,1'-tetralin]-4-yl]-4,6,7,8-tetrahydropyrazolo[1,5-a][1,4]diazepin-2-yl]-3-methyl-1,2,4-oxadiazole Compound 74 was prepared similarly to that of Ex. 22. LCMS calculated for $C_{35}H_{43}FN_9O_2$ (M+H)$^+$ m/z=640.25; found: 640.3. $^1$H NMR (400 MHz, CD$_3$OD) δ 7.49 (d, J=8.0 Hz, 1H), 7.20 (t, J=7.6 Hz, 1H), 7.14 (td, J=7.6, 1.2 Hz, 1H), 7.09 (d, J=7.6 Hz, 1H), 6.99 (s, 1H), 5.25 (d, J=54.8 Hz, 1H), 4.86-4.96 (m, 2H), 4.50-4.67 (m, 2H), 3.96-4.12 (m, 4H), 3.70-3.86 (m, 2H), 3.12-3.24 (m, 3H), 2.89-3.04 (m, 3H), 2.70-2.80 (m, 2H), 2.41 (s, 3H), 2.13-2.37 (m, 3H), 2.12 (s, 3H), 1.73-2.08 (m, 9H).

Example 23. Exemplary Synthesis of 3-chloro-5-[6'-(difluoromethyl)-2-[[(2R,8S)-2-fluoro-1,2,3,5,6,7-hexahydropyrrolizin-8-yl]methoxy]spiro[5,8-dihydropyrano[4,3-d]pyrimidine-7,1'-indane]-4-yl]-N,N-dimethyl-4,6,7,8-tetrahydropyrazolo[1,5-a][1,4]diazepine-2-carboxamide Compound 75

75a

75b

75c

-continued

75d

75e

Compound 75

Step 1. Synthesis of 5-(6'-bromo-2-methylsulfanyl-spiro [5,8-dihydropyrano[4,3-d]pyrimidine-7,1'-indane]-4-yl)-3-chloro-N,N-dimethyl-4,6,7,8-tetrahydropyrazolo[1,5-a][1, 4]diazepine-2-carboxamide (75b). To the solution of 6'-bromo-4-chloro-2-methylsulfanyl-spiro[5,8-dihydropy-rano[4,3-d]pyrimidine-7,1'-indane](75a, 600 mg, 1.51 mmol) DIEA (0.79 mL, 4.53 mmol) and 3-chloro-N,N-dimethyl-5,6,7,8-tetrahydro-4H-pyrazolo[1,5-a][1,4]diaz-epine-2-carboxamide (366.15 mg, 1.51 mmol) in DMF (6 mL) and stirred at 100° C. for 2 h. The mixture was extracted with water (20 mL) and EtOAc (3×10 mL), washed with brine (10 mL), dried with $Na_2SO_4$, concentrated. The crude product was purified by flash chromatography (eluted with $CH_3CN$ in $H_2O$ from 5.0% to 50%) to afford 5-(6'-bromo-2-methylsulfanyl-spiro[5,8-dihydropyrano[4,3-d]pyrimi-dine-7,1'-indane]-4-yl)-3-chloro-N,N-dimethyl-4,6,7,8-tet-rahydropyrazolo[1,5-a][1,4]diazepine-2-carboxamide (75b, 800 mg, 1.3246 mmol, 87.80% yield) as yellow solid. LCMS calcld for $C_{26}H_{28}BrClN_6O_2S$ $(M+H)^+$ m/z=605.2, found: 605.2.

Step 2. Synthesis of 3-chloro-N,N-dimethyl-5-(2-methyl-sulfanyl-6'-vinyl-spiro[5,8-dihydropyrano[4,3-d]pyrimi-dine-7,1'-indane]-4-yl)-4,6,7,8-tetrahydropyrazolo[1,5-a][1, 4]diazepine-2-carboxamide (75c). The mixture of 5-(6'-bromo-2-methylsulfanyl-spiro[5,8-dihydropyrano[4,3-d] pyrimidine-7,1'-indane]-4-yl)-3-chloro-N,N-dimethyl-4,6,7, 8-tetrahydropyrazolo[1,5-a][1,4]diazepine-2-carboxamide (75b, 500 mg, 0.83 mmol), $K_2CO_3$ (343 mg, 2.48 mmol), Pd(Dppf)$Cl_2$ (60.52 mg, 0.08 mmol) and potassium;trifluoro (vinyl)boranuide (277 mg, 2.07 mmol) was added in DMSO (10 mL) and stirred at 100° C. for 16 h under Ar. The crude product was purified by flash chromatography (eluted with $CH_3CN$ in $H_2O$ from 5.0% to 95%) to afford 3-chloro-N, N-dimethyl-5-(2-methylsulfanyl-6'-vinyl-spiro[5,8-dihy-dropyrano[4,3-d]pyrimidine-7,1'-indane]-4-yl)-4,6,7,8-tet-rahydropyrazolo[1,5-a][1,4]diazepine-2-carboxamide (75c, 360 mg, 0.653 mmol, 78.9% yield) as a yellow solid. LCMS calcld for $C_{28}H_{31}ClN_6O_2S$ $(M+H)^+$ m/z=551.2, found: 551.2.

Step 3. Synthesis of 3-chloro-5-(6'-formyl-2-methylsulfo-nyl-spiro[5,8-dihydropyrano[4,3-d]pyrimidine-7,1'-indane]-4-yl)-N,N-dimethyl-4,6,7,8-tetrahydropyrazolo[1,5-a][1,4] diazepine-2-carboxamide (75d). To a solution of 3-chloro-N,N-dimethyl-5-(2-methylsulfanyl-6'-vinyl-spiro[5,8-dihydropyrano[4,3-d]pyrimidine-7,1'-indane]-4-yl)-4,6,7,8-tetrahydropyrazolo[1,5-a][1,4]diazepine-2-carboxamide (75c, 320 mg, 0.58 mmol), Potassium osmate(VI) dihydrate (9.04 mg, 0.03 mmol) and Sodium Periodate (496.79 mg, 2.32 mmol) was added in THF (4 mL) and Water (1 mL) at 25° C. The mixture was stirred at 50° C. for 16 h. The crude product was purified by flash chromatography (eluted with $CH_3CN$ in $H_2O$ from 5.0% to 95%) to afford 3-chloro-5-(6'-formyl-2-methylsulfonyl-spiro[5,8-dihydropyrano[4,3-d]pyrimidine-7,1'-indane]-4-yl)-N,N-dimethyl-4,6,7,8-tet-rahydropyrazolo[1,5-a][1,4]diazepine-2-carboxamide (75d, 120 mg, 0.205 mmol, 35.3% yield) as a white solid. LCMS calcld for $C_{27}H_{29}ClN_6O_5S$ $(M+H)^+$ m/z=585.3, found: 585.3.

Step 4. Synthesis of 3-chloro-5-[6'-(difluoromethyl)-2-methylsulfonyl-spiro[5,8-dihydropyrano[4,3-d]pyrimidine-7,1'-indane]-4-yl]-N,N-dimethyl-4,6,7,8-tetrahydropyrazolo [1,5-a][1,4]diazepine-2-carboxamide (75e). To a solution of 3-chloro-5-(6'-formyl-2-methylsulfonyl-spiro[5,8-dihydro-pyrano[4,3-d]pyrimidine-7,1'-indane]-4-yl)-N,N-dimethyl-4,6,7,8-tetrahydropyrazolo[1,5-a][1,4]diazepine-2-carbox-amide (75d, 100 mg, 0.17 mmol), and DAST (0.23 mL, 1.71 mmol) was added in DCM (1 mL) at 0° C. The mixture was stirred at 25° C. for 16 h. The mixture was quenched with $NH_4Cl$ (5 mL), then the mixture was extracted with DCM (3×5 mL) and water (10 mL), dried over $Na_2SO_4$, concen-trated to afford the crude of 3-chloro-5-[6'-(difluoromethyl)-2-methylsulfonyl-spiro[5,8-dihydropyrano[4,3-d]pyrimi-dine-7,1'-indane]-4-yl]-N,N-dimethyl-4,6,7,8-tetrahydropyrazolo[1,5-a][1,4]diazepine-2-carboxamide (75e, 100 mg, 0.165 mmol, 96.38% yield) was obtained as a yellow solid. LCMS calcld for $C_{27}H_{29}ClF_2N_6O_4$ (M+H)$^+$ m/z=607.3, found: 607.3.

Step 5. Synthesis of 3-chloro-5-[6'-(difluoromethyl)-2-[[(2R,8S)-2-fluoro-1,2,3,5,6,7-hexahydropyrrolizin-8-yl] methoxy]spiro[5,8-dihydropyrano[4,3-d]pyrimidine-7,1'-indane]-4-yl]-N,N-dimethyl-4,6,7,8-tetrahydropyrazolo[1,5-a][1,4]diazepine-2-carboxamide (Compound 75). To a solution of NaH (13.84 mg, 0.35 mmol) and [(2R,8S)-2-fluoro-1,2,3,5,6,7-hexahydropyrrolizin-8-yl]methanol (55.07 mg, 0.35 mmol) in DMF (1 mL) and stirred at 25° C. for 10 min, then 3-chloro-5-[6'-(difluoromethyl)-2-methyl-sulfonyl-spiro[5,8-dihydropyrano[4,3-d]pyrimidine-7,1'-indane]-4-yl]-N,N-dimethyl-4,6,7,8-tetrahydropyrazolo[1,5-a][1,4]diazepine-2-carboxamide (75e, 70 mg, 0.12 mmol) was added at 25° C. The mixture was stirred at 25° C. for 10 min. The mixture was extracted with water (10 mL) and EA (3×15 mL), then washed with brine (10 mL), dried over Na₂SO₄, concentrated. The crude product was purified by Prep-HPLC (eluted with CH₃CN in H₂O (0.1% FA) from 5.0% to 95%) to afford 3-chloro-5-[6'-(difluoromethyl)-2-[[(2R,8S)-2-fluoro-1,2,3,5,6,7-hexahydropyrrolizin-8-yl] methoxy]spiro[5,8-dihydropyrano[4,3-d]pyrimidine-7,1'-indane]-4-yl]-N,N-dimethyl-4,6,7,8-tetrahydropyrazolo[1,5-a][1,4]diazepine-2-carboxamide;formic acid (Compound 75, 25.1 mg, 0.035 mmol, 30.36% yield) as a white solid. LCMS calcld for $C_{34}H_{39}ClF_3N_7O_3$ (M+H)$^+$ m/z=686.2, found: 686.2. $^1$H NMR (400 MHz, CD₃OD) δ 7.45 (dd, J=18.7, 7.8 Hz, 2H), 7.31 (s, 1H), 6.72 (t, J=56.3 Hz, 1H), 5.42-5.15 (m, 1H), 4.83-4.69 (m, 2H), 4.61-4.52 (m, 1H), 4.47-4.33 (m, 2H), 4.14-4.04 (m, 2H), 3.94-3.75 (m, 2H), 3.27-3.11 (m, 4H), 3.09 (d, J=8.1 Hz, 6H), 3.04-2.88 (m, 4H), 2.42-1.82 (m, 11H).

Example 24. Exemplary Synthesis of 3-cyano-5-[(7S)-7'-fluoro-2-[[(2R,8S)-2-fluoro-1,2,3,5,6,7-hexahydropyrrolizin-8-yl]methoxy]-6-methyl-spiro[5,8-dihydropyrido[4,3-d]pyrimidine-7,1'-indane]-4-yl]-N,N-dimethyl-4,6,7,8-tetrahydropyrazolo[1,5-a][1,4]diazepine-2-carboxamide Compound 76

Int-1e

76a

76b

73b

73d

Compound 76

Step 1. Synthesis of 3-iodo-N,N-dimethyl-5-(2-nitrophenyl)sulfonyl-4,6,7,8-tetrahydropyrazolo[1,5-a][1,4]diazepine-2-carboxamide (76a). To a solution of N,N-dimethyl-5-(2-nitrophenyl)sulfonyl-4,6,7,8-tetrahydropyrazolo[1,5-a][1,4]diazepine-2-carboxamide (Int-1e, 200 mg, 0.51 mmol) in HOAc (2 mL, 34.94 mmol) was added N-Iodosuccinimide (228.74 mg, 1.02 mmol). The mixture was stirred at 80° C. for 2 h. The mixture was diluted with water, extracted with DCM, washed with brine, dried over $Na_2SO_4$, concentrated and purified by flash column chromatography (silica gel, eluting with 0% to 5% MeOH/DCM) to afford 3-iodo-N,N-dimethyl-5-(2-nitrophenyl)sulfonyl-4,6,7,8-tetrahydropyrazolo[1,5-a][1,4]diazepine-2-carboxamide (76a, 264 mg, 0.5084 mmol, 100% yield) as a yellow solid. LCMS calcld for $C_{16}H_{19}IN_5O_5S$ (M+H)$^+$ m/z=520.02, found: 520.1.

Step 2. Synthesis of 3-cyano-N,N-dimethyl-5-(2-nitrophenyl)sulfonyl-4,6,7,8-tetrahydropyrazolo[1,5-a][1,4]diazepine-2-carboxamide (76b). The mixture of 3-iodo-N,N-dimethyl-5-(2-nitrophenyl)sulfonyl-4,6,7,8-tetrahydropyrazolo[1,5-a][1,4]diazepine-2-carboxamide (76a, 630 mg, 1.21 mmol), and CuCN (539.85 mg, 6.07 mmol) in DMF (1 mL) was sealed and stirred at 135° C. for 20 h. After completion, the reaction mixture was diluted with water, extracted with EtOAc, washed with brine, dried over $Na_2SO_4$, concentrated and purified by flash column chromatography (silica gel, eluting with 0% to 5% MeOH/DCM) to afford 3-cyano-N,N-dimethyl-5-(2-nitrophenyl)sulfonyl-4,6,7,8-tetrahydropyrazolo[1,5-a][1,4]diazepine-2-carboxamide (76b, 340 mg, 0.8126 mmol, 66.98% yield) as a white solid. LCMS calcld for $C_{17}H_{19}N_6O_5S$ (M+H)$^+$ m/z=419.12; found: 419.2.

Step 3. Synthesis of 3-cyano-N,N-dimethyl-5,6,7,8-tetrahydro-4H-pyrazolo[1,5-a][1,4]diazepine-2-carboxamide (76c). To a solution of 3-cyano-N,N-dimethyl-5-(2-nitrophenyl)sulfonyl-4,6,7,8-tetrahydropyrazolo[1,5-a][1,4]diazepine-2-carboxamide (76b, 340 mg, 0.81 mmol), 4-methoxybenzenethiol (341.76 mg, 2.44 mmol) and cesium carbonate (1056.33 mg, 3.25 mmol) in MeCN (4 mL). The mixture was stirred at 20° C. for 2 h. The mixture was filtered, concentrated and the crude product was purified by silica gel chromatography (eluted with MeOH in DCM from 3% to 10%) to afford 3-cyano-N,N-dimethyl-5,6,7,8-tetrahydro-4H-pyrazolo[1,5-a][1,4]diazepine-2-carboxamide (76c, 164 mg, 0.703 mmol, 86.52% yield) as a white solid. LCMS calcld for $C_{11}H_{16}N_5O$ (M+H)$^+$ m/z=234.14, found: 234.1.

Step 4. Synthesis of 5-[(7S)-2-chloro-7'-fluoro-6-methyl-spiro[5,8-dihydropyrido[4,3-d]pyrimidine-7,1'-indane]-4-yl]-3-cyano-N,N-dimethyl-4,6,7,8-tetrahydropyrazolo[1,5-a][1,4]diazepine-2-carboxamide (76d). The mixture of (7S)-2,4-dichloro-7'-fluoro-6-methyl-spiro[5,8-dihydropyrido[4,3-d]pyrimidine-7,1'-indane](73b, 70 mg, 0.21 mmol), 3-cyano-N,N-dimethyl-5,6,7,8-tetrahydro-4H-pyrazolo[1,5-a][1,4]diazepine-2-carboxamide (53.11 mg, 0.23 mmol) and DIEA (0.14 mL, 0.83 mmol) in DMSO (1.5 mL) was stirred at 30° C. for 20 h. The reaction mixture was filtered and purified by prep-HPLC (0.1% $NH_4HCO_3$) to afford to afford 5-[(7S)-2-chloro-7'-fluoro-6-methyl-spiro[5,8-dihydropyrido[4,3-d]pyrimidine-7,1'-indane]-4-yl]-3-cyano-N,N-dimethyl-4,6,7,8-tetrahydropyrazolo[1,5-a][1,4]diazepine-2-carboxamide (62 mg, 0.116 mmol, 55.99% yield) as a white solid. LCMS calculated for $C_{27}H_{29}ClFN_8O$ (M+H)$^+$ m/z=535.22; found: 535.3.

Step 5. The mixture of 5-[(7S)-2-chloro-7'-fluoro-6-methyl-spiro[5,8-dihydropyrido[4,3-d]pyrimidine-7,1'-indane]-4-yl]-3-cyano-N,N-dimethyl-4,6,7,8-tetrahydropyrazolo[1,5-a][1,4]diazepine-2-carboxamide (50 mg, 0.09 mmol), [(2R,8S)-2-fluoro-1,2,3,5,6,7-hexahydropyrrolizin-8-yl]methanol (22.32 mg, 0.14 mmol), $Pd_2dba_3$ (12.84 mg, 0.01 mmol), Ruphos (13.08 mg, 0.03 mmol) and cesium carbonate (91.12 mg, 0.28 mmol) in Toluene (2 mL) was charged with $N_2$ and sealed. The mixture was stirred at 110° C. for 5 h. LCMS showed OK. The mixture was diluted with water, extracted with EtOAc, washed with brine, dried over $Na_2SO_4$, concentrated and purified by prep-HPLC (0.1% $NH_4HCO_3$) to afford 3-cyano-5-[(7S)-7'-fluoro-2-[[(2R,8S)-2-fluoro-1,2,3,5,6,7-hexahydropyrrolizin-8-yl]methoxy]-6-methyl-spiro[5,8-dihydropyrido[4,3-d]pyrimidine-7,1'-indane]-4-yl]-N,N-dimethyl-4,6,7,8-tetrahydropyrazolo[1,5-a][1,4]diazepine-2-carboxamide (39.09 mg, 0.0587 mmol, 52.99% yield) as a light yellow solid. LCMS calculated for $C_{35}H_{42}F_2N_9O_2$ (M+H)$^+$ m/z=658.35; found: 658.5. $^1$H NMR (400 MHz, $CD_3OD$) δ 7.31 (td, J=8.0, 5.2 Hz, 1H), 7.09 (d, J=7.6 Hz, 1H), 6.93 (dd, J=10.0, 8.4 Hz, 1H), 5.29 (d, J=53.8 Hz, 1H), 4.87-4.97 (m, 2H), 4.37-4.57 (m, 2H), 3.89-4.12 (m, 4H), 3.66, 3.77 (d, J=14.4 Hz, 2H), 3.32 (s, 3H), 3.12-3.28 (m, 4H), 3.10 (s, 3H), 2.94-3.08 (m, 3H), 2.86 (d, J=18.0 Hz, 1H), 2.29-2.55 (m, 3H), 2.27 (s, 3H), 2.03-2.22 (m, 3H), 1.83-1.99 (m, 4H).

Compound 77. 3-cyano-5-[(7S)-2-[[(2R,8S)-2-fluoro-1,2,3,5,6,7-hexahydropyrrolizin-8-yl]methoxy]-6-methyl-spiro[5,8-dihydropyrido[4,3-d]pyrimidine-7,1'-tetralin]-4-yl]-N,N-dimethyl-4,6,7,8-tetrahydropyrazolo[1,5-a][1,4]diazepine-2-carboxamide Compound 78. 3-chloro-5-[(7S)-2-[[(2R,8S)-2-fluoro-1,2,3,5,6,7-hexahydropyrrolizin-8-yl]methoxy]-6-methyl-spiro[5,8-dihydropyrido[4,3-d]pyrimidine-7,1'-tetralin]-4-yl]-N,N-dimethyl-4,6,7,8-tetrahydropyrazolo[1,5-a][1,4]diazepine-2-carboxamide Compound 78 was prepared similarly to that of Ex. 21. LCMS calculated for $C_{33}H_{40}ClFN_7O_3$ (M+H)$^+$ m/z=636.29, 638.29; found: 636.3, 638.3. $^1$H NMR (400 MHz, DMSO) δ=7.46 (d, J=7.7 Hz, 1H), 7.19 (t, J=7.5 Hz, 1H), 7.12 (td, J=7.4, 1.2 Hz, 1H), 7.07 (d, J=6.8 Hz, 1H), 5.23 (d, J=53.4 Hz, 1H), 4.73 (d, J=16.4 Hz, 2H), 4.34-4.53 (m, 2H), 3.87-3.98 (m, 1H), 3.83 (s, 2H), 3.68-3.80 (m, 2H), 3.60 (d, J=14.9 Hz, 1H), 2.86-3.08 (m, 4H), 2.65-2.83 (m, 4H), 2.17-2.32 (m, 1H), 1.94-2.12 (m, 6H), 1.77-1.94 (m, 4H), 1.62-1.77 (m, 4H).

Compound 77 was prepared similarly to that of Ex. 23. LCMS calculated for $C_{36}H_{45}FN_9O_2$ (M+H)$^+$ m/z=654.37; found: 654.2. $^1$H NMR (400 MHz, CD$_3$OD) δ 7.50 (dd, J=8.0, 1.2 Hz, 1H), 7.22 (td, J=7.4, 1.6 Hz, 1H), 7.14 (td, J=7.4, 1.2 Hz, 1H), 7.08 (dd, J=7.6, 1.2 Hz, 1H), 5.28 (d, J=53.6 Hz, 1H), 4.87-4.98 (m, 2H), 4.32-4.62 (m, 2H), 4.11 (d, J=10.8 Hz, 1H), 3.93-4.06 (m, 2H), 3.83-3.92 (m, 2H), 3.70 (d, J=14.8 Hz, 1H), 3.32 (s, 3H), 3.12-3.26 (m, 3H), 3.10 (s, 3H), 2.90-3.07 (m, 3H), 2.71-2.80 (m, 2H), 2.13-2.44 (m, 4H), 2.11 (s, 3H), 1.71-2.08 (m, 8H).

Example 25. Exemplary Synthesis of 3-chloro-5-[(7S)-2-[[(2R,8S)-2-fluoro-1,2,3,5,6,7-hexahydropyrrolizin-8-yl]methoxy]-6-methyl-spiro[5,8-dihydropyrido[4,3-d]pyrimidine-7,1'-tetralin]-4-yl]-4,6,7,8-tetrahydropyrazolo[1,5-a][1,4]diazepin-2-amine (Compound 79)

Compound 78

Compound 79

To a sealed vial was charged a solution of 3-chloro-5-[(7S)-2-[[(2R,8S)-2-fluoro-1,2,3,5,6,7-hexahydropyr-rolizin-8-yl]methoxy]-6-methyl-spiro[5,8-dihydropyrido[4,3-d]pyrimidine-7,1'-tetralin]-4-yl]-4,6,7,8-tetrahydrop-yrazolo[1,5-a][1,4]diazepine-2-carboxylic acid (Compound 78, 30 mg, 0.05 mmol) in 1,4-Dioxane (1 mL), followed by the addition of azido(phenoxy)phosphoryl]oxybenzene (19.47 mg, 0.07 mmol) and t-BuOH (59.42 mg, 0.8 mmol) under N₂. The mixture was heated at 110° C. for 2 hours. The reaction solution was cooled down to rt, and EtOAc was added. The mixture was washed successively with H₂O, NaHCO₃ and brine, dried over MgSO₄ and concentrated in vacuo. The residue was purified by prep-HPLC to afford 3-chloro-5-[(7S)-2-[[(2R,8S)-2-fluoro-1,2,3,5,6,7-hexahy-dropyrrolizin-8-yl]methoxy]-6-methyl-spiro[5,8-dihydro-pyrido[4,3-d]pyrimidine-7,1'-tetralin]-4-yl]-4,6,7,8-tetrahy-dropyrazolo[1,5-a][1,4]diazepin-2-amine (Compound 79, 8.0 mg, 0.0132 mmol, 28.05% yield) as a white solid. LCMS calculated for $C_{32}H_{41}ClFN_8O$ (M+H)⁺ m/z=607.31, 609.31; found: 607.3, 609.31. ¹H NMR (400 MHz, CD₃OD) δ=7.49 (d, J=7.1 Hz, 1H), 7.20 (td, J=7.5, 1.8 Hz, 1H), 7.14 (td, J=7.4, 1.3 Hz, 1H), 7.09 (d, J=7.5 Hz, 1H), 5.26 (d, J=54.4 Hz, 1H), 4.68 (d, J=16.6 Hz, 2H), 3.78-4.23 (m, 7H), 3.67 (d, J=14.9 Hz, 1H), 3.11-3.28 (m, 3H), 2.88-3.07 (m, 3H), 2.70-2.80 (m, 2H), 2.23-2.37 (m, 1H), 1.70-2.21 (m, 14H).

Compound 80. 4-[[1-[[(7S)-6-methyl-4-[(1R,5S)-3,8-diazabicyclo[3.2.1]octan-3-yl]spiro[5,8-dihydro-pyrido[4,3-d]pyrimidine-7,1'-tetralin]-2-yl]oxym-ethyl]cyclopropyl]methyl]morpholine Compound 80 was prepared similarly to that of Ex. 21. LCMS calculated for $C_{32}H_{45}N_6O_2$ (M+H)⁺ m/z=545.4; found: 545.3. ¹H NMR (400 MHz, CD₃OD) δ 7.50 (d, J=7.6 Hz, 1H), 7.19 (t, J=7.2 Hz, 1H), 7.13 (t, J=7.2 Hz, 1H), 7.08 (d, J=6.8 Hz, 1H), 4.14-4.33 (m, 3H), 3.56-3.77 (m, 9H), 3.43 (d, J=12.0 Hz, 1H), 2.86-3.09 (m, 3H), 2.75 (d, J=5.2 Hz, 2H), 2.47 (s, 4H), 2.38 (s, 2H), 2.09 (s, 3H), 1.62-2.04 (m, 8H), 0.63 (t, J=5.6 Hz, 2H), 0.45 (t, J=5.6 Hz, 2H).

Intermediate 3

76a

-continued

Int-3a

Int-3b

Intermediate 3

Step 1. Synthesis of N,N-dimethyl-5-(2-nitrophenyl) sulfonyl-3-(2-trimethylsilylethynyl)-4,6,7,8-tetrahydropyra-zolo[1,5-a][1,4]diazepine-2-carboxamide. To a solution of 3-iodo-N,N-dimethyl-5-(2-nitrophenyl)sulfonyl-4,6,7,8-tet-rahydropyrazolo[1,5-a][1,4]diazepine-2-carboxamide (76a, 500 mg, 0.96 mmol), Trimethylsilylacetylene (0.71 mL, 5.09 mmol) and Triethylamine (292.28 mg, 2.89 mmol) in DMF (10 mL) was added Bis(Triphenylphosphine)Palladiu-m(II) Chloride (135.16 mg, 0.19 mmol) and Copper (I) Iodide % (36.67 mg, 0.19 mmol) under N₂. The mixture was stirred at 45° C. for 20 h. The reaction solution was filtrated, washed by DCM/MeOH=10:1 and concentrated. The resi-due was purified by flash chromatography (DCM/MeOH=20:1) to give N,N-dimethyl-5-(2-nitrophenyl)sulfo-nyl-3-(2-trimethylsilylethynyl)-4,6,7,8-tetrahydropyrazolo [1,5-a][1,4]diazepine-2-carboxamide (Int-3a, 345.5 mg, 0.529 mmol, 54.97% yield). LCMS calculated for $C_{21}H_{28}N_5O_5SiS$ (M+H)⁺ m/z=490.15; found: 490.0.

Step 2. Synthesis of N,N-dimethyl-3-(2-trimethylsilyl-ethynyl)-5,6,7,8-tetrahydro-4H-pyrazolo[1,5-a][1,4]diaz-epine-2-carboxamide. To a solution of N,N-dimethyl-5-(2-nitrophenyl)sulfonyl-3-(2-trimethylsilylethynyl)-4,6,7,8-tetrahydropyrazolo[1,5-a][1,4]diazepine-2-carboxamide (Int-3a, 350 mg, 0.54 mmol), 4-methoxybenzenethiol (225.5 mg, 1.61 mmol) in CH₃CN (3 mL) was added cesium carbonate (696.97 mg, 2.14 mmol). The mixture was stirred at 20° C. for 2 h. The mixture was filtered, concentrated and the crude product was purified by pre-HPLC on a C18 column with a mobile phase (H₂O—NH₄HCO₃/CH₃CN) to afford N,N-dimethyl-3-(2-trimethylsilylethynyl)-5,6,7,8-tet-rahydro-4H-pyrazolo[1,5-a][1,4]diazepine-2-carboxamide (Int-3b, 101 mg, 0.331 mmol, 61.88% yield). LCMS calcld for $C_{15}H_{25}N_4OSi$ (M+H)⁺ m/z=305.17, found: 305.2.

Step 3. Synthesis of 3-ethynyl-N,N-dimethyl-5,6,7,8-tetrahydro-4H-pyrazolo[1,5-a][1,4]diazepine-2-carboxamide. To a solution of N,N-dimethyl-3-(2-trimethylsilylethynyl)-5,6,7,8-tetrahydro-4H-pyrazolo[1,5-a][1,4]diazepine-2-carboxamide (Int-3b, 101 mg, 0.33 mmol) in Methanol (5 mL) was added $K_2CO_3$ (105.29 mg, 0.76 mmol). The mixture was stirred at 20° C. for 1 h. The mixture was filtered, and the filtrate was concentrated and the residue was purified by flash chromatography (DCM/MeOH) to give 3-ethynyl-N,N-dimethyl-5,6,7,8-tetrahydro-4H-pyrazolo[1,5-a][1,4]diazepine-2-carboxamide (Intermediate 3, 75 mg, 0.323 mmol, 97.33% yield). LCMS calculated for $C_{12}H_{17}N_4O$ $(M+H)^+$ m/z=233.13; found: 233.3.

Compound 81. 3-ethynyl-5-[(7S)-2-[[(2R,8S)-2-fluoro-1,2,3,5,6,7-hexahydropyrrolizin-8-yl]methoxy]-6-methyl-spiro[5,8-dihydropyrido[4,3-d]pyrimidine-7,1'-tetralin]-4-yl]-N,N-dimethyl-4,6,7,8-tetrahydropyrazolo[1,5-a][1,4]diazepine-2-carboxamide Compound 81 was prepared similarly to that of Ex. 21 using intermediate 3. LCMS calculated for $C_{37}H_{46}FN_8O_2$ $(M+H)^+$ m/z=653.36; found: 653.3. $^1$H NMR (400 MHz, CD$_3$OD) δ 7.45-7.53 (m, 1H), 7.04-7.24 (m, 3H), 5.26 (d, J=54.4 Hz, 1H), 4.71-4.90 (m, 2H), 4.44-4.54 (m, 1H), 4.30-4.40 (m, 1H), 3.80-4.16 (m, 6H), 3.66 (d, J=14.8 Hz, 1H), 2.89-3.25 (m, 12H), 2.71-2.80 (m, 2H), 2.36-2.51 (m, 1H), 2.05-2.32 (m, 7H), 1.73-2.03 (m, 7H).

Intermediate 4

Int-1c

-continued

Int-4a

Int-4b

Int-4c

Intermediate 4

Step 1. Synthesis of [5-(2-nitrophenyl)sulfonyl-4,6,7,8-tetrahydropyrazolo[1,5-a][1,4]diazepin-2-yl]methanol (Int-4a). To a solution of ethyl 5-(2-nitrophenyl)sulfonyl-4,6,7,8-tetrahydropyrazolo[1,5-a][1,4]diazepine-2-carboxylate (Int-1c 1500 mg, 3.8 mmol) in THF (15 mL) was added 1M DABAL-H in hexane (11.41 mL, 11.41 mmol) at −68° C. under argon. The mixture was stirred at 25° C. for 2 h. The reaction was quenched with water and isopropyl alcohol (1:1.12 mL) and extracted with EtOAc (50 ml×3) and concentrated. The crude product [5-(2-nitrophenyl)sulfonyl-4,6,7,8-tetrahydropyrazolo[1,5-a][1,4]diazepin-2-yl]methanol (Int-4a, 850 mg, 2.39 mmol, 62.79% yield) was carried over without purification. LCMS calcld for $C_{14}H_{17}N_4O_5S$ $(M+H)^+$ m/z=353.1, found: 353.1.

Step 2. Synthesis of 5-(2-nitrophenyl)sulfonyl-4,6,7,8-tetrahydropyrazolo[1,5-a][1,4]diazepine-2-carbaldehyde (Int-4b). To a solution of [5-(2-nitrophenyl)sulfonyl-4,6,7,8-tetrahydropyrazolo[1,5-a][1,4]diazepin-2-yl]methanol (Int-4a, 850 mg, 2.41 mmol) in DMSO (8 mL) was added IBX (514.6 mg, 3.62 mmol) at 25° C. under argon. The mixture was stirred at 25° C. for 16 h. The mixture was filtered to afford a crude solution. The crude product was purified by flash chromatography (eluted with CH$_3$CN in H$_2$O from 50% to 55%). 5-(2-nitrophenyl)sulfonyl-4,6,7,8-tetrahydropyrazolo[1,5-a][1,4]diazepine-2-carbaldehyde (Int-4b, 570 mg, 1.59 mmol, 66.10% yield) was obtained as a white solid. LCMS calcld for C$_{14}$H$_{15}$N$_4$O$_5$S (M+H)$^+$ m/z=351.1, found: 351.1.

Step 3. Synthesis of 2-(1-methylbenzimidazol-2-yl)-5-(2-nitrophenyl)sulfonyl-4,6,7,8-tetrahydropyrazolo[1,5-a][1,4]diazepine (Int-4c). The solution of 5-(2-nitrophenyl)sulfonyl-4,6,7,8-tetrahydropyrazolo[1,5-a][1,4]diazepine-2-carbaldehyde (Int-4b, 250 mg, 1 mmol) and N$_2$-methylbenzene-1,2-diamine (244.34 mg, 2 mmol) in DMF (2 mL) was stirred at 100° C. for 18 h. The mixture was extracted with EtOAc and water, washed with brine and dried over Na$_2$SO$_4$, concentrated and purified by silica gel chromatography (DCM:MeOH=50:1) to get the 2-(1-methylbenzimidazol-2-yl)-5-(2-nitrophenyl)sulfonyl-4,6,7,8-tetrahydropyrazolo[1,5-a][1,4]diazepine (Int-4c, 320 mg, 0.707 mmol, 70.72% yield). LCMS calcld for C$_{21}$H$_{21}$N$_6$O$_4$S (M+H)$^+$ m/z=453.49, found: 453.2.

Step 4. Synthesis of 2-(1-methylbenzimidazol-2-yl)-5,6,7,8-tetrahydro-4H-pyrazolo[1,5-a][1,4]diazepine (Intermediate 4). A solution of Cs$_2$CO$_3$ (230.42 mg, 0.71 mmol), 2-(1-methylbenzimidazol-2-yl)-5-(2-nitrophenyl)sulfonyl-4,6,7,8-tetrahydropyrazolo[1,5-a][1,4]diazepine (Int-4c, 160 mg, 0.35 mmol) and 4-Methoxythiophenol (74.36 mg, 0.53 mmol) in CH$_3$CN (5 mL) was stirred at 25° C. for 3 h. The mixture was filtered, and the solvent was removed. The residue was purified by silica gel chromatography (DCM:MeOH=11:1) to give 2-(1-methylbenzimidazol-2-yl)-5,6,7,8-tetrahydro-4H-pyrazolo[1,5-a][1,4]diazepine (Intermediate 4, 70 mg, 0.262 mmol, 74.05% yield). LCMS calcld for C$_{15}$H$_{18}$N$_5$ (M+H)$^+$ m/z=268.33, found: 268.3.

Compound 82. (7S)-2-[[(2R,8S)-2-fluoro-1,2,3,5,6,7-hexahydropyrrolizin-8-yl]methoxy]-6-methyl-4-[2-(1-methylbenzimidazol-2-yl)-4,6,7,8-tetrahydropyrazolo[1,5-a][1,4]diazepin-5-yl]spiro[5,8-dihydropyrido[4,3-d]pyrimidine-7,1'-tetralin]

Compound 82 was prepared similarly to that of Ex. 21 using intermediate 4. LCMS calculated for C$_{40}$H$_{47}$FN$_9$O (M+H)$^+$ m/z=688.38; found: 688.3. $^1$H NMR (400 MHz, CD$_3$OD) δ 7.61-7.68 (m, 1H), 7.45-7.52 (m, 2H), 7.23-7.33 (m, 2H), 7.03-7.21 (m, 3H), 6.97 (s, 1H), 5.14 (d, J=52.4 Hz, 1H), 4.80-4.95 (m, 2H), 4.50-4.67 (m, 2H), 3.92-4.18 (m, 7H), 3.76, 3.85 (d, J=14.8 Hz, 2H), 2.85-3.15 (m, 6H), 2.67-2.78 (m, 2H), 2.29-2.42 (m, 1H), 1.92-2.22 (m, 9H), 1.69-1.90 (m, 5H).

Compound 83. (7S)-2-[[(2R,8S)-2-fluoro-1,2,3,5,6,7-hexahydropyrrolizin-8-yl]methoxy]-4-[2-(4-fluoro-1-methyl-benzimidazol-2-yl)-4,6,7,8-tetrahydropyrazolo[1,5-a][1,4]diazepin-5-yl]-6-methyl-spiro[5,8-dihydropyrido[4,3-d]pyrimidine-7,1'-tetralin]

Compound 83 was prepared similarly to Compound 82. LCMS calculated for C$_{40}$H$_{46}$F$_2$N$_9$O (M+H)$^+$ m/z=706.38; found: 706.3. $^1$H NMR (400 MHz, CD$_3$OD) δ 7.49-7.51 (m, 1H), 7.35-7.37 (m, 1H), 7.25-7.30 (m, 1H), 7.17-7.21 (m, 1H), 7.11-7.15 (m, 1H), 7.07-7.09 (m, 1H), 7.04 (s, 1H), 6.98-7.03 (m, 1H), 5.20 (d, J=53.6 Hz, 1H), 4.90-4.96 (m, 2H), 4.56-4.68 (m, 2H), 4.19 (s, 3H), 3.97-4.14 (m, 4H), 3.78, 3.86 (d, J=14.4 Hz, 2H), 2.91-3.22 (m, 6H), 2.75-2.78 (m, 2H), 2.23-2.41 (m, 2H), 2.14 (s, 3H), 1.70-2.10 (m, 10H).

Compound 84. (7S)-4-[(1R,5S)-3,8-diazabicyclo[3.2.1]octan-3-yl]-2-[[(2R,8S)-2-fluoro-1,2,3,5,6,7-hexahydropyrrolizin-8-yl]methoxy]-6-methyl-spiro[5,8-dihydropyrido[4,3-d]pyrimidine-7,1'-tetralin]

Compound 84 was prepared similarly to that of Ex. 21. LCMS calculated for $C_{31}H_{42}FN_6O$ (M+H)$^+$ m/z=533.3; found: 533.3. $^1$H NMR (400 MHz, CD$_3$OD) δ 7.49 (d, J=7.6 Hz, 1H), 7.06-7.23 (m, 3H), 5.17-5.36 (m, 1H), 4.21 (d, J=12.0 Hz, 1H), 4.03, 4.15 (d, J=10.4 Hz, 2H), 3.54-3.77 (m, 5H), 3.42 (d, J=12.0 Hz, 1H), 3.13-3.28 (m, 3H), 2.87-3.09 (m, 4H), 2.71-2.80 (m, 2H), 2.11-2.33 (m, 2H), 2.09 (s, 3H), 1.67-2.07 (m, 12H).

Compound 85. (1R,5S)-3-[(7S)-2-[[(2R,8S)-2-fluoro-1,2,3,5,6,7-hexahydropyrrolizin-8-yl]methoxy]-6-methyl-spiro[5,8-dihydropyrido[4,3-d]pyrimidine-7,1'-tetralin]-4-yl]-3-azabicyclo[3.2.1]octan-8-amine Compound 85 was prepared similarly to that of Ex. 21 using intermediate 3. LCMS calculated for $C_{32}H_{44}FN_6O$ (M+H)$^+$ m/z=547.4; found: 547.5. $^1$H NMR (400 MHz, DMSO) δ 7.46 (d, J=8.0 Hz, 1H), 7.20 (t, J=7.2 Hz, 1H), 7.13 (t, J=7.2 Hz, 1H), 7.07 (d, J=7.6 Hz, 1H), 5.24 (d, J=53.6 Hz, 1H), 3.97-4.09 (m, 1H), 3.79, 3.93 (d, J=10.0 Hz, 2H), 3.46-3.66 (m, 4H), 3.15-3.23 (m, 1H), 3.03-3.11 (m, 3H), 2.61-3.02 (m, 8H), 2.04-2.12 (m, 3H), 1.98 (s, 3H), 1.98-2.01 (m, 1H), 1.59-1.95 (m, 11H), 1.30-1.43 (m, 1H).

Example 26. Exemplary Synthesis of [(1R,5S)-3-[(7S)-2-[[(2R,8S)-2-fluoro-1,2,3,5,6,7-hexahydropyrrolizin-8-yl]methoxy]-6-methyl-spiro[5,8-dihydropyrido[4,3-d]pyrimidine-7,1'-tetralin]-4-yl]-3-azabicyclo[3.2.1]octan-8-yl]cyanamide (Compound 86)

-continued

To a solution of (1R,5S)-3-[(7S)-2-[[(2R,8S)-2-fluoro-1,2,3,5,6,7-hexahydropyrrolizin-8-yl]methoxy]-6-methyl-spiro[5,8-dihydropyrido[4,3-d]pyrimidine-7,1'-tetralin]-4-yl]-3-azabicyclo[3.2.1]octan-8-amine (Compound 85, 5 mg, 0.01 mmol) in THF (0.3 mL) were added BrCN (0.93 mg, 0.01 mmol) and Et$_3$N (1.5 uL, 0.01 mmol) at −20° C. The reaction was stirred at −20° C. for 2 h. Then the mixture was filtered and purified by Prep-HPLC on a C18 column (5 uM, 50×150 mm) with mobile phase: H$_2$O (0.1% NH$_4$HCO$_3$)/CH$_3$CN at flow rate of 35 mL/min to afford [(1R,5S)-3-[(7S)-2-[[(2R,8S)-2-fluoro-1,2,3,5,6,7-hexahydropyrrolizin-8-yl]methoxy]-6-methyl-spiro[5,8-dihydropyrido[4,3-d]pyrimidine-7,1'-tetralin]-4-yl]-3-azabicyclo[3.2.1]octan-8-yl]cyanamide (Compound 86, 2.22 mg, 0.0035 mmol, 39.58% yield) as a white solid. LCMS calculated for $C_{33}H_{43}FN_7O$ (M+H)$^+$ m/z=572.4; found: 572.5.

$^1$H NMR (400 MHz, DMSO) δ 7.46 (d, J=7.6 Hz, 1H), 7.20 (t, J=6.8 Hz, 1H), 7.13 (t, J=7.2 Hz, 1H), 7.07 (d, J=7.2 Hz, 1H), 6.87 (d, J=2.8 Hz, 1H), 5.25 (d, J=55.6 Hz, 1H), 3.99-4.08 (m, 1H), 3.91-3.97 (m, 1H), 3.79-3.85 (m, 1H), 3.54-3.64 (m, 4H), 3.20-3.24 (m, 1H), 3.04-3.10 (m, 1H), 2.64-3.02 (m, 8H), 1.42-2.12 (m, 19H).

Intermediate 5. Synthesis of 3-(3-chloro-5,6,7,8-tetrahydro-4H-pyrazolo[1,5-a][1,4]diazepin-2-yl)-5-methyl-1,2,4-oxadiazole Int-1d Int-5a -continued Int-5b Int-5c Int-5d Int-5d Intermediate 5

Step 1. Synthesis of 5-(2-nitrophenyl)sulfonyl-4,6,7,8-tetrahydropyrazolo[1,5-a][1,4]diazepine-2-carboxamide (Int-5a). To a solution of 5-(2-nitrophenyl)sulfonyl-4,6,7,8-tetrahydropyrazolo[1,5-a][1,4]diazepine-2-carboxylic acid (Int-1d, 870 mg, 2.37 mmol), DIEA (1.65 mL, 9.5 mmol) and HATU (1354.48 mg, 3.56 mmol) in DMF (2 mL) was added NH$_4$Cl (171.13 mg, 2.85 mmol). The reaction was stirred at 30° C. for 2 h. The mixture was diluted with DCM (30×2 mL), washed with water (40 mL) and brine (40 mL), dried over Na$_2$SO$_4$. The solvent was removed and the residue was purified by flash chromatography (eluted with CH$_3$CN in H$_2$O from 5.0% to 95%) to afford 5-(2-nitrophenyl)sulfonyl-4,6,7,8-tetrahydropyrazolo[1,5-a][1,4]diazepine-2-carboxamide (Int-5a, 760 mg, 2.08 mmol, 87.59% yield) as a yellowish solid. LCMS calcld for C$_{14}$H$_{16}$N$_5$O$_5$S (M+H)$^+$ m/z=366.0, found: 366.0.

Step 2. Synthesis of 5-(2-nitrophenyl)sulfonyl-4,6,7,8-tetrahydropyrazolo[1,5-a][1,4]diazepine-2-carbonitrile (Int-5b). To a solution of 5-(2-nitrophenyl)sulfonyl-4,6,7,8-tetrahydropyrazolo[1,5-a][1,4]diazepine-2-carboxamide (Int-5a, 1.5 g, 4.11 mmol) and Pyridine (1 mL, 12.32 mmol) in THF (10 mL) was added TFAA (2586.98 mg, 12.32 mmol) slowly at 25° C. The mixture was stirred at 25° C. for 48 h. The mixture was quenched with H$_2$O (20 mL), extracted with EtOAc (20×3 mL), dried over Na$_2$SO$_4$, concentrated. The crude product was purified by silica gel chromatography (eluted with EtOAc in petroleum ether from 10% to 90%) to afford 5-(2-nitrophenyl)sulfonyl-4,6,7,8-tetrahydropyrazolo [1,5-a][1,4]diazepine-2-carbonitrile (Int-5b, 0.8 g, 2.303 mmol, 56.10% yield) as a yellow solid. LCMS calcld for C$_{14}$H$_{14}$N$_5$O$_4$S (M+H)$^+$ m/z=348.07, found: 348.0.

Step 3. Synthesis of 3-chloro-5-(2-nitrophenyl)sulfonyl-4,6,7,8-tetrahydropyrazolo[1,5-a][1,4]diazepine-2-carbonitrile (Int-5c). To a solution of 5-(2-nitrophenyl)sulfonyl-4,6,7,8-tetrahydropyrazolo[1,5-a][1,4]diazepine-2-carbonitrile (500 mg, 1.44 mmol) in CH$_3$CN (5 mL) were added NCS (192.21 mg, 1.44 mmol). The mixture was stirred at 60° C. for 4 h. The mixture was quenched with H$_2$O (10 mL), extracted with EtOAc (30 mL), dried over Na$_2$SO$_4$, concentrated. The crude product was purified by flash chromatography (eluted with EtOAc in petroleum ether from 10% to 90%). The product 3-chloro-5-(2-nitrophenyl)sulfonyl-4,6,7,8-tetrahydropyrazolo[1,5-a][1,4]diazepine-2-carbonitrile (Int-5c, 400 mg, 1.05 mmol, 72.78% yield) was obtained as a white solid. LCMS calcld for C$_{14}$H$_{13}$ClN$_5$O$_4$S (M+H)$^+$ m/z=382.1, found: 382.0.

Step 4. Synthesis of 3-chloro-N-hydroxy-5-(2-nitrophenyl)sulfonyl-4,6,7,8-tetrahydropyrazolo[1,5-a][1,4]diazepine-2-carboxamidine (Int-5d). To a solution of 3-chloro-5-(2-nitrophenyl)sulfonyl-4,6,7,8-tetrahydropyrazolo[1,5-a][1,4]diazepine-2-carbonitrile (Int-5c, 400 mg, 1.05 mmol) and K$_2$CO$_3$ (433.75 mg, 3.14 mmol) in Ethanol (2 mL) was added NH$_2$OH'HCl (144.58 mg, 2.1 mmol). The reaction was stirred at 80° C. for 12 h. The mixture was cooled to rt, filtered, and washed with water (10 ml) to give crude product 3-chloro-N-hydroxy-5-(2-nitrophenyl)sulfonyl-4,6,7,8-tetrahydropyrazolo[1,5-a][1,4]diazepine-2-carboxamidine (Int-5d, 183 mg, 0.441 mmol, 42.11% yield) as a white solid. LCMS calcld for C$_{14}$H$_{16}$ClN$_6$O$_5$S (M+H)$^+$ m/z=415.0, found: 415.2.

Step 5. Synthesis of 3-[3-chloro-5-(2-nitrophenyl)sulfonyl-4,6,7,8-tetrahydropyrazolo[1,5-a][1,4]diazepin-2-yl]-5-methyl-1,2,4-oxadiazole (Int-5e). To a solution of 3-chloro-N-hydroxy-5-(2-nitrophenyl)sulfonyl-4,6,7,8-tetrahydropyrazolo[1,5-a][1,4]diazepine-2-carboxamidine (183 mg, 0.44 mmol) in Acetic acid (2 mL) were added Acetic anhydride (Int-5d, 67.56 mg, 0.66 mmol). The reaction was stirred at 100° C. for 16 h. The mixture was filtered to give crude product. The crude product was purified by flash chromatography (eluted with CH$_3$CN in H$_2$O from 5.0% to 43%). The product 3-[3-chloro-5-(2-nitrophenyl)sulfonyl-4,6,7,8-tetrahydropyrazolo[1,5-a][1,4]diazepin-2-yl]-5-methyl-1,2,4-oxadiazole (Int-5e, 163 mg, 0.371 mmol, 84.19% yield) was obtained as a white solid. LCMS calcld for C$_{16}$H$_{16}$ClN$_6$O$_5$S (M+H)$^+$ m/z=439.1, found: 439.2.

Step 6. Synthesis of 3-(3-chloro-5,6,7,8-tetrahydro-4H-pyrazolo[1,5-a][1,4]diazepin-2-yl)-5-methyl-1,2,4-oxadiazole (Intermediate 5). A solution of 3-[3-chloro-5-(2-nitrophenyl)sulfonyl-4,6,7,8-tetrahydropyrazolo[1,5-a][1,4]diazepin-2-yl]-5-methyl-1,2,4-oxadiazole (Int-5e, 150 mg, 0.34 mmol), 4-methoxybenzenethiol (0.13 mL, 1.03 mmol)

and cesium carbonate (444.34 mg, 1.37 mmol) in CH₃CN (4 mL) was stirred at 20° C. for 1 h. The mixture was filtrated and purified by prep-HPLC on a C18 column with mobile phase: H₂O (0.1% NH₄HCO₃)/CH₃CN to afford 3-(3-chloro-5,6,7,8-tetrahydro-4H-pyrazolo[1,5-a][1,4]diazepin-2-yl)-5-methyl-1,2,4-oxadiazole (Intermediate 5, 80 mg, 0.315 mmol, 92.26% yield) as white solid. LCMS calcld for C₁₀H₁₃ClN₅O (M+H)⁺ m/z=254.07, found: 254.0.

Compound 87. 3-[3-chloro-5-[(7S)-2-[[(2R,8S)-2-fluoro-1,2,3,5,6,7-hexahydropyrrolizin-8-yl]methoxy]-6-methyl-spiro[5,8-dihydropyrido[4,3-d]pyrimidine-7,1'-tetralin]-4-yl]-4,6,7,8-tetrahydropyrazolo[1,5-a][1,4]diazepin-2-yl]-5-methyl-1,2,4-oxadiazole Compound 87 was prepared similarly to that of Ex. 21 using intermediate 5. LCMS calculated for C₃₅H₄₂ClFN₉O₂ (M+H)⁺ m/z=674.31; found: 674.1. ¹H NMR (400 MHz, CD₃OD) δ 7.50 (d, J=7.6 Hz, 1H), 7.00-7.27 (m, 3H), 5.21 (d, J=55.2 Hz, 1H), 4.81-4.84 (m, 2H), 4.51-4.60 (m, 1H), 4.35-4.46 (m, 1H), 3.98-4.09 (m, 2H), 3.85-3.97 (m, 3H), 3.69 (d, J=14.8 Hz, 1H), 2.90-3.21 (m, 6H), 2.71-2.79 (m, 2H), 2.66 (s, 3H), 2.35-2.47 (m, 1H), 1.95-2.27 (m, 9H), 1.72-1.93 (m, 5H).

Intermediate 6

-continued

Int-6b

Int-6c

Intermediate 6

Step 1. Synthesis of ethyl 3-(2-pyridyl)-1H-pyrazole-5-carboxylate (Int-6a). To a solution of 2-Ethynylpyridine (8000 mg, 77.58 mmol) in Toluene (80 mL) was added ethyl 2-diazoacetate (10622.19 mg, 93.1 mmol) and the mixture was stirred and refluxed at 110° C. for 16 h. The reaction was concentrated and purified by flash column chromatography (silica gel, eluting with 27% EtOAc/PE) to afford ethyl 3-(2-pyridyl)-1H-pyrazole-5-carboxylate (9300 mg, 42.8 mmol, 55.19% yield) as a yellow solid. LCMS calculated for C₁₁H₁₂N₃O₂ (M+H)⁺ m/z=218.1; found: 218.1.

Step 2. Synthesis of ethyl 2-[3-(tert-butoxycarbonylamino)propyl]-5-(2-pyridyl)pyrazole-3-carboxylate (Int-6b). To a solution of ethyl 3-(2-pyridyl)-1H-pyrazole-5-carboxylate (6600 mg, 30.38 mmol) in DMF (70 mL) were added tert-butyl N-(3-bromopropyl)carbamate (7958.53 mg, 33.42 mmol), KI (100.88 mg, 0.61 mmol) and cesium carbonate (19749.56 mg, 60.77 mmol). The reaction was stirred at rt overnight. The mixture was diluted with water, extracted with EtOAc, washed with brine, dried over Na₂SO₄, concentrated. The product ethyl 2-[3-(tert-butoxycarbonylamino)propyl]-5-(2-pyridyl)pyrazole-3-carboxylate (Int-6b, 12300 mg) was carried over without further purification. LCMS calculated for C₁₉H₂₇N₄O₄ (M+H)⁺ m/z=375.5; found: 375.1.

Step 3. Synthesis of 2-(2-pyridyl)-5,6,7,8-tetrahydropyrazolo[1,5-a][1,4]diazepin-4-one (Int-6c). A mixture of ethyl 2-[3-(tert-butoxycarbonylamino)propyl]-5-(2-pyridyl)pyrazole-3-carboxylate (Int-6b, 12.3 g, 32.85 mmol) and HCl in Dioxane (120 mL, 480 mmol) was stirred at rt for 4 h. The solvent was removed followed by the addition of Methanol (110 mL) and Et₃N (22.92 mL, 164.25 mmol). The reaction was stirred at 80° C. for 16 h. The mixture was concentrated, Int-6a and the residue was purified by flash column chromatography (silica gel, eluting with 7% MeOH/DCM) to afford 2-(2-pyridyl)-5,6,7,8-tetrahydropyrazolo[1,5-a][1,4]diazepin-4-one (12000 mg, 52.6 mmol, 72.54% yield) as a yellow solid. LCMS calculated for $Cl_2H_{13}N_4O$ (M+H)$^+$ m/z=229.3; found: 229.1. $^1$H NMR (400 MHz, CDCl$_3$) δ 8.66 (dd, J=4.8, 0.8 Hz, 1H), 7.85 (d, J=8.0 Hz, 1H), 7.74 (td, J=8.0, 2.0 Hz, 1H), 7.41 (s, 1H), 7.22-7.25 (m, 1H), 7.12 (s, 1H), 4.61 (t, J=6.8 Hz, 2H), 3.41 (s, 2H), 2.27-2.38 (m, 2H).

Step 4. To a solution of 2-(6-methoxy-2-pyridyl)-5,6,7,8-tetrahydropyrazolo[1,5-a][1,4]diazepin-4-one (100 mg, 0.39 mmol) in THF (10 mL) was added LiAlH$_4$ (132.24 mg, 3.48 mmol) at 0° C. The reaction was stirred at 0° C. to rt overnight. The reaction was quenched with Na$_2$SO$_4$·10H$_2$O. The mixture was filtered and filtrate was concentrated. The residue was purified by flash column chromatography (silica gel, eluting with 7% MeOH/DCM) to afford 2-(6-methoxy-2-pyridyl)-5,6,7,8-tetrahydro-4H-pyrazolo[1,5-a][1,4]diazepine (70 mg, 0.287 mmol, 74.01% yield) as a yellow oil. LCMS calculated for $C_{13}H_{17}N_4O$ (M+H)$^+$ m/z=245.1; found: 245.1. $^1$H NMR (400 MHz, DMSO) δ 7.68 (td, J=8.0, 7.6 Hz, 1H), 7.44 (dd, J=7.6, 0.8 Hz, 1H), 6.67 (dd, J=8.4, 0.8 Hz, 1H), 6.62 (s, 1H), 4.32-4.39 (m, 2H), 3.89 (s, 3H), 3.82 (s, 2H), 2.99-3.07 (m, 2H), 1.68-1.78 (m, 2H), 1.40-1.46 (m, 1H).

Compound 88. (7S)-2-[[(2R,8S)-2-fluoro-1,2,3,5,6,7-hexahydropyrrolizin-8-yl]methoxy]-6-methyl-4-[2-(2-pyridyl)-4,6,7,8-tetrahydropyrazolo[1,5-a][1,4]diazepin-5-yl]spiro[5,8-dihydropyrido[4,3-d]pyrimidine-7,1'-tetralin]

Compound 88 was prepared similarly to that of Ex. 21 using Intermediate 6. LCMS calculated for $C_{37}H_{44}FN_8O$ (M+H)$^+$ m/z=635.4; found: 635.5. $^1$H NMR (400 MHz, CD$_3$OD) δ 8.52 (dd, J=4.8, 0.8 Hz, 1H), 7.93 (d, J=8.0 Hz, 1H), 7.82 (td, J=7.6, 1.6 Hz, 1H), 7.49 (d, J=7.6 Hz, 1H), 7.28-7.33 (m, 1H), 7.05-7.22 (m, 3H), 6.88 (s, 1H), 5.16 (d, J=52.4 Hz 1H), 4.47-4.60 (m, 2H), 3.94-4.15 (m, 4H), 3.73-3.89 (m, 2H), 3.07-3.22 (m, 3H), 2.87-3.03 (m, 3H), 2.71-2.80 (m, 2H), 2.19-2.40 (m, 3H), 2.12 (s, 3H), 1.69-2.11 (m, 11H).

Compound 89. (7S)-2-[[(2R,8S)-2-fluoro-1,2,3,5,6,7-hexahydropyrrolizin-8-yl]methoxy]-4-[2-(6-methoxy-2-pyridyl)-4,6,7,8-tetrahydropyrazolo[1,5-a][1,4]diazepin-5-yl]-6-methyl-spiro[5,8-dihydropyrido[4,3-d]pyrimidine-7,1'-tetralin]

Compound 89 was prepared similarly to Compound 88. LCMS calculated for $C_{38}H_{46}FN_8O_2$ (M+H)$^+$ m/z=665.4; found: 665.5. $^1$H NMR (400 MHz, CD$_3$OD) δ 7.66 (t, J=7.6 Hz, 1H), 7.49 (d, J=7.6 Hz, 1H), 7.45 (dd, J=7.6, 0.4 Hz, 1H), 7.20 (td, J=7.2, 1.2 Hz, 1H), 7.14 (td, J=7.6, 1.2 Hz, 1H), 7.09 (dd, J=7.6, 1.2 Hz, 1H), 6.87 (s, 1H), 6.68 (d, J=8.4 Hz, 1H), 5.17 (d, J=53.2 Hz, 1H), 4.43-4.60 (m, 2H), 3.99-4.15 (m, 4H), 3.96 (s, 3H), 3.78, 3.87 (d, J=14.8 Hz, 2H), 3.14-3.21 (m, 2H), 3.08-3.12 (m, 1H), 2.89-3.03 (m, 3H), 2.73-2.79 (m, 2H), 2.13 (s, 3H), 1.64-2.50 (m, 14H).

Intermediate 7

Int-1c

Int-7a

-continued

Int-7b

Int-7c

Intermediate 7

Step 1. Synthesis of ethyl 3-chloro-5-(2-nitrophenyl) sulfonyl-4,6,7,8-tetrahydropyrazolo[1,5-a][1,4]diazepine-2-carboxylate (Int-7a). A solution of ethyl 5-(2-nitrophenyl) sulfonyl-4,6,7,8-tetrahydropyrazolo[1,5-a][1,4]diazepine-2-carboxylate (Int-1c 1000 mg, 2.54 mmol) in DMF (10 mL) was added NCS (372.42 mg, 2.79 mmol) at 25° C. Then the mixture was stirred at 80° C. for 1 h. The solution was extracted with EtOAc (10 ml), the organic phase was concentrated. The residue was purified by silica gel chromatography (eluting with EtOAc in PE from 5% to 85%). The product ethyl 3-chloro-5-(2-nitrophenyl)sulfonyl-4,6,7, 8-tetrahydropyrazolo[1,5-a][1,4]diazepine-2-carboxylate (Int-7a, 914 mg, 2.131 mmol, 84.06% yield) was obtained as an oil. LCMS calculated for $C_{16}H_{18}ClN_4O_6S$ $(M+H)^+$ m/z=429.06, found: 429.2.

Step 2. Synthesis of 3-chloro-5-(2-nitrophenyl)sulfonyl-4,6,7,8-tetrahydropyrazolo[1,5-a][1,4]diazepine-2-carbox-amide (Int-7b). A solution of ethyl 3-chloro-5-(2-nitrophe-nyl)sulfonyl-4,6,7,8-tetrahydropyrazolo[1,5-a][1,4] diazepine-2-carboxylate (Int-7a, 500 mg, 1.17 mmol) in Ethanol (5 mL) was added $NH_2NH_2 \cdot H_2O$ (594.85 mg, 11.66 mmol) at 25° C. The mixture was stirred at 85° C. for 2 h. The solution was extracted with EtOAc (5 ml), the organic phase was concentrated. The residue was purified by silica gel chromatography (eluting with EtOAc in PE from 5% to 95%). The product 3-chloro-5-(2-nitrophenyl)sulfonyl-4,6, 7,8-tetrahydropyrazolo[1,5-a][1,4]diazepine-2-carbohy-drazide (Int-7b, 300 mg, 0.723 mmol, 62.03% yield) was obtained as a white solid. LCMS calculated for $C_{14}H_{16}ClN_6O_5S$ $(M+H)^+$ m/z=415.06, found: 415.0.

Step 3. Synthesis of 3-chloro-2-(4,5-dimethyl-1,2,4-tri-azol-3-yl)-5-(2-nitrophenyl)sulfonyl-4,6,7,8-tetrahydropy-razolo[1,5-a][1,4]diazepine (Int-7c). To a solution of 3-chloro-5-(2-nitrophenyl)sulfonyl-4,6,7,8-tetrahydropyra-zolo[1,5-a][1,4]diazepine-2-carbohydrazide (Int-7b, 150 mg, 0.36 mmol) in 1,4-Dioxane (3 mL) was added 1,1,1-trimethoxyethane (65.17 mg, 0.54 mmol), Methylamine in EtOH (0.17 mL, 1.08 mmol) and a drop of AcOH (21.7 mg, 0.36 mmol) at rt. The mixture was stirred at 120° C. for 16 h in a sealed vial. The solution was extracted with EtOAc (2 ml), The water phase was concentrated. The residue was purified by silica gel chromatography (eluting with MeOH in DCM from 1% to 3%). The product 3-chloro-2-(4,5-dimethyl-1,2,4-triazol-3-yl)-5-(2-nitrophenyl)sulfonyl-4,6, 7,8-tetrahydropyrazolo[1,5-a][1,4]diazepine (95 mg, 0.210 mmol, 58.14% yield) was obtained as a white solid. LCMS calculated for $C_{17}H_{19}ClN_7O_4S$ $(M+H)^+$ m/z=452.09, found: 452.2.

Step 4. Synthesis of 3-chloro-2-(4,5-dimethyl-1,2,4-tri-azol-3-yl)-5,6,7,8-tetrahydro-4H-pyrazolo[1,5-a][1,4]diaz-epine (Intermediate 7). To a solution of 3-chloro-2-(4,5-dimethyl-1,2,4-triazol-3-yl)-5-(2-nitrophenyl)sulfonyl-4,6, 7,8-tetrahydropyrazolo[1,5-a][1,4]diazepine (Int-7c, 75 mg, 0.17 mmol) in $CH_3CN$ (0.5 mL) was added 4-Methoxythio-phenol (44.21 mg, 0.32 mmol) and $CS_2CO_3$ (137.07 mg, 0.42 mmol) at rt. The mixture was stirred at 25° C. for 2 h. The solution was concentrated. The residue was purified by silica gel on chromatography (eluting with MeOH in DCM from 3% to 11%). The 3-chloro-2-(4,5-dimethyl-1,2,4-tri-azol-3-yl)-5,6,7,8-tetrahydro-4H-pyrazolo[1,5-a][1,4]diaz-epine (Intermediate 7, 40 mg, 0.15 mmol, 71.33% yield) was obtained as a white solid. LCMS calculated for $C_{11}H_{16}ClN_6$ $(M+H)^+$ m/z=267.11, found: 267.1.

Compound 90. (7S)-4-[3-chloro-2-(4,5-dimethyl-1, 2,4-triazol-3-yl)-4,6,7,8-tetrahydropyrazolo[1,5-a][1, 4]diazepin-5-yl]-2-[[(2R,8S)-2-fluoro-1,2,3,5,6,7-hexahydropyrrolizin-8-yl]methoxy]-6-methyl-spiro [5,8-dihydropyrido[4,3-d]pyrimidine-7,1'-tetralin]

Compound 90 was prepared similarly to that of Ex. 21 using Intermediate 7. LCMS calcld for $C_{36}H_{45}ClFN_{10}O$ $(M+H)^+$ m/z=687.34; found: 687.4. $^1H$ NMR (400 MHz, $CD_3OD$) δ 7.50 (d, J=8.0 Hz, 1H), 7.04-7.24 (m, 3H), 5.23 (d, J=52.0 Hz, 1H), 4.79-4.96 (m, 2H), 4.42-4.64 (m, 2H), 3.85-4.15 (m, 5H), 3.77 (s, 3H), 3.70 (d, J=14.8 Hz, 1H), 2.90-3.22 (m, 6H), 2.71-2.80 (m, 2H), 2.37-2.53 (m, 4H), 1.72-2.29 (m, 14H).

Compound 91. (7S)-4-(6,8-dihydro-5H-imidazo[1,5-a]pyrazin-7-yl)-2-[[(2R,8S)-2-fluoro-1,2,3,5,6,7-hexahydropyrrolizin-8-yl]methoxy]-6-methyl-spiro[5,8-dihydropyrido[4,3-d]pyrimidine-7,1'-tetralin]

-continued

Compound 92

Compound 91 was prepared similarly to that of Ex. 21. LCMS calculated for $C_{31}H_{39}FN_7O$ (M+H)$^+$ m/z=544.31; found: 544.4. $^1$H NMR (400 MHz, CD$_3$OD) δ 7.63 (s, 1H), 7.51 (d, J=7.6 Hz, 1H), 7.06-7.24 (m, 3H), 6.84 (s, 1H), 5.28 (d, J=53.6 Hz, 1H), 4.77-4.83 (m, 2H), 4.30-4.40 (m, 1H), 4.05-4.25 (m, 4H), 3.68-3.78 (m, 3H), 3.15-3.27 (m, 3H), 2.91-3.09 (m, 3H), 2.71-2.81 (m, 2H), 2.15-2.31 (m, 2H), 2.05-2.14 (m, 4H), 1.91-2.04 (m, 4H), 1.74-1.90 (m, 3H).

Example 27. Exemplary Synthesis of 6-[5-[(7S)-2-[[(2R,8S)-2-fluoro-1,2,3,5,6,7-hexahydropyrrolizin-8-yl]methoxy]-6-methyl-spiro[5,8-dihydropyrido[4,3-d]pyrimidine-7,1'-tetralin]-4-yl]-4,6,7,8-tetrahydropyrazolo[1,5-a][1,4]diazepin-2-yl]pyridin-2-ol (Compound 92)

To a solution of (7S)-2-[[(2R,8S)-2-fluoro-1,2,3,5,6,7-hexahydropyrrolizin-8-yl]methoxy]-4-[2-(6-methoxy-2-pyridyl)-4,6,7,8-tetrahydropyrazolo[1,5-a][1,4]diazepin-5-yl]-6-methyl-spiro[5,8-dihydropyrido[4,3-d]pyrimidine-7,1'-tetralin](Compound 89, 8 mg, 0.01 mmol) in THF (5 mL) was added HBr (0.5 mL, 0.01 mmol) and the reaction was stirred at 60° C. for 24 h. The pH was adjusted to 8 by saturated NaHCO$_3$ aqueous solution. Then this mixture was concentrated and purified by Prep-HPLC on a C18 column (5 uM, 50×150 mm) with mobile phase: H$_2$O (0.1% NH$_4$HCO$_3$)/CH$_3$CN at flow rate: 35 mL/min to afford 6-[5-[(7S)-2-[[(2R,8S)-2-fluoro-1,2,3,5,6,7-hexahydropyrrolizin-8-yl]methoxy]-6-methyl-spiro[5,8-dihydropyrido[4,3-d]pyrimidine-7,1'-tetralin]-4-yl]-4,6,7,8-tetrahydropyrazolo[1,5-a][1,4]diazepin-2-yl]pyridin-2-ol (Compound 92, 3.25 mg, 0.005 mmol, 39.05% yield) as a white solid. LCMS calculated for $C_{37}H_{44}FN_8O_2$ (M+H)$^+$ m/z=651.4; found: 651.4. $^1$H NMR (400 MHz, CD$_3$OD) δ 7.60 (dd, J=9.2, 7.2 Hz, 1H), 7.49 (dd, J=7.6, 0.8 Hz, 1H), 7.17-7.22 (m, 1H), 7.14 (td, J=7.6, 1.6 Hz, 1H), 7.09 (dd, J=7.6, 0.8 Hz, 1H), 6.86 (s, 1H), 6.77 (dd, J=7.2, 1.2 Hz, 1H), 6.46 (dd, J=9.2, 0.8 Hz, 1H), 5.23 (d, J=53.2 Hz, 1H), 4.46-4.62 (m, 3H), 3.95-4.10 (m, 4H), 3.74, 3.83 (d, J=14.8 Hz, 2H), 3.10-3.23 (m, 3H), 2.88-3.04 (m, 3H), 2.72-2.80 (m, 2H), 2.14-2.40 (m, 2H), 2.12 (s, 3H), 1.67-2.11 (m, 11H).

Compound 89

Intermediate 8

Int-6c

-continued

Int-8a

Intermediate 8

Step 1. Synthesis of 3-chloro-2-(2-pyridyl)-5,6,7,8-tetra-hydropyrazolo[1,5-a][1,4]diazepin-4-one (Int-8a). To a solution of 2-(2-pyridyl)-5,6,7,8-tetrahydropyrazolo[1,5-a][1,4]diazepin-4-one (Int-6c, 2500 mg, 10.95 mmol) in DMF (23 mL) was added NCS (1755.05 mg, 13.14 mmol) at 50° C., then the mixture was stirred at 50° C. for 16 h. Then the mixture was concentrate and purified by Prep-HPLC on a C18 column (5 uM, 50×150 mm) with mobile phase: $H_2O$ (0.1% HCOOH)/$CH_3CN$ at flow rate: 65 mL/min to afford 3-chloro-2-(2-pyridyl)-5,6,7,8-tetrahydropyrazolo[1,5-a][1,4]diazepin-4-one (Int-8a, 2690 mg, 10.2 mmol, 93.49% yield) as a white solid. $^1$H NMR (400 MHz, $CDCl_3$) δ 8.79 (d, J=4.4 Hz, 1H), 8.05 (d, J=8.0 Hz, 1H), 7.84 (td, J=8.0, 1.6 Hz, 1H), 7.30-7.38 (m, 1H), 6.46 (s, 1H), 4.60 (t, J=7.2 Hz, 2H), 3.34-3.44 (m, 2H), 2.24-2.37 (m, 2H). LCMS calculated for $Cl_2H_{12}ClN_4O$ (M+H)+ m/z=263.7; found: 263.2/265.2.

Step 2. 3-chloro-2-(2-pyridyl)-5,6,7,8-tetrahydro-4H-pyrazolo[1,5-a][1,4]diazepine (Intermediate 8). To a solution of 3-chloro-2-(2-pyridyl)-5,6,7,8-tetrahydropyrazolo[1,5-a][1,4]diazepin-4-one (Int-8a, 1000 mg, 3.81 mmol) in THF (100 mL) was added $NaBH_4$ (845.1 mg, 22.84 mmol) at 0° C. The mixture was stirred at rt for 1 h, followed by the addition of Boron trifluoride diethyl etherate (4322.05 mg, 30.45 mmol). The reaction was allowed to rt and stirred overnight. Methanol was added to quenched the reaction at 0° C. and then refluxed at 45° C. for 16 h. The mixture was concentrated and purified by flash column chromatography (silica gel, eluting with MeOH/DCM=10/1) to afford 3-chloro-2-(2-pyridyl)-5,6,7,8-tetrahydro-4H-pyrazolo[1,5-a][1,4]diazepine (Intermediate 8,710 mg, 2.85 mmol, 74.99% yield) as a colorless oil. LCMS calculated for $Cl_2H_{14}ClN_4$(M+H)+ m/z=249.7; found: 249.2/251.2.

Compound 93. (7S)-4-[3-chloro-2-(2-pyridyl)-4,6,7,8-tetrahydropyrazolo[1,5-a][1,4]diazepin-5-yl]-2-[[(2R,8S)-2-fluoro-1,2,3,5,6,7-hexahydropyrrolizin-8-yl]methoxy]-6-methyl-spiro[5,8-dihydropyrido[4,3-d]pyrimidine-7,1'-tetralin]

Compound 93 was prepared similarly to Compound 88 using Intermediate 8. LCMS calculated for $C_{37}H_{43}ClFN_8O$ (M+H)+ m/z=670.3; found: 669.4, 671.4. $^1$H NMR (400 MHz, $CD_3OD$) δ 8.61 (d, J=4.8 Hz, 1H), 7.85-7.95 (m, 2H), 7.50 (d, J=8.0 Hz, 1H), 7.35-7.42 (m, 1H), 7.06-7.23 (m, 3H), 5.18 (d, J=55.2 Hz, 1H), 4.77 (d, J=28.4 Hz, 2H), 4.50-4.61 (m, 1H), 4.35-4.47 (m, 1H), 4.01-4.12 (m, 2H), 3.87-4.00 (m, 3H), 3.71 (d, J=15.2 Hz, 1H), 2.89-3.25 (m, 6H), 2.76 (dd, J=8.0, 2.8 Hz, 2H), 2.37-2.49 (m, 1H), 2.14-2.28 (m, 2H), 2.11 (s, 3H), 1.70-2.08 (m, 9H).

Intermediate 9

Int-9a

Int-9b

-continued

Int-9c        Intermediate 9

Step 1. Synthesis of methyl 3-[(2R)-2-(tert-butoxycarbo-nylamino)propyl]imidazole-4-carboxylate (Int-9a) To a solution of tert-butyl N-[(1R)-2-hydroxy-1-methyl-ethyl] carbamate (1.75 g, 9.99 mmol), methyl 1H-imidazole-4-carboxylate (1.51 g, 11.98 mmol) and $PPh_3$ (3705.38 mg, 16.98 mmol) in THF (100 mL) was added DIAD (3.34 mL, 16.98 mmol) dropwise at −50° C. under $N_2$. The reaction mixture was allowed to warm to rt and stirred for 16 h. The reaction mixture was concentrated under reduced pressure and then adjusted the pH to 1 by 1M HCl, extracted with EtOAc (3×50 mL). The aqueous layer was neutralized to pH 7-8 with sat. aq $NaHCO_3$, and was extracted with EtOAc (3×70 mL). The combined organic phases were dried ($Na_2SO_4$), concentrated under reduced pressure and the crude residue was purified by silica gel column chromatography (DCM:EtOAc, 1:1) to afford methyl 3-[(2R)-2-(tert-butoxycarbonylamino)propyl]imidazole-4-carboxylate (Int-9a, 1.20 g, 4.24 mmol, 42.41% yield) as a white solid. LCMS calculated for $C_{13}H_{22}N_3O_4$ $(M+H)^+$ m/z=284.32; found: 284.2.

Step 2. Synthesis of methyl 3-[(2R)-2-aminopropyl] imidazole-4-carboxylate (Int-9b)

A solution of methyl 3-[(2R)-2-(tert-butoxycarbo-nylamino)propyl]imidazole-4-carboxylate (Int-9a, 1.2 g, 4.24 mmol) and HCl/Dioxane (6 mL, 24 mmol) in Methanol (4 mL) was stirred at 25° C. for 1 h. The reaction mixture was concentrated under reduced pressure to give the crude methyl 3-[(2R)-2-aminopropyl]imidazole-4-carboxylate (Int-9b, 0.80 g) as a white solid.

Step 3. Synthesis of (6R)-6-methyl-6,7-dihydro-5H-imidazo[1,5-a]pyrazin-8-one (Int-9c). A solution of methyl 3-[(2R)-2-aminopropyl]imidazole-4-carboxylate (Int-9b, 0.8 g, 4.37 mmol) and TEA (6 mL, 43.25 mmol) in Methanol (30 mL) was stirred at 50° C. overnight. The reaction mixture was concentrated under reduced pressure. The crude residue was purified by column (DCM:MeOH) to afford (6R)-6-methyl-6,7-dihydro-5H-imidazo[1,5-a]pyrazin-8-one (Int-9c, 1.20 g, 7.94 mmol, 95.19% yield) as a white solid.

Step 4. Synthesis of (Intermediate 9). To a solution of (6R)-6-methyl-6,7-dihydro-5H-imidazo[1,5-a]pyrazin-8-one (Int-9c, 600 mg, 3.97 mmol) in THF (30 mL) was added $LiAlH_4$ (451.88 mg, 11.91 mmol). The mixture reaction was stirred at 80° C. overnight. The reaction was quenched with $Na_2SO_4$·$10H_2O$ and dried over $MgSO_4$. the mixture was filtered, and the filter cake was washed with THF twice. The filtrate was concentrated under reduced pressure to give not the title product(6R)-6-methyl-5,6,7,8-tetrahydroimidazo[1,5-a]pyrazine (Intermediate 9, 150 mg, 1.09 mmol, 27.55% yield) as a white solid. LCMS calculated for $C_7H_{12}N_3$(M+H)$^+$ m/z=138.10; found: 138.2. $^1$H NMR (400 MHz, $CD_3OD$) δ 7.53 (s, 1H), 6.70 (s, 1H), 4.21-4.15 (m, 1H), 4.13 (d, J=16.0 Hz, 1H), 3.93 (d, J=15.5 Hz, 1H), 3.58-3.50 (m, 1H), 3.18-3.08 (m, 1H), 1.25 (d, J=6.4 Hz, 3H).

Compound 94. (7S)-2-[[(2R,8S)-2-fluoro-1,2,3,5,6, 7-hexahydropyrrolizin-8-yl]methoxy]-6-methyl-4-[(6R)-6-methyl-6,8-dihydro-5H-imidazo[1,5-a] pyrazin-7-yl]spiro[5,8-dihydropyrido[4,3-d] pyrimidine-7,1'-tetralin]

Compound 94 was prepared similarly to that of Ex. 21 using Intermediate 9. LCMS calculated for $C_{32}H_{41}FN_7O$ $(M+H)^+$ m/z=558.3; found: 558.4. $^1$H NMR (400 MHz, $CD_3OD$) δ 7.66 (s, 1H), 7.51 (d, J=6.8 Hz, 1H), 7.19-7.24 (m, 1H), 7.15 (td, J=7.6, 1.6 Hz, 1H), 7.10 (dd, J=7.6, 0.8 Hz, 1H), 6.88 (s, 1H), 5.40 (d, J=52.8 Hz, 1H), 4.76-4.82 (m, 3H), 4.42-4.49 (m, 1H), 4.15-4.36 (m, 3H), 3.89 (d, J=15.2 Hz, 1H), 3.61-3.75 (m, 2H), 3.50-3.59 (m, 1H), 3.38-3.47 (m, 1H), 3.14-3.23 (m, 1H), 2.94-3.12 (m, 2H), 2.74-2.80 (m, 2H), 2.15-2.51 (m, 4H), 2.13 (s, 3H), 1.93-2.11 (m, 4H), 1.74-1.88 (m, 2H), 1.27 (d, J=6.8 Hz, 3H).

Compound 95. 3-chloro-N,N-dimethyl-5-[(7S)-6-methyl-2-[[1-(morpholinomethyl)cyclopropyl] methoxy]spiro[5,8-dihydropyrido[4,3-d]pyrimidine-7,1'-tetralin]-4-yl]-4,6,7,8-tetrahydropyrazolo[1,5-a] [1,4]diazepine-2-carboxamide Compound 95 was prepared similarly to that of Ex. 21. LCMS calculated for $C_{36}H_{48}ClN_8O_3$ $(M+H)^+$ m/z=675.3; found: 675.1/677.1. $^1$H NMR (400 MHz, $CD_3OD$) δ 7.50 (d, J=8.0 Hz, 1H), 7.19 (t, J=7.2 Hz, 1H), 7.13 (td, J=7.6, 1.2 Hz, 1H), 7.08 (d, J=7.6 Hz, 1H), 4.77 (d, J=16.8 Hz, 1H), 4.35-4.61 (m, 2H), 4.22 (d, J=11.2 Hz, 1H), 4.02-4.15 (m, 2H), 3.81-3.98 (m, 2H), 3.68 (d, J=14.4 Hz, 1H), 3.61 (t, J=4.4 Hz, 4H), 3.09 (d, J=10.0 Hz, 6H), 2.97 (dd, J=38.4, 18.4 Hz, 2H), 2.70-2.79 (m, 2H), 2.34-2.52 (m, 6H), 2.30 (d, J=12.8 Hz, 1H), 2.13-2.24 (m, 1H), 2.11 (s, 3H), 1.92-2.06 (m, 3H), 1.71-1.86 (m, 2H), 0.54-0.66 (m, 2H), 0.37-0.48 (m, 2H).

Compound 96. 3-chloro-5-[(7S)-2-[[(2R,8S)-2-fluoro-1,2,3,5,6,7-hexahydropyrrolizin-8-yl]methoxy]-7'-hydroxy-6-methyl-spiro[5,8-dihydro-pyrido[4,3-d]pyrimidine-7,1'-indane]-4-yl]-N,N-dimethyl-4,6,7,8-tetrahydropyrazolo[1,5-a][1,4]diazepine-2-carboxamide Compound 96 was prepared similarly to that of Ex. 21. LCMS calculated for $C_{34}H_{43}ClFN_8O_3$ (M+H)$^+$ m/z=665.3; found: 665.8. $^1$H NMR (400 MHz, CD$_3$OD) δ 7.11 (t, J=8.0 Hz, 1H), 6.73 (d, J=7.6 Hz, 1H), 6.60 (d, J=8.0 Hz, 1H), 5.28 (d, J=54.4 Hz, 1H), 4.80 (d, J=16.8 Hz, 2H), 4.33-4.53 (m, 2H), 3.95-4.13 (m, 3H), 3.71-3.91 (m, 3H), 3.05-3.29 (m, 10H), 2.90-3.04 (m, 3H), 2.75 (d, J=18.4 Hz, 1H), 2.05-2.45 (m, 9H), 1.82-2.01 (m, 3H), 1.72-1.81 (m, 1H).

Compound 97. 3-chloro-5-[(7S)-2-[[1-[(dimethyl-amino)methyl]-2,2-difluoro-cyclopropyl]methoxy]-6-methyl-spiro[5,8-dihydropyrido[4,3-d]pyrimidine-7,1'-tetralin]-4-yl]-N,N-dimethyl-4,6,7,8-tetrahydropyrazolo[1,5-a][1,4]diazepine-2-carboxamide Compound 97 was prepared similarly to that of Ex. 21. LCMS calculated for $C_{34}H_{44}ClF_2N_8O_2$ (M+H)$^+$ m/z=669.3; found: 669.0/671.1. $^1$H NMR (400 MHz, CD$_3$OD) δ 7.50 (d, J=7.6 Hz, 1H), 7.20 (t, J=7.2 Hz, 1H), 7.13 (td, J=7.6, 1.2 Hz, 1H), 7.08 (d, J=7.2 Hz, 1H), 4.87-4.93 (m, 1H), 4.75-4.82 (m, 1H), 4.47-4.54 (m, 1H), 4.37-4.46 (m, 2H), 4.23-4.29 (m, 1H), 4.03-4.13 (m, 1H), 3.84-3.98 (m, 2H), 3.68 (d, J=14.8 Hz, 1H), 3.06-3.11 (m, 6H), 2.89-3.06 (m, 2H), 2.63-2.79 (m, 3H), 2.34-2.51 (m, 2H), 2.21-2.26 (m, 6H), 2.12-2.20 (m, 1H), 2.10 (s, 3H), 1.93-2.04 (m, 2H), 1.72-1.87 (m, 2H), 1.51-1.66 (m, 1H), 1.30-1.40 (m, 1H).

Intermediate 10. Synthesis of 2-(3-chloro-5,6,7,8-tetrahydro-4H-pyrazolo[1,5-a][1,4]diazepin-2-yl)acetonitrile Int-9a Int-9b Intermediate 9

Step 1. Synthesis of tert-butyl 3-chloro-2-(methylsulfo-nyloxymethyl)-4,5,7,8-tetrahydropyrazolo[1,5-d][1,4]diaz-epine-6-carboxylate (Int-10a)

To a solution of tert-butyl 3-chloro-2-(hydroxymethyl)-4,5,7,8-tetrahydropyrazolo[1,5-d][1,4]diazepine-6-carboxy-late (500 mg, 1.66 mmol) in DCM (5 mL) were added Et$_3$N (0.35 mL, 2.49 mmol) and Methanesulfonyl Chloride (0.15 mL, 1.99 mmol) at 0° C. The reaction was stirred at 0° C. for 2 h. Then the mixture was extracted with EtOAc/H$_2$O. The combined organic layer was washed with brine, dried over Na$_2$SO$_4$ and concentrated. The residue was purified by flash column chromatography (silica gel, eluting with 5% MeOH/DCM) to afford tert-butyl 3-chloro-2-(methylsulfonyloxym-ethyl)-4,5,7,8-tetrahydropyrazolo[1,5-d][1,4]diazepine-6- carboxylate (Int-10a, 490 mg, 0.645 mmol, 38.93% yield) as an oil. LCMS calculated for $C_{14}H_{23}ClN_3O_5S$ (M+H)$^+$ m/z=380.1; found: 380.2/382.2.

Step 2. Synthesis of tert-butyl 3-chloro-2-(cyanomethyl)-4,5,7,8-tetrahydropyrazolo[1,5-d][1,4]diazepine-6-carboxylate (Int-10b). To a solution of tert-butyl 3-chloro-2-(methylsulfonyloxymethyl)-4,5,7,8-tetrahydropyrazolo[1,5-d][1,4]diazepine-6-carboxylate (Int-10a, 490 mg, 1.29 mmol) in DMF was added NaCN (316.1 mg, 6.45 mmol) and the reaction was stirred at rt for 2 h. Then the mixture was extracted with EtOAc/H$_2$O. The combined organic layer was washed with brine, dried over Na$_2$SO$_4$ and concentrated. The residue was purified by Prep-HPLC on a C18 column (5 uM, 50×150 mm) with mobile phase: H$_2$O (0.1% NH$_4$HCO$_3$)/CH$_3$CN at flow rate: 35 mL/min to afford tert-butyl 3-chloro-2-(cyanomethyl)-4,5,7,8-tetrahydropyrazolo[1,5-d][1,4]diazepine-6-carboxylate (Int-10b, 200 mg, 0.644 mmol, 49.89% yield) as a yellow oil. LCMS calculated for $C_{14}H_{20}ClN_4O_2$ (M+H)$^+$ m/z=311.1; found: 311.2. $^1$H NMR (400 MHz, DMSO) δ 4.49 (s, 2H), 4.35-4.42 (m, 2H), 3.96 (s, 2H), 3.61-3.70 (m, 2H), 1.72-1.85 (m, 2H), 1.36 (s, 9H).

Step 3. Synthesis of 2-(3-chloro-5,6,7,8-tetrahydro-4H-pyrazolo[1,5-a][1,4]diazepin-2-yl)acetonitrile (Intermediate 10). A mixture of tert-butyl 3-chloro-2-(cyanomethyl)-4,6,7,8-tetrahydropyrazolo[1,5-a][1,4]diazepine-5-carboxylate (Int-9b, 100 mg, 0.32 mmol) and HCl in Dioxane (2 mL, 8 mmol) was stirred at 0° C. to rt for 2 h. Then the mixture was concentrated to afford a crude product for the next step. LCMS calculated for $C_9H_{12}ClN_4$ (M+H)$^+$ m/z=211.1; found: 211.1/213.1.

Compound 98. 2-[3-chloro-5-[(7S)-2-[[(2R,8S)-2-fluoro-1,2,3,5,6,7-hexahydropyrrolizin-8-yl]methoxy]-6-methyl-spiro[5,8-dihydropyrido[4,3-d]pyrimidine-7,1'-tetralin]-4-yl]-4,6,7,8-tetrahydropyrazolo[1,5-a][1,4]diazepin-2-yl]acetonitrile Compound 98 was prepared similarly to that of Ex. 21 using Intermediate 10. LCMS calculated for $C_{34}H_{41}ClFN_8O$ (M+H)$^+$ m/z=631.3; found: 631.1/633.1. $^1$H NMR (400 MHz, CD$_3$OD) δ 7.49 (d, J=7.2 Hz, 1H), 7.17-7.23 (m, 1H), 7.14 (td, J=7.6, 1.2 Hz, 1H), 7.08 (d, J=7.6 Hz, 1H), 5.26 (d, J=54.8 Hz, 1H), 4.74, 4.80 (d, J=16.4 Hz, 2H), 4.41-4.50 (m, 1H), 4.29-4.38 (m, 1H), 3.84-4.09 (m, 5H), 3.82 (s, 2H), 3.66 (d, J=14.8 Hz, 1H), 3.09-3.28 (m, 3H), 2.89-3.06 (m, 3H), 2.71-2.81 (m, 2H), 2.12-2.42 (m, 4H), 2.10 (s, 3H), 1.93-2.08 (m, 5H), 1.74-1.92 (m, 3H).

Intermediate 11. Synthesis of 3-chloro-2-(1-methyl-tetrazol-5-yl)-5,6,7,8-tetrahydro-4H-pyrazolo[1,5-a][1,4]diazepine Int-11a Int-11b Int-11c Intermediate 11

Step 1. Synthesis of tert-butyl 2-(1H-tetrazol-5-yl)-4,6,7,8-tetrahydropyrazolo[1,5-a][1,4]diazepine-5-carboxylate (Int-11a). To a solution of tert-butyl 2-cyano-4,6,7,8-tetrahydropyrazolo[1,5-a][1,4]diazepine-5-carboxylate (400 mg, 1.52 mmol), sodium azide (495.67 mg, 7.62 mmol) and Triethylamine Hydrochloride (472.28 mg, 3.43 mmol) in Toluene (10 mL). The mixture was stirred at 120° C. for 36 h. The crude product was purified by silica gel chromatography (eluted with MeOH in DCM from 1% to 10%). The crude tert-butyl 2-(1H-tetrazol-5-yl)-4,6,7,8-tetrahydropyrazolo[1,5-a][1,4]diazepine-5-carboxylate (Int-11a, 275 mg, 0.901 mmol, 59.06% yield) was obtained as yellow solid. LCMS calcld for $C_{13}H_{20}N_7O_2$ (M+H)$^+$ m/z=306.1, found: 306.1.

Step 2. Synthesis of tert-butyl 2-(1-methyltetrazol-5-yl)-4,6,7,8-tetrahydropyrazolo[1,5-a][1,4]diazepine-5-carboxylate (Int-11b). To a solution of tert-butyl 2-(1H-tetrazol-5-yl)-4,6,7,8-tetrahydropyrazolo[1,5-a][1,4]diazepine-5-carboxylate (Int-11a, 100 mg, 0.33 mmol) and NaH (15.72 mg, 0.39 mmol) in DMF (0.5 ml) at 0° C., followed by the addition of MeI (0.02 mL, 0.39 mmol). The reaction was stirred at 25° C. for 16 h. The crude product was purified by prep-HPLC. The product tert-butyl 2-(2-methyltetrazol-5-yl)-4,6,7,8-tetrahydropyrazolo[1,5-a][1,4]diazepine-5-carboxylate (28 mg, 0.0877 mmol, 26.77% yield) and tert-butyl 2-(1-methyltetrazol-5-yl)-4,6,7,8-tetrahydropyrazolo[1,5-a][1,4]diazepine-5-carboxylate (Int-11b, 60 mg, 0.188 mmol, 57.37% yield) was obtained as white solid. LCMS calcld for $C_{14}H_{22}N_7O_2$ $(M+H)^+$ m/z=320.1, found: 320.1.

Step 3. Synthesis of tert-butyl 3-chloro-2-(1-methyltetrazol-5-yl)-4,6,7,8-tetrahydropyrazolo[1,5-a][1,4]diazepine-5-carboxylate (Int-11c). To a solution of tert-butyl 2-(1-methyltetrazol-5-yl)-4,6,7,8-tetrahydropyrazolo[1,5-a][1,4]diazepine-5-carboxylate (Int-11b, 190 mg, 0.44 mmol) in DMF (4 mL) was added NCS (70.24 mg, 0.53 mmol) at 0° C., then the mixture was stirred at 50° C. for 16 h. Then the mixture was concentrated and purified by Prep-HPLC on a C18 column (5 uM, 50×150 mm) with mobile phase: $H_2O$ (0.1% $NH_4HCO_3$)/MeOH at flow rate 50 mL/min to afford tert-butyl 3-chloro-2-(1-methyltetrazol-5-yl)-4,6,7,8-tetrahydropyrazolo[1,5-a][1,4]diazepine-5-carboxylate (Int-11c, 162 mg, 0.458 mmol, 77.09% yield) as a white solid. LCMS calculated for $C_{14}H_{21}ClN_7O_2(M+H)^+$ m/z=354.1; found: 354.2/356.1.

Step 4. Synthesis of 3-chloro-2-(1-methyltetrazol-5-yl)-5,6,7,8-tetrahydro-4H-pyrazolo[1,5-a][1,4]diazepine (Intermediate 11). To a solution of tert-butyl 3-chloro-2-(1-methyltetrazol-5-yl)-4,6,7,8-tetrahydropyrazolo[1,5-a][1,4]diazepine-5-carboxylate (Int-11c, 50 mg, 0.14 mmol) in DCM (1.5 mL) was added HCl in dioxane (1.41 mL, 5.65 mmol) at 0° C. The reaction was stirred at rt for 1 h. Then the mixture was concentrated to afford 70 mg crude of Intermediate 11. LCMS calculated for $C_9H_{13}ClN_7$ $(M+H)^+$ m/z=254.7; found: 254.3/256.3.

Compound 99. (7S)-4-[3-chloro-2-(1-methyltetrazol-5-yl)-4,6,7,8-tetrahydropyrazolo[1,5-a][1,4]diazepin-5-yl]-2-[[(2R,8S)-2-fluoro-1,2,3,5,6,7-hexahydropyrrolizin-8-yl]methoxy]-6-methyl-spiro[5,8-dihydropyrido[4,3-d]pyrimidine-7,1'-tetralin]

Compound 99 was prepared similarly to that of Ex. 21 using Intermediate 11. LCMS calculated for $C_{34}H_{42}ClFN_{11}O$ $(M+H)^+$ m/z=674.3; found: 674.5. $^1H$ NMR (400 MHz, $CD_3OD$) δ 7.50 (d, J=7.6 Hz, 1H), 7.20 (td, J=7.2, 1.6 Hz, 1H), 7.14 (td, J=7.6, 1.6 Hz, 1H), 7.09 (d, J=6.8 Hz, 1H), 5.23 (d, J=53.2 Hz, 1H), 4.60-4.66 (m, 2H), 4.41-4.54 (m, 1H), 4.33 (s, 3H), 4.02-4.11 (m, 2H), 3.89-3.98 (m, 3H), 3.71 (d, J=14.8 Hz, 1H), 3.10-3.20 (m, 2H), 3.00-3.10 (m, 2H), 2.90-2.99 (m, 2H), 2.76 (d, J=5.2 Hz, 2H), 2.36-2.51 (m, 1H), 2.14-2.31 (m, 3H), 2.11 (s, 3H), 1.77-2.06 (m, 9H).

Example 28. Exemplary Synthesis of 3-chloro-5-[(7S)-6-ethyl-2-[[(2R,8S)-2-fluoro-1,2,3,5,6,7-hexahydropyrrolizin-8-yl]methoxy]spiro[5,8-dihydropyrido[4,3-d]pyrimidine-7,1'-tetralin]-4-yl]-N,N-dimethyl-4,6,7,8-tetrahydropyrazolo[1,5-a][1,4]diazepine-2-carboxamide (Compound 100)

100a

100b

100c

-continued

100d

Compound 100

Step 1. Synthesis of (7S)-6-ethylspiro[5,8-dihydropyrido[4,3-d]pyrimidine-7,1'-tetralin]-2,4-diol (100b). To a solution of (7S)-spiro[6,8-dihydro-5H-pyrido[4,3-d]pyrimidine-7,1'-tetralin]-2,4-diol (100a prepared similarly to that of 64h, 400 mg, 1.41 mmol) in Ethanol (6.7 mL) was added acetaldehyde (0.8 mL, 14.12 mmol) and NaBH$_3$CN (266.15 mg, 4.24 mmol). The mixture was stirred at 30° C. for 2 days. NaBH$_3$CN (266.15 mg, 4.24 mmol) and acetaldehyde (0.8 mL, 14.12 mmol) were added, and the reaction was continued to stir at 30° C. for 6 h. The reaction mixture was quenched with water and filtered, dry over in vacuum to afford (7S)-6-ethylspiro[5,8-dihydropyrido[4,3-d]pyrimidine-7,1'-tetralin]-2,4-diol (100b, 430 mg, 0.884 mmol, 62.60% yield) as yellow solid. LCMS calculated for C$_{18}$H$_{22}$N$_3$O$_2$ (M+H)$^+$ m/z=312.17; found: 312.0.

Step 2. Synthesis of (7S)-2,4-dichloro-6-ethyl-spiro[5,8-dihydropyrido[4,3-d]pyrimidine-7,1'-tetralin](100c). A solution of (7S)-6-ethylspiro[5,8-dihydropyrido[4,3-d]pyrimidine-7,1'-tetralin]-2,4-diol (100b, 430 mg, 0.88 mmol) in POCl$_3$ (4065.43 mg, 26.51 mmol) was stirred at 100° C. for 5 h. The reaction mixture was concentrated, diluted with DCM and DIEA, extracted with DCM, dried over Na$_2$SO$_4$, concentrated and purified by flash column chromatography (silica gel, eluting with 0% to 10% EtOAc/PE) to afford (7S)-2,4-dichloro-6-ethyl-spiro[5,8-dihydropyrido[4,3-d]pyrimidine-7,1'-tetralin (100c, 120 mg, 0.345 mmol, 38.99% yield) as a yellow solid. LCMS calculated for C$_{18}$H$_{20}$Cl$_2$N$_3$ (M+H)$^+$ m/z=348.10, 350.10; found: 348.1, 350.1.

Step 3. Synthesis of 3-chloro-5-[(7S)-2-chloro-6-ethyl-spiro[5,8-dihydropyrido[4,3-d]pyrimidine-7,1'-tetralin]-4-yl]-N,N-dimethyl-4,6,7,8-tetrahydropyrazolo[1,5-a][1,4]diazepine-2-carboxamide (100d). A solution of (7S)-2,4-dichloro-6-ethyl-spiro[5,8-dihydropyrido[4,3-d]pyrimidine-7,1'-tetralin](100c, 120 mg, 0.34 mmol), 3-chloro-N,N-dimethyl-5,6,7,8-tetrahydro-4H-pyrazolo[1,5-a][1,4]diazepine-2-carboxamide (83.63 mg, 0.34 mmol) and DIEA (133.59 mg, 1.03 mmol) in DMSO (1.2 mL) was stirred at 30° C. for 16 h. The reaction mixture was filtered, the filtrate was purified by prep-HPLC (0.1% NH$_4$HCO$_3$), to afford 3-chloro-5-[(7S)-2-chloro-6-ethyl-spiro[5,8-dihydropyrido[4,3-d]pyrimidine-7,1'-tetralin]-4-yl]-N,N-dimethyl-4,6,7,8-tetrahydropyrazolo[1,5-a][1,4]diazepine-2-carboxamide (100d, 110 mg, 0.198 mmol, 57.57% yield) as a white solid. LCMS calculated for C$_{28}$H$_{34}$Cl$_2$N$_7$O (M+H)$^+$ m/z=554.22, 556.22; found: 554.0, 556.0. $^1$H NMR (400 MHz, DMSO) δ=7.47 (d, J=7.5 Hz, 1H), 7.19 (t, J=6.9 Hz, 1H), 7.13 (t, J=6.8, 1H), 7.07 (d, J=6.9, 1H), 4.85-4.71 (m, 2H), 4.51-4.38 (m, 2H), 4.02-3.86 (m, 2H), 3.74 (dd, J=45.1, 15.6 Hz, 2H), 3.02-2.91 (m, 7H), 2.82 (d, J=18.3 Hz, 1H), 2.82 (d, J=18.3 Hz, 1H), 2.76-2.62 (m, 2H), 2.37-1.99 (m, 4H), 1.94-1.64 (m, 4H), 0.84 (t, J=7.0 Hz, 3H).

Step 4. Synthesis of 3-chloro-5-[(7S)-6-ethyl-2-[[(2R,8S)-2-fluoro-1,2,3,5,6,7-hexahydropyrrolizin-8-yl]methoxy]spiro[5,8-dihydropyrido[4,3-d]pyrimidine-7,1'-tetralin]-4-yl]-N,N-dimethyl-4,6,7,8-tetrahydropyrazolo[1,5-a][1,4]diazepine-2-carboxamide (Compound 100)

The mixture of 3-chloro-5-[(7S)-2-chloro-6-ethyl-spiro[5,8-dihydropyrido[4,3-d]pyrimidine-7,1'-tetralin]-4-yl]-N,N-dimethyl-4,6,7,8-tetrahydropyrazolo[1,5-a][1,4]diazepine-2-carboxamide (100d, 30 mg, 0.05 mmol), [(2R,8S)-2-fluoro-1,2,3,5,6,7-hexahydropyrrolizin-8-yl]methanol (43.07 mg, 0.27 mmol) and Sodium Tert-Butoxide (7.8 mg, 0.08 mmol) in DMSO (1 mL) was stirred at 20° C. for 3 h until the reaction mixture is clear. The reaction mixture was purified by prep-HPLC (0.1% NH$_4$HCO$_3$) to afford 3-chloro-5-[(7S)-6-ethyl-2-[[(2R,8S)-2-fluoro-1,2,3,5,6,7-hexahydropyrrolizin-8-yl]methoxy]spiro[5,8-dihydropyrido[4,3-d]pyrimidine-7,1'-tetralin]-4-yl]-N,N-dimethyl-4,6,7,8-tetrahydropyrazolo[1,5-a][1,4]diazepine-2-carboxamide (Compound 100, 16 mg, 0.0237 mmol, 43.88% yield) as a white solid. LCMS calculated for C$_{36}$H$_{46}$ClFN$_8$O$_2$ (M+H)$^+$ m/z=677.35; found: 677.0. $^1$H NMR (400 MHz, CD$_3$OD) δ=7.52 (d, J=7.7 Hz, 1H), 7.17 (dd, J=10.7, 4.3 Hz, 1H), 7.12 (td, J=7.3, 1.3 Hz, 1H), 7.07 (d, J=6.5 Hz, 1H), 5.26 (d, J=53.8 Hz, 1H), 4.93-4.86 (m, 1H), 4.76 (dd, J=16.7, 6.5 Hz, 1H), 4.56-4.34 (m, 2H), 4.16-3.72 (m, 6H), 3.16 (m, 3H), 3.10 (d, J=2.1 Hz, 3H), 3.08 (s, 3H), 3.06-2.86 (m, 3H), 2.75 (d, J=7.0 Hz, 2H), 2.53-1.71 (m, 14H), 0.95 (t, J=7.0 Hz, 3H).

Example 29. Exemplary Synthesis of 3-chloro-5-[(7S)-6-ethyl-2-[[(2R,8S)-2-fluoro-1,2,3,5,6,7-hexa-hydropyrrolizin-8-yl]methoxy]spiro[5,8-dihydro-pyrido[4,3-d]pyrimidine-7,1'-tetralin]-4-yl]-N,N-dimethyl-4,6,7,8-tetrahydropyrazolo[1,5-a][1,4] diazepine-2-carboxamide (Compound 101)

100a

101b

101c

101d

-continued

Compound 101

Step 1. Synthesis of (7S)-2,4-dichloro-7'-fluoro-spiro[6,8-dihydro-5H-pyrido[4,3-d]pyrimidine-7,1'-indane](101b)

The mixture of (7S)-7'-fluorospiro[6,8-dihydro-5H-pyrido[4,3-d]pyrimidine-7,1'-indane]-2,4-diol (100a, 1.2 g, 4.18 mmol) in POCl$_3$ (12.59 mL, 137.49 mmol) was added DIEA (1.46 mL, 8.35 mmol) and heated at 100° C. for 5 h. The reaction was cooled down to rt, concentrated and dissolved in DCM (20 mL) at 0'° C. The mixture was added DIEA (1.5 mL) and was stirred at 0° C. for 2 h, followed by the addition of NH$_4$HCO$_3$ (aq, 20 mL). The organic layer was dried over Na$_2$SO$_4$ and concentrated and purified by flash column chromatography (silica gel, eluting with 0% to 100% EtOAc/PE) to afford (7S)-2,4-dichloro-7'-fluoro-spiro[6,8-dihydro-5H-pyrido[4,3-d]pyrimidine-7,1'-indane] (101b, 1.14 g, 3.52 mmol, 84.19% yield as brown solid. LCMS calculated for C$_{15}$H$_{13}$Cl$_2$FN$_3$ (M+H)$^+$ m/z=324.1, 326.1; found: 324.1, 326.1.

Step 2. Synthesis of 3-chloro-5-[(7S)-2-chloro-7'-fluoro-spiro[6,8-dihydro-5H-pyrido[4,3-d]pyrimidine-7,1'-indane]-4-yl]-N,N-dimethyl-4,6,7,8-tetrahydropyrazolo[1,5-a][1,4]diazepine-2-carboxamide (101c). The mixture of (7S)-2,4-dichloro-7'-fluoro-spiro[6,8-dihydro-5H-pyrido[4,3-d]pyrimidine-7,1'-indane](101b, 300 mg, 0.93 mmol), 3-chloro-N,N-dimethyl-5,6,7,8-tetrahydro-4H-pyrazolo[1,5-a][1,4]diazepine-2-carboxamide (Int-, 224.61 mg, 0.93 mmol) and DIEA (0.64 mL, 3.7 mmol) in DMSO (2 mL) was stirred at 20° C. for 30 h. The reaction mixture was purified by prep-HPLC on a C18 column (20-35 uM, 100 A, 40 g) with mobile phase: H$_2$O (0.1% NH$_4$HCO$_3$)/MeCN at flowrate: 50 mL/min to give 3-chloro-5-[(7S)-2-chloro-7'-fluoro-spiro[6,8-dihydro-5H-pyrido[4,3-d]pyrimidine-7,1'-indane]-4-yl]-N,N-dimethyl-4,6,7,8-tetrahydropyrazolo[1,5-a][1,4]diazepine-2-carboxamide (364 mg, 0.686 mmol, 74.16% yield). LCMS calculated for C$_{25}$H$_{27}$Cl$_2$FN$_7$O (M+H)$^+$ m/z=530.2/532.2; found: 530.1/532.2.

Step 3. Synthesis of 3-chloro-5-[(7S)-2-chloro-6-(cya-nomethyl)-7'-fluoro-spiro[5,8-dihydropyrido[4,3-d]pyrimi-dine-7,1'-indane]-4-yl]-N,N-dimethyl-4,6,7,8-tetrahydropy-razolo[1,5-a][1,4]diazepine-2-carboxamide (101d). To a solution of 3-chloro-5-[(7S)-2-chloro-7'-fluoro-spiro[6,8-di-hydro-5H-pyrido[4,3-d]pyrimidine-7,1'-indane]-4-yl]-N,N-dimethyl-4,6,7,8-tetrahydropyrazolo[1,5-a][1,4]diazepine-2-carboxamide (101c, 364 mg, 0.69 mmol) in DMF (2 mL)

was added Cesium carbonate (670.78 mg, 2.06 mmol) and bromoacetonitrile (0.1 mL, 1.37 mmol). The reaction was heated at 50° C. overnight. The reaction mixture was purified by prep-HPLC on a C18 column (20-35 uM, 100 A, 40 g) with mobile phase: $H_2O$ (0.1% $NH_4HCO_3$)/MeCN to give 3-chloro-5-[(7S)-2-chloro-6-(cyanomethyl)-7'-fluoro-spiro[5,8-dihydropyrido[4,3-d]pyrimidine-7,1'-indane]-4-yl]-N,N-dimethyl-4,6,7,8-tetrahydropyrazolo[1,5-a][1,4]diazepine-2-carboxamide (370 mg, 0.650 mmol, 94.68% yield). LCMS calculated for $C_{27}H_{28}Cl_2FN_8O$ (M+H)$^+$ m/z=569.17; found: 569.2.

Step 4. Synthesis of 3-chloro-5-[(7S)-6-(cyanomethyl)-7'-fluoro-2-[[(2R,8S)-2-fluoro-1,2,3,5,6,7-hexahydropyrrolizin-8-yl]methoxy]spiro[5,8-dihydropyrido[4,3-d]pyrimidine-7,1'-indane]-4-yl]-N,N-dimethyl-4,6,7,8-tetrahydropyrazolo[1,5-a][1,4]diazepine-2-carboxamide (Compound 101). The mixture of 3-chloro-5-[(7S)-2-chloro-6-(cyanomethyl)-7'-fluoro-spiro[5,8-dihydropyrido[4,3-d]pyrimidine-7,1'-indane]-4-yl]-N,N-dimethyl-4,6,7,8-tetrahydropyrazolo[1,5-a][1,4]diazepine-2-carboxamide (101d, 30 mg, 0.05 mmol), [(2R,8S)-2-fluoro-1,2,3,5,6,7-hexahydropyrrolizin-8-yl]methanol (41.93 mg, 0.26 mmol) and sodium tert-butoxide (7.59 mg, 0.08 mmol) in DMSO (1 mL) was stirred at 20° C. under Argon for 2 h. The reaction mixture was purified by prep-HPLC $H_2O$ (0.1% $NH_4HCO_3$)/MeCN to afford 3-chloro-5-[(7S)-6-(cyanomethyl)-7'-fluoro-2-[[(2R,8S)-2-fluoro-1,2,3,5,6,7-hexahydropyrrolizin-8-yl]methoxy]spiro[5,8-dihydropyrido[4,3-d]pyrimidine-7,1'-indane]-4-yl]-N,N-dimethyl-4,6,7,8-tetrahydropyrazolo[1,5-a][1,4]diazepine-2-carboxamide (Compound 101, 10 mg, 0.0135 mmol, 25.60% yield) as a white solid. LCMS calculated for $C_{35}H_{41}ClF_2N_9O_2$ (M+H)$^+$ m/z=692.3; found: 692.3. 1H NMR (400 MHz, CD$_3$OD) δ 7.34-7.39 (m, 1H), 7.12-7.14 (m, 1H), 6.95-7.00 (m, 1H), 5.26 (d, J=53.8, 1H), 4.82, 4.88 (d, J=16.8 Hz, 2H), 4.39-4.53 (m, 2H), 3.87-4.16 (m, 6H), 3.56, 3.73 (d, J=17.6 Hz, 2H), 3.12-3.25 (m, 4H), 3.10 (s, 3H), 3.08 (s, 3H), 2.96-3.04 (m, 2H), 2.80 (d, J=17.6, 1H), 2.57-2.65 (m, 1H), 1.83-2.44 (m, 10H).

Compound 102. 3-chloro-5-[(7S)-6-(cyanomethyl)-2-[[(2R,8S)-2-fluoro-1,2,3,5,6,7-hexahydropyrrolizin-8-yl]methoxy]spiro[5,8-dihydropyrido[4,3-d]pyrimidine-7,1'-tetralin]-4-yl]-N,N-dimethyl-4,6,7,8-tetrahydropyrazolo[1,5-a][1,4]diazepine-2-carboxamide Compound 102 was prepared similarly to that of Ex. 28. LCMS calculated for $C_{36}H_{44}ClFN_9O_2$ (M+H)$^+$ m/z=688.33, 690.33; found: 689.5, 691.6. 1H NMR (400 MHz, CD$_3$OD) δ=7.50 (d, J=7.8, 1H), 7.26 (dd, J=10.6, 4.4, 1H), 7.20 (td, J=7.4, 1.4, 1H), 7.15 (d, J=7.4, 1H), 5.27 (d, J=54.4, 1H), 4.91 (d, J=16.6, 1H), 4.80 (d, J=16.6, 1H), 4.36-4.56 (m, 2H), 4.04-4.22 (m, 3H), 3.86-4.03 (m, 3H), 3.45 (m, J=17.2, 2H), 3.12-3.26 (m, 3H), 3.10 (s, 3H), 3.07 (s, 3H), 2.92-3.06 (m, 3H), 2.73-2.83 (m, 2H), 2.33-2.47 (m, 1H), 1.73-2.33 (m, 11H).

Compound 103. 3-chloro-5-[(7S)-6-ethyl-7'-fluoro-2-[[(2R,8S)-2-fluoro-1,2,3,5,6,7-hexahydropyrrolizin-8-yl]methoxy]spiro[5,8-dihydropyrido[4,3-d]pyrimidine-7,1'-indane]-4-yl]-N,N-dimethyl-4,6,7,8-tetrahydropyrazolo[1,5-a][1,4]diazepine-2-carboxamide Compound 103 was prepared similarly to that of Ex. 28. LCMS calculated for $C_{35}H_{44}ClF_2N_8O_2$ (M+H)$^+$ m/z=681.32; found: 681.3, 683.3. 1H NMR (400 MHz, CD$_3$OD) δ=7.26-7.31 (m, 1H), 7.04-7.08 (m, 1H), 6.89-6.93 (m, 1H), 5.26 (d, J=53.8, 1H), 4.73-4.82 (m, 2H), 4.36-4.52 (m, 2H), 3.66-4.14 (m, 6H), 3.14-3.25 (m, 3H), 3.10 (s, 3H), 3.08 (s, 3H), 2.91-3.04 (m, 3H), 2.80 (d, J=17.6, 1H), 2.55-2.65 (m, 1H), 1.81-2.46 (m, 12H), 1.07 (t, J=7.2, 3H).

Example 30: Nucleotide Exchange Assay

Ras proteins cycle between an active, GTP bound state, and an inactive GDP-bound state. This activity is tightly regulated by GTPase activating proteins (GAPs) and guanine nucleotide exchange factors (GEFs). GEFs, such as SOS1/2, activate Ras proteins by exchanging GDP for GTP, thus returning Ras to its active conformation (Simanshu, Nissley, & McCormick, 2017). Therefore, a small molecule that binds K-Ras in a manner that prevents SOS-mediated nucleotide exchange locks KRas in its inactive state. Homogenous time resolved fluorescence (HTRF) was used to detect SOS-mediated binding of a fluorescent GTP analog, GTP-DY-647P1 (Jena Biosciences NU-820-647P1) to GST-tagged KRAS$^{G12D}$ (2-169, Reaction Biology, MSC-11-539).

GST-tagged KRAS$^{G12D}$ (2-169) and anti-GST MAb Tb Cryptate Gold (CisBio 61GSTTLB) were diluted into assay buffer (20 mM HEPES, pH 7.3, 150 mM NaCl, 5 mM $MgCl_2$, 0.05% BSA 0.0025% NP40, 1 mM DTT) to prepare a 2.5× donor solution. 5× compound was added to the protein mixture and incubated for 1 h at RT. 2.5× acceptor solution containing $SOS1_{cat}$ (564-1049, Reaction Biology MSC-11-502) and GTP-DY-647P1 were then added to the donor KRAS mixture such that the final concentration of the reaction contained 5 nM GST-tagged $KRAS^{G12D}$ (2-169), 20 nM $SOS_{cat}$, and 150 nM GTP. The reaction was monitored using at RT with the Envision multimode plate reader (Ex/Em 337/665, 620 nM) up to 90 minutes at 5 minute intervals. Data was blanked to reactions without SOS1 and 0% inhibition was calculated such that DMSO only=0% and blank=100%. Curve fitting was done using a 4 parameter fit. NEA KRAS G12D $IC_{50}$ (uM) values of selected compounds are depicted in Table 2 with compounds having a value<0.01 uM as ++++; >0.01 uM to 0.1 uM as +++; >0.1 uM to 1 uM as ++; >1 uM to 20 uM as +; and >20 uM as NA.

Example 31: Protein Constructs for Protein-Protein Interaction

TABLE 1

Assay, Protein construct, and protein construct sequences

| Assay | Protein Construct | Protein Construct Sequence |
|-------|-------------------|----------------------------|
| PPI | Biotinylated Avi-KRAS-G12D (1-169) | SGLNDIFEAQKIEWHEMTEYKLVVV GADGVGKSALTIQLIQNHFVDEYDP TIEDSYRKQVVIDGETCLLDILDTA GQEEYSAMRDQYMRTGEGFLCVFAI NNTKSFEDIHHYREQIKRVKDSEDV PMVLVGNKCDLPSRTVDTKQAQDLA RSYGIPFIETSAKTRQGVDDAFYTL VREIRKHKEK |
| PPI | Biotinylated Avi-KRAS-G12V (1-169) | SGLNDIFEAQKIEWHEMTEYKLVVV GAVGVGKSALTIQLIQNHFVDEYDP TIEDSYRKQVVIDGETCLLDILDTA GQEEYSAMRDQYMRTGEGFLCVFAI NNTKSFEDIHHYREQIKRVKDSEDV PMVLVGNKCDLPSRTVDTKQAQDLA RSYGIPFIETSAKTRQGVDDAFYTL VREIRKHKEK |
| PPI | Biotinylated Avi-KRAS wt (1-169) | SGLNDIFEAQKIEWHEMTEYKLVVV GAGGVGKSALTIQLIQNHFVDEYDP TIEDSYRKQVVIDGETCLLDILDTA GQEEYSAMRDQYMRTGEGFLCVFAI NNTKSFEDIHHYREQIKRVKDSEDV PMVLVGNKCDLPSRTVDTKQAQDLA RSYGIPFIETSAKTRQGVDDAFYTL VREIRKHKEK |
| PPI | Biotinylated Avi-NRAS (1-169) | SGLNDIFEAQKIEWHEMTEYKLVVV GAGGVGKSALTIQLIQNHFVDEYDP TIEDSYRKQVVIDGETCLLDILDTA GQEEYSAMRDQYMRTGEGFLCVFAI NNSKSFADINLYREQIKRVKDSDDV PMVLVGNKCDLPTRTVDTKQAHELA KSYGIPFIETSAKTROGVEDAFYTL VREIRQYRMK |
| PPI | His8-RAF1 RBD (52-131) | SHHHHHHHHSKTSNTIRVFLPNKQR TVVNVRNGMSLHDCLMKALKVRGLQ PECCAVFRLLHEHKGKKARLDWNTD AASLIGEELQVDFL |

Example 32. Recombinant Protein Production

Biotinylated KRAS wt and KRAS G12D/V proteins were expressed and purified in conditions similar to those previously reported (Tran, et al., 2021) (Zhang, et al., 2020).

Briefly, KRAS (1-169) proteins were expressed in *E. coli* at 18° C. with an upstream TEV cleavage site (ENLFYQS) followed an Avi tag sequence (GLNDIFEAQKIEHE). KRAS expression constructs contained both a His6 and maltose-binding protein (MBP) tags at the N-terminus for Ni-NTA column purification prior to overnight TEV cleavage and MBP column purification. The avi-tagged NRAS expression construct contained both a His6 tag and SUMO cleavage sige at the N-terminus for Ni-NTA column purification followed by His-ULP1 digestion overnight. All avi-tagged RAS proteins were dialyzed into buffer containing ATP, biotin, and BirA followed by purification over a second Ni-NTA column and then run over a size exclusion HiLoad™ 26/600 Superdex™ column in 20 mM HEPES, pH 7.5, 300 mM NaCl, 5 mM $MgCl_2$, and 1 mM TCEP. Fractions containing the protein of interest were pooled, concentrated, and confirmed by intact mass spectrometry. To prepare 'GTP' loaded KRAS and NRAS, biotinylated KRAS or NRAS was nucleotide exchanged from GDP-bound protein to GppNHp-bound (Jena Biosciences, NU-401-50) protein in the presence of alkaline phosphatase and excess GppNHp as previously described and the resulting nucleotide content was confirmed by HPLC reverse phase analytical chromatography (Donohue, et al., 2019) (Tran, et al., 2021).

His-tagged RAF1 (52-131) was similarly expressed in *E. coli* at 18° C. overnight with an upstream TEV cleavage site. His-tagged RAF1 expression construct contained both a His6 and MBP tags at the N-terminus for Ni-NTA column purification followed by MBP-tagged TEV digestion overnight. RAF1 protein samples were further purified over a MBP column followed by a Ni-NTA column and a second MBP column. The fractions containing the protein of interest were pooled, concentrated, and further purified over a HiLoad™ 16/600 Superdex™ 75 pg size exclusion column into 20 mM HEPES, pH8.0, 200 mM NaCl, 5 mM TCEP.

Example 33: Protein-Protein Interaction (PPI) Assay

When RAS proteins are in the active GTP-bound conformation, they bind the effector protein RAF1 at the N-terminus Ras-binding domain (RBD, residues 52-131) (Tran, et al., 2021). Homogenous time resolved fluorescence (HTRF) was used to monitor the interaction between wt or mutant KRAS and RAF1 or wt NRAS and RAF1. Compounds were assayed in the presence of KRAS G12D/V and RAF1 versus wt KRAS to assess activity against mutant and w.t. KRAS. Similarly, compounds were then assayed in the presence of w.t. NRAS and RAF1 to assess RAS isoform selectivity. In all assay formats, His-tagged RAF1 protein was incubated with the HTRF donor, anti-6His Tb Cryptate gold (Cisbio 61DB10RDF), and biotinylated RAS proteins were incubated with the HTRF acceptor, streptavidin-d2 (CisBio 610SADLA). The intensity of the fluorescence signal emitted is proportional to binding between the two proteins. The donor solution was prepared by mixing 16 nM His-tagged RAF1 in protein dilution buffer with 1:100 anti-6His Tb cryptate in PPI-Terbium detection buffer. 16 nM biotinylated RAS protein was diluted into protein dilution buffer (50 mM Tris-HCl pH 7.5, 150 mM NaCl, 0.1 mM MgCl2, 1 mM TCEP, 0.005% Tween20) and mixed with 1:2000 Streptavidin-d2 diluted in PPI-Terbium detection buffer (CisBio 61DB10RDF). 50× compound in DMSO was mixed with 16 nM KRAS-acceptor solution and incubated for 30 minutes at room temperature. After compound pre-incubation with KRAS, the RAF1 donor solution was added to the KRAS-acceptor solution and incubated for 1 hour at room temperature. The fluorescence signal emitted was monitored at 665 nm and 615 nm using an Envision multimode plate reader. The HTRF ratio (665/615) was calculated and normalized to 0% inhibition in the absence of compound and 100% inhibition in the presence of untagged RAF1 protein. PPI KRAS G12D/RAF1, KRAS G12V/RAF1, w.t.KRAS/RAF1 and NRAS/RAF1 $IC_{50}$ (uM) values of selected compounds are depicted in Table 4 and Table 5 with compounds having a value <0.1 uM as ++++; >0.1 uM to 1 uM as +++; >1 uM to 10 uM as ++; >10 uM to 100 uM as +; and >100 uM as NA.

Compounds described herein are active against KRAS G12 mutant and other alleles representative by PPI-G12D, PPI-G12V and PPI-w.t.KRAS potency for broad activity against mutant KRAS and wtKRAS amplification driven malignancies.

Example 34. pERK Inhibition Cellular HTRF Assay in AGS Cell Lines (Method A)

The Phospho-ERK cellular HTRF assay measures ERK protein phosphorylated at Thr202/Tyr204 as a readout of MAPK pathway activation (Cisbio 64ERKPEH). AGS cells (ATCC CRL-1739) are cultured in the complete medium containing 10% fetal bovine serum and 1×Penicillin/Streptomycin at 37° C. in a humid atmosphere of 5% $CO_2$ in the air (AGS cells: RPMI 1640 medium).

On day 1, the cells are plated in tissue-culture treated 96-well plates at the specified densities and allowed to attach for overnight (AGS: 30,000 cells/well). On day 2, the cells are treated with the serially diluted compound solutions in a final concentration of 0.5% DMSO. After the treatment for the specified time (AGS cells: 3 hours), the supernatant is removed, and the cells are lysed by the lysis buffer supplied with the kit. Then, the cell lysates are treated with the detection reagents overnight at 4° C. in darkness. On day 3, the fluorescence intensities at the wavelengths 665 and 620 nm are measured by the Envision plate reader (Perkin Elmer). The data are processed and fitted to a 4-parameter logistic model for $IC_{50}$ calculations (GraphPad Prism 9).

Example 35. pERK in Cell Western (ICW) Assay (Method B)

pERK ICW is a high throughput screening assay to evaluate the cellular potency of mutant KRAS small molecule inhibitors. KRAS mutant cell line AGS ($KRAS^{G12D}$) were purchased from ATCC and maintained in DMEM and RPMI medium supplemented with 10% fetal bovine serum and Penicillin/Streptomycin.

Cells grown in exponential phase were trypsinized, resuspended in fresh media, and viable cells were counted using a cell counter with Trypan Blue (BioRad TC20). Cells were seeded into 384-well plate (Greiner 781091) at density of 5,000 cells/well for AGS and allowed to grow overnight in a 37° C. $CO_2$ incubator. The next day, compounds were dispensed into wells with a ½ log, 10-point serial dilution and top concentration of 10 µM using Tecan D300e dispenser and incubated for 3 hours in a 37° C. $CO_2$ incubator. Cells were then fixed with paraformaldehyde (Electron Microscopy Sciences, 15710, 4% final concentration) for 30 min, permeabilized with wash buffer (1×PBS+0.1% Triton X-100) for 30 min and blocked with Odyssey blocking buffer (Li—COR 927-70001) for 1 hour, all at room temperature (RT). Phospho-ERK antibody (CST 4370L) was diluted 1:500 in Odyssey blocking+0.2% Tween 20 and incubated with cells overnight at 4° C. The next day, plates were washed 5× with wash buffer, incubated with IRDye 800 CW, Goat anti-Rabbit secondary antibody (Li—COR 926-32211, 1:500) and DRAQ5 (CST 4084L, 1:5,000) diluted in in Odyssey blocking+0.2% Tween 20 for 1 hour, washed 5×, and imaged on an Odyssey CLx imaging system.

For data analysis, signal intensities from 800 (phosphor-ERK) and 700 (DRAQ5) channels were extracted, and phospho-ERK signals were normalized to DRAQ5 signals for each well and percent of DMSO control values were computed. Data were then imported into Graphpad Prism to compute half-maximal inhibitory concentrations ($IC_{50}$) using a 4-parameter variable slope model. Z-factor for each plate was computed from signals derived from wells treated with either DMSO or 5 µM of Trametinib. AGS pERK ICW (Method B) $IC_{50}$ (uM) values of selected compounds are depicted in Table 2 with compounds having a value 0.001 uM to 0.01 uM as ++++; >0.01 uM to 0.1 uM as +++; >0.1 uM to 1 uM as ++; 1 uM to 10 uM as + and >10 uM as NA.

Table 2 includes NEA KRAS G12D $IC_{50}$ (uM) values (<0.01 uM as ++++; >0.01 uM to 0.1 uM as +++; >0.1 uM to 1 uM as ++; >1 uM to 20 uM as +; and >20 uM as NA), PPI KRAS G12D/RAF1 $IC_{50}$ (uM) values (<0.1 uM as ++++; >0.1 uM to 1 uM as +++; >1 uM to 10 uM as ++; >10 uM to 100 uM as +; and >100 uM as NA), AGS pERK HTRF (Method A) $IC_{50}$ (uM) values (<0.01 uM as ++++; >0.01 uM to 0.1 uM as +++; 0.1 uM to 1 uM as ++; 1 uM to 20 uM as + and >20 uM as NA), and AGS pERK ICW (Method B) $IC_{50}$ (uM) values (0.001 uM to 0.01 uM as ++++; >0.01 uM to 0.1 uM as +++; >0.1 uM to 1 uM as ++; 1 uM to 10 uM as + and >10 uM as NA) of selected compounds. ND indicates not determined.

TABLE 2

| | $IC_{50}$ (uM) values for various assays | | |
| --- | --- | --- | --- |
| cpd# | NEA-G12D (uM) | PPI-G12D (uM) | PERK-AGS (uM) Method B |
| 1 | + | NA | NA |
| 2 | +++ | + | + |
| 3 | + | NA | ND |
| 4 | + | NA | NA |
| 5 | + | + | NA |
| 6 | + | NA | NA |
| 7 | + | NA | NA |
| 8 | ++ | NA | NA |
| 9 | + | ND | + |
| 10 | +++ | NA | NA |
| 11 | + | ND | ND |
| 12 | + | ND | ND |
| 13 | + | + | ND |
| 14 | + | NA | NA |
| 15 | + | NA | NA |
| 16 | + | NA | NA |
| 17 | + | + | + |
| 18 | NA | + | NA |
| 19 | + | NA | ND |
| 20 | + | NA | ND |
| 21 | + | ND | ND |
| 22 | + | ND | ND |
| 23 | + | + | ND |
| 24 | ++ | + | ND |
| 21 | + | ND | ND |
| 22 | + | ND | ND |
| 23 | + | + | ND |
| 24 | ++ | + | ND |
| 21 | + | ND | ND |
| 22 | + | ND | ND |
| 23 | + | + | ND |
| 24 | ++ | + | ND |
| 25 | + | NA | ND |
| 24A | +++ | + | + |

TABLE 2-continued

| | IC$_{50}$ (uM) values for various assays | | |
| --- | --- | --- | --- |
| cpd# | NEA-G12D (uM) | PPI-G12D (uM) | PERK-AGS (uM) Method B |
| 26 | + | ND | ND |
| 23A | ++ | NA | ND |
| 23B | + | ND | ND |
| 27A | ++ | NA | ND |
| 27B | ++++ | + | ++ |
| 28A | + | NA | NA |
| 29 | ++ | + | + |
| 30 | + | NA | ND |
| 31 | +++ | NA | ND |
| 32 | +++ | NA | ND |
| 33 | ++ | + | ND |
| 34 | ++++ | NA | ND |
| 35 | +++ | NA | ND |
| 36 | ++++ | + | ND |
| 37 | ++++ | NA | ND |
| 38 | ++++ | + | ND |
| 39 | ++++ | NA | + |
| 39A | ++++ | + | ++ |
| 39B | + | ND | NA |
| 40 | +++ | NA | ND |
| 41 | + | ND | NA |
| 42 | ++++ | + | ++ |
| 43 | +++ | + | + |
| 44 | + | ND | ND |
| 45 | ++++ | + | ++ |
| 46A | ++ | + | NA |
| 46B | + | ND | ND |
| 47 | ++++ | NA | + |
| 48 | + | ND | NA |
| 49 | ++++ | + | ++ |
| 50 | ++++ | + | ++ |
| 51A | + | ND | ND |
| 51B | +++ | + | ND |
| 52 | ++++ | + | ND |
| 53 | ++++ | + | +++ |
| 54 | ++++ | + | ++ |
| 55 | ++++ | + | ++ |
| 56 | +++ | ND | ND |
| 58 | +++ | ND | ND |
| 59 | +++ | NA | ND |
| 60 | ++ | + | NA |
| 61 | ++++ | + | +++ |
| 62 | +++ | NA | ND |
| 63 | ++++ | + | +++ |
| 64 | ++++ | + | +++ |
| 64B | ++ | NA | ND |
| 65 | ++++ | + | +++ |
| 66 | +++ | ND | NA |
| 67 | +++ | ND | NA |
| 68 | +++ | ND | NA |
| 69 | ++++ | + | +++ |
| 70 | +++ | ND | + |
| 71 | ++ | NA | ND |
| 72 | ++++ | + | ++ |
| 73 | +++ | NA | ND |
| 74 | +++ | NA | ND |
| 75 | ++ | ND | ND |
| 76 | ++++ | + | ND |
| 77 | ++++ | + | ND |
| 78 | ++++ | + | ND |
| 79 | ++++ | NA | + |
| 80 | +++ | + | ND |
| 81 | ++++ | + | +++ |
| 82 | +++ | NA | ND |
| 83 | +++ | NA | ND |
| 84 | ++++ | NA | + |
| 85 | + | NA | ND |
| 86 | ++++ | NA | ND |
| 87 | ++++ | + | ++ |
| 88 | +++ | NA | ND |
| 89 | ++ | NA | ND |
| 90 | ++++ | + | +++ |
| 91 | + | NA | ND |
| 92 | ++ | NA | ND |
| 93 | ++++ | + | ND |

TABLE 2-continued

| | IC$_{50}$ (uM) values for various assays | | |
| --- | --- | --- | --- |
| cpd# | NEA-G12D (uM) | PPI-G12D (uM) | PERK-AGS (uM) Method B |
| 94 | + | NA | ND |
| 95 | ++++ | NA | ND |
| 96 | ++++ | + | +++ |
| 97 | ++++ | NA | + |
| 98 | ++++ | NA | ND |
| 99 | ++++ | NA | ++ |
| 100 | +++ | NA | ND |
| 101 | ++ | ND | ND |
| 102 | +++ | ND | ND |
| 103 | +++ | ND | ND |

Table 3 includes KRASG12V/RAF1, wtKRAS/RAF1 and wtNRAS/RAF1 PPI IC$_{50}$ (uM) values of selected compounds; with compounds having a value <0.1 uM as ++++; 0.1 uM to 1 uM as +++; >1 uM to 10 uM as ++; >10 uM to 100 uM as +; and >100 uM as NA.

TABLE 3

| | IC$_{50}$ (uM) values for KRASG12V/RAF1, wtKRAS/RAF1 and wtNRAS/RAF1 PPI | | |
| --- | --- | --- | --- |
| cpd# | PPI-G12V (uM) | PPI-w.t.KRAS (uM) | PPI-w.t.NRAS (uM) |
| 23 | + | NA | NA |
| 24 | + | + | NA |
| 53 | + | + | NA |
| 64 | + | ND | NA |
| 81 | + | + | NA |
| 90 | + | NA | NA |
| 96 | + | NA | NA |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

We claim:

1. A compound of Formula (II):

Formula (II)

or a pharmaceutically acceptable salt thereof wherein:

M is selected from O, NH, and NMe;

n is 0;

R$^1$ is selected from an unsaturated 5- to 12-membered heterocycle, which is optionally substituted with one or more substituents independently selected from halogen, —B(OR$^{20}$)$_2$, —OR$^{20}$, —SR$^{20}$, —S(O)$_2$ $(R^{20})$, —$S(O)_2N(R^{20})_2$, —$NR^{20}S(O)_2R^{20}$, —$C(O)N$ $(R^{20})_2$, —$N(R^{20})C(O)R^{20}$, —$N(R^{20})C(O)N(R^{20})_2$, —$N(R^{20})C(O)OR^{20}$, —$N(R^{20})_2$, —$C(O)R^{20}$, —$C(O)OR^{20}$, —$OC(O)R^{20}$, —$OC(O)N(R^{20})_2$, —$NO_2$, =O, =$NO(R^{20})$, —CN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, and $C_{2-6}$ alkynyl;

or $R^1$ is selected from a 7- to 10-membered heterocycle, which is optionally substituted with one or more substituents independently selected from halogen, —$OR^{20}$, —$C(O)N(R^{20})_2$, —$N(R^{20})_2$, —$C(O)R^{20}$, —$S(O)_2(R^{20})$, =O, $C_{1-6}$ cyanoalkyl, and $C_{1-6}$ alkyl;

B is selected from a heterocycle and carbocycle, wherein the heterocycle or carbocycle is optionally substituted with one or more substituents independently selected from halogen, cyano, hydroxy, =O, —$NO_2$, $C_1$-$C_4$ alkyl, $C_{1-6}$ aminoalkyl, —S—$C_1$-$C_3$ alkyl, $C_2$-$C_4$ alkenyl, $C_2$-$C_4$ alkynyl, $C_2$-$C_4$ hydroxy-alkynyl, $C_1$-$C_3$ cyanoalkyl, triazolyl, $C_1$-$C_3$ haloalkyl, —O—$C_1$-$C_3$ haloalkyl, —S—$C_1$-$C_3$ haloalkyl, $C_1$-$C_3$ alkoxy, $C_1$-$C_3$ hydroxyalkyl, —$CH_2C(=O)N(R^5)_2$, —$C_3$-$C_4$ alkynyl-$N(R^5)_2$, —$N(R^5)_2$, ($C_1$-$C_3$ alkoxy)halo$C_1$-$C_3$ alkyl-, $C_3$-$C_{12}$ carbocycle, and 5- to 12-membered heterocycle, wherein the $C_3$-$C_{12}$ carbocycle and 5- to 12-membered heterocycle are each optionally substituted with one or more sub-stituents selected from halogen, —OH, —$NO_2$, —$NH_2$, —O, —S, —CN, $C_{1-6}$ aminoalkyl, $C_{1-6}$ alkoxy, $C_{1-6}$ hydroxyalkyl, and $C_{1-6}$ haloalkyl;

Y is O;

$R^2$ is selected from -L-heterocycle, wherein the hetero-cycle portion of -L-heterocycle is optionally substi-tuted with one or more $R^6$;

each L is independently selected from a $C_1$-$C_4$ alkylene optionally substituted with one or more substituents selected from hydroxy, $C_1$-$C_4$ hydroxyalkyl, $C_1$-$C_4$ alkyl, $C_3$-$C_6$ carbocycle, and 3- to 8-membered het-erocycle, wherein the $C_3$-$C_6$ carbocycle and 3- to 8-membered heterocycle are each optionally substi-tuted with one or more substituents selected from halogen, —OH, —$NO_2$, =O, =S, —CN, $C_{1-6}$ ami-noalkyl, $C_{1-6}$ alkoxy, $C_{1-6}$ hydroxyalkyl, and $C_{1-6}$ haloalkyl; and wherein optionally two substituents on the same carbon atom of L come together to form a $C_3$-$C_6$ carbocycle or 3- to 8-membered heterocycle wherein the $C_3$-$C_6$ carbocycle and 3- to 8-membered heterocycle are each optionally substituted with one or more substituents selected from halogen, —OH, —$NO_2$, —O, =S, —CN, $C_{1-6}$ aminoalkyl, $C_{1-6}$ alkoxy, $C_{1-6}$ hydroxyalkyl, and $C_{1-6}$ haloalkyl;

each $R^6$ is independently selected from halogen, hydroxy, $C_1$-$C_3$ hydroxyalkyl, $C_1$-$C_3$ alkyl, $C_1$-$C_3$ haloalkyl, $C_1$-$C_3$ alkoxy, cyano, $C_1$-$C_3$ aminoalkyl, -Q-phenyl, -Q-phenylSO$_2$F, —NHC(O)phenyl, —NHC(O)phenylSO$_2$F, $C_1$-$C_3$ alkyl substituted pyrazolyl, tert-butyldimethylsilyloxyCH$_2$—, —$N(R^5)_2$, ($C_1$-$C_3$ alkoxy) $C_1$-$C_3$ alkyl-, ($C_1$-$C_3$ alkyl) C(=O)—, oxo, ($C_1$-$C_3$ haloalkyl) C(=O)—, —SO$_2$F, ($C_1$-$C_3$ alkoxy) $C_1$-$C_3$ alkoxy, —CH$_2$OC (O)N(R$^5$)$_2$, —CH$_2$NHC(O)OC$_1$-C$_6$ alkyl, —CH$_2$NHC(O)N(R$^5$)$_2$, —CH$_2$NHC(O)C$_1$-C$_6$ alkyl, —CH$_2$(pyrazolyl), —CH$_2$NHSO$_2$C$_1$-C$_6$ alkyl, —CH$_2$OC(O)heterocycle, —OC(O)N(R$^5$)$_2$, —OC (O)NH(C$_1$-C$_3$ alkyl)O(C$_1$-C$_3$ alkyl), —OC(O)NH (C$_1$-C$_3$ alkyl)O(C$_1$-C$_3$ alkyl)phenyl(C$_1$-C$_3$ alkyl)N (CH$_3$)$_2$, —OC(O)NH(C$_1$-C$_3$ alkyl)O(C$_1$-C$_3$ alkyl) phenyl, —OC(O)heterocycle, and —CH$_2$heterocycle, wherein the phenyl of —NHC (O)phenyl or —OC(O)NH(C$_1$-C$_3$ alkyl)(C$_1$-C$_3$ alkyl)phenyl is optionally substituted with —C(O) H or —OH and wherein the heterocycle of —CH$_2$heterocyclyl is optionally substituted with oxo, wherein Q is O or S;

each $R^{20}$ is independently selected from hydrogen; and $C_{1-6}$ alkyl, $C_{3-12}$ carbocycle, and 3- to 12-membered heterocycle, each of which is optionally substituted with one or more substituents independently selected from halogen, —OH, —CN, —$NO_2$, —$NH_2$, —$N(C_{1-6}$ alkyl)$_2$, $C_{1-10}$ alkyl, —$C_{1-10}$ haloalkyl, —O—$C_{1-10}$ alkyl, oxo, $C_{3-12}$ carbocycle, and 3- to 12-membered heterocycle; and each $R^5$ is independently selected from hydrogen and $C_1$-$C_6$ alkyl.

2. The compound or salt of claim 1, wherein Mis O.

3. The compound or salt of claim 1, wherein Mis NMe.

4. The compound or salt of claim 1, wherein $R^1$ is selected from a 7- to 10-membered heterocycle, which is optionally substituted with one or more substituents independently selected from halogen, —$OR^{20}$, —$C(O)N(R^{20})_2$, —$N(R^{20})_2$, —$C(O)R^{20}$, —$S(O)_2 (R^{20})$, =O, $C_{1-6}$ cyanoalkyl, and $C_{1-6}$ alkyl.

5. The compound or salt of claim 1, wherein $R^1$ is selected from an unsaturated 5- to 12-membered heterocycle, which is optionally substituted with one or more substituents independently selected from halogen, —$B(OR^{20})_2$, —$OR^{20}$, —$SR^{20}$, —$S(O)_2 (R^{20})$, —$S(O)_2N(R^{20})_2$, —$NR^{20}S(O)_2R^{20}$, —$C(O)N(R^{20})_2$, —$N(R^{20})C(O)R^{20}$, —$N(R^{20})C(O)N(R^{20})_2$, —$N(R^{20})C(O)OR^{20}$, —$N(R^{20})_2$, —$C(O)R^{20}$, —$C(O)OR^{20}$, —$OC(O)R^{20}$, —$OC(O)N(R^{20})_2$, —$NO_2$, =O, =$NO(R^{20})$, —CN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, and $C_{2-6}$ alkynyl.

6. The compound or salt of claim 5, wherein $R^1$ is selected from

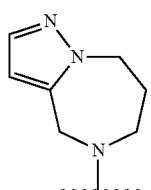

which is optionally substituted.

7. The compound or salt of claim 6, wherein $R^1$ is selected from which is optionally substituted with one or more substituents independently selected from halogen, —$C(O)N(R^{20})_2$, —$N(R^{20})_2$, —$C(O)R^{20}$, —$C(O)OR^{20}$, —CN, $C_{1-6}$ cyanoal-kyl, $C_{1-6}$ alkyl, and $C_{2-6}$ alkynyl.

8. The compound or salt of claim 7, wherein $R^1$ is

9. The compound or salt of claim 7, wherein $R^1$ is

10. The compound or salt of claim 1, wherein B is selected from each of which is optionally substituted with one or more substituents.

11. The compound or salt of claim 10, wherein B is selected from each of which is optionally substituted with one or more substituents.

12. The compound or salt of claim 11, wherein the one or more optional substituents are independently selected from oxo, —NH$_2$, —CN, halogen, and C$_1$-C$_3$ alkyl.

13. The compound or salt of claim 11, wherein B is selected from

14. The compound or salt of claim 1, wherein L is selected from C$_1$-C$_4$ alkylene.

15. The compound or salt of claim 14, wherein L is selected from unsubstituted C$_1$-C$_4$ alkylene.

16. The compound or salt of claim 15, wherein Y—R$^2$ is selected from wherein the heterocycle portion is optionally substituted with one or more R$^6$.

17. The compound or salt of claim 16, wherein R$^6$ of R$^2$ is independently selected at each occurrence from C$_1$-C$_3$ alkyl and halogen.

18. The compound or salt of claim 1, wherein Y—R$^2$ is selected from

19. The compound or salt of claim 1, wherein Y—R$^2$ is

361

362

20. The compound or salt of claim 1, wherein Y—R² is

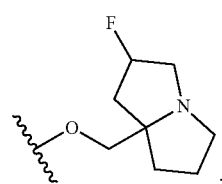 [SMILES: *OCC12CCCN1CC(F)C2]

21. The compound or salt of claim 1, wherein Mis O; R¹ is selected from which is optionally substituted with one or more substituents independently selected from halogen and —C(O)N(R²⁰)₂; B is selected from which is optionally substituted with one or more substituents selected from —NH₂, —CN, and C₁-C₃ alkyl; and Y—R² is

22. The compound or salt of claim 1, wherein Mis NMe; R¹ is selected from which is optionally substituted with one or more substituents independently selected from halogen and —C(O)N(R²⁰)₂; B is selected from which is optionally substituted with one or more substituents selected from —NH₂, —CN, and C₁-C₃ alkyl; and Y—R² is

23. The compound or salt of claim 1, wherein the compound is selected from

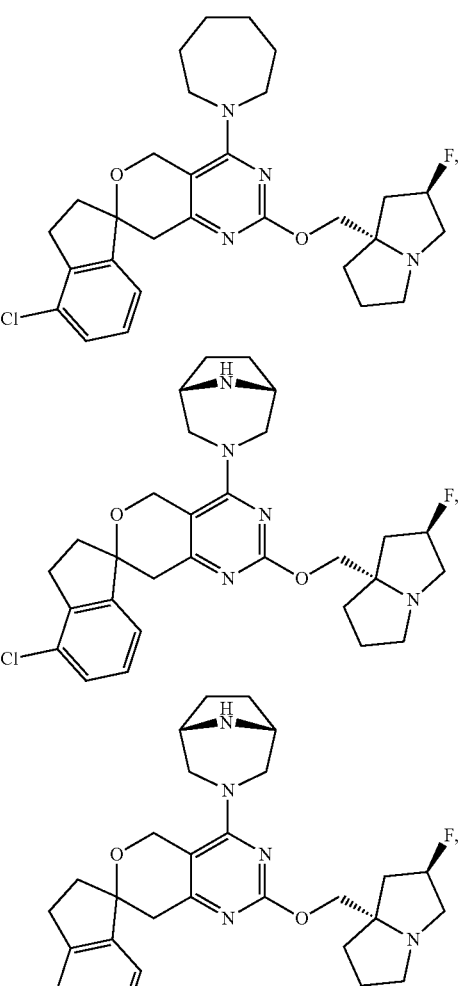

363

-continued

364

-continued

365

-continued

366

-continued

367

-continued

368

-continued

369

370

US 12,624,052 B2

371
-continued

372
-continued

373

-continued

374

-continued

or a salt of any one thereof.

24. The compound or salt of claim 1, wherein the compound is selected from

375

376

377

-continued

378

-continued

379

-continued

380

-continued or a salt of any one thereof.

25. The compound or salt of claim 1, the compound is selected from

381

382

383

384

-continued carcinoma), alveolar (bronchiolar) carcinoma, bronchial adenoma, sarcoma, lymphoma, chondromatous hamartoma, mesothelioma;

Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma);

Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma);

Liver: hepatoma (hepatocellular carcinoma), cholangiocarcinoma, hepatoblastoma, angiosarcoma, hepatocellular adenoma, hemangioma;

Biliary tract: gall bladder carcinoma, ampullary carcinoma, cholangiocarcinoma;

Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors;

Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma);

Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma);

Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma);

Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma.

or a salt of any one thereof.

26. A pharmaceutical composition comprising a compound or salt of claim 1 and a pharmaceutically acceptable excipient.

27. A method of treating a disease or disorder, comprising administering to a patient in need thereof the pharmaceutical composition of claim 26, wherein the disease or disorder is a cancer selected from:

Cardiac: sarcoma (angiosarcoma, fibrosarcoma, rhabdomyosarcoma, liposarcoma), myxoma, rhabdomyoma, fibroma, lipoma and teratoma;

Lung: bronchogenic carcinoma (squamous cell, undifferentiated small cell, undifferentiated large cell, adeno-

28. The compound or salt of claim 1, wherein $R^1$ is selected from an optionally substituted 7- to 10-membered fused heterocycle.

\* \* \* \* \*